(12) United States Patent
Young et al.

(10) Patent No.: US 11,873,496 B2
(45) Date of Patent: Jan. 16, 2024

(54) METHODS OF ALTERING GENE EXPRESSION BY PERTURBING TRANSCRIPTION FACTOR MULTIMERS THAT STRUCTURE REGULATORY LOOPS

(71) Applicant: Whitehead Institute for Biomedical Research, Cambridge, MA (US)

(72) Inventors: Richard A. Young, Boston, MA (US); Abraham S. Weintraub, Somerville, MA (US); Charles H. Li, Waban, MA (US); Alla A. Sigova, Newton, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 824 days.

(21) Appl. No.: 16/476,868

(22) PCT Filed: Jan. 9, 2018

(86) PCT No.: PCT/US2018/013003
§ 371 (c)(1),
(2) Date: Jul. 9, 2019

(87) PCT Pub. No.: WO2018/129544
PCT Pub. Date: Jul. 12, 2018

(65) Prior Publication Data
US 2019/0352648 A1    Nov. 21, 2019

Related U.S. Application Data

(60) Provisional application No. 62/596,093, filed on Dec. 7, 2017, provisional application No. 62/444,341, filed on Jan. 9, 2017.

(51) Int. Cl.
| | |
|---|---|
| *C07H 21/02* | (2006.01) |
| *C12N 15/67* | (2006.01) |
| *C07K 14/47* | (2006.01) |
| *C12N 15/113* | (2010.01) |
| *G01N 33/50* | (2006.01) |
| *C12N 15/85* | (2006.01) |

(52) U.S. Cl.
CPC .......... *C12N 15/67* (2013.01); *C07K 14/4702* (2013.01); *C12N 15/113* (2013.01); *C12N 15/85* (2013.01); *G01N 33/5023* (2013.01); *C12N 2015/859* (2013.01); *C12N 2310/51* (2013.01); *C12N 2310/53* (2013.01); *C12N 2830/001* (2013.01); *C12N 2830/15* (2013.01)

(58) Field of Classification Search
CPC .................. C12N 15/113; C12N 2830/001
See application file for complete search history.

(56) References Cited

U.S. PATENT DOCUMENTS

| | | |
|---|---|---|
| 6,780,986 B1 | 8/2004 | Heintz et al. |
| 8,513,207 B2 | 8/2013 | Brown |
| 9,801,877 B2 | 10/2017 | Yao et al. |
| 10,378,027 B2 | 8/2019 | Joung et al. |
| 11,312,955 B2 | 4/2022 | Berry et al. |
| 11,434,476 B2 | 9/2022 | Jaenisch et al. |
| 2008/0311039 A1* | 12/2008 | Bonavida ......... G01N 33/57426 424/9.1 |
| 2009/0082470 A1 | 3/2009 | Farjo |
| 2012/0115227 A1 | 5/2012 | Cohen-Haguenauer et al. |
| 2014/0273226 A1 | 9/2014 | Wu |
| 2014/0322707 A1 | 10/2014 | He et al. |
| 2015/0071906 A1 | 3/2015 | Liu et al. |
| 2015/0353885 A1 | 12/2015 | Sourdive |
| 2015/0376612 A1 | 12/2015 | Lee et al. |
| 2016/0010076 A1 | 1/2016 | Joung et al. |
| 2016/0024474 A1 | 1/2016 | Conway et al. |
| 2016/0186208 A1 | 6/2016 | Jaenisch et al. |
| 2016/0215281 A1 | 7/2016 | Fanucchi et al. |
| 2016/0340749 A1 | 11/2016 | Stelzer et al. |
| 2017/0014449 A1 | 1/2017 | Bangera et al. |
| 2017/0130247 A1 | 5/2017 | Dowen |
| 2017/0362649 A1 | 12/2017 | Lieberman-Aiden et al. |
| 2018/0245079 A1 | 8/2018 | Lieberman Aiden et al. |
| 2019/0024086 A1 | 1/2019 | Lande et al. |
| 2019/0127713 A1 | 5/2019 | Gersbach |

(Continued)

FOREIGN PATENT DOCUMENTS

| | | | |
|---|---|---|---|
| EP | 3382018 A1 | 10/2018 | |
| WO | WO 2006/025802 A1 * | 3/2006 | ........... C12N 15/113 |

(Continued)

OTHER PUBLICATIONS

Lopez-Bertoni et al. (Oncogene, 2015, 34, 3994-4004).*

(Continued)

*Primary Examiner* — Amy H Bowman
(74) *Attorney, Agent, or Firm* — Morse, Barnes-Brown & Pendleton, P.C.; Lisa M. Warren, Esq.; Erin E. Bryan, Esq.

(57) ABSTRACT

The invention relates to methods of modulating the expression of one or more genes in a cell by modulating the multimerization of a transcription factor and/or modulating the formation of enhancer-promoter DNA loops, and thereby modulating the expression of the one or more genes. The invention also relates to treating diseases and conditions involving aberrant gene expression by modulating the multimerization of a transcription factor and/or modulating the formation of enhancer-promoter DNA loops. The invention also relates to methods for screening for compounds that modulate expression of one or more genes in a cell.

18 Claims, 33 Drawing Sheets

Specification includes a Sequence Listing.

(56) References Cited

U.S. PATENT DOCUMENTS

| | | | |
|---|---|---|---|
| 2019/0241964 | A1 | 8/2019 | Hunter et al. |
| 2019/0309291 | A1 | 10/2019 | Lee et al. |
| 2019/0359959 | A1 | 11/2019 | Jaenisch et al. |
| 2020/0002558 | A1 | 1/2020 | Iwasaki et al. |
| 2020/0149039 | A1 | 5/2020 | Schuijers et al. |
| 2020/0224274 | A1 | 7/2020 | Bernstein et al. |

FOREIGN PATENT DOCUMENTS

| | | | |
|---|---|---|---|
| WO | WO-2009/146033 | A2 | 12/2009 |
| WO | WO-2012/019168 | A3 | 7/2012 |
| WO | WO-2013/176772 | A1 | 11/2013 |
| WO | WO 2014/071247 | A1 | 5/2014 |
| WO | WO-2014/172470 | A2 | 10/2014 |
| WO | WO 2015/033293 | A1 | 3/2015 |
| WO | WO-2015/038892 | A1 | 3/2015 |
| WO | WO-2015/191780 | A2 | 12/2015 |
| WO | WO-2015/196128 | A2 | 12/2015 |
| WO | WO-2016/063264 | A1 | 4/2016 |
| WO | WO-2016/022363 | A3 | 5/2016 |
| WO | WO-2016/081798 | A1 | 5/2016 |
| WO | WO-2016/070037 | A3 | 6/2016 |
| WO | WO-2016/103233 | A2 | 6/2016 |
| WO | WO-2016/115326 | A1 | 7/2016 |
| WO | WO-2016/073990 | A3 | 8/2016 |
| WO | WO-2016/154330 | A1 | 9/2016 |
| WO | WO-2016/164356 | A1 | 10/2016 |
| WO | WO-2016/174250 | A1 | 11/2016 |
| WO | WO-2016/130600 | A9 | 12/2016 |
| WO | WO-2017/031370 | A1 | 2/2017 |
| WO | WO-2017/040793 | A1 | 3/2017 |
| WO | WO-2017/011710 | A3 | 4/2017 |
| WO | WO-2017/064546 | A1 | 4/2017 |
| WO | WO-2017/106290 | A1 | 6/2017 |
| WO | WO-2017/143042 | A3 | 10/2017 |
| WO | WO-2017/208247 | A1 | 12/2017 |
| WO | WO-2018/035495 | A1 | 2/2018 |
| WO | WO-2018/049073 | A1 | 3/2018 |
| WO | WO-2018/049075 | A1 | 3/2018 |
| WO | WO-2018/049077 | A1 | 3/2018 |
| WO | WO-2018/049079 | A1 | 3/2018 |
| WO | WO 2018/111944 | A1 | 6/2018 |
| WO | WO-2018/129544 | A1 | 7/2018 |
| WO | WO-2018/204764 | A1 | 11/2018 |
| WO | WO-2019/036430 | A1 | 2/2019 |
| WO | WO-2019/071054 | A1 | 4/2019 |

OTHER PUBLICATIONS

Issad et al. (Trends in Endocrinology and Metabolism, 19, 10, 2008, 380-389).*

Lee, Jeng-Shin, Katherine M. Galvin, and Yang Shi. "Evidence for physical interaction between the zinc-finger transcription factors YY1 and Sp1." *Proceedings of the National Academy of Sciences* 90.13 (1993): 6145-6149.

Narlikar, Leelavati, and Ivan Ovcharenko. "Identifying regulatory elements in eukaryotic genomes." *Briefings in functional genomics and proteomics* 8.4 (2009): 215-230.

McClellan, Michael J., et al. "Modulation of enhancer looping and differential gene targeting by Epstein-Barr virus transcription factors directs cellular reprogramming." *PLoS Pathog* 9.9 (2013): e1003636.

Bonavida, Benjamin. "Therapeutic YY1 inhibitors in cancer: ALL in ONE." *Critical Reviews™ in Oncogenesis* 22.1-2 (2017).

Weintraub, Abraham S., et al. "YY1 is a structural regulator of enhancer-promoter loops." *Cell* 171.7 (2017): 1573-1588.

Phillips, J.E., and Corces, V.G. (2009). CTCF: master weaver of the genome. Cell 137, 1194-1211.

Beagan JA, Duong MT, Titus KR, et al. YY1 and CTCF orchestrate a 3D chromatin looping switch during early neural lineage commitment. *Genome Res.* 2017;27(7):1139-1152.

International Search Report issued in PCT/US2018/013003 dated Jun. 1, 2018.

Amabile, A. et al., "Inheritable Silencing of Endogenous Genes by Hit-and-Run Targeted Epigenetic Editing," Cell, 167:219-232. 2016.

Banani et al. "Biomolecular condensates: organizers of cellular biochemistry," Nature Reviews Molecular Cell Biology, vol. 18, No. 5, pp. 285-298, 2017.

Barrera, L. et al., "Survey of variation in human transcription factors reveals prevalent DNA binding changes," Science, 351 (6280):1450-1454, 2016.

Bell, A.C., et al., "Methylation of a CTCF-dependent boundary controls imprinted expression of the Igf2 gene," Nature 405, 482-485, 2000.

Brunk, Brian P., et al., "Regulated demethylation of the myoD distal enhancer during skeletal myogenesis," Developmental biology, 177.2: 490-503, 1996.

Chen, W.G., et al., "Derepression of BDNF transcription involves calcium-dependent phosphorylation of MeCP2," Science 302, 885-889, 2003.

Cho et al., "Antisense Transcription and Short Article Heterochromatin at the DM1 CTG Repeats Are Constrained by CTCF," Molecular Cell, vol. 20, pp. 483-489, 2005.

Choudhury et al., "CRISPR-dCas9 mediated TET1 targeting for selective DNA demethylation at BRCA1 promoter," Oncotarget, vol. 7, No. 29, pp. 46545-46556, 2016.

Cong et al., "Multiplex Genome Engineering Using CRISPR/Cas Systems," Science, vol. 339, pp. 819-823, 2013.

De Groote et al., "Epigenetic Editing: targeted rewriting of epigenetic marks to modulate expression of selected target genes" Nucleic Acids Res., vol. 40, No. 21, pp. 10596-10613, 2012.

De Souza et al., "DNA methylation profiling in human Huntington's disease brain," Human Molecular Genetics, vol. 25, No. 10, pp. 2013-2030, 2016.

De Wit, et al., "CTCF Binding Polarity Determines Chromatin Looping," Molecular Cell, vol. 60. No. 4, pp. 676-684, 2015.

Deng et al., "Controlling Long-Range Genomic Interactions at a Native Locus by Targeted Tethering of a Looping Factor," Cell, vol. 149, pp. 1233-1244, 2012.

Dowen, J. et al., "Control of Cell Identity Genes Occurs in Insulated Neighborhoods in Mammalian Chromosomes," Cell, 159:374-387, 2014.

Dávalos-Salas, Mercedes, et al., "Gain of DNA methylation is enhanced in the absence of CTCF at the human retinoblastoma gene promoter," BMC cancer, 11.1: 1-11, 2011.

Ecker et al., "Genomics: ENCODE explained," Nature, vol. 489, 7414, pp. 52-55, 2012.

Extended European Search Report for application No. 17849560.2 dated Mar. 31, 2020.

Filippova, et al., "Tumor-associated Zinc Finger Mutations in the CTCF Transcription Factor Selectively Alter Its DNA-binding Specificity," Cancer Research, 62, 48-52, 2002.

Flavahan, et al., "Insulator dysfunction and oncogene activation in IDH mutant gliomas," Nature, vol. 529, No. 7584, pp. 110-114, 2015.

Guo et al., "YY1 Target DB: an integral information resource for Yin Yang 1 target loci," Database, vol. pp. 1-10, 2013.

Guo, C. et al., "CTCF Binding Elements Mediate Control of V(D)J Recombination," Nature, 477(7365):424-430, 2011.

Herold, M. et al., "CTCF: insights into insulator function during development," Development, 139:1045-1057, 2012.

Hnisz, D. et al., "Activation of proto-oncogenes by disruption of chromosome neighborhoods," Science, 351(6280):1454-1458, 2016.

Hnisz, D. et al., "Convergence of Developmental and Oncogenic Signaling Pathways at Transcriptional Super-Enhancers," Molecular Cell, 58:362-370, 2015.

Hnisz, D. et al., "Super-Enhancers in the Control of Cell Identity and Disease," Cell, 155:934-947, 2013.

Hsu, "Completion of a Programmable DNA-Binding Small Molecule Library," Thesis, California Institute of Technology, retrieved from thesis.library.caltech.edu/4398, 153 pages, 2008.

International Preliminary Report on Patentability for International Application No. PCT/US2017/047674, dated Feb. 19, 2019.

(56) References Cited

OTHER PUBLICATIONS

International Preliminary Report on Patentability for International Application No. PCT/US2017/050553, dated Mar. 12, 2019.
International Preliminary Report on Patentability for International Application No. PCT/US2017/065918, dated Jun. 18, 2019.
International Search Report and Written Opinion issued in PCT/US2017/050553, dated Jan. 30, 2018.
International Search Report for International Application No. PCT/US2017/047674, dated Jan. 4, 2018.
International Search Report for International Application No. PCT/US2017/065918, dated Apr. 30, 2018.
International Search Report for PCT/US2017/50556 (Methods and Compositions for Modulating Gene Expression, filed Sep. 7, 2017), issued by ISA/US, 5 pages (dated Dec. 26, 2017).
International Search Report for PCT/US2017/50558 (Methods and Compositions for Modulating Gene Expression, filed Sep. 7, 2017), issued by ISA/US, 5 pages (dated Dec. 18, 2017).
International Search Report for PCT/US2017/50561 (Methods and Compositions for Modulating Gene Expression, filed Sep. 7, 2017), issued by ISA/US, 5 pages (dated Dec. 18, 2017).
Ishimaru, Naoki, et al., "Differential epigenetic regulation of BDNF and NT-3 genes by trichostatin A and 5-aza-2'-deoxycytidine in Neuro-2a cells," Biochemical and biophysical research communications, 394.1: 173-177, 2010.
Ji, X. et al., "3D Chromosome Regulatory Landscape of Human Pluripotent Cells," Cell Stem Cell, 18:262-275, 2016.
Ji, X. et al., "Chromatin proteomic profiling reveals novel proteins associated with histone-marked genomic regions," PNAS, 112(12):3841-3846, 2015.
Jinek et al., "A Programmable Dual-RNA-Guided DNA Endonuclease in Adaptive Bacterial Immunity," Science, vol. 337, pp. 816-821, 2012.
Kang, J.Y., et al., "Disruption of CTCF/cohesin-mediated highorder chromatin structures by DNA methylation downregulates PTGS2 expression," Oncogene 34, 5677-5684, 2015.
Kearns et al., "Functional annotation of native enhancers with a Cas9-histone demethylase fusion," Nature Methods, vol. 12, No. 5, pp. 401-403, 2015.
Kim et al., "Genome-wide target specificities of CRISPR RNAguided programmable deaminases," Nat Biotechnol, vol. 35, pp. 475-480, 2017.
Koferle et al., "Brave new epigenomes: the dawn of epigenetic engineering," Genome Medicine, vol. 7, No. 59, pp. 1-3, 2015.
Komor et al., "Programmable editing of a target base in genomic DNA without double-stranded DNA cleavage," Nature, vol. 533, pp. 420-424, Supplement, 2016.
Krylov et al., "A general method to design dominant negatives to B-HLHZip proteins that abolish DNA binding," PNAS, vol. 94, No. 23, pp. 12274-12279, 1997.
Kungulovski, et al., "Epigenome editing: state of the art, concepts, and perspectives," Trends in Genetics, 32.2: 101-113, 2015.
Lei, et al., "Targeted DNA methylation in vivo using an engineered dCas9-MQ1 fusion protein," Nature Communications, 8, Article No. 16026, 2017.
Li et al., "An alternative CTCF isoform antagonizes canonical CTCF occupancy and changes chromatin architecture to promote apoptosis," Nature Communications, article No. 1535; pp. 1-13, 2019.
Lin et al., "Formation and Maturation of Phase-Separated Liquid Droplets by RNA-Binding Proteins" Molecular Cell, vol. 60, pp. 208-219, 2015.
Ling J Q et al., "Long-range DNA interactions are specifically altered by locked nucleic acid- targeting of a CTFC binding site," Biochimica et Biophysica Acta. Gene Regulatory Mechanisms, vol. 1809, No. 1. pp. 24-33, 2011.
Liu, et al., "Editing DNA Methylation in the Mammalian Genome," Cell, 167(1):233-247, 2016.
Lo, Albert, et al., "Genetic and epigenetic control of gene expression by CRISPR-Cas systems," F1000Research, 6: 747, 2017.
Ma et al., "Targeted Gene Suppression by Inducing De Novo DNA Methylation in the Gene Promotor," Epigenetics & Chromatin, vol. 7:20, pp. 1-11, 2014.
Mansour, M. et al., "An oncogenic super-enhancer formed through somatic mutation of a noncoding intergenic element," Science, 346(6215):1373-7, Nov. 13, 2014.
Martinowich, K., et al., "DNA methylation-related chromatin remodeling in activity-dependent BDNF gene regulation," Science 302, 890-893, 2003.
McDonald, James I., et al., "Reprogrammable CRISPR/Cas9-based system for inducing site-specific DNA methylation," Biology open, 5.6: 866-874, 2016.
Morgan et al., "Manipulation of nuclear architecture through CRISPR-mediated chromosomal looping," Nature Communications, vol. 8, Article 15993, 9 pages, 2017.
Morita, Sumiyo, et al., "Targeted DNA demethylation in vivo using dCas9-peptide repeat and scFv-TET1 catalytic domain fusions," Nature biotechnology, 34.10: 1060-1065, 2016.
Narenda, et al., "CTCF establishes discrete functional chromatin domains at the Hox clusters during differentiation," Science, vol. 347, No. 6225, pp. 1017-1021, 2015.
Patterson et al., "DNA Methylation: Bisulphite Modification and Analysis," J Vis Exp., vol. 56, e3170, pp. 1-9, 2011.
Rada-Iglesias et al., "Whole-genome maps of USFI and USF2 binding and histone H3 acetylation reveal new aspects of promoter structure and candidate genes for common human disorders," Genome Research, vol. 18(3), pp. 380-392, 2008.
Ran et al., "Genome engineering using the CRISPR-Cas9 system," Nature Protocols, vol. 8, No. 11, pp. 2281-2308, 2013.
Rodriguez, et al., "CTCF is a DNA methylation-sensitive positive regulator of the INK/ARF locus," Biochem. Biophys. Res. Commun., 392(2):129-34, 2010.
Rudolph Jaenish, In Vitro Reprogramming of Somatic Cells Into Pluripotent ES-Like Cells, National Institutes of Health Grant No. HD045022; Funding date: Jun. 15, 2008, Abstract.
Rudolph Jaenish, Nuclear Cloning and the Reprogramming of the Genome, National Institutes of Health Grant No. HD045022; Funding date: Jul. 28, 2003, Abstract.
Sabari et al., "Coactivator condensation at super-enhancers links phase separation and gene control," Science, 361(6400): eaar3958, pp. 1-16, 2018.
Schultz, M.D., et al., "Human body epigenome maps reveal noncanonical DNA methylation variation," Nature 523, 212-216, 2015.
Shin et al., "Spatiotemporal control of intracellular phase transitions using light-activated optoDroplets," Cell, vol. 168, No. 1-2, pp. 159-171, 2017.
Singh, et al., "Protein Engineering Approaches in the Post-Genomic Era," Current Protein and Peptide Science, 18, 1-11, 2017.
Spencer, R. et al., "A Boundary Element Between Tsix and Xist Binds the Chromatin Insulator Ctcf and Contributes to Initiation of X-Chromosome Inactivation," Genetics, 189:441-454, 2011.
Stelzer, Y., et al., "Tracing dynamic changes of DNA methylation at single-cell resolution," Cell 163, 218-229, 2015.
Stepper, Peter, et al., "Efficient targeted DNA methylation with chimeric dCas9-Dnmt3a-Dnmt3L methyltransferase," Nucleic acids research, 45.4: 1703-1713, 2016.
Subramaniam, et al., "DNA methyltransferases: a novel target for prevention and therapy," Frontiers in Oncology, 4, May 1, 2014.
Supplementary Partial European Search Report in Application No. EP 17 88 1835, dated Jul. 30, 2020.
Sweatt, J.D., "The emerging field of neuroepigenetics," Neuron 80, 624-632, 2013.
Szabó, P. et al., "Role of CTCF Binding Sites in the Igf2/H19 Imprinting Control Region," Molecular and Cellular Biology, 24(11):4791-4800, 2004.
Tang, Z. et al., "CTCF-Mediated Human 3D Genome Architecture Reveals Chromatin Topology for Transcription," Cell, 163:1-17, 2015.
Thakore et al., "Highly Specific Epigenome Editing by CRISPR/Cas9 Repressors for Silencing of Distal Regulatory Elements," Nat Methods, vol. 12, No. 12, pp. 1143-1149, 2015.

(56) References Cited

OTHER PUBLICATIONS

The ENCODE Project Consortium, "An Integrated Encyclopedia of DNA Elements in the Human Genome" Nature, vol. 6; 489 (7414):57-74, 2012.

Torres, A. et al., "Potent and sustained cellular inhibition of miR-122 by lysine-derivatized peptide nucleic acids (PNA) and phosphorothioate locked nucleic acid (LNA)/2'-O-methyl (OMe) mixmer anti-miRs in the absence of transfection agents," Artificial DNA: PNA & XNA, 2(3):71-78, 2011.

Viscidi et al., "Novel Chemical Method for the Preparation of Nucleic Acids for Nonisotopic Hybridization," J Clin Microbiol, vol. 23, No. 2, pp. 311-317, 1986.

Votja et al., "Repurposing the CRISPR-Cas9 system for targeted DNA methylation," Nucleic Acids Research, 2016, vol. 44, No. 12 5615-5628, published on Mar. 11, 2016.

Wang, H., et al., "Widespread plasticity in CTCF occupancy linked to DNA methylation," Genome Res 22, 1680-1688, 2012.

Woloszynska-Read et al., "DNA Methylation-dependent Regulation of BORIS/CTCFL Expression in Ovarian Cancer," Cancer Immunity, vol. 7, 1 pp. 1-10, 2007.

Written Opinion for PCT/US2017/50556 (Methods and Compositions for Modulating Gene Expression, filed Sep. 7, 2017), issued by ISA/US, 8 pages (dated Dec. 26, 2017).

Written Opinion for PCT/US2017/50558 (Methods and Compositions for Modulating Gene Expression, filed Sep. 7, 2017), issued by ISA/US, 6 pages (dated Dec. 18, 2017).

Written Opinion for PCT/US2017/50561 (Methods and Compositions for Modulating Gene Expression, filed Sep. 7, 2017), issued by ISA/US, 6 pages (dated Dec. 18, 2017).

Wu et al., "MicroRNAs direct rapid deadenylation of mRNA," Proc Natl Acad Sci, vol. 103, pp. 4034-4039, 2006.

Wu, H., "Reversing DNA methylation: mechanisms, genomics, and biological functions," Cell 156, 45-68, 2014.

Xiong, Tina, et al. "Targeted DNA methylation in human cells using engineered dCas9-methyltransferases," Scientific reports, 7.1: 1-14, 2017.

Xu, Xingxing, et al., "A CRISPR-based approach for targeted DNA demethylation," Cell discovery, 2.1: 1-12, 2016.

Yan, et al., "DNA methylation reactivates GAD1 expression in cancer by preventing CTCF-mediated polycomb repressive complex 2 recruitment," Oncogene, 35(30):3995-4008, 2016.

Zhang, et al., "Propagated Perturbations from a Peripheral Mutation Show Interactions Supporting WW Domain Thermostability," Structure, 26, 1474-1485, 2018.

Zhao, et al., "CTCF cooperates with noncoding RNA MYCNOS to promote neuroblastoma progression through facilitating MYCN expression," Oncogene, 35, 3565-3576, 2016.

Ziebarth et al., "CTCFBSDB 2.0: a database for CTCF-binding sites and genome organization," Nucleic Acid Research, vol. 41; D188-94, 2013.

\* cited by examiner

1A

1B

1E

1F

1G

1H

2C

2D

3A

3B

3C

3D

3E

3F

FIGS. 6A-6B
6A
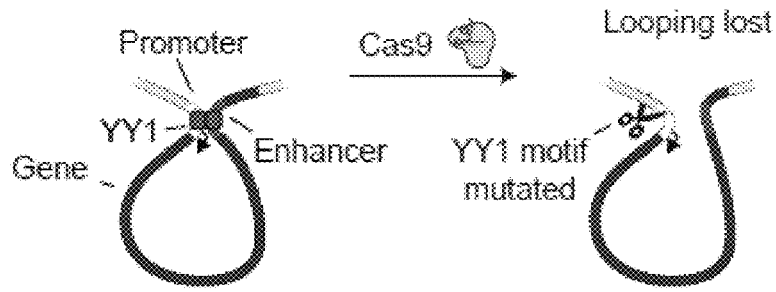
6B
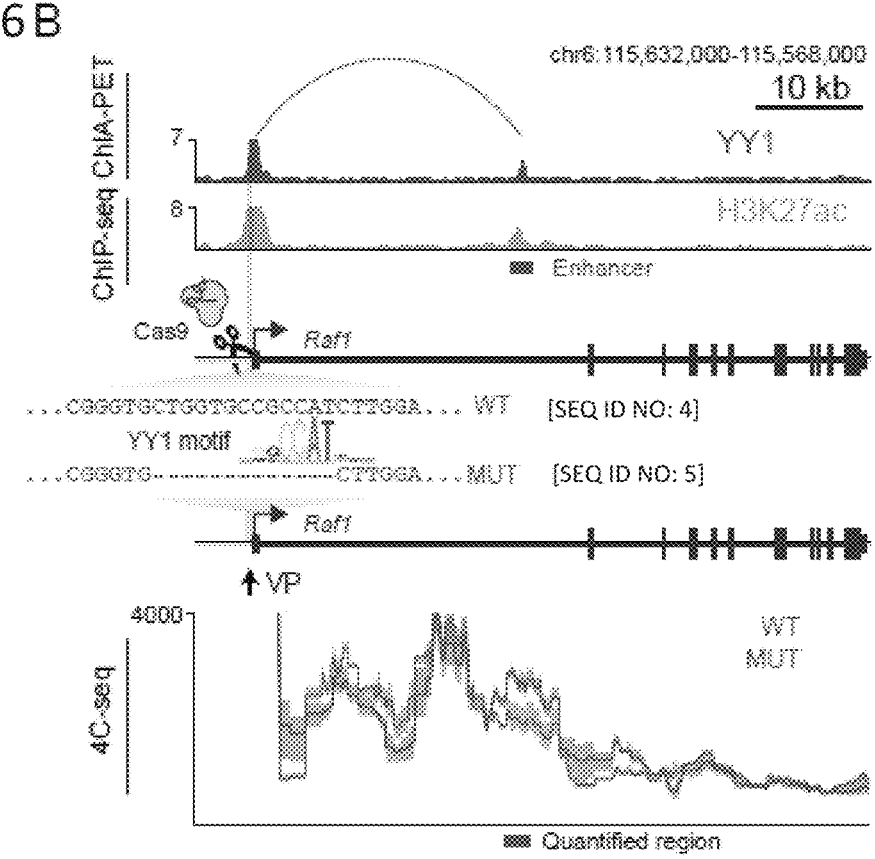
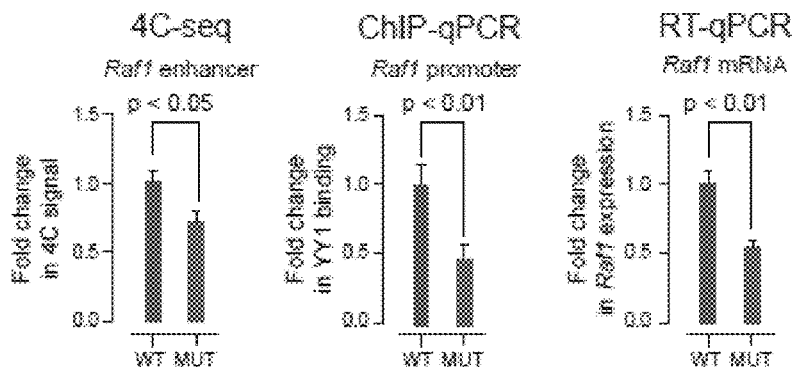

16A  This study

16B

16C  Nora et al. 2017

SEQUENCE LISTING

```
<160> NUMBER OF SEQ ID NOS: 45

<210> SEQ ID NO 1
<211> LENGTH: 20
<212> TYPE: RNA
<213> ORGANISM: Artificial Sequence
<220> FEATURE:
<223> OTHER INFORMATION: Guide RNA

<400> SEQUENCE: 1
acugucaaug uaggcccaua                                                    20

<210> SEQ ID NO 2
<211> LENGTH: 40
<212> TYPE: DNA
<213> ORGANISM: Mus musculus

<400> SEQUENCE: 2
gcgtcggcca tgacagttac atccgggtat gatgcctagc                              40

<210> SEQ ID NO 3
<211> LENGTH: 35
<212> TYPE: DNA
<213> ORGANISM: Mus musculus

<400> SEQUENCE: 3
gcgtcggcct gtgacatccg ggtatgatgc ctagc                                   35

<210> SEQ ID NO 4
<211> LENGTH: 25
<212> TYPE: DNA
<213> ORGANISM: Mus musculus

<400> SEQUENCE: 4
cgggtgctgg tgccgccatc ttgga                                              25
```

<210> SEQ ID NO 5
<211> LENGTH: 12
<212> TYPE: DNA
<213> ORGANISM: Mus musculus

<400> SEQUENCE: 5
cgggtgcttg ga                                                        12

<210> SEQ ID NO 6
<211> LENGTH: 22
<212> TYPE: DNA
<213> ORGANISM: Mus musculus

<400> SEQUENCE: 6
actgtgcctc catttgtttt ca                                             22

<210> SEQ ID NO 7
<211> LENGTH: 12
<212> TYPE: DNA
<213> ORGANISM: Mus musculus

<400> SEQUENCE: 7
actgtgtttt ca                                                        12

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
caccgactcc cgccatccaa gatgg                                          25

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
aaacccatct tggatggcgg gagtc                                          25

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
caccgagcta cttgaaaaca aatgg                                          25

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
aaacccattt gttttcaagt agctc                                          25

```
<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
caccgtcttc tctcttcttt tcac                                              24

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
aaacgtgaaa agaagagaga agac                                              24

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ctgtgcagtg attgggtcct                                                   20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
ttgccgctct gcacttaagt                                                   20

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
gcttcctcac attgaaacag aa                                                22

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
gggaagctct gagagtcctt at                                                22

<210> SEQ ID NO 18
<211> LENGTH: 17
<212> TYPE: DNA
<213> ORGANISM: Artificial Sequence
<220> FEATURE:
<223> OTHER INFORMATION: primer
```

```
<400> SEQUENCE: 18
cgccaccagg atgacag                                                    17

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
gaatgtgacc gcaaccaac                                                  19

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cattttacct gcccccagta                                                 20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
cagccttaaa cagcctggaa                                                 20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
tttcaaagcc accaaggtct                                                 20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
caagtagctc ggggtctcag                                                 20

<210> SEQ ID NO 24
<211> LENGTH: 19
<212> TYPE: DNA
<213> ORGANISM: Artificial Sequence
<220> FEATURE:
<223> OTHER INFORMATION: Bridge linker
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (10)..(10)
```

<223> OTHER INFORMATION: biotinylation

<400> SEQUENCE: 24
cgcgatatct tatctgact                                               19

<210> SEQ ID NO 25
<211> LENGTH: 19
<212> TYPE: DNA
<213> ORGANISM: Artificial Sequence
<220> FEATURE:
<223> OTHER INFORMATION: bridge linker
<220> FEATURE:
<221> NAME/KEY: misc_feature
<222> LOCATION: (1)..(1)
<223> OTHER INFORMATION: 5' phosphorylation

<400> SEQUENCE: 25
gtcagataag atatcgcgt                                               19

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
gtctggatcc tcgtcttgag cc                                           22

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
ccaaggatcc gtaagctagg ct                                           22

<210> SEQ ID NO 28
<211> LENGTH: 199
<212> TYPE: DNA
<213> ORGANISM: Artificial Sequence
<220> FEATURE:
<223> OTHER INFORMATION: competitor DNA

<400> SEQUENCE: 28
gagcaacaac aacaacgaac cggttcgacc tccccggcca tctttcgacc tccccggcca    60
tctttcgacc tccccggcca tctttcgacc tccccggcca tctttcgacc tccccggcca   120
tctttcgacc tccccggcca tctttcgacc tccccggcca tctttcgacc tcccgtcgac   180
agaggcagca aaagccaga                                              199

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
caagggcaag taacccgatc                                              20

<210> SEQ ID NO 30
<211> LENGTH: 20

-continued

<212> TYPE: DNA
<213> ORGANISM: Artificial Sequence
<220> FEATURE:
<223> OTHER INFORMATION: primer

<400> SEQUENCE: 30
aatagataca tcccccacct                                           20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
caagggcaag taacccgatc                                           20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
aatagataca tcccccacct                                           20

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
tcgctccccg gccatcttgg cggctggtgt                                30

<210> SEQ ID NO 34
<211> LENGTH: 30
<212> TYPE: DNA
<213> ORGANISM: Artificial Sequence
<220> FEATURE:
<223> OTHER INFORMATION: primer

<400> SEQUENCE: 34
acaccagccg ccaagatggc cggggagcga                                30

<210> SEQ ID NO 35
<211> LENGTH: 25
<212> TYPE: DNA
<213> ORGANISM: Artificial Sequence
<220> FEATURE:
<223> OTHER INFORMATION: primer

<400> SEQUENCE: 35
caccgaagta gctcggggtc tcaga                                     25

<210> SEQ ID NO 36
<211> LENGTH: 25
<212> TYPE: DNA
<213> ORGANISM: Artificial Sequence
<220> FEATURE:
<223> OTHER INFORMATION: primer

<400> SEQUENCE: 36
aaactctgag accccgagct acttc                                       25

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
caccggtgct cagtaaatgt aaac                                        24

<210> SEQ ID NO 38
<211> LENGTH: 24
<212> TYPE: DNA
<213> ORGANISM: Artificial Sequence
<220> FEATURE:
<223> OTHER INFORMATION: primer

<400> SEQUENCE: 38
aaacgtttac atttactgag cacc                                        24

<210> SEQ ID NO 39
<211> LENGTH: 23
<212> TYPE: DNA
<213> ORGANISM: Mus musculus

<400> SEQUENCE: 39
actcccgcca tccaagatgg cgg                                         23

<210> SEQ ID NO 40
<211> LENGTH: 24
<212> TYPE: DNA
<213> ORGANISM: Mus musculus

<400> SEQUENCE: 40
gagctacttg aaaacaaatg gagg                                        24

<210> SEQ ID NO 41
<211> LENGTH: 23
<212> TYPE: DNA
<213> ORGANISM: Mus musculus

<400> SEQUENCE: 41
gtcttctctc ttcttttcac tgg                                         23

<210> SEQ ID NO 42
<211> LENGTH: 20
<212> TYPE: DNA
<213> ORGANISM: Artificial Sequence
<220> FEATURE:
<223> OTHER INFORMATION: linker sequence

<400> SEQUENCE: 42
acgcgatatc ttatctgact                                             20

<210> SEQ ID NO 43
<211> LENGTH: 20
<212> TYPE: DNA
<213> ORGANISM: Artificial Sequence
<220> FEATURE:
<223> OTHER INFORMATION: linker sequence

<400> SEQUENCE: 43
agtcagataa gatatcgcgt                                             20

```
<210> SEQ ID NO 44
<211> LENGTH: 11
<212> TYPE: DNA
<213> ORGANISM: Artificial Sequence
<220> FEATURE:
<223> OTHER INFORMATION: YY1 binding motif
<220> FEATURE:
<221> NAME/KEY: misc_feature
<222> LOCATION: (9)..(9)
<223> OTHER INFORMATION: n is a, c, t, or g

<400> SEQUENCE: 44
ggcgccatnt t                                                          11

<210> SEQ ID NO 45
<211> LENGTH: 12
<212> TYPE: DNA
<213> ORGANISM: Artificial Sequence
<220> FEATURE:
<223> OTHER INFORMATION: YY1 binding motif

<400> SEQUENCE: 45
gccgccattt tg                                                         12
```

METHODS OF ALTERING GENE EXPRESSION BY PERTURBING TRANSCRIPTION FACTOR MULTIMERS THAT STRUCTURE REGULATORY LOOPS

RELATED APPLICATIONS

This application is a national stage filing under 35 U.S.C. 371 of International Application No.: PCT/US2018/013003, filed Jan. 9, 2018, which claims the benefit of U.S. Provisional Application No. 62/444,341, filed Jan. 9, 2017, and U.S. Provisional Application No. 62/596,093, filed Dec. 7, 2017, the contents of which are hereby incorporated by reference in their entirety. International Application No.: PCT/US2018/013003 was published under PCT Article 21(2) in English.

GOVERNMENT SUPPORT

This invention was made with government support under Grant No. HG002668 awarded by the National Institutes of Health. The government has certain rights in the invention.

BACKGROUND OF THE INVENTION

Cell-type specific gene expression programs in humans are generally controlled by gene regulatory elements called enhancers (Buecker and Wysocka, 2012; Bulger and Groudine, 2011; Levine et al., 2014; Ong and Corces, 2011; Ren and Yue, 2016). Transcription factors (TFs) bind these enhancer elements and regulate transcription from the promoters of nearby or distant genes through physical contacts that involve looping of DNA between enhancers and promoters (Bonev and Cavalli, 2016; Fraser et al., 2015; Heard and Bickmore, 2007; de Laat and Duboule, 2013; Pombo and Dillon, 2015; Spitz, 2016). Despite the fundamental importance of proper gene control to cell identity and development, the proteins that contribute to structural interactions between enhancers and promoters are poorly understood.

There is considerable evidence that enhancer-promoter interactions can be facilitated by transcriptional cofactors such as Mediator, structural maintenance of chromosomes (SMC) protein complexes such as cohesin, and DNA binding proteins such as CTCF. Mediator can physically bridge enhancer-bound transcription factors (TFs) and the promoter-bound transcription apparatus (Allen and Taatjes, 2015; Jeronimo et al., 2016; Kagey et al., 2010; Malik and Roeder, 2010; Petrenko et al., 2016). Cohesin is loaded at active enhancers and promoters by the Mediator-associated protein NIPBL, and may transiently stabilize enhancer-promoter interactions (Kagey et al., 2010; Schmidt et al., 2010). CTCF proteins bound at enhancers and promoters can interact with one another, and may thus facilitate enhancer-promoter interactions (Guo et al., 2015; Splinter et al., 2006), but CTCF does not generally occupy these interacting elements (Cuddapah et al., 2009; Kim et al., 2007; Phillips-Cremins et al., 2013; Wendt et al., 2008).

Enhancer-promoter interactions generally occur within larger chromosomal loop structures formed by the interaction of CTCF proteins bound to each of the loop anchors (Gibcus and Dekker, 2013; Gorkin et al., 2014; Hnisz et al., 2016a; Merkenschlager and Nora, 2016). These loop structures, variously called TADs, loop domains, CTCF contact domains and insulated neighborhoods, tend to insulate enhancers and genes within the CTCF-CTCF loops from elements outside those loops (Dixon et al., 2012; Dowen et al., 2014; Hnisz et al., 2016b; Ji et al., 2016; Lupiáñez et al., 2015; Narendra et al., 2015; Nora et al., 2012; Phillips-Cremins et al., 2013; Rao et al., 2014; Tang et al., 2015). Constraining DNA interactions within CTCF-CTCF loop structures in this manner may facilitate proper enhancer-promoter contacts.

Evidence that CTCF-CTCF interactions play important global roles in chromosome loop structures but are only occasionally directly involved in enhancer-promoter contacts (Phillips and Corces, 2009), led us to consider the possibility that a bridging protein analogous to CTCF might generally participate in enhancer-promoter interactions.

SUMMARY OF THE INVENTION

It is demonstrated herein that the transcription factor YY1 acts to structure looping interactions between enhancers and promoters. YY1 is a broadly expressed and essential zinc-finger transcription factor that occupies most enhancers and promoters. YY1 structures enhancer-promoter looping interactions, and perturbation of YY1 binding disrupts enhancer-promoter loops. YY1 may structure enhancer-promoter loops by the multimerization (e.g., dimerization) of YY1 molecules bound at two distant DNA elements. Given the ability of other transcription factors to form multimers (e.g., dimers), transcription factor multimerization (e.g., dimerization) may be a common mechanism for the structuring of enhancer-promoter loops.

Disclosed herein are methods of modulating the expression of one or more genes in a cell, comprising modulating the multimerization (e.g., dimerization) of a transcription factor and thereby modulating the expression of the one or more genes. In some aspects, the transcription factor is YY1. In some aspects, the transcription factor binds to an enhancer and a promoter region of the genome of the cell. In some aspects, the method comprises modulating multimerization (e.g., dimerization) of the transcription factor, thereby modulating formation of enhancer-promoter DNA loops in the genome of the cell. In some aspects, multimerization (e.g., dimerization) is modulated with a composition comprising a nucleic acid, polypeptide and/or a small molecule.

Also disclosed herein are methods of modulating the expression of one or more genes in a cell, comprising modulating formation of a enhancer-promoter DNA loop in the genome of the cell, wherein formation is transcription factor dependent. In some aspects, formation is modulated by modulating binding of the transcription factor to the promoter and/or enhancer region of the enhancer-promoter DNA loop. In some aspects, formation of the enhancer-promoter DNA loop is modulated by modulating the multimerization (e.g., dimerization) of a transcription factor in the cell. In some aspects, multimerization (e.g., dimerization) is modulated by contacting the cell with a nucleic acid, polypeptide and/or a small molecule.

Also disclosed herein are methods for treating a disease or condition associated with aberrant gene expression in a subject in need thereof, comprising administering a composition that modulates formation of enhancer-promoter DNA loops, wherein formation of the enhancer-promoter DNA loop is transcription factor dependent. In some aspects, the disease or condition associated with aberrant gene expression is cancer.

Also disclosed herein are methods treating a disease or condition associated with aberrant activity of a gene product in a subject in need thereof, comprising administering a composition that modulates formation of enhancer-promoter DNA loops, wherein formation of the enhancer-promoter DNA loop is transcription factor dependent. In some embodiments, the aberrant activity of a gene product is increased activity and the methods decrease the expression of a gene encoding the gene product to treat the disease or condition. In some embodiments, the aberrant activity of a gene product is decreased activity and the methods increase the expression of a gene encoding the gene product to treat the disease or condition.

Also disclosed herein is a method of screening for a compound that modulates the expression of one or more genes in a cell, comprising contacting the cell with a test agent, and measuring enhancer-promoter DNA loop formation in the cell, wherein the test agent is identified as a gene expression modulator if the level of enhancer-promoter DNA loop formation in the cell contacted with the test agent is different than the level enhancer-promoter DNA loop formation in a control cell not contacted with the test agent.

Also disclosed herein are methods of identifying one or more genes with expression dependent on an enhancer in a cell, comprising identifying one or more enhancer-promoter DNA loops comprising the enhancer in the cell, and identifying the one or more genes expressed in the enhancer-promoter DNA loop, wherein the one or more genes expressed in the enhancer-promoter DNA loop are identified as genes with expression dependent on the enhancer.

Disclosed herein are also methods of identifying genomic enhancer-promoter specificity, comprising identifying transcription factor dependent DNA loop formation and promoters and enhancers brought into proximity by the transcription factor, thereby identifying enhancer-promoter specificity.

BRIEF DESCRIPTION OF THE DRAWINGS

(FIG. 1B) CRISPR scores (CS) of all genes in KBM7 cells from Wang et al. (2015). Candidate enhancer-promoter structuring factors identified by ChIP-MS are indicated as dots and those identified as cell-essential (CS<−1) are shown in red. (FIG. 1C) Histogram showing the number of tissues in which each candidate enhancer-promoter structuring factor is expressed across 53 tissues surveyed by GTEx. Candidates that are both broadly expressed (expressed in greater than 90% of tissues surveyed) and cell-essential are shown in red. (FIG. 1D) Metagene analysis showing the occupancy of YY1 and CTCF at enhancers, promoters, and insulator elements in mouse ESCs. (FIG. 1E) Summary of the classes of high-confidence interactions identified by YY1 and CTCF ChIA-PET in mES cells. (FIG. 1F) Example of a YY1-YY1 enhancer-promoter interaction at the Raf1 locus in mES cells. (FIG. 1G) Model depicting co-immunoprecipitation assay to detect YY1 dimerization and evaluate dependence on RNA for YY1 dimerization. (FIG. 1H) Western blot results showing co-immunoprecipitation of FLAG-tagged YY1 and HA-tagged YY1 protein from nuclear lysates prepared from transfected cells. Quantification of the remaining signal normalized to input after RNase A treatment for the co-immunoprecipitated tagged YY1 is displayed under the relevant bands. See also Table 11, FIG. 18. See STAR methods for detailed description of genomics analyses. Datasets used in this figure are listed in Table S4.

(FIG. 2A) YY1 ChIA-PET detects interactions between the Sox2 super-enhancer (red bars) and the Sox2 promoter. (FIG. 2B) Histogram showing the Sox2 transcripts per cell as determined by single molecule FISH for cells infected with a small hairpin targeting either GFP (shGFP, n=195 cells) or YY1 (shYY1, n=224 cells) (FIG. 2C) YY1 ChIA-PET detects interactions between the Oct4 super-enhancer (red bars) and the Oct4 promoter. (FIG. 2D) Histogram showing the Oct4 transcripts per cell as determined by single molecule FISH for cells infected with a small hairpin targeting either GFP (shGFP, n=195 cells) or YY1 (shYY1, n=224 cells).

(FIG. 3A and FIG. 3D) Models depicting the in vitro DNA circularization assays used to detect the ability of YY1 to enhance DNA looping interactions. (FIG. 3B and FIG. 3E) Results of the in vitro DNA circularization assay visualized by gel electrophoresis. The dominant lower band reflects the starting linear DNA template, while the upper band corresponds to the circularized DNA ligation product. (FIG. 3C and FIG. 3F) Quantifications of DNA template circularization as a function of incubation time with T4 DNA ligase. Values correspond to the percent of DNA template that is circularized and represents the mean and standard deviation of four experiments. See also FIG. 17.

(FIG. 4A) Gene track for the Zfp518a gene showing ChIA-PET, ChIP-seq, and GRO-seq data. Schematic depicts the promoter and enhancer. The sequence of the Zfp518a enhancer that was targeted by CRISPR is shown with the guide RNA sequence highlighted in blue and the PAM sequence highlighted in red [GCGTCGGC-CATGACAGTTACATCCGGGTATGATGCCTAGC (SEQ ID NO: 2)]. At the bottom is the sequence of the homozygous mutant obtained after CRISPR targeting [GCGTCGGCCTGTGACATCCGGGTATGATGCCTAGC (SEQ ID NO:3)] and analyzed in FIG. 4C through FIG. 4E. The guide RNA sequence is also shown [ACUGUCAAU-GUAGGCCCAUA (SEQ ID NO: 1)] (FIG. 4B) 4C-seq analysis detects a decreased interaction frequency between the Zfp518a enhancer and the Zfp518a promoter in the mutant cell line. The thick line indicates the mean interaction frequency from two biological replicate experiments. (FIG. 4C) ChIP-qPCR shows decreased YY1 binding at the Zfp518a enhancer in the mutant cell line. (FIG. 4D) RT-qPCR shows decreased Zfp518a expression in the mutant cell line. (FIG. 4E) Quantification of the change in interaction frequency (4C-seq signal) between mutated enhancer and the promoter shown in b (boxed region).

FIG. 6A-6C. Deletion of YY1 binding sites causes loss of enhancer-promoter interactions: (FIG. 6A) Model depicting CRISPR/Cas9-mediated deletion of a YY1 binding motif in the regulatory region of a gene. (FIG. 6B and FIG. 6C) CRISPR/Cas9-mediated deletion of YY1 binding motifs in the regulatory regions of two genes, Raf1 (FIG. 6B) and Etv4 (FIG. 6C), was performed and the effects on YY1 occupancy, enhancer-promoter looping, and mRNA levels were measured. The positions of the targeted YY1 binding motifs, the genotype of the wildtype and mutant lines, and the 4C-seq viewpoint are indicated. The mean 4C-seq signal is represented as a line (individual replicates are shown in FIG. 14) and the shaded area represents the 95% confidence interval. Three biological replicates were assayed for 4C-seq and ChIP-qPCR experiments, and six biological replicates were assayed for RT-qPCR experiments. SEQ ID NO: 4 in FIG. 6B is a portion of the wildtype Raf1 gene. SEQ ID NO: 5 in FIG. 6B is a portion of the mutated Raf1 gene. SEQ ID NO: 6 in FIG. 6C is a portion of the wildtype Etv4 gene. SEQ ID NO: 7 in FIG. 6C is a portion of the mutated Etv4 gene. Error bars represent the standard deviation. All p-values were determined using the Student's t test. See also FIG. 13. See STAR methods for detailed description of genomics analyses. Datasets used in this figure are listed in Table S4.

(FIG. 7A) Model depicting dTAG system used to rapidly deplete YY1 protein. (FIG. 7B) Western blot validation of knock-in of FKBP degron tag and ability to inducibly degrade YY1 protein. (FIG. 7C) Change in gene expression ($\log_2$ fold-change) upon degradation of YY1 for all genes plotted against the expression in untreated cells. Genes that displayed significant changes in expression (FDR adjusted p-value<0.05) are colored with upregulated genes plotted in red and downregulated genes plotted in blue. (FIG. 7D) Heatmaps displaying the change in expression of each gene upon degradation of YY1 and wild type YY1 ChIP-seq signal in a ±2 kb region centered on the TSS of each gene. Each row represents a single gene and genes are ranked by their adjusted p-value for change in expression upon YY1 degradation. (FIG. 7E) Model depicting experimental outline to test the effect of YY1 degradation on embryonic stem cell differentiation into the three germ layers via embryoid body formation from untreated cells (YY1$^+$) and cells treated with dTAG compound to degrade YY1 (YY1$^-$). (FIG. 7F) Microscopy images of embryoid bodies formed from YY1$^+$ and YY1$^-$ cells. (FIG. 7G) Immunohistochemistry images of embryoid bodies formed from YY1$^+$ and YY1$^-$ cells. GATA4 is displayed in green and DNA stained using DAPI is displayed in blue. The scale bar represents 50 µm. (FIG. 7H) Quantification of single-cell RNA-seq results for embryoid bodies formed from YY1$^+$ and YY1$^-$ cells. The percentage of cells expressing various differentiation-specific genes is displayed for YY1$^+$ and YY1$^-$ embryoid bodies. See also Table S3, and FIG. 15. See STAR methods for detailed description of genomics analyses. Datasets used in this figure are listed in Table S4.

(FIG. 8A) Scatter plot displaying for all YY1-YY1 enhancer-promoter interactions the change in normalized interaction frequency ($\log_2$ fold change) upon degradation of YY1, as measured by H3K27ac HiChIP, and plotted against the normalized interaction frequency in untreated cells. (FIG. 8B) Change in normalized interaction frequency ($\log_2$ fold change) upon degradation of YY1 for three different classes of interactions: all interactions, interactions not associated with YY1 ChIP-seq peaks, and YY1-YY1 enhancer-promoter interactions. (FIG. 8C) Scatter plot displaying for each gene associated with a YY1-YY1 enhancer-promoter interaction the change in gene expression ($\log_2$ fold-change) upon degradation of YY1 plotted against the expression in untreated cells. Genes that showed significant changes in expression (FDR adjusted p-value<0.05) are colored with upregulated genes plotted in red and downregulated genes plotted in blue. (FIG. 8D and FIG. 8E) Effect of YY1 degradation at the Slc7a5 locus (FIG. 8D) and Klf9 locus (FIG. 8E) on enhancer-promoter interactions and gene expression. The top of each panel shows an arc representing an enhancer-promoter interaction detected in the HiChIP data. Signal in the outlined pixels was used to quantify the change in normalized interaction frequency upon YY1 degradation. Three biological replicates were assayed per condition for H3K27ac HiChIP and two biological replicates were assayed for RNA-seq. Error bars represent the standard deviation. P-values for HiChIP were determined using the Student's t test. P-values for RNA-seq were determined using a Wald test. See also FIG. 14. See STAR methods for detailed description of genomics analyses. Datasets used in this figure are listed in Table S4.

(FIG. 9A) Model depicting use of dCas9-YY1 to artificially tether YY1 to a site adjacent to the YY1 binding site mutation in the promoter-proximal region of Etv4 in order to determine if artificially tethered YY1 can rescue enhancer-promoter interactions. (FIG. 9B) Model depicting dCas9-YY1 rescue experiments. Etv4 promoter-proximal YY1 binding motif mutant cells were transduced with lentivirus to stably express either dCas9 or dCas9-YY1, and two sgRNAs to direct their localization to the sequences adjacent to the deleted YY1 binding motif in the Etv4 promoter-proximal region. The ability to rescue enhancer-promoter looping was assayed by 4C-seq. (FIG. 9C) Western blot results showing that Etv4 promoter-proximal YY1 binding motif mutant cells transduced with lentivirus to stably express either dCas9 or dCas9-YY1 successfully express dCas9 or dCas9-YY1. (FIG. 9D) Artificial tethering of YY1 using dCas9-YY1 was performed at sites adjacent to the YY1 binding site mutation in the promoter-proximal region of Etv4. The effects of tethering YY1 using dCas9-YY1 on enhancer-promoter looping and expression of the Etv4 gene were measured and compared to dCas9 alone. The genotype of the Etv4 promoter-proximal YY1 binding motif mutant cells and the 4C-seq viewpoint (VP) is shown. The 4C-seq signal is displayed as the smoothed average reads per million per base pair. The mean 4C-seq signal is represented as a line and the shaded area represents the 95% confidence interval. Three biological replicates were assayed for 4C-seq and CAS9 ChIP-qPCR experiments, and six biological replicates were assayed for RT-qPCR experiments. Error bars represent the standard deviation. All p-values were determined using the Student's t test. (FIG. 9E) Model depicting the loss of looping interactions after the inducible degradation of the structuring factors CTCF and YY1 followed by restoration of looping upon washout of degradation compounds. (FIG. 9F) Change in normalized interaction frequency ($\log_2$ fold change) after YY1 and CTCF degradation (treated) and recovery (washout) relative to untreated cells. For YY1 degradation, change in normalized interaction frequency is plotted for YY1-YY1 enhancer-promoter interactions. For CTCF degradation, change in normalized interaction frequency is plotted for CTCF-CTCF interactions. See also FIG. 14. See STAR methods for detailed description of genomics analyses. Datasets used in this figure are listed in Table S4.

(FIG. 10A-FIG. 10B) Heatmaps displaying the YY1 occupancy at enhancers (FIG. 10A) and active promoters (FIG. 10B) in six human cell types. (FIG. 10C-FIG. 10E) Summaries of the major classes of high-confidence interactions identified with YY1 HiChIP in three human cell types. (FIG. 10E-FIG. 10K) Examples of YY1-YY1 enhancer-promoter interactions in three human cell types: colorectal cancer (FIG. 10F and FIG. 10I), T cell acute lymphoblastic leukemia (FIG. 10G and FIG. 10J), and chronic myeloid leukemia (FIG. 10H and FIG. 10K). Displayed examples show YY1-YY1 enhancer-promoter interactions involving typical enhancers (FIG. 10E-FIG. 10H) and involving super-enhancers (FIG. 10I-FIG. 10K). See also FIG. 12. See STAR methods for detailed description of genomics analyses. Datasets used in this figure are listed in Table S4.

(FIG. 11A) Reads per million transcript (RPKM) for YY1 across a range of primary human tissues and cell types. (FIG. 11B) Reads per million transcript (RPKM) for CTCF across a range of primary human tissues and cell types. (FIG. 11C) CRISPR scores from a genome wide CRISPR screen in KBM7 cells for YY1 and CTCF FIG. 12—YY1 multimerizes in vivo. Co-immunoprecipitation (Co-IP) of FLAG and HA tagged YY1 constructs show YY1 dimerizes in vivo.

(FIG. 13A and FIG. 13B) CRISPR/Cas9-mediated deletion of YY1 binding motifs in the regulatory regions of two genes, Raf1 (FIG. 13A) and Etv4 (FIG. 13B). The top of each panel shows a high-confidence YY1-YY1 enhancer-promoter interaction and ChIP-seq binding profiles for YY1 and H3K27ac displayed as reads per million per base pair. Position of the targeted YY1 DNA binding motif and the genotype of the wildtype and mutant lines are shown. The bottom of each panel shows chromatin interaction profiles in wildtype and mutant cells anchored on the indicated viewpoint (VP) for three biological replicates. 4C-seq signal is displayed as smoothed reads per million per base pair. SEQ ID NO: 4 in FIG. 13A is a portion of the wildtype Raf1 gene. SEQ ID NO: 5 in FIG. 13A is a portion of the mutated Raf1 gene. SEQ ID NO: 6 in FIG. 13B is a portion of the wildtype Etv4 gene. SEQ ID NO: 7 in FIG. 13B is a portion of the mutated Etv4 gene. The sources of the datasets used in this figure are listed in Table S4.

(FIG. 14A and FIG. 14B) Summaries of the major classes of high-confidence interactions identified by YY1 ChIA-PET (FIG. 14A) and H3K27ac HiChIP (FIG. 14B). Interactions are classified based on the presence of enhancer, promoter, and insulator elements at the anchors of each interaction. Interactions are displayed as arcs between these elements and the thickness of the arcs approximately reflects the percentage of interactions of that class relative to the total number of interactions that were classified. (FIG. 14C) Percent of YY1 ChIP-seq peaks in mES cells that are associated with enhancer-promoter interactions, associated with non-enhancer-promoter interactions, and not associated with a detected interaction for high confidence interactions identified by YY1 ChIA-PET and H3K27ac HiChIP. (FIG. 14D) Percent of genes that significantly increase in expression, significantly decrease in expression, or are not differentially expressed in response to YY1 degradation for three classes of genes: all genes, genes involved in enhancer-promoter interactions that do not have YY1 peaks at both ends, and genes involved in YY1-YY1 enhancer-promoter interactions. (FIG. 14E) Expression of Raf1 and Etv4 genes before (0 hr) and after YY1 degradation (24 hr) as measured by RNA-seq. The sources of the datasets used in this figure are listed in Table S4.

(FIG. 15A) Model depicting differentiation of pluripotent ES cells into cells of the three germ layers. Pluripotency and differentiation specific markers that were examined are indicated. (FIG. 15B) Immunohistochemistry images of embryoid bodies formed from untreated cells (YY1+) and cells treated with dTAG compound to degrade YY1 (YY1−). GFAP and TUBB3, which are expressed in cells belonging to the ectoderm lineage, are displayed in green and red, respectively. DNA stained using DAPI is displayed as blue. (FIG. 15C) Principle component analysis (PCA) based representation of single-cell RNA-seq data for embryoid bodies formed from untreated cells (YY1+) and cells treated with dTAG compound to degrade YY1 (YY1−). Each dot represents a single-cell and dots are arranged based on PCA. Cells from YY1+ embryoid bodies are shown in beige and cells from YY1-embryoid bodies are shown in blue. (FIG. 15D) Expression of pluripotency and differentiation specific genes (FIG. 15A) as measured by single-cell RNA-seq of embryoid bodies formed from untreated cells (YY1+) and cells treated with dTAG compound to degrade YY1 (YY1−). Each dot represents a single-cell and dots are shaded based on their normalized expression value. The sources of the datasets used in this figure are listed in Table S4.

(FIG. 16A) Model depicting dTAG system used to rapidly degrade YY1 protein. The FKBP degron tag was knocked-in to both alleles of the endogenous Yy1 gene locus. Addition of dTAG compound results in recruitment of the cereblon E3 ligase to FKBP degron-tagged YY1 protein, resulting in rapid proteasome-mediated degradation. The effects of YY1 degradation were examined 24 hours after treatment with dTAG compound. Washout of the dTAG compound for 5 days allowed recovery of YY1 protein. (FIG. 16B) Western blot validation of YY1 degradation after 24 hour treatment with dTAG compound and YY1 recovery after 5 day washout of the dTAG compound. (FIG. 16C) Model depicting AID degradation system used to rapidly degrade CTCF protein in Nora et al. (2017). The AID tag was knocked-in at the endogenous Ctcf gene locus. Addition of auxin results in the recruitment of the TIR1 E3 ligase to AID-tagged CTCF protein, resulting in proteasome-mediated degradation. The effects of CTCF degradation were examined 48 hours after treatment with dTAG compound. Washout of auxin for 2 days allowed recovery of CTCF protein.

(FIG. 17A) Purity of recombinant His6-YY1 protein was validated by gel electrophoresis of the purified material followed by Coomassie blue staining and western blot analysis with anti-YY1 antibody. (FIG. 17B) Activity of purified recombinant YY1 protein was validated by EMSA. Purified YY1 was incubated with biotinylated DNA probe in the presence or absence of a non-biotinylated competitor DNA. Activity of the recombinant protein was assessed by the ability to bind DNA and was determined by resolution on a native gel. Unbound "free" biotinylated probe is found at the bottom of the gel, while probe bound by YY1 migrates slower and appears as a higher band. Addition of competitor DNA abrogates this effect indicating that the activity is specific.

(FIG. 18A) Heatmap displaying YY1, H3K27ac, and CTCF ChIP-seq signal and GRO-seq signal at promoters, enhancers, and insulators in mouse embryonic stem cells (mES cells). ChIP-seq and GRO-seq signal is plotted as reads per million per base pair in a ±2 kb region centered on each promoter, enhancer, and insulator. (FIG. 18B) Expanded metagene analysis showing the occupancy of YY1 and CTCF at enhancers, promoters, and insulator elements in mES cells.

In addition, occupancy of YY1 was plotted at YY1 peaks that were not classified as an enhancer, promoter, or insulator, and occupancy of CTCF was plotted at CTCF peaks that were not classified as an enhancer, promoter, or insulator. ChIP-seq profiles are shown as mean reads per million per base pair for elements of each class in a ±2 kb region centered on each region. The number of enhancers, promoters, and insulators surveyed are noted in parentheses. To facilitate comparisons of the same factor between different regions the total ChIP-seq signal in the region was quantified and is displayed in the top right corner of the plot for each metagene analysis. (FIG. 18C) Metagene analysis showing GRO-seq signal and H3K27ac ChIP-seq signal at YY1 and CTCF peaks in mES cells that were not classified as part of an enhancer, promoter, or insulator. ChIP-seq profiles are shown as mean reads per million per base pair for elements of each class in a ±2 kb region centered on each region. The number of YY1 and CTCF peaks surveyed are noted in parentheses. To facilitate comparisons of the same factor between different regions the total ChIP-seq signal in the region was quantified and is displayed in the top right corner of the plot for each metagene analysis. (FIG. 18D) Expanded summary of the major classes of high-confidence interactions identified in YY1 and CTCF ChIA-PET datasets presented in FIG. 1E. Interactions are classified based on the presence of enhancer, promoter, and insulator elements at the anchors of each interaction. Interactions are displayed as arcs between these elements and the thickness of the arcs approximately reflects the percentage of interactions of that class relative to the total number of interactions that were classified. (FIG. 18E) An example of extensive YY1-associated enhancer-promoter interactions. The high-confidence YY1 interactions are depicted as red arcs, while high-confidence CTCF interactions are depicted as blue arcs. ChIP-seq binding profiles for YY1, CTCF, and H3K27ac, and stranded GRO-seq signal are displayed as reads per million per base pair at the Klf9 locus in mES cells. The Klf9 gene is indicated in the gene model and the interacting super-enhancers are labeled under the H3K27ac ChIP-seq track. (FIG. 18F) Metagene analysis showing the occupancy of YY1 at typical enhancer constituents and super-enhancer constituents. ChIP-seq profiles are shown in mean reads per million per base pair for elements of each class in a ±2 kb region centered on each region. To facilitate comparisons of the same factor between different regions the total ChIP-seq signal in the region was quantified and is displayed in the top right corner of the plot for each metagene analysis. The number of elements surveyed is listed at the top of the plot. Both plots are floored at the minimum amount of typical enhancer constituent signal. (FIG. 18G) Heatmaps displaying for each high-confidence YY1 interaction the number of PETs that support the interaction, for interactions that have at least one anchor overlapping a super-enhancer (left) and for interactions that have no ends overlapping a super-enhancer (right). Each row represents an interaction and the color intensity of each row represents the PET count for that interaction. (FIG. 18H) Box plot displaying the PET counts of high confidence YY1 ChIA-PET interactions that are either not associated with super-enhancers or associated with super-enhancers. (FIG. 18I) Model depicting co-immunoprecipitation assay to detect YY1 dimerization. (FIG. 18J) Western blot results showing co-immunoprecipitation of FLAG-tagged YY1 and HA-tagged YY1 protein from nuclear lysates prepared from transfected cells. Interaction between FLAG-tagged YY1 and HA-tagged YY1 protein is observed, while interaction with OCT4 protein is not observed. The sources of the datasets used in this figure are listed in Table S4.

DETAILED DESCRIPTION OF THE INVENTION

Figure 1A:
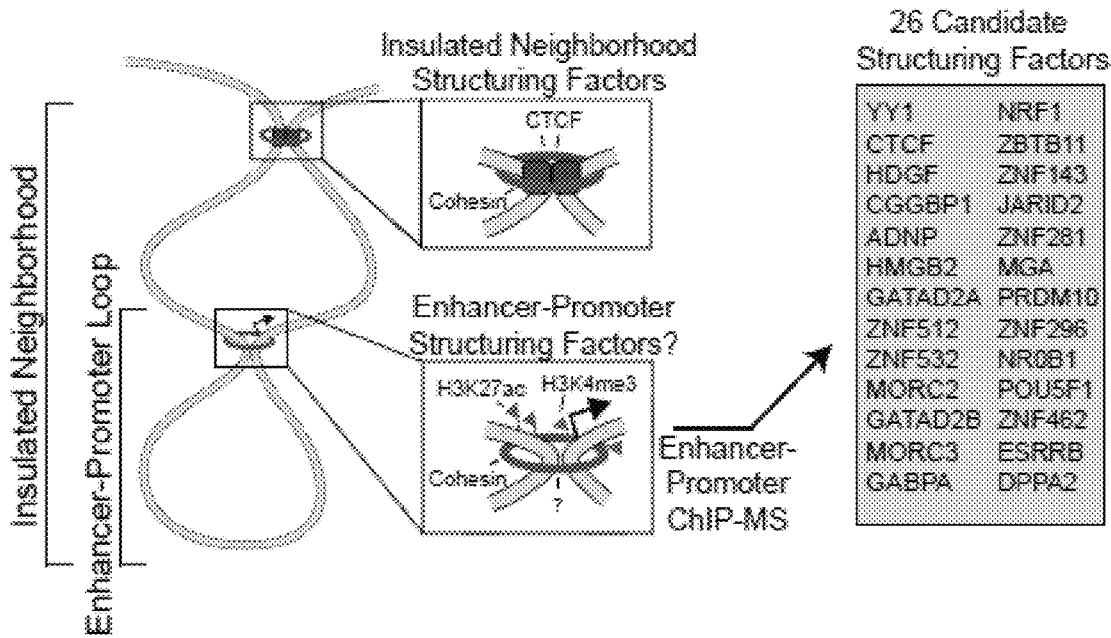
FIG. 1A-1H. YY1 is a candidate enhancer-promoter structuring factor (FIG. 1A) Model depicting an enhancer-promoter loop contained within a larger insulated neighborhood loop. Candidate enhancer-promoter structuring transcription factors were identified by ChIP-MS of histones with modifications characteristic of enhancer and promoter chromatin.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R I., "Culture of Animal Cells, A Manual of Basic Technique", 5th ed., John Wiley & Sons, Hoboken, NJ, 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, MD) and National Center for Biotechnology Information, National Library of Medicine (Bethesda, MD), as of May 1, 2010, ncbi.nlm.nih.gov/omim/ and in Online Mendelian Inheritance in Animals (OMIA), a database of genes, inherited disorders and traits in animal species (other than human and mouse), at omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

The disclosure herein demonstrates that the multimerization (e.g., dimerization) of transcription factors bound at enhancers and promoters can structure looping interactions between enhancers and promoters that that are functionally important in gene control. Enhancers are frequently dysregulated in disease including the acquisition of disease-specific enhancer elements via aberrant expression of transcription factors or acquisition of DNA variants that nucleate enhancer formation. The discovery that transcription factors mediate their activity via multimerization (e.g., dimerization) to structure looping interactions between two distinct DNA elements implies that perturbing transcription factor protein multimerization (e.g., dimerization) interfaces, or perturbing the interaction with DNA (for example, by methylating DNA) may be used to disrupt disease specific enhancer-promoter loops. With multiple transcription factors binding at different enhancers it may also imply a mechanism for determining enhancer-promoter specificity that can be used to identify the target genes of disease-associated enhancer elements.

Modulating Multimerization of Transcription Factor

In one aspect, the invention is directed to methods of modulating the expression of one or more genes in a cell, comprising modulating the multimerization (e.g., dimerization) of a transcription factor and thereby modulating the expression of the one or more genes.

"Modulate" or "modify" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" or "modifier" is an agent that causes or facilitates a qualitative or quantitative change, alteration, or modification in a process, pathway, or phenomenon of interest. In certain embodiments, modulating refers to reducing, slowing or otherwise eliminating the expression of one or more genes. Modulating expression of a gene may be accomplished or facilitated, for example, by any agent (e.g., a nucleic acid molecule or compound) that causes or facilitates a qualitative or quantitative change, alteration, or modification in the expression of the gene in a subject.

Transcription factors (TFs) contain DNA binding domains that recognize and bind recognition sites or sequences in the promoters of transcriptionally active genes, and also contain activation or repression domains that activate or suppress gene transcription when the TF binds to the recognition site or sequence. TF binding motifs are known in the art. See, for example, PCT/US16/59399, filed Oct. 28, 2016, the methods, teachings, and embodiments in this application can be freely combined with those disclosed herein. TF binding motif sequences can also be found in publicly available databases. In some embodiments, the TF binding motif is a YY1 Binding motif. In some embodiments, the YY1 binding motif is GGCGCCATnTT (SEQ ID NO: 44), CCGCCATnTT, CGCCATnTT, GCCGCCATTTTG (SEQ ID NO: 45), GCCAT, or CCAT.

In some embodiments, the transcription factor of the methods and compositions disclosed herein is a zinc finger protein. In some embodiments, the transcription factor of the methods and compositions disclosed herein belongs to the GLI-Kruppel class of zinc finger proteins. In some embodiments, the transcription factor of the methods and compositions disclosed herein is YY1. YY1 (Gene ID: 7528 (human); Gene ID: 22632 (mouse)) is a widely or ubiquitously distributed transcription factor belonging to the GLI-Kruppel class of zinc finger proteins and is involved in repressing and activating a diverse number of promoters. The transcription factor of the methods and compositions disclosed herein is not limited and may be any transcription factor that associates with an enhancer-promoter DNA loop.

In some embodiments, the transcription factor binds to an enhancer and a promoter region of the genome of the cell. In some embodiments, the enhancer and promoter regions are both located in the same insulated neighborhood of the genome of the cell.

The term "binding" is intended to mean throughout the disclosure a physical association between a target molecule (e.g., a DNA sequence, a transcription factor binding site in an enhancer or promoter region of a genome, genomic DNA binding site on a transcription factor) or complex and a binding agent (e.g., transcription factor, interfering nucleic acid, small molecule, antibody). The association is typically dependent upon the presence of a particular structural feature of the target (e.g., transcription factor binding site, DNA binding site on transcription factor). It is to be understood that binding specificity need not be absolute but generally refers to the context in which the binding occurs. As used herein, a "transcription factor binding site" refers to a region of genomic DNA that associates with a transcription factor. It is understood that each nucleotide of the genomic DNA may not interact with the transcription factor; instead only portions of the binding site may interact. As used herein, a compound that binds to a transcription factor binding site and modulates transcription factor binding may or may not bind to nucleotides that interact with the transcription factor.

As used herein, an "insulated neighborhood" is a region of a chromosome bounded by one or more markers. In some aspects, an "insulated neighborhood" is a chromosomal loop structure formed by the interaction of two DNA sites bound by the CTCF protein and occupied by the cohesin complex. See Hnisz, et al., "Insulated Neighborhoods: Structural and Functional Units of Mammalian Gene Control," Cell. 2016 Nov. 17; 167(5):1188-1200. doi: 10.1016/j.cell.2016.10.024.

The term "small molecule" refers to an organic molecule that is less than about 2 kilodaltons (kDa) in mass. In some embodiments, the small molecule is less than about 1.5 kDa, or less than about 1 kDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups. In some embodiments a small molecule is an artificial (non-naturally occurring) molecule. In some embodiments, a small molecule is non-polymeric. In some embodiments, a small molecule is not an amino acid. In some embodiments, a small molecule is not a nucleotide. In some embodiments, a small molecule is not a saccharide. In some embodiments, the term "small molecule" excludes molecules that are ingredients found in standard tissue culture medium.

The term "enhancer" refers to a region of genomic DNA to which proteins (e.g., transcription factors) bind to enhance (increase) transcription of a gene. Enhancers may be located some distance away from the promoters and transcription start site (TSS) of genes whose transcription they regulate and may be located upstream or downstream of the TSS. Enhancers can be identified using methods known to those of ordinary skill in the art based on one or more characteristic properties. For example, H3K27Ac is a histone modification associated with active enhancers (Creyghton et al., (2010) "Histone H3K27ac separates active from poised enhancers and predicts developmental state," Proc Natl Acad Sci USA 107, 21931-21936; Rada-Iglesias et al., "A unique chromatin signature uncovers early developmental enhancers in humans," Nature 470, 279-283). In some embodiments enhancers are identified as regions of genomic DNA that when present in a cell show enrichment for acetylated H3K27 (H3K27Ac), enrichment for methylated H3K4 (H3K4me1), or both. Enhancers can additionally or alternately be identified as regions of genomic DNA that when present in a cell are enriched for occupancy by transcription factors. Histone modifications can be detected using chromatin immunoprecipitation (ChIP) followed by microarray hybridization (ChIP-Chip) or followed by sequencing (ChIP-Seq) or other methods known in the art. These methods may also or alternately be used to detect occupancy of genomic DNA by transcription factors (or other proteins). A peak-finding algorithm such as that implemented in MACS version 1.4.2 (model-based analysis of ChIP-seq) or subsequent versions thereof may be used to identify regions of ChIP-seq enrichment over background (Zhang, Y., et al. (2008) "Model-based Analysis of ChIP-Seq (MACS)," Genome Biol. 9:R137). In some embodiments a p-value threshold of enrichment of $10^{-9}$ may be used. In some embodiments, the enhancer region is a distal enhancer region. In some embodiments, the enhancer is a super-enhancer. See, for example, US20160237490 published Aug. 18, 2016.

In some embodiments, multimerization (e.g., dimerization) of the transcription factor is modulated in a cell, thereby modulating formation of enhancer-promoter DNA loops in the genome of the cell. In some embodiments, multimerization (e.g., dimerization) of the transcription factor is decreased. Multimerization (e.g., dimerization) of the transcription factor in the cell can be decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some embodiments, multimerization (e.g., dimerization) of the transcription factor is increased. Multimerization (e.g., dimerization) of the transcription factor in the cell can be increased by about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 500%, 600% or more. In some embodiments, multimerization (e.g., dimerization) of the transcription factor in the cell can be increased or decreased by about 1-fold, 2-fold, 3-fold, 4-fold, 5-fold, 6-fold or more.

In some embodiments, the expression of one or more genes is decreased. The expression of one or more genes can be decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some embodiments, the expression of one or more genes is increased. The expression of one or more genes can be increased by about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 500%, 600% or more. In some embodiments, expression of one or more genes can be increased or decreased by about 1-fold, 2-fold, 3-fold, 4-fold, 5-fold, 6-fold or more.

In some embodiments, multimerization (e.g., dimerization) is modulated with a composition comprising a small molecule, peptide, polypeptide, nucleic acid, and/or oligonucleotide. In some embodiments, multimerization (e.g., dimerization) of the transcription factor is decreased. Multimerization (e.g., dimerization) of the transcription factor in the cell can be decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some embodiments, multimerization (e.g., dimerization) of the transcription factor is increased. Multimerization (e.g., dimerization) of the transcription factor in the cell can be increased by about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 500%, 600% or more. In some embodiments, multimerization (e.g., dimerization) of the transcription factor in the cell can be increased or decreased by about 1-fold, 2-fold, 3-fold, 4-fold, 5-fold, 6-fold or more.

In some embodiments, the composition comprises a polypeptide or a nucleic acid encoding for a polypeptide that is a transcription factor variant (e.g., YY1 variant) with increased, decreased or no affinity (e.g., multimerization affinity) for a transcription factor. In some embodiments, the transcription factor variant (e.g., YY1 variant) has decreased or no binding affinity for the transcription factor binding site. In some embodiments, the composition comprises a polypeptide that binds to a transcription factor (e.g., YY1) and decreases or increases transcription factor multimerization (e.g., dimerization).

In some embodiments, the transcription factor variant (e.g., YY1 variant) is a dominant negative variant. The transcription factor variant (e.g., YY1 variant) may (i) lack at least a portion of the DNA binding domain and/or (ii) lack at least a portion of the region that mediates multimerization. The first type could inhibit multimerization by binding to the fully functional transcription factor. The second type could inhibit formation of the enhancer-promoter loop structure by binding to a fully functional transcription factor (e.g., a fully functional transcription factor that is bound at a promoter or enhancer). In some embodiments, the composition comprises a small molecule that binds to a transcription factor (e.g., YY1) and decreases or increases transcription factor multimerization (e.g., dimerization). In some embodiments, the composition comprises an antibody that binds to a transcription factor (e.g., YY1) and decreases transcription factor multimerization (e.g., dimerization).

In some embodiments, the cell is a stem cell (e.g., an embryonic stem cell, a mammalian embryonic stem cell, a human embryonic stem cell, a murine embryonic stem cell). In some embodiments, the cell is an embryonic stem cell. In some embodiments, the cell is an induced pluripotent stem cell.

In some embodiments of the methods and compositions disclosed herein, cells include somatic cells, stem cells, mitotic or post-mitotic cells, neurons, fibroblasts, or zygotes. A cell, zygote, embryo, or post-natal mammal can be of vertebrate (e.g., mammalian) origin. In some aspects, the vertebrates are mammals or avians. Particular examples include primate (e.g., human), rodent (e.g., mouse, rat), canine, feline, bovine, equine, caprine, porcine, or avian (e.g., chickens, ducks, geese, turkeys) cells, zygotes, embryos, or post-natal mammals. In some embodiments, the cell, zygote, embryo, or post-natal mammal is isolated (e.g., an isolated cell; an isolated zygote; an isolated embryo). In some embodiments, a mouse cell, mouse zygote, mouse embryo, or mouse post-natal mammal is used. In some embodiments, a rat cell, rat zygote, rat embryo, or rat post-natal mammal is used. In some embodiments, a human cell, human zygote or human embryo is used. The methods described herein can be used in a mammal (e.g., a mouse, a human) in vivo.

Stem cells may include totipotent, pluripotent, multipotent, oligipotent and unipotent stem cells. Specific examples of stem cells include embryonic stem cells, fetal stem cells, adult stem cells, and induced pluripotent stem cells (iPSCs) (e.g., see U.S. Published Application Nos. 2010/0144031, 2011/0076678, 2011/0088107, 2012/0028821 all of which are incorporated herein by reference).

Somatic cells may be primary cells (non-immortalized cells), such as those freshly isolated from an animal, or may be derived from a cell line capable of prolonged proliferation in culture (e.g., for longer than 3 months) or indefinite proliferation (immortalized cells). Adult somatic cells may be obtained from individuals, e.g., human subjects, and cultured according to standard cell culture protocols available to those of ordinary skill in the art. Somatic cells of use in aspects of the invention include mammalian cells, such as, for example, human cells, non-human primate cells, or rodent (e.g., mouse, rat) cells. They may be obtained by well-known methods from various organs, e.g., skin, lung, pancreas, liver, stomach, intestine, heart, breast, reproductive organs, muscle, blood, bladder, kidney, urethra and other urinary organs, etc., generally from any organ or tissue containing live somatic cells. Mammalian somatic cells useful in various embodiments include, for example, fibroblasts, Sertoli cells, granulosa cells, neurons, pancreatic cells, epidermal cells, epithelial cells, endothelial cells, hepatocytes, hair follicle cells, keratinocytes, hematopoietic cells, melanocytes, chondrocytes, lymphocytes (B and T lymphocytes), macrophages, monocytes, mononuclear cells, cardiac muscle cells, skeletal muscle cells, etc.

In some embodiments, the one or more genes that are modulated comprise cell regulator genes. In some embodiments, the one or more genes comprise Oct4, Nanog and/or Sox2. In some embodiments the cell is a cancer cell and gene is an oncogene or tumor suppressor gene. In some embodiments, the cell (e.g., cancer cell) may harbor a mutation or polymorphic variant associated with increased or aberrant enhancer activity.

Modulating Formation of Enhancer-Promoter DNA Loops

Some aspects of the invention are directed to methods of modulating the expression of one or more genes in a cell, comprising modulating formation and/or stability of an enhancer-promoter DNA loop in the genome of the cell, wherein formation and/or stability is transcription factor (e.g., YY1) dependent. As used herein, indications that the enhancer-promoter DNA loop formation is "transcription factor dependent" is intended to mean that the transcription factor is partially or wholly responsible for formation and/or stability of the enhancer-promoter DNA loop. In some instances, the transcription factor is necessary but not sufficient for formation and/or stability of the enhancer-promoter DNA loop. In some instances, the transcription factor is necessary and sufficient for formation and/or stability of the enhancer-promoter DNA loop. In some embodiments, expression of one or more genes in a cell can be decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some embodiments, expression of one or more genes in a cell can be increased by about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 500%, 600% or more. In some embodiments, expression of one or more genes in a cell can be increased or decreased by about 1-fold, 2-fold, 3-fold, 4-fold, 5-fold, 6-fold or more.

In some embodiments, formation of the enhancer-promoter DNA loop is modulated by modulating binding of the transcription factor (e.g., YY1) to the promoter and/or enhancer region (e.g., transcription factor binding site in the promoter and/or enhancer region) of the enhancer-promoter DNA loop. In some embodiments, binding of the transcription factor can be decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some embodiments, binding of the transcription factor can be increased by about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 500%, 600% or more. In some embodiments binding of the transcription factor can be increased or decreased by about 1-fold, 2-fold, 3-fold, 4-fold, 5-fold, 6-fold or more.

In some embodiments, binding of the transcription factor (e.g., YY1) to the promoter and/or enhancer region of the enhancer-promoter DNA loop is modulated by modifying a promoter and/or enhancer region (e.g., transcription factor binding site in a promoter and/or enhancer region). In some embodiments, the modification comprises modifying the degree of methylation of the promoter and/or enhancer region or a region within about 25 bases, 50 bases, 100 bases, 200 bases, 300 bases, 400 bases, 500 bases, 600 bases, 700 bases, 800 bases, 900 bases, 1000 bases, 1500 bases, 2000 bases, 5000 bases, 10000 bases, 20000 bases, 50000 bases or more upstream or downstream of the promoter and/or enhancer region. In some embodiments, binding of the transcription factor (e.g., YY1) to the promoter and/or enhancer region of the enhancer-promoter DNA loop is modulated by modifying the methylation of one or more transcription binding sites or motifs (e.g., YY1 binding sites or motifs) in a promoter and/or enhancer region. In some embodiments, binding of the transcription factor (e.g., YY1) to the promoter and/or enhancer region of the enhancer-promoter DNA loop is modulated by modifying the methylation within about 25 bases, 50 bases, 100 bases, 200 bases, 300 bases, 400 bases, 500 bases, 600 bases, 700 bases, 800 bases, 900 bases, 1000 bases, 1500 bases, 2000 bases, 5000 bases, 10000 bases, 20000 bases, 50000 bases or more upstream or downstream of one or more transcription binding sites/motifs (e.g., YY1 binding sites/motifs) in a promoter and/or enhancer region. In some embodiments, the degree of methylation can be increased or decreased by about 1-fold, 2-fold, 3-fold, 4-fold, 5-fold, 6-fold or more. Methods of modulating methylation of DNA are known in the art. See Liu et al., "Editing DNA methylation in the mammalian genome," Cell, Vol. 167 (1):233-247.e17, which is incorporated by reference in its entirety. In some aspects, the degree of methylation may be modified by one or more methods disclosed in Application No. 62/377,520 (Rudolf Jaenisch, et al., filed Aug. 19, 2016) and PCT/US2017/047674 (Rudolf Jaenisch, et al., filed Aug. 18, 2017) which are hereby incorporated by reference in its entirety. In some embodiments, the degree of methylation may be modified using a catalytically inactive targetable nuclease (e.g., catalytically inactive site specific nuclease). In some embodiments, the binding of YY1 to a YY1 binding site or motif is enhanced by reducing methylation of the YY1 binding site or motif. In some embodiments, the binding of YY1 to a YY1 binding site or motif is enhanced by reducing the level or degree of methylation of the YY1 binding site or motif. In some embodiments, the binding of YY1 to a YY1 binding site or motif is reduced by increasing the level or degree of methylation of the YY1 binding site or motif.

In some embodiments, the modification comprises modifying the nucleotide sequence of one or more promoter and/or enhancer regions. In some embodiments, the modification comprises modifying the nucleotide sequence of a transcription factor binding site (e.g., YY1 binding site) in one or more promoter and/or enhancer regions. In some embodiments, the nucleotide sequence of the enhancer or promoter region (e.g., transcription binding site in a promoter or enhancer region) is modified with a targetable nuclease (e.g., site specific nuclease).

In some embodiments, the modification is a deletion of all or part of a binding motif, substitution of one or more nucleotides in a binding motif wherein the substitution reduces TF binding, or altering a binding motif to increase binding. In some embodiments, a catalytically inactive site-specific nuclease targeted to or near a binding motif (e.g., up to about 5, 10, 15, 20, 25, 50, 75, 100, 150, 200, 300, or 500 nucleotides away from either end of the binding motif) sterically blocks binding of the TF to the binding motif or blocks association of the TF (e.g., multimerization of the TF) and formation of DNA looping structures. In some embodiments, a catalytically inactive site-specific nuclease targeted to or near a binding motif (e.g., up to about 5, 10, 15, 20, 25, 50, 75, 100, 150, 200, 300, or 500 nucleotides away from either end of the binding motif) modulates (e.g., increases or decreases) binding of the TF by modulating DNA methylation of the binding motif or near the binding motif. In some embodiments, the modification is a DNA modification that inhibits or blocks TF binding.

There are currently four main types of targetable nucleases (sometimes also referred to as "site specific nucleases") in use: zinc finger nucleases (ZFNs), transcription activator-like effector nucleases (TALENs), and RNA-guided nucleases (RGNs) such as the Cas proteins of the CRISPR/Cas Type II system, and engineered meganucleases. ZFNs and TALENs comprise the nuclease domain of the restriction enzyme FokI (or an engineered variant thereof) fused to a site-specific DNA binding domain (DBD) that is appropriately designed to target the protein to a selected DNA sequence. In the case of ZFNs, the DNA binding domain comprises a zinc finger DBD. In the case of TALENs, the site-specific DBD is designed based on the DNA recognition code employed by transcription activator-like effectors (TALEs), a family of site-specific DNA binding proteins found in plant-pathogenic bacteria such as *Xanthomonas* species. The Clustered Regularly Interspaced Short Palindromic Repeats (CRISPR) Type II system is a bacterial adaptive immune system that has been modified for use as an RNA-guided endonuclease technology for genome engineering. The bacterial system comprises two endogenous bacterial RNAs called crRNA and tracrRNA and a CRISPR-associated (Cas) nuclease, e.g., Cas9. The tracrRNA has partial complementarity to the crRNA and forms a complex with it. The Cas protein is guided to the target sequence by the crRNA/tracrRNA complex, which forms a RNA/DNA hybrid between the crRNA sequence and the complementary sequence in the target. For use in genome modification, the crRNA and tracrRNA components are often combined into a single chimeric guide RNA (sgRNA or gRNA) in which the targeting specificity of the crRNA and the properties of the tracrRNA are combined into a single transcript that localizes the Cas protein to the target sequence so that the Cas protein can cleave the DNA. The sgRNA often comprises an approximately 20 nucleotide guide sequence complementary or homologous to the desired target sequence followed by about 80 nt of hybrid crRNA/tracrRNA. One of ordinary skill in the art appreciates that the guide RNA need not be perfectly complementary or homologous to the target sequence. For example, in some embodiments it may have one or two mismatches. The genomic sequence which the gRNA hybridizes is typically flanked on one side by a Protospacer Adjacent Motif (PAM) sequence although one of ordinary skill in the art appreciates that certain Cas proteins may have a relaxed requirement for a PAM sequence. The PAM sequence is present in the genomic DNA but not in the sgRNA sequence. The Cas protein will be directed to any DNA sequence with the correct target sequence and PAM sequence. The PAM sequence varies depending on the species of bacteria from which the Cas protein was derived. Specific examples of Cas proteins include Cas1, Cas2, Cas3, Cas4, Cas5, Cas6, Cas7, Cas8, Cas9 and Cas10. In some embodiments, the site specific nuclease comprises a Cas9 protein. For example, Cas9 from *Streptococcus pyogenes* (Sp), *Neisseria meningitides, Staphylococcus aureus, Streptococcus thermophiles*, or *Treponema denticola* may be used. The PAM sequences for these Cas9 proteins are NGG, NNNNGATT, NNAGAA, NAAAAC, respectively. A number of engineered variants of the site-specific nucleases have been developed and may be used in certain embodiments. For example, engineered variants of Cas9 and Fok1 are known in the art. Furthermore, it will be understood that a biologically active fragment or variant can be used. Other variations include the use of hybrid site specific nucleases. For example, in CRISPR RNA-guided FokI nucleases (RFNs) the FokI nuclease domain is fused to the amino-terminal end of a catalytically inactive Cas9 protein (dCas9) protein. RFNs act as dimers and utilize two guide RNAs (Tsai, Q S, et al., Nat Biotechnol. 2014; 32(6): 569-576). Site-specific nucleases that produce a single-stranded DNA break are also of use for genome editing. Such nucleases, sometimes termed "nickases" can be generated by introducing a mutation (e.g., an alanine substitution) at key catalytic residues in one of the two nuclease domains of a site specific nuclease that comprises two nuclease domains (such as ZFNs, TALENs, and Cas proteins). Examples of such mutations include D10A, N863A, and H840A in SpCas9 or at homologous positions in other Cas9 proteins. A nick can stimulate HDR at low efficiency in some cell types. Two nickases, targeted to a pair of sequences that are near each other and on opposite strands can create a single-stranded break on each strand ("double nicking"), effectively generating a DSB, which can optionally be repaired by HDR using a donor DNA template (Ran, F. A. et al. Cell 154, 1380-1389 (2013). In some embodiments, the Cas protein is a SpCas9 variant. In some embodiments, the SpCas9 variant is a R661A/Q695A/Q926A triple variant or a N497A/R661A/Q695A/Q926A quadruple variant. See Kleinstiver et al., "High-fidelity CRISPR-Cas9 nucleases with no detectable genome-wide off-target effects," Nature, Vol. 529, pp. 490-495 (and supplementary materials)(2016); incorporated herein by reference in its entirety. In some embodiments, the Cas protein is C2c1, a class 2 type V-B CRISPR-Cas protein. See Yang et al., "PAM-Dependent Target DNA Recognition and Cleavage by C2c1 CRISPR-Cas Endonuclease," Cell, Vol. 167, pp. 1814-1828 (2016); incorporated herein by reference in its entirety. In some embodiments, the Cas protein is one described in US 20160319260 "Engineered CRISPR-Cas9 nucleases with Altered PAM Specificity" incorporated herein by reference.

In some embodiments, the targetable nuclease (e.g., site specific nuclease) has at least 90%, 95% or 99% polypeptide sequence identity to a naturally occurring targetable nuclease.

In some embodiments, the nucleotide sequence of the enhancer or promoter region is modified with a site specific nuclease (i.e., a targetable nuclease) and one or more guide sequences. In some embodiments, the site specific nuclease is a Cas protein. A variety of CRISPR associated (Cas) genes or proteins which are known in the art can be used in the methods of the invention and the choice of Cas protein will depend upon the particular situation (e.g., www.ncbi.nlm.nih.gov/gene/?term=cas9). In a particular aspect, the Cas nucleic acid or protein used in the compositions is Cas9. In some embodiments a Cas protein, e.g., a Cas9 protein, may be from any of a variety of prokaryotic species. In some embodiments a particular Cas protein, e.g., a particular Cas9 protein, may be selected to recognize a particular protospacer-adjacent motif (PAM) sequence. In certain embodiments a Cas protein, e.g., a Cas9 protein, may be obtained from a bacteria or archaea or synthesized using known methods. In certain embodiments, a Cas protein may be from a gram positive bacteria or a gram negative bacteria. In certain embodiments, a Cas protein may be from a *Streptococcus*, (e.g., a *S. pyogenes*, a *S. thermophilus*) a *Cryptococcus*, a *Corynebacterium*, a *Haemophilus*, a *Eubacterium*, a *Pasteurella*, a *Prevotella*, a *Veillonella*, or a *Marinobacter*. In some embodiments nucleic acids encoding two or more different Cas proteins, or two or more Cas proteins, may be present in the composition, e.g., to allow for recognition and modification of sites comprising the same, similar or different PAM motifs.

In some embodiments, the Cas protein is Cpf1 protein or a functional portion thereof. In some embodiments, the Cas protein is Cpf1 from any bacterial species or functional portion thereof. In certain embodiments, a Cpf1 protein is a *Francisella novicida* U112 protein or a functional portion thereof, a *Acidaminococcus* sp. BV3L6 protein or a functional portion thereof, or a Lachnospiraceae bacterium ND2006 protein or a function portion thereof. Cpf1 protein is a member of the type V CRISPR systems. Cpf1 protein is a polypeptide comprising about 1300 amino acids. Cpf1 contains a RuvC-like endonuclease domain. See Zetsche B, et al., "Cpf1 is a single RNA-guided endonuclease of a class 2 CRISPR-Cas system," Cell. 2015 Oct. 22; 163(3):759-71. doi: 10.1016/j.cell.2015.09.038. Epub 2015 Sep. 25.) and US20160208243, incorporated herein by reference in their entirities. One of ordinary skill in the art appreciates that Cpf1 does not utilize tracrRNA, and thus requires only a crRNA that contains a single stem-loop, which tolerates sequence changes that retain secondary structure.

In some embodiments a Cas9 nickase may be generated by inactivating one or more of the Cas9 nuclease domains. In some embodiments, an amino acid substitution at residue 10 in the RuvC I domain of Cas9 converts the nuclease into a DNA nickase. For example, the aspartate at amino acid residue 10 can be substituted for alanine (Cong et al, Science, 339:819-823).

In some embodiments, the targetable nuclease may be a catalytically inactive targetable nuclease (e.g., catalytically inactive site specific nuclease). In some embodiments, a catalytically inactive targetable nuclease can be utilized along with an effector domain to modulate binding of a transcription factor to a promoter or enhancer region by modifying the degree of methylation of the promoter or enhancer region. Amino acids mutations that create a catalytically inactive Cas9 protein include mutating at residue 10 and/or residue 840. Mutations at both residue 10 and residue 840 can create a catalytically inactive Cas9 protein, sometimes referred herein as dCas9. In some embodiments, dCas9 is a D10A and a H840A Cas9 mutant that is catalytically inactive. As used herein an "effector domain" is a molecule (e.g., protein) that modulates the expression and/or activation of a genomic sequence (e.g., gene). The effector domain may have methylation activity (e.g., DNA methylation activity). In some aspects, the effector domain targets one or both alleles of a gene. The effector domain can be introduced as a nucleic acid sequence and/or as a protein. In some aspects, the effector domain can be a constitutive or an inducible effector domain. In some aspects, a Cas (e.g., dCas) nucleic acid sequence or variant thereof and an effector domain nucleic acid sequence are introduced into the cell as a chimeric sequence. In some aspects, the effector domain is fused to a molecule that associates with (e.g., binds to) Cas protein (e.g., the effector molecule is fused to an antibody or antigen binding fragment thereof that binds to Cas protein). In some aspects, a Cas (e.g., dCas) protein or variant thereof and an effector domain are fused or tethered creating a chimeric protein and are introduced into the cell as the chimeric protein. In some aspects, the Cas (e.g., dCas) protein and effector domain bind as a protein-protein interaction. In some aspects, the Cas (e.g., dCas) protein and effector domain are covalently linked. In some aspects, the effector domain associates non-covalently with the Cas (e.g., dCas) protein. In some aspects, a Cas (e.g., dCas) nucleic acid sequence and an effector domain nucleic acid sequence are introduced as separate sequences and/or proteins. In some aspects, the Cas (e.g., dCas) protein and effector domain are not fused or tethered.

A site specific nuclease or polypeptide (e.g., fusion polypeptide comprising a site-specific nuclease and an effector domain, fusion polypeptide comprising a site-specific nuclease and an effector domain having methylation or de-methylation activity) may be targeted to a unique site in the genome (e.g., a transcription factor binding site, a YY1 binding site) of a mammalian cell by appropriate design of the nuclease, guide RNA, or polypeptide. A polypeptide, nuclease and/or guide RNA may be introduced into cells by introducing a nucleic acid that encodes it into the cell. Standard methods such as plasmid DNA transfection, viral vector delivery, transfection with modified or synthetic mRNA (e.g., capped, polyadenylated mRNA), or microinjection can be used. In some embodiments, the modified or synthetic mRNA comprises one or more modifications that stabilize the mRNA or provide other improvements over naturally occurring mRNA (e.g., increased cellular uptake). Examples of modified or synthetic mRNA are described in Warren et al. (Cell Stem Cell 7(5):618-30, 2010, Mandal P K, Rossi D J. Nat Protoc. 2013 8(3):568-82, US Pat. Pub. No. 20120046346 and/or PCT/US2011/032679 (WO/2011/130624). mRNA is also discussed in R. E. Rhoads (Ed.), "Synthetic mRNA: Production, Introduction Into Cells, and Physiological Consequences," Series: Methods in Molecular Biology, Vol. 1428. Additional examples are found in numerous PCT and US applications and issued patents to Moderna Therapeutics, e.g., PCT/US2011/046861; PCT/US2011/054636, PCT/US2011/054617, U.S. Ser. No. 14/390,100 (and additional patents and patent applications mentioned in these.) If DNA encoding the nuclease or guide RNA is introduced, the coding sequences should be operably linked to appropriate regulatory elements for expression, such as a promoter and termination signal. In some embodiments a sequence encoding a guide RNA is operably linked to an RNA polymerase III promoter such as U6 or tRNA promoter. In some embodiments one or more guide RNAs and Cas protein coding sequences are transcribed from the same nucleic acid (e.g., plasmid). In some embodiments multiple guide RNAs are transcribed from the same plasmid or from different plasmids or are otherwise introduced into the cell. The multiple guide RNAs may direct Cas9 to different target sequences in the genome, allowing for multiplexed genome editing. In some embodiments a nuclease protein (e.g., Cas9) may comprise or be modified to comprise a nuclear localization signal (e.g., SV40 NLS). A nuclease protein may be introduced into cells, e.g., using protein transduction. Nuclease proteins, guide RNAs, or both, may be introduced using microinjection. Methods of using site specific nucleases, e.g., to perform genome editing, are described in numerous publications, such as Methods in Enzymology, Doudna J A, Sontheimer E J. (eds), The use of CRISPR/Cas9, ZFNs, and TALENs in generating site-specific genome alterations. Methods Enzymol. 2014, Vol. 546 (Elsevier); Carroll, D., Genome Editing with Targetable Nucleases, Annu. Rev. Biochem. 2014. 83:409-39, and references in either of these. See also U.S. Pat. Pub. Nos. 20140068797, 20140186919, 20140170753 and/or PCT/US2014/034387 (WO/2014/172470).

In some embodiments, the one or more guide sequences include sequences that recognize DNA in a site-specific manner. For example, guide sequences can include guide ribonucleic acid (RNA) sequences utilized by a CRISPR system or sequences within a TALEN or zinc finger system that recognize DNA in a site-specific manner. The guide sequences comprise a portion that is complementary to a portion of each of the one or more genomic sequences and comprise a binding site for the catalytically inactive site specific nuclease. In some embodiments, the RNA sequence is referred to as guide RNA (gRNA) or single guide RNA (sgRNA).

In some aspects, a guide sequence can be complementary to one or more (e.g., all) of the genomic sequences that are being modulated or modified. In one aspect, a guide sequence is complementary to a single target genomic sequence. In a particular aspect in which two or more target genomic sequences are to be modulated or modified, multiple (e.g., 2, 3, 4, 5, 6, 7, 8, 9, 10, or more) guide sequences are introduced wherein each guide sequence is complementary to (specific for) one target genomic sequence. In some aspects, two or more, three or more, four or more, five or more, or six or more guide sequences are complementary to (specific for) different parts of the same target sequence. In one aspect, two or more guide sequences bind to different sequences of the same region of DNA. In some aspects, a single guide sequence is complementary to at least two target or more (e.g., all) of the genomic sequences. It will also be apparent to those of skill in the art that the portion of the guide sequence that is complementary to one or more of the genomic sequences and the portion of the guide sequence that binds to the catalytically inactive site specific nuclease can be introduced as a single sequence or as 2 (or more) separate sequences into a cell.

Each guide sequence can vary in length from about 8 base pairs (bp) to about 200 bp. In some embodiments, the RNA sequence can be about 9 to about 190 bp; about 10 to about 150 bp; about 15 to about 120 bp; about 20 to about 100 bp; about 30 to about 90 bp; about 40 to about 80 bp; about 50 to about 70 bp in length.

The portion of each genomic sequence (e.g., a promoter or enhancer region, a transcription factor binding site in a promoter or enhancer region) to which each guide sequence is complementary can also vary in size. In particular aspects, the portion of each genomic sequence to which the guide sequence is complementary can be about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 39, 40, 41, 42, 43, 44, 45, 46 47, 48, 49, 50, 51, 52, 53, 54, 55, 56, 57, 58, 59 60, 61, 62, 63, 64, 65, 66, 67, 68, 69, 70, 71, 72, 73, 74, 75, 76, 77, 78, 79, 80 81, 82, 83, 84, 85, 86, 87 88, 89, 90, 81, 92, 93, 94, 95, 96, 97, 98, or 100 nucleotides (contiguous nucleotides) in length. In some embodiments, each guide sequence can be at least about 70%, 75%, 80%, 85%, 90%, 95%, 100%, etc. identical or similar to the portion of each genomic sequence. In some embodiments, each guide sequence is completely or partially identical or similar to each genomic sequence. For example, each guide sequence can differ from perfect complementarity to the portion of the genomic sequence by about 1, 2, 3, 4, 5, 6, 7, 8, 9, 10, 11, 12, 13, 14, 15, 16, 17, 18, 19, 20, etc. nucleotides. In some embodiments, one or more guide sequences are perfectly complementary (100%) across at least about 10 to about 25 (e.g., about 20) nucleotides of the genomic sequence.

In some embodiments, one or more nucleotide sequences (e.g., guide sequences) is complementary or homologous to a region of genomic DNA involved in transcription factor binding or enhancer-promoter DNA loop formation. In some embodiments, one or more nucleotide sequences are complementary or homologous to an enhancer or promoter region of an enhancer-promoter DNA loop. In some embodiments, one or more nucleotide sequences are complementary or homologous to a transcription factor (e.g., YY1) binding site (e.g., transcription factor binding site in a promoter or enhancer region). In some embodiments, one or more nucleotide sequences are complementary or homologous to a region of genomic DNA that, based on the degree of methylation, modulates transcription factor binding (e.g., YY1 binding), enhancer-promoter DNA loop formation, and/or enhancer-promoter DNA loop stability. In some embodiments, the one or more nucleotide sequences are complementary or homologous to 1, 2, 3, 4, 5, 6, 7, 8, 9, 10 or more genomic DNA sequences. In some embodiments, one or more nucleotide sequences are complementary or homologous to a unique genomic DNA sequence, and can be utilized to modulate the expression of one or more genes associated with a specific enhancer-promoter DNA loop.

In some embodiments, a site specific nuclease (e.g., Talen, Zinc Finger Protein) binds to a region of genomic DNA involved in transcription factor binding or enhancer-promoter DNA loop formation. In some embodiments, a site specific nuclease (e.g., Talen, Zinc Finger Protein) binds to an enhancer or promoter region of an enhancer-promoter DNA loop. In some embodiments, a site specific nuclease (e.g., Talen, Zinc Finger Protein) binds to a transcription factor (e.g., YY1) binding site (e.g., transcription factor binding site in a promoter or enhancer region). In some embodiments, a site specific nuclease (e.g., Talen, Zinc Finger Protein) binds to a region of genomic DNA that, based on the degree of methylation, modulates transcription factor binding (e.g., YY1 binding), enhancer-promoter DNA loop formation, and/or enhancer-promoter DNA loop stability. In some embodiments, a site specific nuclease (e.g., Talen, Zinc Finger Protein) binds to 1, 2, 3, 4, 5, 6, 7, 8, 9, 10 or more genomic DNA sequences. In some embodiments, a site specific nuclease (e.g., Talen, Zinc Finger Protein) binds to a unique genomic DNA sequence, and can be utilized to modulate the expression of one or more genes associated with a specific enhancer-promoter DNA loop.

In some embodiments, nucleic acids (e.g., enhanced nucleic acids) (e.g., DNA constructs, synthetic RNAs, e.g., homologous or complementary RNAs described herein, mRNAs described herein, etc.) herein may be introduced into cells of interest via transfection, electroporation, cationic agents, polymers, or lipid-based delivery molecules well known to those of ordinary skill in the art. As used herein, an "enhanced nucleic acid" has an enhanced property (e.g., enhanced stability, enhanced cellular uptake, enhanced binding, enhanced specificity) compared to a naturally occurring counterpart nucleic acid.

In some embodiments, methods of the present disclosure enhance nucleic acid delivery into a cell population, in vivo, ex vivo, or in culture. For example, a cell culture containing a plurality of host cells (e.g., eukaryotic cells such as yeast or mammalian cells) is contacted with a composition that contains an enhanced nucleic acid having at least one nucleoside modification and, optionally, a translatable region. In some embodiments, the composition also generally contains a transfection reagent or other compound that increases the efficiency of enhanced nucleic acid uptake into the host cells. The enhanced nucleic acid exhibits enhanced retention in the cell population, relative to a corresponding unmodified nucleic acid. In some embodiments, the retention of the enhanced nucleic acid is greater than the retention of the unmodified nucleic acid. In some embodiments, it is at least about 50%, 75%, 90%, 95%, 100%, 150%, 200%, or more than 200% greater than the retention of the unmodified nucleic acid. Such retention advantage may be achieved by one round of transfection with the enhanced nucleic acid, or may be obtained following repeated rounds of transfection.

The synthetic RNAs (e.g., modified mRNAs, enhanced nucleic acids) of the presently disclosed subject matter may be optionally combined with a reporter gene (e.g., upstream or downstream of the coding region of the mRNA) which, for example, facilitates the determination of modified mRNA delivery to the target cells or tissues. Suitable reporter genes may include, for example, Green Fluorescent Protein mRNA (GFP mRNA), *Renilla* Luciferase mRNA (Luciferase mRNA), Firefly Luciferase mRNA, or any combinations thereof. For example, GFP mRNA may be fused with a mRNA encoding a nuclear localization sequence to facilitate confirmation of mRNA localization in the target cells where the RNA transcribed from the at least one regulatory element is taking place.

In some embodiments, RNA can be modified further post-transcription, e.g., by adding a cap or other functional group. In an aspect, a synthetic RNA (enhanced nucleic acid) comprises a 5' and/or a 3'-cap structure. Synthetic RNA can be single stranded (e.g., ssRNA) or double stranded (e.g., dsRNA). The 5' and/or 3'-cap structure can be on only the sense strand, the antisense strand, or both strands. By "cap structure" is meant chemical modifications, which have been incorporated at either terminus of the oligonucleotide (see, for example, Adamic et al., U.S. Pat. No. 5,998,203, incorporated by reference herein). These terminal modifications protect the nucleic acid molecule from exonuclease degradation, and can help in delivery and/or localization within a cell. The cap can be present at the 5'-terminus (5'-cap) or at the 3'-terminal (3'-cap) or can be present on both termini.

Non-limiting examples of the 5'-cap include, but are not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, Tetrahedron 49, 1925; incorporated by reference herein).

The synthetic RNA may comprise at least one modified nucleoside, such as pseudouridine, m5U, s2U, m6A, and m5C, N1-methylguanosine, N1-methyladenosine, N7-methylguanosine, 2'-)-methyluridine, and 2'-O-methylcytidine. Polymerases that accept modified nucleosides are known to those of skill in the art. Modified polymerases can be used to generate synthetic, modified RNAs. Thus, for example, a polymerase that tolerates or accepts a particular modified nucleoside as a substrate can be used to generate a synthetic, modified RNA including that modified nucleoside.

In some embodiments, the synthetic RNA provokes a reduced (or absent) innate immune response in vivo or reduced interferon response in vivo by the transfected tissue or cell population. mRNA produced in eukaryotic cells, e.g., mammalian or human cells, is heavily modified, the modifications permitting the cell to detect RNA not produced by that cell. The cell responds by shutting down translation or otherwise initiating an innate immune or interferon response. Thus, to the extent that an exogenously added RNA can be modified to mimic the modifications occurring in the endogenous RNAs produced by a target cell, the exogenous RNA can avoid at least part of the target cell's defense against foreign nucleic acids. Thus, in some embodiments, synthetic RNAs include in vitro transcribed RNAs including modifications as found in eukaryotic/mammalian/human RNA in vivo. Other modifications that mimic such naturally occurring modifications can also be helpful in producing a synthetic RNA molecule that will be tolerated by a cell.

In some embodiments, the synthetic RNA has one or more modifications (e.g., modified 5' and/or 3' UTR sequences, optimized codons) that can enhance mRNA stability and/or translation efficiency in mammalian (e.g., human) cells. See US Pat. Publ. No. 20140206753, incorporated herein by reference in its entirety.

As used herein, the terms "transfect" or "transfection" mean the introduction of a nucleic acid, e.g., a synthetic RNA, e.g., modified mRNA into a cell, or preferably into a target cell. The introduced synthetic RNA (e.g., modified mRNA) may be stably or transiently maintained in the target cell. The term "transfection efficiency" refers to the relative amount of synthetic RNA (e.g., modified mRNA) taken up by the target cell which is subject to transfection. In practice, transfection efficiency may be estimated by the amount of a reporter nucleic acid product expressed by the target cells following transfection. Preferred embodiments include compositions with high transfection efficacies and in particular those compositions that minimize adverse effects which are mediated by transfection of non-target cells. In some embodiments, compositions of the present invention that demonstrate high transfection efficacies improve the likelihood that appropriate dosages of the synthetic RNA (e.g., modified mRNA) will be delivered to the target cell, while minimizing potential systemic adverse effects.

In some embodiments a cell may be genetically modified (in vitro or in vivo) (e.g., using a nucleic acid construct, e.g., a DNA construct) to cause it to express (i) an agent that modulates transcription factor (e.g., YY1) multimerization or binding to a promoter or enhancer region or (ii) an mRNA that encodes such an agent. For example, the present disclosure contemplates generating a cell or cell line that transiently or stably expresses an RNA that inhibits binding to a promoter or enhancer region or multimerization of the TF or that transiently stably expresses an mRNA that encodes an antibody (or other protein capable of specific binding) that inhibits binding to a promoter or enhancer region or multimerization of the TF. The genetically modified cells and constructs may be useful, e.g., in gene therapy approaches. For example, in some embodiments, such a nucleic acid construct is administered to an individual in need thereof. In other embodiments, cells (e.g., autologous) that have been contacted ex vivo with such a construct can be administered to an individual in need thereof. The construct may include a promoter operably linked to a sequence that encodes the agent or mRNA.

The synthetic RNA (e.g., modified mRNA, enhanced nucleic acid) can be formulated with one or more acceptable reagents, which provide a vehicle for delivering such synthetic RNA to target cells. Appropriate reagents are generally selected with regard to a number of factors, which include, among other things, the biological or chemical properties of the synthetic RNA, the intended route of administration, the anticipated biological environment to which such synthetic RNA (e.g., modified mRNA) will be exposed and the specific properties of the intended target cells. In some embodiments, transfer vehicles, such as liposomes, encapsulate the synthetic RNA without compromising biological activity. In some embodiments, the transfer vehicle demonstrates preferential and/or substantial binding to a target cell relative to non-target cells. In a preferred embodiment, the transfer vehicle delivers its contents to the target cell such that the synthetic RNA are delivered to the appropriate subcellular compartment, such as the cytoplasm.

In some embodiments, the transfer vehicle in the compositions of the invention is a liposomal transfer vehicle, e.g. a lipid nanoparticle. In one embodiment, the transfer vehicle may be selected and/or prepared to optimize delivery of the nucleic acid (e.g., enhanced nucleic acid, synthetic RNA (e.g., modified mRNA)) to a target cell. For example, if the target cell is a hepatocyte the properties of the transfer vehicle (e.g., size, charge and/or pH) may be optimized to effectively deliver such transfer vehicle to the target cell, reduce immune clearance and/or promote retention in that target cell. Alternatively, if the target cell is in the central nervous system (e.g., for the treatment of neurodegenerative diseases, the transfer vehicle may specifically target brain or spinal tissue), selection and preparation of the transfer vehicle must consider penetration of, and retention within the blood brain barrier and/or the use of alternate means of directly delivering such transfer vehicle to such target cell. In one embodiment, the compositions of the present invention may be combined with agents that facilitate the transfer of exogenous synthetic RNA (e.g., modified mRNA) (e.g., agents which disrupt or improve the permeability of the blood brain barrier and thereby enhance the transfer of exogenous mRNA to the target cells).

The use of liposomal transfer vehicles to facilitate the delivery of nucleic acids to target cells is contemplated by the present disclosure. Liposomes (e.g., liposomal lipid nanoparticles) are generally useful in a variety of applications in research, industry, and medicine, particularly for their use as transfer vehicles of diagnostic or therapeutic compounds in vivo (Lasic, Trends Biotechnol., 16: 307-321, 1998; Drummond et al., Pharmacol. Rev., 51: 691-743, 1999) and are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.).

In the context of the present disclosure, a liposomal transfer vehicle typically serves to transport the nucleic acid (e.g., modified mRNA) to the target cell. For the purposes of the present invention, the liposomal transfer vehicles are prepared to contain the desired nucleic acids. The process of incorporation of a desired entity (e.g., a nucleic acid) into a liposome is often referred to as "loading" (Lasic, et al., FEBS Lett., 312: 255-258, 1992). The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a nucleic acid into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in a preferred embodiment of the present invention, the selected transfer vehicle is capable of enhancing the stability of the nucleic acid contained therein. The liposome can allow the encapsulated nucleic acid (e.g., modified mRNA) to reach the target cell and/or may preferentially allow the encapsulated nucleic acid (e.g., modified mRNA) to reach the target cell, or alternatively limit the delivery of such nucleic acid (e.g., modified mRNA) to other sites or cells where the presence of the administered nucleic acid (e.g., modified mRNA) may be useless or undesirable. Furthermore, incorporating the synthetic RNA (e.g., modified mRNA) into a transfer vehicle, such as for example, a cationic liposome, also facilitates the delivery of such synthetic RNA (e.g., modified mRNA) into a target cell.

Liposomal transfer vehicles can be prepared to encapsulate one or more desired synthetic RNA (e.g., modified mRNA) such that the compositions demonstrate a high transfection efficiency and enhanced stability. While liposomes can facilitate introduction of nucleic acids into target cells, the addition of polycations (e.g., poly L-lysine and protamine), as a copolymer can facilitate, and in some instances markedly enhance the transfection efficiency of several types of cationic liposomes by 2-28 fold in a number of cell lines both in vitro and in vivo. (See N. J. Caplen, et al., Gene Ther. 1995; 2: 603; S. Li, et al., Gene Ther. 1997; 4, 891.)

In some embodiments, the transfer vehicle is formulated as a lipid nanoparticle. As used herein, the phrase "lipid nanoparticle" refers to a transfer vehicle comprising one or more lipids (e.g., cationic lipids, non-cationic lipids, and PEG-modified lipids). Preferably, the lipid nanoparticles are formulated to deliver one or more synthetic RNAs (e.g., modified mRNAs) to one or more target cells.

Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides). Also contemplated is the use of polymers as transfer vehicles, whether alone or in combination with other transfer vehicles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, dendrimers and polyethylenimine. In one embodiment, the transfer vehicle is selected based upon its ability to facilitate the transfection of a nucleic acid (e.g., modified mRNA) to a target cell.

The present disclosure contemplates the use of lipid nanoparticles as transfer vehicles comprising a cationic lipid to encapsulate and/or enhance the delivery of nucleic acid (e.g., modified mRNA) into the target cell, e.g., that will act as a depot for production of a peptide, polypeptide, or protein (e.g., antibody or antibody fragment) as described herein. As used herein, the phrase "cationic lipid" refers to any of a number of lipid species that carry a net positive charge at a selected pH, such as physiological pH. The contemplated lipid nanoparticles may be prepared by including multi-component lipid mixtures of varying ratios employing one or more cationic lipids, non-cationic lipids and PEG-modified lipids. Several cationic lipids have been described in the literature, many of which are commercially available.

Suitable cationic lipids of use in the compositions and methods herein include those described in international patent publication WO 2010/053572, incorporated herein by reference, e.g., C12-200 described at paragraph [00225] of WO 2010/053572. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g., (15Z,18Z)—N,N-dimethyl-6-(9Z,12Z)-octadeca-9,12-dien-1-yl)tetracosa-15,18-dien-1-amine (HGT5000), (15Z, 18Z)—N,N-dimethyl-6-((9Z,12Z)-octadeca-9,12-dien-1-yl) tetracosa-4,15,18-trien-1-amine (HGT5001), and (15Z, 18Z)—N,N-dimethyl-6-49Z,12Z)-octadeca-9,12-dien-1-yl) tetracosa-5,15,18-trien-1-amine (HGT5002).

In some embodiments, the cationic lipid N-[1-(2,3-dioleyloxy)propyl]-N,N,N-trimethylammonium chloride or "DOTMA" is used. (Felgner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-1-(cis,cis-9', 1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-K-DMA", 2,2-dilinoleyl-4-dimethylaminoethyl[1,3]-dioxolane or "DLin-K-XTC2-DMA", and 2-(2,2-di((9Z, 12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28:172-176 (2010)), or mixtures thereof (Heyes, J., et al., J Controlled Release 107: 276-287 (2005); Morrissey, D V., et al., Nat. Biotechnol. 23(8): 1003-1007 (2005); PCT Publication WO2005/121348A1).

The use of cholesterol-based cationic lipids is also contemplated by the present disclosure. Such cholesterol-based cationic lipids can be used, either alone or in combination with other cationic or non-cationic lipids. Suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE.

The skilled artisan will appreciate that various reagents are commercially available to enhance transfection efficacy. Suitable examples include LIPOFECTIN (DOTMA:DOPE) (Invitrogen, Carlsbad, Calif.), LIPOFECTAMINE (DOSPA: DOPE) (Invitrogen), LIPOFECTAMINE2000. (Invitrogen), FUGENE, TRANSFECTAM (DOGS), and EFFECTENE.

Also contemplated are cationic lipids such as the dialkylamino-based, imidazole-based, and guanidinium-based lipids. For example, certain embodiments are directed to a composition comprising one or more imidazole-based cationic lipids, for example, the imidazole cholesterol ester or "ICE" lipid (3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(1H-imidazol-4-yl)propanoate. In a preferred embodiment, a transfer vehicle for delivery of synthetic RNA (e.g., modified mRNA) may comprise one or more imidazole-based cationic lipids, for example, the imidazole cholesterol ester or "ICE" lipid (3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(1H-imidazol-4-yl)propanoate.

The imidazole-based cationic lipids are also characterized by their reduced toxicity relative to other cationic lipids. The imidazole-based cationic lipids (e.g., ICE) may be used as the sole cationic lipid in the lipid nanoparticle, or alternatively may be combined with traditional cationic lipids, non-cationic lipids, and PEG-modified lipids. The cationic lipid may comprise a molar ratio of about 1% to about 90%, about 2% to about 70%, about 5% to about 50%, about 10% to about 40% of the total lipid present in the transfer vehicle, or preferably about 20% to about 70% of the total lipid present in the transfer vehicle.

In some embodiments, the lipid nanoparticles comprise the HGT4003 cationic lipid 2-((2,3-Bis((9Z,12Z)-octadeca-9,12-dien-1-yloxy)propyl)disulfanyl)-N,N-dimethyl-ethanamine, as further described in US Pub. No. 20140288160 the entire teachings of which are incorporated herein by reference in their entirety.

In other embodiments the compositions and methods described herein are directed to lipid nanoparticles comprising one or more cleavable lipids, such as, for example, one or more cationic lipids or compounds that comprise a cleavable disulfide (S—S) functional group (e.g., HGT4001, HGT4002, HGT4003, HGT4004 and HGT4005), as further described in US Pub. No. 20140288160, the entire teachings of which are incorporated herein by reference in their entirety.

The use of polyethylene glycol (PEG)-modified phospholipids and derivatized lipids such as derivatized cerarmides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipids together which comprise the transfer vehicle (e.g., a lipid nanoparticle). Contemplated PEG-modified lipids include, but is not limited to, a polyethylene glycol chain of up to 5 kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613). In some embodiments, exchangeable lipids comprise PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in the liposomal transfer vehicle.

The present disclosure also contemplates the use of non-cationic lipids. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. Such non-cationic lipids may be used alone, but are preferably used in combination with other excipients, for example, cationic lipids. When used in combination with a cationic lipid, the non-cationic lipid may comprise a molar ratio of 5% to about 90%, or preferably about 10% to about 70% of the total lipid present in the transfer vehicle.

In some embodiments, the transfer vehicle (e.g., a lipid nanoparticle) is prepared by combining multiple lipid and/or polymer components. For example, a transfer vehicle may be prepared using C12-200, DOPE, chol, DMG-PEG2K at a molar ratio of 40:30:25:5, or DODAP, DOPE, cholesterol, DMG-PEG2K at a molar ratio of 18:56:20:6, or HGT5000, DOPE, chol, DMG-PEG2K at a molar ratio of 40:20:35:5, or HGT5001, DOPE, chol, DMG-PEG2K at a molar ratio of 40:20:35:5. The selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the synthetic RNA (e.g., modified mRNA) to be delivered. Additional considerations include, for example, the saturation of the alkyl chain, as well as the size, charge, pH, pKa, fusogenicity and toxicity of the selected lipid(s). Thus the molar ratios may be adjusted accordingly. For example, in embodiments, the percentage of cationic lipid in the lipid nanoparticle may be greater than 10%, greater than 20%, greater than 30%, greater than 40%, greater than 50%, greater than 60%, or greater than 70%. The percentage of non-cationic lipid in the lipid nanoparticle may be greater than 5%, greater than 10%, greater than 20%, greater than 30%, or greater than 40%. The percentage of cholesterol in the lipid nanoparticle may be greater than 10%, greater than 20%, greater than 30%, or greater than 40%. The percentage of PEG-modified lipid in the lipid nanoparticle may be greater than 1%, greater than 2%, greater than 5%, greater than 10%, or greater than 20%.

In certain embodiments, the lipid nanoparticles of the present disclosure comprise at least one of the following cationic lipids: C12-200, DLin-KC2-DMA, DODAP, HGT4003, ICE, HGT5000, or HGT5001. In embodiments, the transfer vehicle comprises cholesterol and/or a PEG-modified lipid. In some embodiments, the transfer vehicles comprises DMG-PEG2K. In certain embodiments, the transfer vehicle comprises one of the following lipid formulations: C12-200, DOPE, chol, DMG-PEG2K; DODAP, DOPE, cholesterol, DMG-PEG2K; HGT5000, DOPE, chol, DMG-PEG2K, HGT5001, DOPE, chol, DMG-PEG2K.

The liposomal transfer vehicles for use in the compositions of the disclosure can be prepared by various techniques which are presently known in the art. Multi-lamellar vesicles (MLV) may be prepared conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments, the compositions of the present disclosure comprise a transfer vehicle wherein the synthetic RNA (e.g., modified mRNA) is associated on both the surface of the transfer vehicle and encapsulated within the same transfer vehicle. For example, during preparation of the compositions of the present invention, cationic liposomal transfer vehicles may associate with the synthetic RNA (e.g., modified mRNA) through electrostatic interactions.

In certain embodiments, the compositions of the invention may be loaded with diagnostic radionuclide, fluorescent materials or other materials that are detectable in both in vitro and in vivo applications. For example, suitable diagnostic materials for use in the present invention may include Rhodamine-dioleoylphospha-tidylethanolamine (Rh-PE), Green Fluorescent Protein mRNA (GFP mRNA), *Renilla* Luciferase mRNA and Firefly Luciferase mRNA.

Selection of the appropriate size of a liposomal transfer vehicle may take into consideration the site of the target cell or tissue and to some extent the application for which the liposome is being made. In some embodiments, it may be desirable to limit transfection of the synthetic RNA (e.g., modified mRNA) to certain cells or tissues. For example, to target hepatocytes a liposomal transfer vehicle may be sized such that its dimensions are smaller than the fenestrations of the endothelial layer lining hepatic sinusoids in the liver; accordingly the liposomal transfer vehicle can readily penetrate such endothelial fenestrations to reach the target hepatocytes. Alternatively, a liposomal transfer vehicle may be sized such that the dimensions of the liposome are of a sufficient diameter to limit or expressly avoid distribution into certain cells or tissues. For example, a liposomal transfer vehicle may be sized such that its dimensions are larger than the fenestrations of the endothelial layer lining hepatic sinusoids to thereby limit distribution of the liposomal transfer vehicle to hepatocytes. Generally, the size of the transfer vehicle is within the range of about 25 to 250 nm, preferably less than about 250 nm, 175 nm, 150 nm, 125 nm, 100 nm, 75 nm, 50 nm, 25 nm or 10 nm.

A variety of alternative methods known in the art are available for sizing of a population of liposomal transfer vehicles. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method which relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, Ann. Rev. Biophys. Bioeng., 10:421-450 (1981), incorporated herein by reference. Average liposome diameter may be reduced by sonication of formed liposomes. Intermittent sonication cycles may be alternated with QELS assessment to guide efficient liposome synthesis.

As used herein, the term "target cell" refers to a cell or tissue to which a composition of the invention is to be directed or targeted. For example, where it is desired to deliver a nucleic acid to a hepatocyte, the hepatocyte represents the target cell. In some embodiments, the compositions of the invention transfect the target cells on a discriminatory basis (i.e., do not transfect non-target cells). The compositions of the invention may also be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells. In some embodiments, the target cells are deficient in or have an overabundance of a protein or enzyme of interest. In some embodiments the protein or enzyme of interest is encoded by a target gene, and the composition comprises an agent that modulates the expression of the target gene.

The compositions of the invention may be prepared to preferentially distribute to target cells such as in the heart, lungs, kidneys, liver, and spleen. In some embodiments, the compositions of the invention distribute into the cells of the liver to facilitate the delivery and the subsequent expression of the nucleic acid (e.g., modified mRNA) comprised therein by the cells of the liver (e.g., hepatocytes). The targeted hepatocytes may function as a biological "reservoir" or "depot" capable of producing a functional protein or enzyme. Accordingly, in one embodiment of the invention the liposomal transfer vehicle may target hepatocytes and/or preferentially distribute to the cells of the liver upon delivery. Following transfection of the target hepatocytes, the synthetic RNA (e.g., modified mRNA) loaded in the liposomal vehicle are translated and a functional protein product is produced. In other embodiments, cells other than hepatocytes (e.g., lung, spleen, heart, ocular, or cells of the central nervous system) can serve as a depot location for protein production.

The expressed or translated peptides, polypeptides, or proteins may also be characterized by the in vivo inclusion of native post-translational modifications which may often be absent in recombinantly-prepared proteins or enzymes, thereby further reducing the immunogenicity of the translated peptide, polypeptide, or protein.

The present disclosure also contemplates the discriminatory targeting of target cells and tissues by both passive and active targeting means. The phenomenon of passive targeting exploits the natural distributions patterns of a transfer vehicle in vivo without relying upon the use of additional excipients or means to enhance recognition of the transfer vehicle by target cells. For example, transfer vehicles which are subject to phagocytosis by the cells of the reticulo-endothelial system are likely to accumulate in the liver or spleen, and accordingly may provide means to passively direct the delivery of the compositions to such target cells.

The present disclosure contemplates active targeting, which involves the use of additional excipients, referred to herein as "targeting ligands" that may be bound (either covalently or non-covalently) to the transfer vehicle to encourage localization of such transfer vehicle at certain target cells or target tissues. For example, targeting may be mediated by the inclusion of one or more endogenous targeting ligands (e.g., apolipoprotein E) in or on the transfer vehicle to encourage distribution to the target cells or tissues. Recognition of the targeting ligand by the target tissues actively facilitates tissue distribution and cellular uptake of the transfer vehicle and/or its contents in the target cells and tissues (e.g., the inclusion of an apolipoprotein-E targeting ligand in or on the transfer vehicle encourages recognition and binding of the transfer vehicle to endogenous low density lipoprotein receptors expressed by hepatocytes). As provided herein, the composition can comprise a ligand capable of enhancing affinity of the composition to the target cell. Targeting ligands may be linked to the outer bilayer of the lipid particle during formulation or post-formulation. These methods are well known in the art. In addition, some lipid particle formulations may employ fusogenic polymers such as PEAA, hemagluttinin, other lipopeptides (see U.S. patent application Ser. Nos. 08/835,281, and 60/083,294, which are incorporated herein by reference) and other features useful for in vivo and/or intracellular delivery. In other some embodiments, the compositions of the present invention demonstrate improved transfection efficacies, and/or demonstrate enhanced selectivity towards target cells or tissues of interest. Contemplated therefore are compositions which comprise one or more ligands (e.g., peptides, aptamers, oligonucleotides, a vitamin or other molecules) that are capable of enhancing the affinity of the compositions and their nucleic acid contents for the target cells or tissues. Suitable ligands may optionally be bound or linked to the surface of the transfer vehicle. In some embodiments, the targeting ligand may span the surface of a transfer vehicle or be encapsulated within the transfer vehicle. Suitable ligands and are selected based upon their physical, chemical or biological properties (e.g., selective affinity and/or recognition of target cell surface markers or features.) Cell-specific target sites and their corresponding targeting ligand can vary widely. Suitable targeting ligands are selected such that the unique characteristics of a target cell are exploited, thus allowing the composition to discriminate between target and non-target cells. For example, compositions of the invention may include surface markers (e.g., apolipoprotein-B or apolipoprotein-E) that selectively enhance recognition of, or affinity to hepatocytes (e.g., by receptor-mediated recognition of and binding to such surface markers). Additionally, the use of galactose (e.g., as a galactose derivative such as N-acetylgalactosamine) as a targeting ligand would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting ligands that have been conjugated to moieties present in the transfer vehicle (e.g., a lipid nanoparticle) therefore facilitate recognition and uptake of the compositions of the present invention in target cells and tissues. Examples of suitable targeting ligands include one or more peptides, proteins, aptamers, small molecules, vitamins and oligonucleotides.

In some embodiments, the binding of the transcription factor to the promoter and/or enhancer region of the enhancer-promoter DNA loop (e.g., a transcription factor binding site in a promoter or enhancer region) is modulated by contacting the cell with a composition or compound comprising a small molecule, peptide, polypeptide, nucleic acid, and/or oligonucleotide. In some embodiments, binding of the transcription factor can be decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some embodiments, binding of the transcription factor can be increased by about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 500%, 600% or more. In some embodiments binding of the transcription factor can be increased or decreased by about 1-fold, 2-fold, 3-fold, 4-fold, 5-fold, 6-fold or more.

In some embodiments, a composition modulating binding of the transcription factor to the promoter and/or enhancer region (e.g., a transcription factor binding site in a promoter or enhancer region) of the enhancer-promoter DNA loop comprises a polypeptide or a nucleic acid encoding a polypeptide. In some embodiments, the polypeptide is a transcription factor variant (e.g., YY1 variant) with increased, decreased or no binding activity to the promoter and/or enhancer region (e.g., promoter or enhancer transcription factor binding site) of the enhancer-promoter DNA loop. In some embodiments, the polypeptide (e.g., variant transcription factor, YY1 variant) has a higher affinity (e.g., multimerization affinity) for the transcription factor than with the transcription factor itself. In some embodiments, the polypeptide (e.g., transcription factor variant, YY1 variant) has decreased binding activity to the promoter and/or enhancer region (e.g., promoter or enhancer transcription factor binding site) of the enhancer-promoter DNA loop and increased affinity (e.g., multimerization affinity) to the transcription factor.

In some embodiments, the polypeptide is a transcription factor variant (e.g., YY1 variant) with increased, decreased or no affinity (e.g., multimerization affinity) for a transcription factor, and binding activity to a promoter and/or enhancer region (e.g., promoter or enhancer transcription binding site) of an enhancer-promoter DNA loop. In some embodiments, the polypeptide has decreased or no affinity (e.g., multimerization affinity) for a transcription factor (e.g., YY1) and the same or increased binding activity to a promoter and/or enhancer region (e.g., promoter or enhancer transcription binding site) of an enhancer-promoter DNA loop. In some embodiments, the polypeptide is a transcription factor variant (e.g., YY1 variant) having increased affinity (e.g., multimerization affinity) for the transcription factor (e.g., YY1).

In some embodiments, the polypeptide binds to a promoter or enhancer transcription factor binding site and modulates transcription factor binding. In some embodiments, the polypeptide has the same, increased or reduced binding affinity to a promoter or enhancer transcription factor binding site as the cognate transcription factor.

In some embodiments, a composition modulating binding of the transcription factor to the promoter and/or enhancer region of the enhancer-promoter DNA loop comprises an antibody. In some embodiments, the antibody binds to the transcription factor (e.g., YY1) and modulates (e.g., decreases) binding to a transcription factor binding site (e.g., YY1 binding site) in the promoter and/or enhancer region of the enhancer-promoter DNA loop. In some embodiments, the antibody binds to a transcription factor binding site (e.g., YY1 binding site) in the promoter and/or enhancer region of the enhancer-promoter DNA loop and modulates (e.g., decreases) binding of the cognate transcription factor (e.g., YY1).

The term "antibody" encompasses immunoglobulins and derivatives thereof containing an immunoglobulin domain capable of binding to an antigen. An antibody can originate from any mammalian or avian species, e.g., human, rodent (e.g., mouse, rabbit), goat, chicken, camelid, etc., or can be generated using, e.g., phage display. The antibody may be a member of any immunoglobulin class, e.g., IgG, IgM, IgA, IgD, IgE, or subclasses thereof such as IgG1, IgG2, etc. In various embodiments of the invention "antibody" refers to an antibody fragment such as an Fab', F(ab')2, scFv (single-chain variable) or other fragment that retains an antigen binding site, or a recombinantly produced scFv fragment, including recombinantly produced fragments. An antibody can be monovalent, bivalent or multivalent in various embodiments. In some embodiments an antibody is a single domain antibody, e.g., comprising one variable domain ($V_H$) of a heavy-chain antibody. The antibody may be a chimeric or "humanized" antibody, which can be generated using methods known in the art. An antibody may be polyclonal or monoclonal, though monoclonal antibodies may be preferred. Methods for producing antibodies that specifically bind to virtually any molecule of interest are known in the art. In some aspects the antibody is an intrabody, which may be expressed intracellularly. In some embodiments the composition comprises a single-chain antibody and a protein transduction domain (e.g., as a fusion polypeptide).

In some embodiments, the composition modulating of the transcription factor (e.g., YY1) to the promoter and/or enhancer region of the enhancer-promoter DNA loop comprises an interfering nucleic acid. In some embodiments, the interfering nucleic acid binds to a promoter and/or enhancer region of the genome of the cell and inhibits binding of a transcription factor (e.g., YY1) to the promoter or enhancer. In some embodiments, the interfering nucleic acid binds to a transcription factor binding site (e.g., YY1 binding site) in a promoter and/or enhancer region and inhibits binding of a transcription factor (e.g., YY1) to the transcription factor binding site. In some embodiments, the interfering nucleic acid binds to the transcription factor (e.g., YY1) and inhibits binding of the transcription factor to an enhancer or promoter region of the genome of a cell. In some embodiments, the interfering nucleic acid binds to a transcription factor (e.g., YY1) and inhibits multimerization (e.g., dimerization) of the transcription factor.

An interfering nucleic acid may be produced in any of variety of ways in various embodiments. For example, nucleic acid strands may be chemically synthesized (e.g., using standard nucleic acid synthesis techniques) or may be produced in cells or using an in vitro transcription system.

In some embodiments, the interfering nucleic acid is a naturally occurring RNA sequence, a modified RNA sequence (e.g., a RNA sequence comprising one or more modified bases), a synthetic RNA sequence, or a combination thereof. As used herein a "modified RNA" is an RNA comprising one or more modifications to the RNA (e.g., RNA comprising one or more non-standard and/or non-naturally occurring bases and/or modifications to the backbone and or sugar). Methods of modifying bases of RNA are well known in the art. Examples of such modified bases include those contained in the nucleosides 5-methylcytidine (5mC), pseudouridine (Ψ), 5-methyluridine, 2'0-methyluridine, 2-thiouridine, N-6 methyladenosine, hypoxanthine, dihydrouridine (D), inosine (I), and 7-methylguanosine (m7G). It should be noted that any number of bases, sugars, or internucleoside linkages in a RNA sequence can be modified in various embodiments. It should further be understood that combinations of different modifications may be used.

In some aspects, the nucleic acid is a morpholino. Morpholinos are typically synthetic molecules, of about 25 bases in length. Morpholinos have standard nucleic acid bases, but those bases are bound to morpholine rings instead of deoxyribose rings and are linked through phosphorodiamidate groups instead of phosphates.

In some aspects of the invention, formation of the enhancer-promoter DNA loop is modulated by modulating the multimerization (e.g., dimerization) of a transcription factor (e.g., YY1) in the cell. Any method of modulating multimerization (e.g., dimerization) disclosed herein may be used. In some embodiments multimerization (e.g., dimerization) can be decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some embodiments, multimerization (e.g., dimerization) can be increased by about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 500%, 600% or more. In some embodiments multimerization (e.g., dimerization) can be increased or decreased by about 1-fold, 2-fold, 3-fold, 4-fold, 5-fold, 6-fold or more.

In some embodiments, multimerization (e.g., dimerization) is modulated by contacting the cell with a small molecule, peptide, polypeptide, nucleic acid, and/or oligonucleotide. In some embodiments, the small molecule, peptide, polypeptide, nucleic acid, and/or oligonucleotide binds to the transcription factor (e.g., YY1) and inhibits multimerization (e.g., dimerization). In some embodiments, the transcription factor is a zinc finger protein. In some embodiments, the transcription factor is YY1.

In some aspects of the invention, modulation of the expression of one or more genes comprises modulating the expression of a transcription factor (e.g., YY1) that binds to an enhancer and promoter region of DNA (e.g., a transcription factor binding site in a promoter or enhancer region) and forms an enhancer-promoter DNA loop. In some embodiments, the method comprises contacting a cell with a small molecule or nucleic acid that reduces expression of the transcription factor (e.g., YY1). In some embodiments, the expression of the transcription factor (e.g., YY1) is decreased. The expression of the transcription factor can be decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some embodiments, the expression of the transcription factor (e.g., YY1) is increased. The expression of the transcription factor can be increased by about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 500%, 600% or more. In some embodiments, expression of the transcription factor (e.g., YY1) can be increased or decreased by about 1-fold, 2-fold, 3-fold, 4-fold, 5-fold, 6-fold or more.

In some aspects, the method comprises contacting a cell with a nucleic acid that reduces expression of the transcription factor (e.g., YY1). The nucleic acid is a polymer of ribose nucleotides or deoxyribose nucleotides having more than three nucleotides in length. The nucleic acid may include naturally-occurring nucleotides; synthetic, modified, or pseudo-nucleotides such as phosphorothiolates; as well as nucleotides having a detectable label such as $P^{32}$, biotin, fluorescent dye or digoxigenin. A nucleic acid that can reduce the expression of a transcription factor may be completely complementary to the transcription factor nucleic acid. Alternatively, some variability between the sequences may be permitted.

The nucleic acid of the invention can hybridize to transcription factor (e.g., YY1) nucleic acid under intracellular conditions or under stringent hybridization conditions. The nucleic acids of the invention are sufficiently complementary to transcription factor (e.g., YY1) nucleic acids to inhibit expression of the transcription factor under either or both conditions. Intracellular conditions refer to conditions such as temperature, pH and salt concentrations typically found inside a cell, e.g. a mammalian cell.

Generally, stringent hybridization conditions are selected to be about 5° C. lower than the thermal melting point ($T_m$) for the specific sequence at a defined ionic strength and pH. However, stringent conditions encompass temperatures in the range of about 1° C. to about 20° C. lower than the thermal melting point of the selected sequence, depending upon the desired degree of stringency as otherwise qualified herein. Nucleic acids that comprise, for example, 2, 3, 4, or 5 or more stretches of contiguous nucleotides that are precisely complementary to a transcription factor coding sequence, each separated by a stretch of contiguous nucleotides that are not complementary to adjacent coding sequences, may inhibit the function of a transcription factor nucleic acid. In general, each stretch of contiguous nucleotides is at least 4, 5, 6, 7, or 8 or more nucleotides in length. Non-complementary intervening sequences may be 1, 2, 3, or 4 nucleotides in length. One skilled in the art can easily use the calculated melting point of an nucleic acid hybridized to a sense nucleic acid to estimate the degree of mismatching that will be tolerated for inhibiting expression of a particular target nucleic acid. Nucleic acids of the invention include, for example, a ribozyme or an antisense nucleic acid molecule.

An antisense nucleic acid molecule may be single or double stranded (e.g. a small interfering RNA (siRNA)), and may function in an enzyme-dependent manner or by steric blocking. Antisense molecules that function in an enzyme-dependent manner include forms dependent on RNase H activity to degrade target mRNA. These include single-stranded DNA, RNA and phosphorothioate molecules, as well as the double-stranded RNAi/siRNA system that involves target mRNA recognition through sense-antisense strand pairing followed by degradation of the target mRNA by the RNA-induced silencing complex. Steric blocking antisense, which are RNase-H independent, interferes with gene expression or other mRNA-dependent cellular processes by binding to a target mRNA and interfering with other processes such as translation. Steric blocking antisense includes 2'-0 alkyl (usually in chimeras with RNase-H dependent antisense), peptide nucleic acid (PNA), locked nucleic acid (LNA) and morpholino antisense.

Small interfering RNAs, for example, may be used to specifically reduce the level of mRNA encoding a transcription factor (e.g., YY1) and/or reduce translation of mRNA encoding a transcription factor (e.g., YY1) such that the level of transcription factor (e.g., YY1) is reduced. siRNAs mediate post-transcriptional gene silencing in a sequence-specific manner. See, for example, Carthew et al., "Origins and Mechanisms of miRNAs and siRNAs," Cell, Volume 136, Issue 4, p 642-655, 20 Feb. 2009. Once incorporated into an RNA-induced silencing complex, siRNA mediate cleavage of the homologous endogenous mRNA transcript by guiding the complex to the homologous mRNA transcript, which is then cleaved by the complex. The siRNA may be homologous to any region of the transcription factor (e.g., YY1) mRNA transcript. The region of homology may be 30 nucleotides or less in length, less than 25 nucleotides, about 21 to 23 nucleotides in length or less, e.g., 19 nucleotides in length. SiRNA is typically double stranded and may have nucleotide 3' overhangs. The 3' overhangs may be up to about 5 or 6 nucleotide '3 overhangs, e.g., two nucleotide 3' overhangs, such as, 3' overhanging UU dinucleotides, for example. In some embodiments, the siRNAs may not include any nucleotide 3' overhangs. Methods for designing siRNAs are known to those skilled in the art. See, for example, Elbashir et al. Nature 411: 494-498 (2001); Harborth et al. Antisense Nucleic Acid Drug Dev. 13: 83-106 (2003). In some embodiments a target site is selected that begins with AA, has 3' UU overhangs for both the sense and antisense siRNA strands and has an approximate 50% G/C content. In some embodiments, a target site is selected that is unique to one or more target mRNAs and not in other mRNAs whose degradation or translational inhibition is not desired. siRNAs may be chemically synthesized, created by in vitro transcription, or expressed from an siRNA expression vector or a PCR expression cassette. See, e.g., http://www.thermofisher.com/us/en/home/life-science/rnai.html.

When an siRNA is expressed from an expression vector or a PCR expression cassette, the insert encoding the siRNA may be expressed as an RNA transcript that folds into an siRNA hairpin. Thus, the RNA transcript may include a sense siRNA sequence that is linked to its reverse complementary antisense siRNA sequence by a spacer sequence that forms the loop of the hairpin as well as a string of U's at the 3' end. The loop of the hairpin may be any appropriate length, for example, up to 30 nucleotides in length, e.g., 3 to 23 nucleotides in length, and may be of various nucleotide sequences. SiRNAs also may be produced in vivo by cleavage of double-stranded RNA introduced directly or via a transgene or virus. Amplification by an RNA-dependent RNA polymerase may occur in some organisms. The siRNA may be further modified according to any methods known to those having ordinary skill in the art.

An antisense inhibitory nucleic acid may also be used to specifically reduce transcription factor (e.g., YY1) expression, for example, by inhibiting transcription and/or translation. An antisense inhibitory nucleic acid is complementary to a sense nucleic acid encoding a transcription factor (e.g., YY1). For example, it may be complementary to the coding strand of a double-stranded cDNA molecule or complementary to an mRNA sequence. It may be complementary to an entire coding strand or to only a portion thereof. It may also be complementary to all or part of the noncoding region of a nucleic acid encoding a transcription factor (e.g., YY1). The non-coding region includes the 5' and 3' regions that flank the coding region, for example, the 5' and 3' untranslated sequences. An antisense inhibitory nucleic acid is generally at least six nucleotides in length, but may be up to about 8, 12, 15, 20, 25, 30, 35, 40, 45, or 50 nucleotides long. Longer inhibitory nucleic acids may also be used.

An antisense inhibitory nucleic acid may be prepared using methods known in the art, for example, by expression from an expression vector encoding the antisense inhibitory nucleic acid or from an expression cassette. Alternatively, it may be prepared by chemical synthesis using naturally-occurring nucleotides, modified nucleotides or any combinations thereof. In some embodiments, the inhibitory nucleic acids are made from modified nucleotides or non-phosphodiester bonds, for example, that are designed to increase biological stability of the inhibitory nucleic acid or to increase intracellular stability of the duplex formed between the antisense inhibitory nucleic acid and the sense nucleic acid.

Naturally-occurring nucleotides, nucleosides and nucleobases include the ribose or deoxyribose nucleotides adenosine, guanine, cytosine, thymine, and uracil. Examples of modified nucleotides, nucleosides and nucleobases include those comprising 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladeninje, uracil-5oxyacetic acid, butoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl)uracil, (acp3)w, and 2,6-diaminopurine.

Thus nucleic acids of the invention may include modified nucleotides, as well as natural nucleotides such as combinations of ribose and deoxyribose nucleotides, and a nucleic acid of the invention may be of any length discussed above and that is complementary to the nucleic acid sequences of a transcription factor (e.g., YY1).

In some embodiments, a nucleic acid modulating expression of a transcription factor is a small hairpin RNA (i.e., short hairpin RNA) (shRNA).

shRNA is a sequence of RNA that makes a tight hairpin turn that can be used to silence gene expression by means of RNA interference. The shRNA hairpin structure is cleaved by the cellular machinery into a siRNA, which then binds to and cleaves the target mRNA. shRNA can be introduced into cells via a vector encoding the shRNA, where the shRNA coding region is operably linked to a promoter. The selected promoter permits expression of the shRNA. For example, the promoter can be a U6 promoter, which is useful for continuous expression of the shRNA. The vector can, for example, be passed on to daughter cells, allowing the gene silencing to be inherited. See, McIntyre G, Fanning G, Design and cloning strategies for constructing shRNA expression vectors, BMC BIOTECHNOL. 6:1 (2006); Paddison et al., Short hairpin RNAs (shRNAs) induce sequence-specific silencing in mammalian cells, GENES DEV. 16 (8): 948-58 (2002).

In some embodiments, a nucleic acid modulating expression of a transcription factor (e.g., YY1) is a ribozyme. A ribozyme is an RNA molecule with catalytic activity and is capable of cleaving a single-stranded nucleic acid such as an mRNA that has a homologous region. See, for example, Cech, Science 236: 1532-1539 (1987); Cech, Ann. Rev. Biochem. 59:543-568 (1990); Cech, Curr. Opin. Struct. Biol. 2: 605-609 (1992); Couture and Stinchcomb, Trends Genet. 12: 510-515 (1996).

Methods of designing and constructing a ribozyme that can cleave an RNA molecule in trans in a highly sequence specific manner have been developed and described in the art. See, for example, Haseloff et al., Nature 334:585-591 (1988). A ribozyme may be targeted to a specific RNA by engineering a discrete "hybridization" region into the ribozyme. The hybridization region contains a sequence complementary to the target RNA that enables the ribozyme to specifically hybridize with the target. See, for example, Gerlach et al., EP 321,201. The target sequence may be a segment of about 5, 6, 7, 8, 9, 10, 12, 15, 20, or 50 contiguous nucleotides. Longer complementary sequences may be used to increase the affinity of the hybridization sequence for the target.

In some embodiments, the cell of the compositions and methods described herein is a stem cell. In some embodiments, the cell is an embryonic stem cell. The type of cell is not limited and can be any cell described herein or known in the art.

In some embodiments, modulation of the expression of one or more genes by the compositions and methods described herein comprises modulation of the expression of Oct4, Nanog and/or Sox2. Genes modulated by the methods of the invention are not limited and can comprise any gene expressed in an enhancer-promoter DNA loop.

In some embodiments, the methods and compositions disclosed herein can be used to modulate the expression of genes dependent upon the formation of an enhancer-promoter DNA loop mediated by a transcription factor. In some embodiments, the methods and compositions disclosed herein can be used to modulate the expression of genes dependent upon the formation of one or more specific enhancer-promoter DNA loops mediated by a transcription factor. For example, the methods and compositions disclosed herein can specifically target promoter and/or enhancer regions unique to one or more enhancer-promoter DNA loops, thereby modulating the expression of genes under control of the one or more enhancer-promoter DNA loops but not modulating the expression of genes in other enhancer-promoter DNA loops dependent upon the same transcription factor.

Treating Diseases and Conditions Associated with Aberrant Gene Expression

In some aspects, disclosed herein are methods for treating a disease or condition associated with aberrant gene expression or aberrant gene product activity in a subject in need thereof (e.g., human), comprising administering a composition that modulates formation and/or stability of enhancer-promoter DNA loops, wherein formation and/or stability of the enhancer-promoter DNA loop is transcription factor (e.g., YY1) dependent. Any disease associated with increased or decreased expression or activity of a gene or gene product, wherein expression of the gene is regulated at least in part by formation of an enhancer-promoter DNA loop mediated at least in part by TF multimerization may be treated by the methods disclosed herein. In some embodiments, the diseases are neurodegenerative diseases, neurodevelopmental disorders, autoimmune diseases, metabolic diseases, etc. In some embodiments, the disease is cancer.

In some aspects, formation of the enhancer-promoter DNA loop is modulated by modulating binding of a transcription factor (e.g., YY1) to a promoter and/or enhancer region of the enhancer-promoter DNA loop (e.g., a transcription factor binding site in a promoter or enhancer region). Binding may be modulated by any method or composition disclosed herein. In some embodiments, binding of the transcription factor (e.g., YY1) can be decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some embodiments, binding of the transcription factor (e.g., YY1) can be increased by about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 500%, 600% or more. In some embodiments binding of the transcription factor (e.g., YY1) can be increased or decreased by about 1-fold, 2-fold, 3-fold, 4-fold, 5-fold, 6-fold or more.

In some aspects, binding is modulated by modifying the promoter and/or enhancer region (e.g., a transcription factor binding site in a promoter or enhancer region). Modification of the promoter or enhancer region may be by any method or composition disclosed herein.

In some aspects, the modification comprises modifying the methylation of the promoter and/or enhancer region (e.g., a transcription factor binding site in a promoter or enhancer region). Modulation of methylation may be by any method or composition disclosed herein. In some embodiments methylation can be increased or decreased by about 1-fold, 2-fold, 3-fold, 4-fold, 5-fold, 6-fold or more. In some embodiments, the degree of methylation is modified with a catalytically inactive site specific nuclease and an effector domain having methylase or demethylase activity as described herein or known in the art. In some embodiments, the effector domain has DNA demethylation activity and is Tet1, ACID A, MBD4, Apobec1, Apobec2, Apobec3, Tdg, Gadd45a, Gadd45b, and/or ROS1. In some embodiments, the effector domain has DNA methylation activity and is Dnmt1, Dnmt3a, Dnmt3b, CpG Methyltransferase M.SssI, and/or M.EcoHK31I. In some embodiments, the catalytically inactive site specific nuclease and an effector domain are fused.

In some aspects, the modification comprises modifying the nucleotide sequence of the promoter and/or enhancer region (e.g., a transcription factor binding site in a promoter or enhancer region). The method of modifying the nucleotide sequence of the promoter and/or enhancer region may be by any composition or method disclosed herein.

In some embodiments, the binding of the transcription factor (e.g., YY1) to the promoter and/or enhancer region (e.g., a transcription factor binding site in a promoter or enhancer region) is modulated by administering to the subject a composition comprising a small molecule, peptide, polypeptide, nucleic acid, and/or oligonucleotide. Any composition for modulating binding of the transcription factor disclosed herein may be used. In some embodiments, the composition comprises an interfering nucleic acid.

In some embodiments, formation of the enhancer-promoter DNA loop is modulated by modulating the multimerization (e.g., dimerization) of a transcription factor (e.g., YY1) in the subject. Modulation of the multimerization (e.g., dimerization) of the transcription factor (e.g., YY1) may be by any method or composition disclosed herein. In some embodiments, multimerization (e.g., dimerization) is modulated by administering to the subject a small molecule, peptide, polypeptide, nucleic acid, and/or oligonucleotide. In some embodiments multimerization (e.g., dimerization) can be decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some embodiments, multimerization (e.g., dimerization) can be increased by about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 500%, 600% or more. In some embodiments multimerization (e.g., dimerization) can be increased or decreased by about 1-fold, 2-fold, 3-fold, 4-fold, 5-fold, 6-fold or more.

In some embodiments, the transcription factor is a zinc finger protein. In some embodiments, the transcription factor is YY1. In some embodiments, aberrant gene expression is decreased. In some embodiments, aberrant gene expression is increased.

In some embodiments, the disease or condition associated with aberrant gene expression is cancer. "Cancer" is generally used to refer to a disease characterized by one or more tumors, e.g., one or more malignant or potentially malignant tumors. The term "tumor" as used herein encompasses abnormal growths comprising aberrantly proliferating cells. As known in the art, tumors are typically characterized by excessive cell proliferation that is not appropriately regulated (e.g., that does not respond normally to physiological influences and signals that would ordinarily constrain proliferation) and may exhibit one or more of the following properties: dysplasia (e.g., lack of normal cell differentiation, resulting in an increased number or proportion of immature cells); anaplasia (e.g., greater loss of differentiation, more loss of structural organization, cellular pleomorphism, abnormalities such as large, hyperchromatic nuclei, high nuclear to cytoplasmic ratio, atypical mitoses, etc.); invasion of adjacent tissues (e.g., breaching a basement membrane); and/or metastasis. Malignant tumors have a tendency for sustained growth and an ability to spread, e.g., to invade locally and/or metastasize regionally and/or to distant locations, whereas benign tumors often remain localized at the site of origin and are often self-limiting in terms of growth. The term "tumor" includes malignant solid tumors, e.g., carcinomas (cancers arising from epithelial cells), sarcomas (cancers arising from cells of mesenchymal origin), and malignant growths in which there may be no detectable solid tumor mass (e.g., certain hematologic malignancies). Cancer includes, but is not limited to: breast cancer; biliary tract cancer; bladder cancer; brain cancer (e.g., glioblastomas, medulloblastomas); cervical cancer; choriocarcinoma; colon cancer; endometrial cancer; esophageal cancer; gastric cancer; hematological neoplasms including acute lymphocytic leukemia and acute myelogenous leukemia; T-cell acute lymphoblastic leukemia/lymphoma; hairy cell leukemia; chronic lymphocytic leukemia, chronic myelogenous leukemia, multiple myeloma; adult T-cell leukemia/lymphoma; intraepithelial neoplasms including Bowen's disease and Paget's disease; liver cancer; lung cancer; lymphomas including Hodgkin's disease and lymphocytic lymphomas; neuroblastoma; melanoma; oral cancer including squamous cell carcinoma; ovarian cancer including ovarian cancer arising from epithelial cells, stromal cells, germ cells and mesenchymal cells; neuroblastoma, pancreatic cancer; prostate cancer; rectal cancer; sarcomas including angiosarcoma, gastrointestinal stromal tumors, leiomyosarcoma, rhabdomyosarcoma, liposarcoma, fibrosarcoma, and osteosarcoma; renal cancer including renal cell carcinoma and Wilms tumor; skin cancer including basal cell carcinoma and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullary carcinoma. It will be appreciated that a variety of different tumor types can arise in certain organs, which may differ with regard to, e.g., clinical and/or pathological features and/or molecular markers. Tumors arising in a variety of different organs are discussed, e.g., the WHO Classification of Tumours series, $4^{th}$ ed, or $3^{rd}$ ed (Pathology and Genetics of Tumours series), by the International Agency for Research on Cancer (IARC), WHO Press, Geneva, Switzerland, all volumes of which are incorporated herein by reference. In some embodiments, the cancer is lung cancer, breast cancer, cervical cancer, colon cancer, gastric cancer, kidney cancer, leukemia, liver cancer, lymphoma, (e.g., a Non-Hodgkin lymphoma, e.g., diffuse large B-cell lymphoma, Burkitts lymphoma) ovarian cancer, pancreatic cancer, prostate cancer, rectal cancer, sarcoma, skin cancer, testicular cancer, or uterine cancer. The type of cancer is not limited. In some embodiments, the cancer exhibits aberrant gene expression. In some embodiments, the cancer exhibits aberrant gene product activity. In some embodiments, the cancer expresses a gene product at a normal level but harbor a mutation that alters its activity. In the case of an oncogene that has an aberrantly increased activity, the methods of the invention can be used to reduce expression of the oncogene. In the case of a tumor suppressor gene that has aberrantly reduced activity (e.g., due to a mutation), the methods of the invention can be used to increase expression of the tumor suppressor gene.

A cancer may be associated with increased expression of an oncogene and/or decreased expression of a tumor suppression gene. In some embodiments a method of the invention comprises decreasing expression of an oncogene that is overexpressed in the cancer by reducing formation and/or maintenance of a loop between an enhancer and the promoter of the oncogene. In some embodiments a method of the invention comprises increasing expression of a tumor suppressor gene by increasing formation and/or maintenance of a DNA loop between an enhancer and the promoter of the tumor suppressor gene. Oncogenes and tumor suppressor genes are known in the art and listed in publically available databases.

In some embodiments, the methods and compositions of the invention are used in combination with other compositions or methods. In some embodiments, the methods disclosed herein are used to treat disease (e.g., cancer) in combination with other agents (e.g., anti-cancer agents) or therapies (e.g., radiation).

In some embodiments a method of the invention may comprise analyzing a sample obtained from a tumor, identifying one or more genes that is aberrantly expressed or encodes an a gene product with aberrant activity in the tumor, and modulating expression of the gene using a composition or method described herein Administration of the compositions described herein may be by any route (e.g., oral, intravenous, intraperitoneal, gavage, topical, transdermal, intramuscular, enteral, subcutaneous), may be systemic or local, may include any dose (e.g., from about 0.01 mg/kg to about 500 mg/kg), may involve a single dose or multiple doses. In some embodiments administration may be performed by direct administration to a tissue or organ (e.g., skin, heart, liver, lung, kidney, brain, eye, muscle, bone, nerve) or tumor. The nucleic acid(s) or protein(s) may be physically associated with, e.g., encapsulated, e.g., in lipid-containing particles, e.g., solid lipid nanoparticles, liposomes, polymeric particles (e.g., PLGA particles). In some embodiments one or more nucleic acids may be administered using a vector (e.g., a viral vector such as an adenoviral vector, lentiviral vector, or adeno-associated virus vector). In some embodiments one or more nucleic acids, proteins, and/or vectors may be combined with a pharmaceutically acceptable carrier to produce a pharmaceutical composition, which may be administered to a subject.

In some embodiments a nucleic acid, polypeptide, antibody or particle may be targeted to cells of a particular type, e.g., cancer cells of a particular type or expressing a particular cell surface marker. For example, a nucleic acid, protein, or a particle comprising a nucleic acid or vector may comprise or be conjugated to a targeting moiety that binds to a marker expressed at the surface of a target cell (e.g., binds to a tumor antigen or a receptor expressed by the target cell). A targeting moiety may comprise, e.g., an antibody or antigen-binding portion thereof, an engineered protein capable of specific binding, a nucleic acid aptamer, a ligand, etc.

In some embodiments, nucleic acids encoding one or more components (e.g., site specific nuclease, catalytically inactive site specific nuclease, effector domain, catalytically inactive site specific nuclease-effector domain fusion protein, one or more guide sequences, one or more nucleic acids) are delivered by one or more viral vectors e.g., a retroviral vector such as a lentiviral vector or gamma retroviral vector, or an adenoviral or AAV vector.

The compositions disclosed herein used to modulate TF multimerization and/or TF binding to an enhancer or promoter may be targeted to a particular cell type, tissue, or organ of interest. In some embodiments the agent comprises a targeting moiety or is delivered using a delivery vehicle that comprises a targeting moiety. A targeting moiety may, for example, comprise an antibody or ligand that binds to a protein (e.g., a receptor) present at the surface of a target cell of interest. In some embodiments the targeting moiety is present at the surface of a cancer cell.

Compositions and compounds described herein may be administered in a pharmaceutical composition. In addition to the active agent, the pharmaceutical compositions typically comprise a pharmaceutically-acceptable carrier. The term "pharmaceutically-acceptable carrier", as used herein, means one or more compatible solid or liquid vehicles, fillers, diluents, or encapsulating substances which are suitable for administration to a human or non-human animal. In preferred embodiments, a pharmaceutically-acceptable carrier is a non-toxic material that does not interfere with the effectiveness of the biological activity of the active ingredients. The term "compatible", as used herein, means that the components of the pharmaceutical compositions are capable of being comingled with an agent, and with each other, in a manner such that there is no interaction which would substantially reduce the pharmaceutical efficacy of the pharmaceutical composition under ordinary use situations. Pharmaceutically-acceptable carriers should be of sufficiently high purity and sufficiently low toxicity to render them suitable for administration to the human or non-human animal being treated.

Some examples of substances which can serve as pharmaceutically-acceptable carriers are pyrogen-free water; isotonic saline; phosphate buffer solutions; sugars such as lactose, glucose, and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobrama; polyols such as propylene glycol, glycerin, sorbitol, mannitol, and polyethylene glycol; sugar; alginic acid; cocoa butter (suppository base); emulsifiers, such as the Tweens; as well as other non-toxic compatible substances used in pharmaceutical formulation. Wetting agents and lubricants such as sodium lauryl sulfate, as well as coloring agents, flavoring agents, excipients, tableting agents, stabilizers, antioxidants, and preservatives, can also be present. It will be appreciated that a pharmaceutical composition can contain multiple different pharmaceutically acceptable carriers.

A pharmaceutically-acceptable carrier employed in conjunction with the compounds described herein is used at a concentration or amount sufficient to provide a practical size to dosage relationship. The pharmaceutically-acceptable carriers, in total, may, for example, comprise from about 60% to about 99.99999% by weight of the pharmaceutical compositions, e.g., from about 80% to about 99.99%, e.g., from about 90% to about 99.95%, from about 95% to about 99.9%, or from about 98% to about 99%.

Pharmaceutically-acceptable carriers suitable for the preparation of unit dosage forms for oral administration and topical application are well-known in the art. Their selection will depend on secondary considerations like taste, cost, and/or shelf stability, which are not critical for the purposes of the subject invention, and can be made without difficulty by a person skilled in the art.

Pharmaceutically acceptable compositions can include diluents, fillers, salts, buffers, stabilizers, solubilizers and other materials which are well-known in the art. The choice of pharmaceutically-acceptable carrier to be used in conjunction with the compounds of the present invention is basically determined by the way the compound is to be administered. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof in certain embodiments. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. It will also be understood that a compound can be provided as a pharmaceutically acceptable pro-drug, or an active metabolite can be used. Furthermore it will be appreciated that agents may be modified, e.g., with targeting moieties, moieties that increase their uptake, biological half-life (e.g., pegylation), etc.

The agents may be administered in pharmaceutically acceptable solutions, which may routinely contain pharmaceutically acceptable concentrations of salt, buffering agents, preservatives, compatible carriers, adjuvants, and optionally other therapeutic ingredients.

The agents may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

In some embodiments, agents may be administered directly to a tissue, e.g., a tissue in which the cancer cells are found or one in which a cancer is likely to arise. Direct tissue administration may be achieved by direct injection. The agents may be administered once, or alternatively they may be administered in a plurality of administrations. If administered multiple times, the peptides may be administered via different routes. For example, the first (or the first few) administrations may be made directly into the affected tissue while later administrations may be systemic.

For oral administration, compositions can be formulated readily by combining the active agent(s) with pharmaceutically acceptable carriers well known in the art. Such carriers enable the agents to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration. For buccal administration, the compositions may take the form of tablets or lozenges formulated in conventional manner.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated in some embodiments to achieve appropriate systemic levels of compounds.

In some embodiments a method comprises decreasing expression of an oncogene that is overexpressed or has aberrantly increased activity in the cancer by reducing formation and/or stability of a loop between an enhancer and the promoter of the oncogene. In some embodiments a method comprises increasing expression of a tumor suppressor gene by increasing formation and/or maintenance of a DNA loop between an enhancer and the promoter of the tumor suppressor gene. In some embodiments a method may comprise analyzing a sample obtained from a tumor, identifying one or more genes that is aberrantly expressed or encodes a gene product with aberrant activity in the tumor, and modulating expression of the gene using a composition of method described herein (e.g., reducing expression of an oncogene that is aberrantly overexpressed or has aberrantly increased activity relative to expression or activity of the normal counterpart in normal cells).

In some embodiments, compositions and methods herein that comprise reducing enhancer-promoter DNA looping may be used to treat any disease associated with increased expression of a gene or increased activity of a gene product. In some embodiments, compositions and methods herein that comprise increasing enhancer-promoter DNA looping may be used to treat any disease associated with decreased expression of a gene or decreased activity of a gene product relative to normal levels. Such diseases include, e.g., neurodegenerative diseases, neurodevelopmental disorders, autoimmune diseases, metabolic diseases, etc. Any disease associated with increased or decreased expression or activity of a gene or gene product, wherein expression of the gene is regulated at least in part by formation of an enhancer-promoter DNA loop mediated at least in part by TF multimerization could be treated.

Method of Screening

Some aspects of the invention are directed to methods of screening for a compound that modulates the expression of one or more genes in a cell, comprising contacting the cell with a test agent (e.g., a small molecule, nucleic acid, antibody or polypeptide), and measuring enhancer-promoter DNA loops in the cell, wherein the test agent is identified as a gene expression modulator if the level of enhancer-promoter DNA loop in the cell contacted with the test agent is different than the level enhancer-promoter DNA loop formation in a control cell not contacted with the test agent. In some embodiments, the enhancer-promoter DNA loop formation is transcription factor dependent. In some embodiments, the transcription factor is a zinc finger protein. In some embodiments, the transcription factor is YY1. In some embodiments, the transcription factor is capable of homomultimerization (e.g., homodimerization). In some embodiments the method comprises measuring DNA looping between an enhancer and a promoter of a particular gene of interest in a cell, wherein the test agent is identified as a modulator of expression of the particular gene of interest if the level of DNA looping between an enhancer and the promoter of the gene in the cell contacted with the test agent is different than the level of DNA looping between an enhancer and the promoter of the gene in a control cell not contacted with the test agent. In some embodiments any of the methods disclose herein further comprise measuring expression of the gene(s) in cells contacted with the test agent. In some embodiments the method further comprises comparing expression of the gene(s) by cells contacted with the test agent with expression of the gene by cells not contacted with the test agent.

Methods of measuring enhancer-promoter DNA loop formation in a cell are known in the art. See Hepelev, et al., (2012) "Characterization of genome-wide enhancer-promoter interactions reveals co-expression of interacting genes and modes of higher order chromatin organization," Cell Res. 22, 490-503, incorporated by reference in its entirety Some aspects of the invention are directed to methods of screening for modulators of DNA loop formation and/or stability (e.g., enhancer-promoter DNA loop formation and/or stability) comprising contacting a linear DNA comprising 2 or more TF binding sites with a cognate transcription factor capable of multimerization and a test agent and measuring the degree of circularization of the DNA. In some embodiments, the test agent is contacted with the linear DNA at the same time as the TF is contacted. In some embodiments, the test agent is contacted with the linear DNA after the TF is contacted. In some embodiments, the test agent is contacted with the linear DNA before the TF is contacted. The activity of the test agent to modulate DNA loop formation and/or stability can be assessed by comparison with a control comprising the DNA and transcription factor but not the test agent.

Some aspects of the invention are directed to methods of identifying one or more genes with expression dependent on an enhancer in a cell, comprising identifying one or more enhancer-promoter DNA loops comprising the enhancer in the cell, and identifying the one or more genes expressed in the enhancer-promoter DNA loop, wherein the one or more genes expressed in the enhancer-promoter DNA loop are identified as genes with expression dependent on the enhancer. In some embodiments, the enhancer-promoter DNA loop formation is transcription factor dependent. In some embodiments, the transcription factor is a zinc finger protein. In some embodiments, the transcription factor is YY1. In some embodiments, the transcription factor is capable of homomultimerization (e.g., homodimerization). In some embodiments, the step of identifying one or more enhancer-promoter DNA loops comprising the enhancer comprises performing a ChIP-MS assay.

It has been found that transcription factors can bind to different enhancers and multiple transcription factors can bind to the same enhancer. By the above method, genes with expression controlled by a particular enhancer can be identified. In the case of enhancers associated with a disease or condition, the above method can be used to identify expressed genes that may be targets for further study or for therapeutics.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

Specific examples of these methods are set forth below in the Examples.

EXAMPLES

Chromosome structure is thought to play important roles in gene control, but we have limited understanding of the proteins that contribute to structuring enhancer-promoter interactions. We report here that Yin Yang 1 (YY1) contributes to enhancer-promoter interactions in a manner analogous to DNA looping mediated by CTCF. YY1 and CTCF share many features: both are essential, ubiquitously expressed, zinc-coordinating proteins that bind hypo-methylated DNA sequences, form homodimers and thus facilitate loop formation. The two proteins differ in that YY1 preferentially occupies interacting enhancers and promoters, whereas CTCF preferentially occupies sites distal from these regulatory elements that tend to form larger loops and participate in insulation. Deletion of YY1 binding sites or depletion of YY1 can disrupt enhancer-promoter contacts and normal gene expression. Thus, YY1-mediated structuring of enhancer-promoter loops is analogous to CTCF-mediated structuring of TADs, CTCF contact domains, and insulated neighborhoods. This model of YY1-mediated structuring of enhancer-promoter loops accounts for diverse functions reported previously for YY1, including contributions to both gene activation and repression, and to gene dysregulation in cancer. Thus we propose that YY1 is a structural regulator of enhancer-promoter loops and that YY1 structured enhancer-promoter loops may be a general mechanism of mammalian gene control.

Analysis of Enhancer Promoter DNA Looping Interactions

Figure 1B:
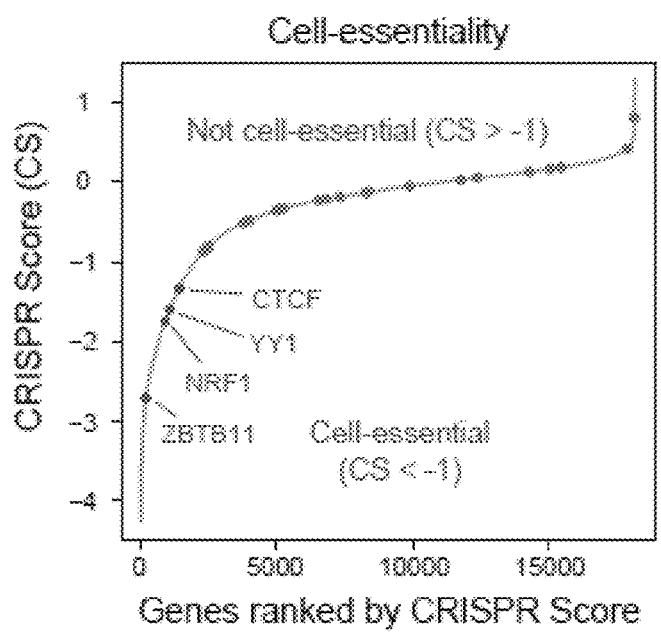
Figures 1C, 1D:
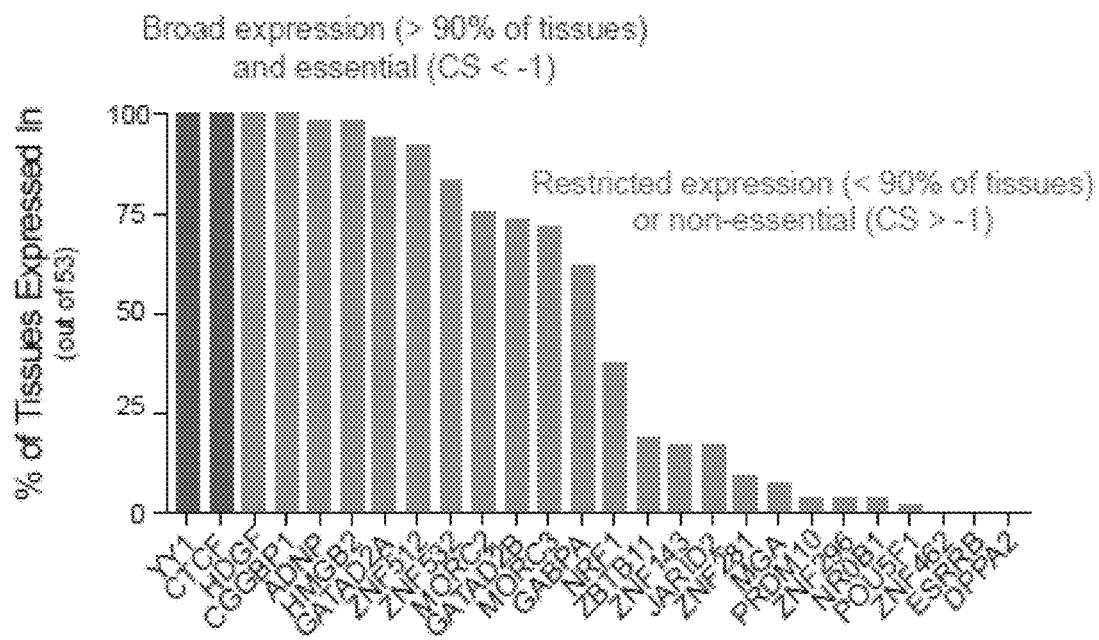

We sought to identify a protein factor that might contribute to enhancer-promoter interactions in a manner analogous to that of CTCF at insulators. Such a protein would be expected to bind active enhancers and promoters, be essential for cell viability, show ubiquitous expression, and be capable of dimerization. To identify proteins that bind active enhancers and promoters, we sought candidates from chromatin immunoprecipitation with mass spectrometry (ChIP-MS), using antibodies directed towards histones with modifications characteristic of enhancer and promoter chromatin (H3K27ac and H3K4me3, respectively) (Creyghton et al., 2010), conducted previously in murine embryonic stem cells (mES cells) (Ji et al., 2015). Of 26 transcription factors that occupy both enhancers and promoters (FIG. 1A), four (CTCF, YY1, NRF1 and ZBTB11) are essential based on a CRISPR cell-essentiality screen (FIG. 1B) (Wang et al., 2015) and two (CTCF, YY1) are expressed in >90% of tissues examined (FIG. 1C). YY1 and CTCF share additional features: like CTCF, YY1 is a zinc-finger transcription factor (Klenova et al., 1993; Shi et al., 1991), essential for embryonic and adult cell viability (Donohoe et al., 1999; Heath et al., 2008) and capable of forming homodimers (Lopez-Perrote et al., 2014; Saldaña-Meyer et al., 2014) (Table S1). YY1, however, tends to occupy active enhancers and promoters, as well as some insulators, whereas CTCF preferentially occupies insulator elements (FIG. 1D, FIG. 18A-C).

Figure 1E:
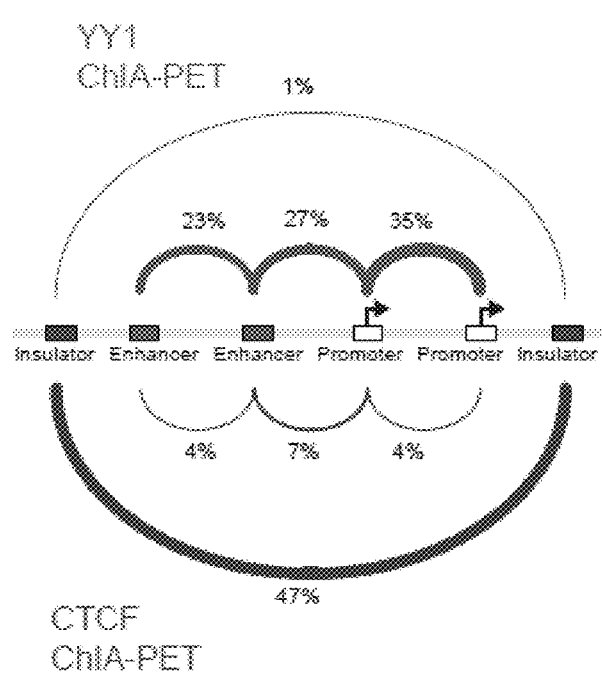
Figure 1F:
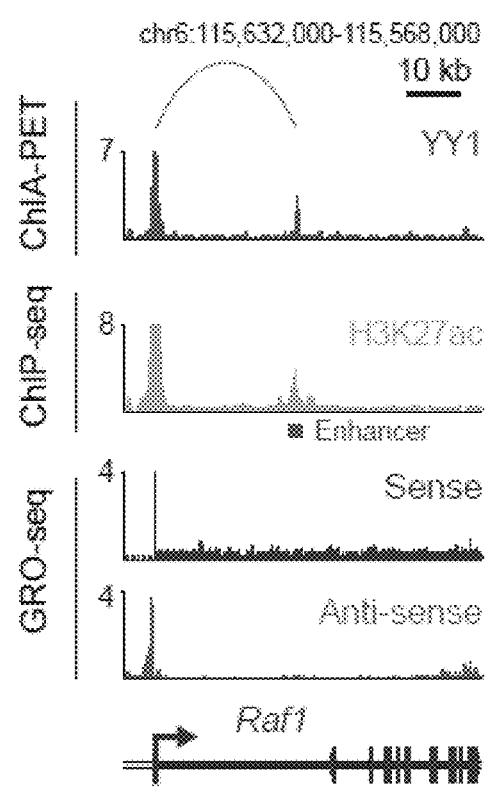
Figure 11A:
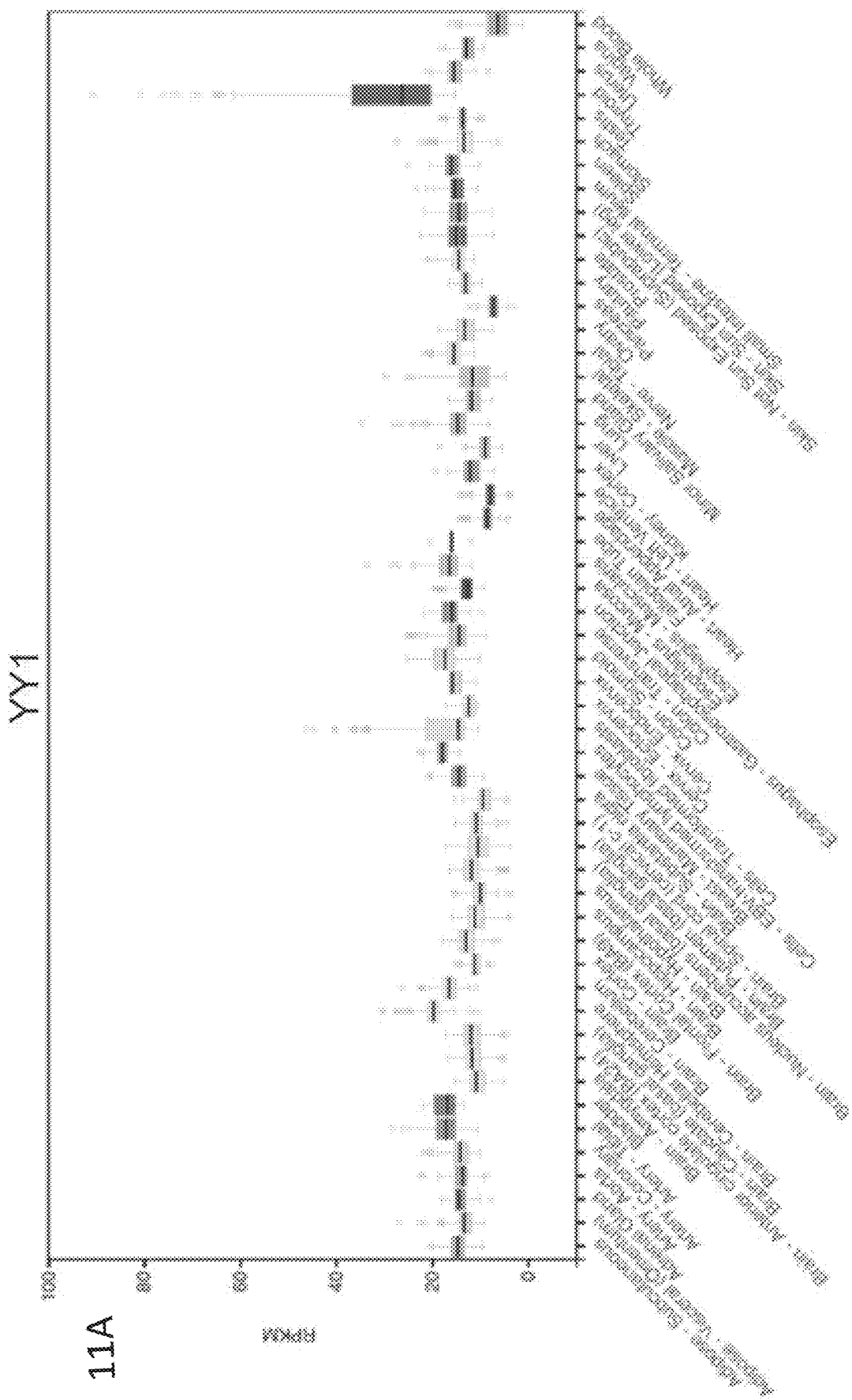
FIG. 11A-11C—YY1 and CTCF are ubiquitously expressed and essential.
Figures 18A, 18B, 18C:
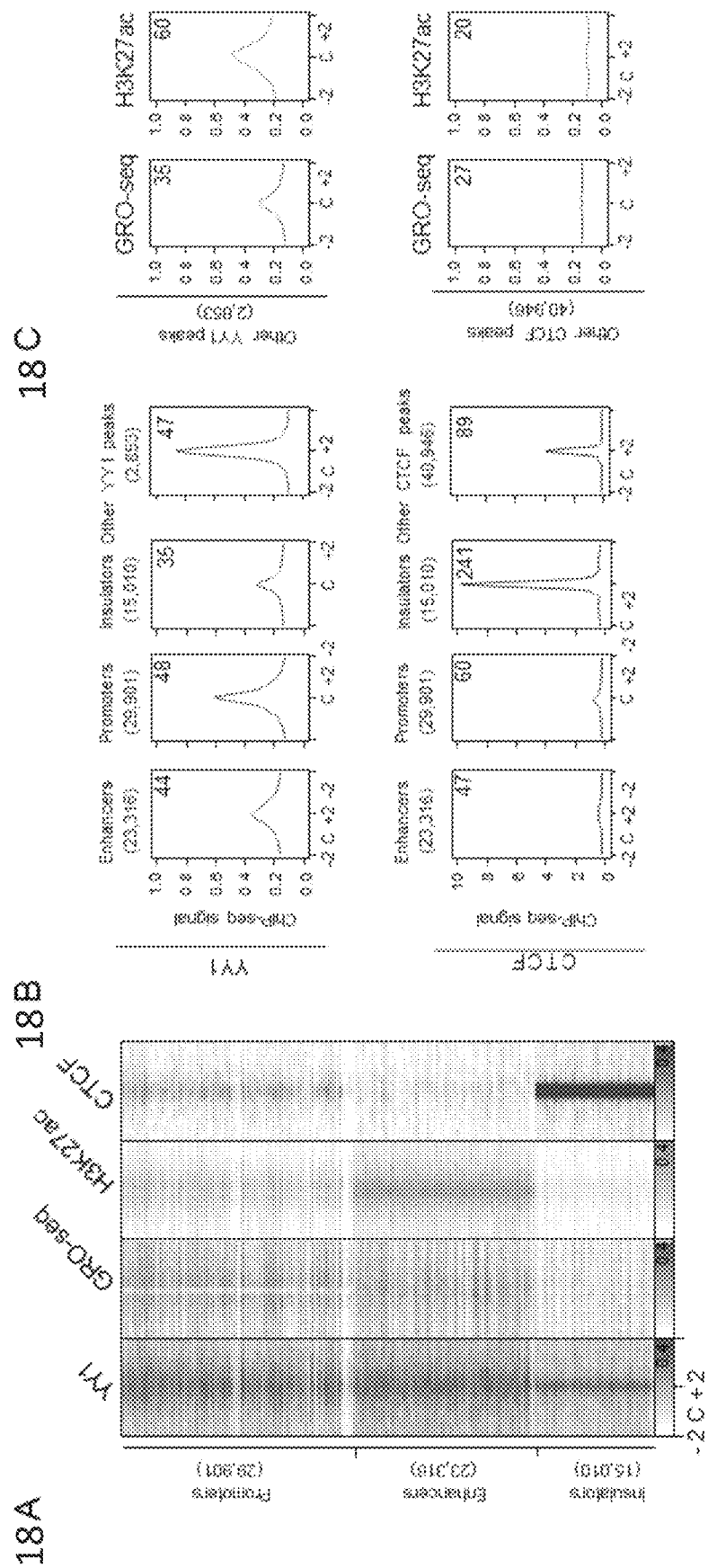
FIG. 18A-18J. YY1-associated interactions connect enhancers and promoters, related to FIG. 1.
Figures 18D, 18E:
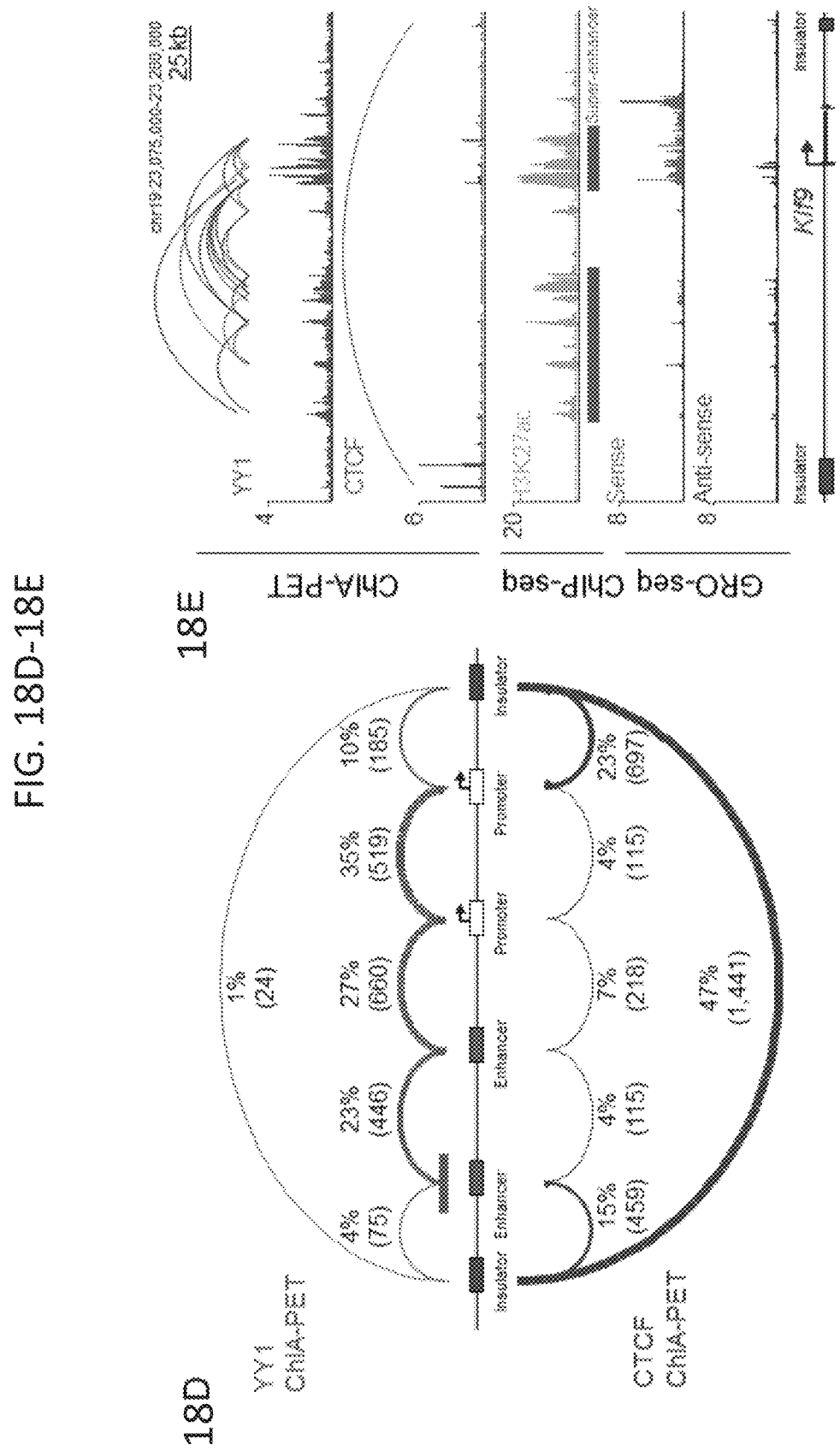

If YY1 contributes to enhancer-promoter interactions, then chromatin interaction analysis by paired-end tag sequencing (ChIA-PET) (Fullwood et al., 2009) for YY1 should show that YY1 is preferentially associated with these interactions. CTCF ChIA-PET, in contrast, should show that CTCF is preferentially associated with insulator DNA interactions. We generated ChIA-PET data for YY1 and CTCF in mES cells and compared these two datasets. The results showed that the majority of YY1-associated interactions connect active regulatory elements (enhancer-enhancer, enhancer-promoter, and promoter-promoter, which we will henceforth call enhancer-promoter interactions), whereas the majority of CTCF-associated interactions connect insulator elements (FIG. 1E, FIG. 18D). Some YY1-YY1 interactions involved simple enhancer-promoter contacts, as seen in the Raf1 locus (FIG. 1F) and others involved more complex contacts among super-enhancer constituents and their target promoters, as seen in the Klf9 locus (FIG. 11E). Super-enhancers were generally occupied by YY1 at relatively high densities and exhibited relatively high YY1-YY1 interaction frequencies (FIG. 18E-H). For both YY1 and CTCF, there was also evidence of enhancer-insulator and promoter-insulator interactions, but these were more pronounced for CTCF (FIG. 18D).

Figure 1G:
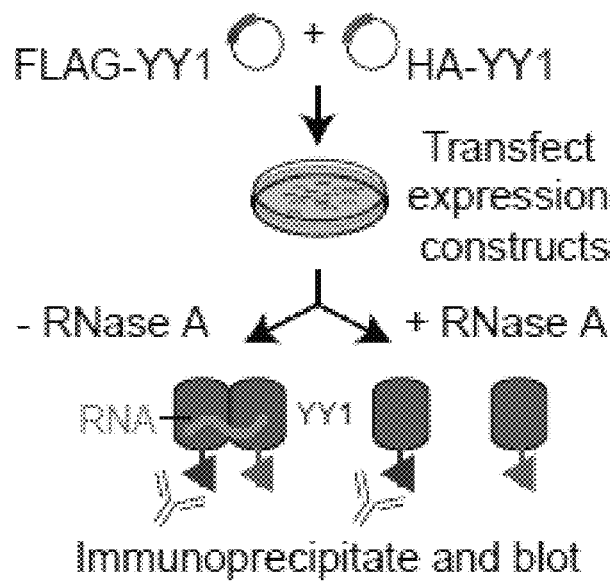
Figure 1H:
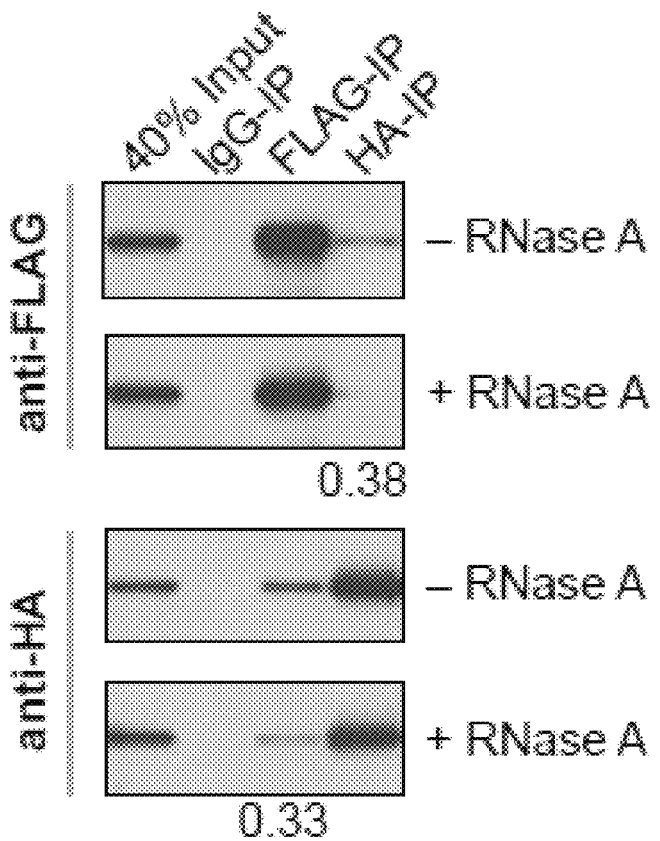
Figure 2A:
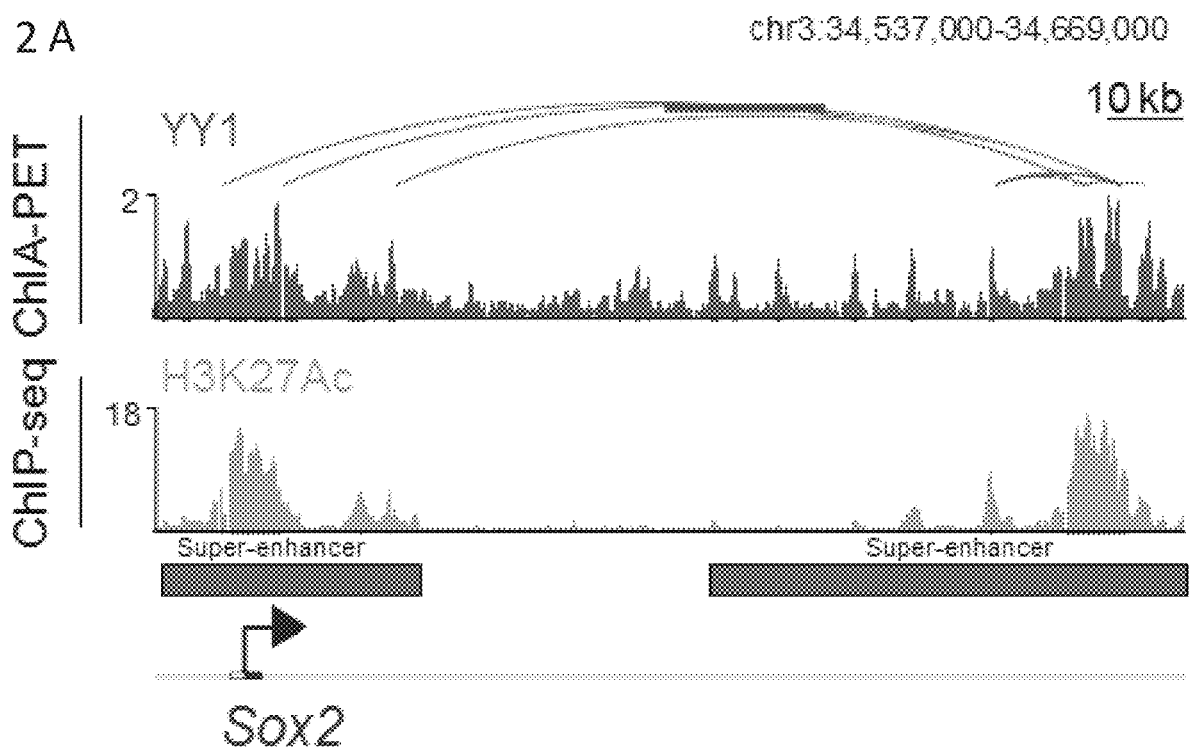
FIG. 2A-2D—Depletion of YY1 causes loss of enhancer-promoter interactions.
Figure 2B:
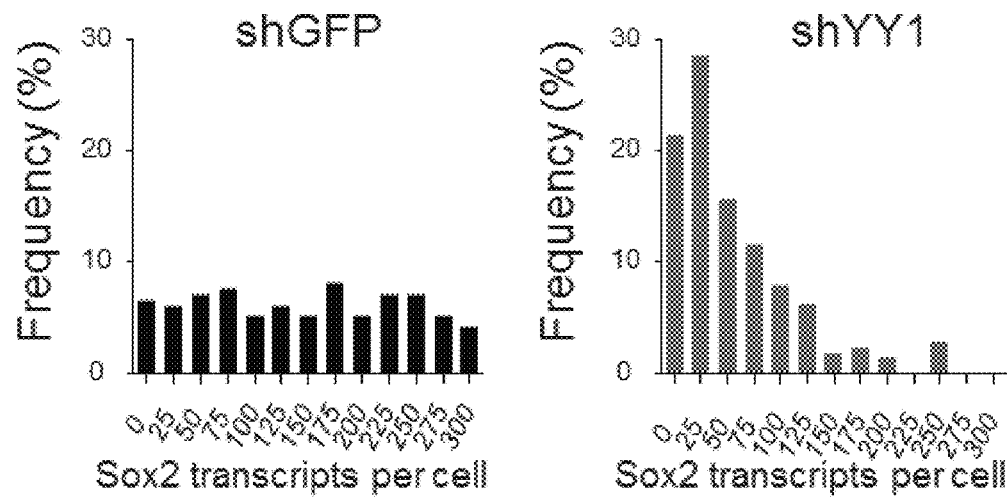
Figure 2C:
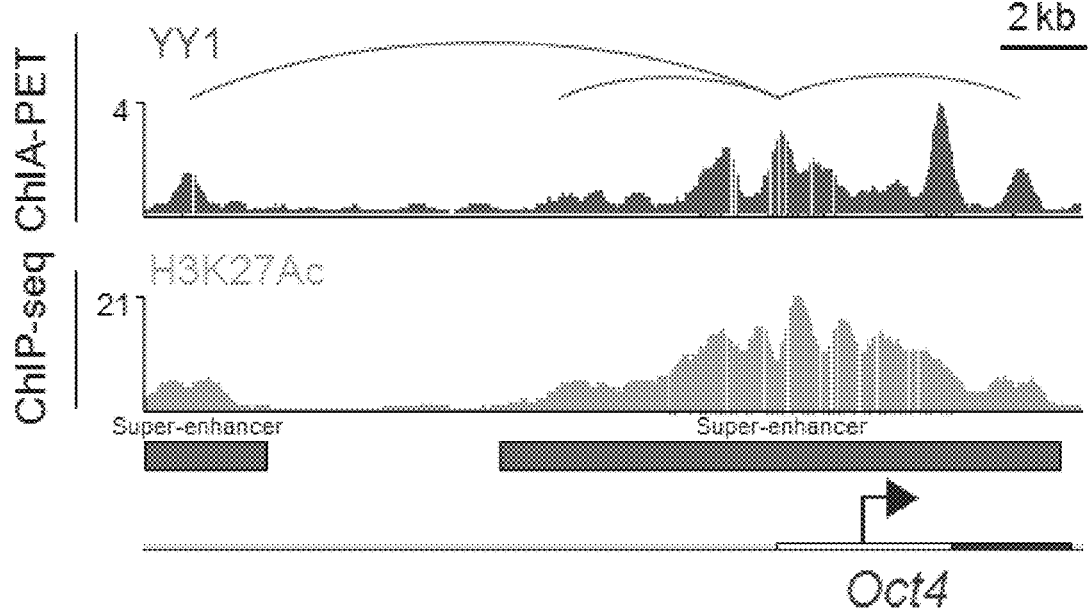
Figure 2D:
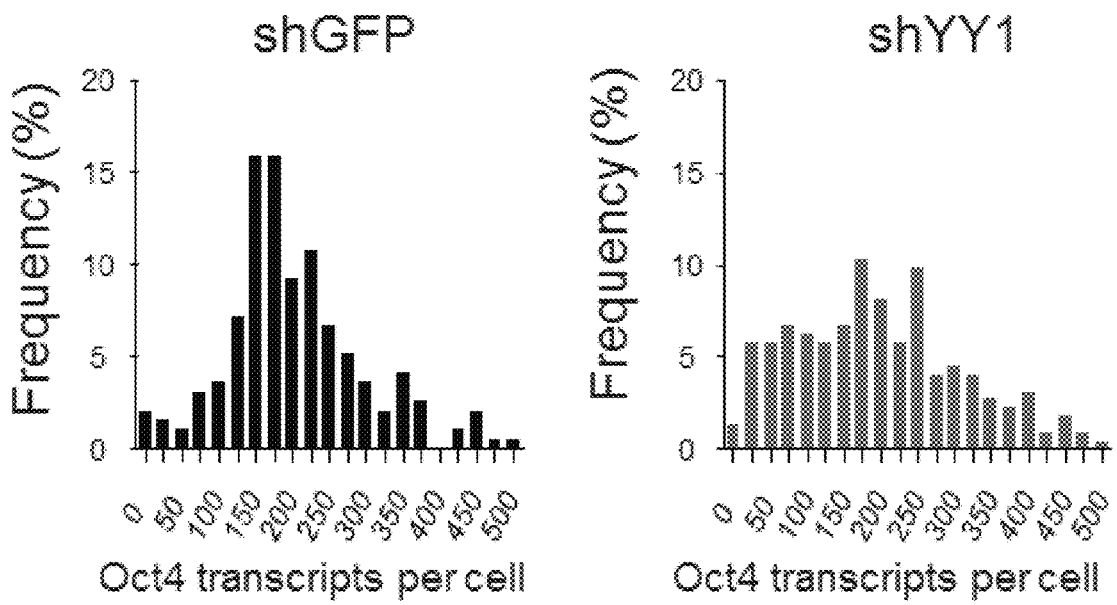
Figures 18F, 18G, 18H, 18I, 18J:
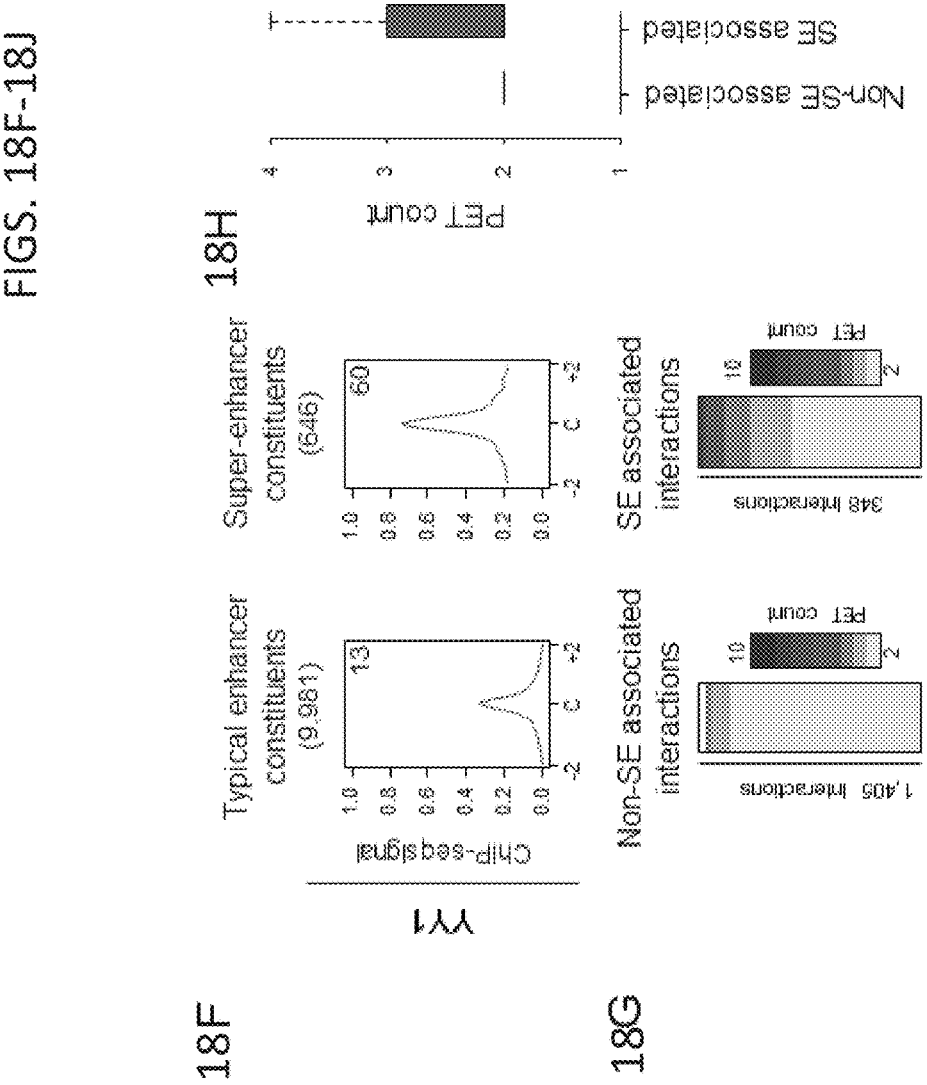

Previous studies have reported that YY1 can form dimers (Lopez-Perrote et al., 2014). To confirm that YY1 dimerization occurs, FLAG-tagged and HA-tagged versions of YY1 protein were expressed in cells, nuclei were isolated and the tagged YY1 proteins in nuclear extracts were immunoprecipitated with either anti-FLAG or anti-HA antibodies. The results show that the FLAG-tagged and HA-tagged YY1 proteins interact (FIG. 1G, H, FIG. 18I, J), consistent with prior reports that YY1 proteins oligomerize (Lopez-Perrote et al., 2014). Other highly expressed nuclear proteins such as OCT4 did not co-precipitate, indicating that the assay was specific (FIG. 18J). We previously reported that YY1 can bind both DNA and RNA independently, and that YY1 binding of active regulatory DNA elements is enhanced by the binding of RNA species that are transcribed at these loci (Sigova et al., 2015). It is therefore possible that YY1-YY1 interactions may be enhanced by the ability of each of the YY1 proteins to bind RNA species. Indeed, when we repeated the experiment described above with nuclear extracts containing the tagged YY1 proteins, and a portion of the sample was treated with RNase A prior to immuno-precipitation with anti-tag antibodies, there was a ~60% reduction in the amount of co-immunoprecipitated YY1 partner protein (FIG. 1G, H). These results suggest that stable YY1-YY1 interactions may be facilitated by RNA.

TABLE S1

Comparison of YY1 and CTCF

| | CTCF Citation | YY1 Citation |
|---|---|---|
| Shared Features | | |
| Zinc-coordinating DNA-binding domain TF | (Klenova et al., 1993) | (Shi et al., 1991) |
| Ubiquitously expressed in mammalian cells | (Mele et al., 2015) | (Mele et al., 2015) |
| Essential roles in normal development | (Heath et al., 2008; Moore et al., 2012; Splinter et al., 2006) | (Donohoe et al., 1999) |
| Reported as activator | (Klenova et al., 1993; Lobanenkov et al., 1990) | (Seto et al., 1991) |
| Reported as repressor | (Baniahmad et al., 1990; Kohne et al., 1993) | (Shi et al., 1991) |
| Binds RNA | (Saldaña-Meyer et al., 2014) | (Jeon and Lee, 2011; Sigova et al., 2015) |
| Can form dimers | (Saldaña-Meyer et al., 2014; Yusufzai et al., 2004) | (Lopez-Perrote et al., 2014; Wu et al., 2007) |
| Involved in V(D)J recombination | (Liu et al., 2007) | (Guo et al., 2011) |
| Reported to bend the DNA | (Arnold et al., 1996) | (Natesan and Gilman, 1993) |
| Enriched at loop anchors | (Heidari et al., 2014; Rao et al., 2014) | (Heidari et al., 2014; Rao et al., 2014) |
| Misexpressed in cancer | (Filippova et al., 1998, 2002) | (Castellano et al., 2009) |
| Involved in XCI | (Xu et al., 2007) | (Jeon and Lee, 2011) |
| Distinguishing Features | | |
| Binds predominantly to insulators | | FIG. 1C, this study |
| Binds predominantly to active enhancers and promoters | | |

YY1 is Associated with Active Regulatory Elements

If YY1 is an enhancer-promoter structuring protein then we would expect that YY1 would both occupy and connect active regulatory elements. We examined global binding of YY1 in murine embryonic stem cells (mESCs) and found that YY1 is predominantly localized to active promoters and enhancers (FIG. 1c, 1e). We next performed chromatin interaction analysis by paired-end tag sequencing (ChIA-PET) for YY1 and CTCF. We found that the majority of YY1-associated interactions connect active regulatory elements, which is in stark contrast to the CTCF-associated interactions where the majority connect insulator elements (FIG. 1d). FIG. 1e shows an example of a gene with enhancer-promoter loops associated with YY1 binding. These results show that YY1 is associated with active regulatory elements and suggest that it may be involved in structuring enhancer-promoter loops.

YY1 is Critical for Proper Gene Expression

Gene expression is thought to be controlled by loops between enhancers and promoters thus if YY1 is involved in structuring these loops then perturbation of YY1 should perturb gene expression. To test this, we used an inducible small hairpin RNA (shRNA) to knockdown YY1 and assayed gene expression with single molecule RNA fluorescent in situ hybridization (smRNA FISH). We found there was a decrease in the transcripts of the key ES cell regulators Oct4 and Sox2 (FIG. 2). The promoters and enhancers of these genes are all densely occupied by YY1. These genes also all have YY1-associated enhancer-promoter loops (FIG. 2). This shows that YY1 is critical for proper gene expression, and supports the idea that YY1 regulates gene expression by connecting enhancers and promoters.

YY1 can Enhance DNA Interactions In Vitro

Figure 3A:
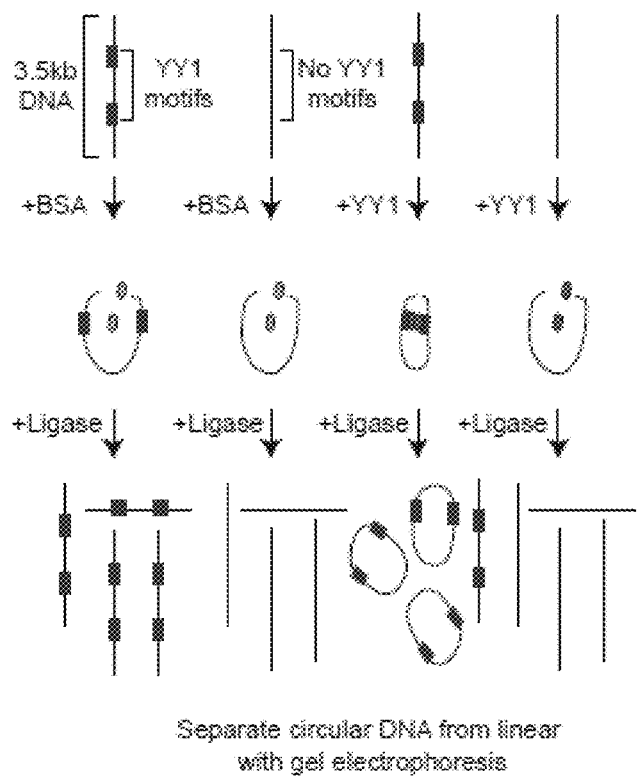
FIG. 3A-3F. YY1 can enhance DNA interactions in vitro.
Figure 3B:
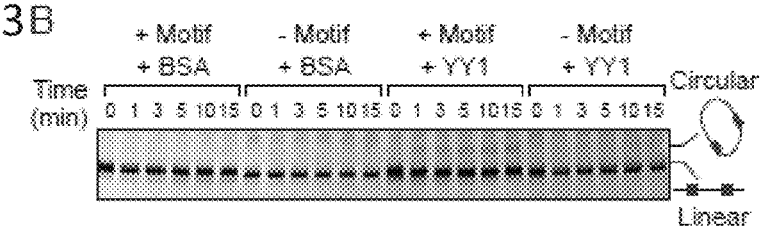
Figure 3C:
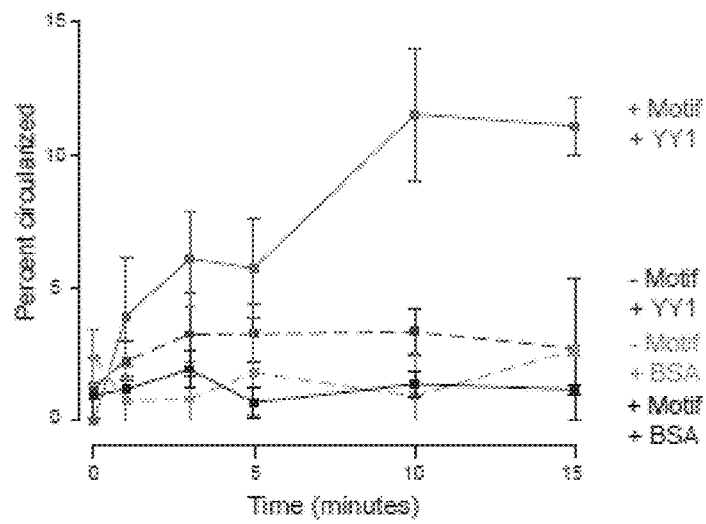
Figure 3D:
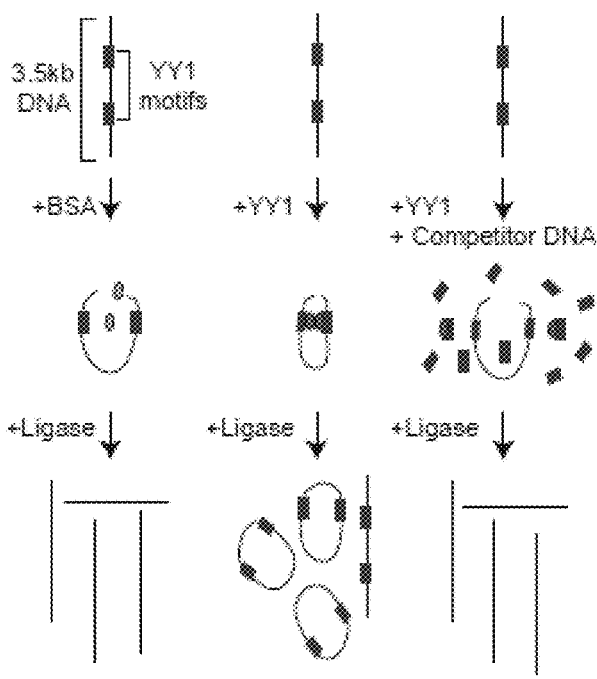
Figure 3E:
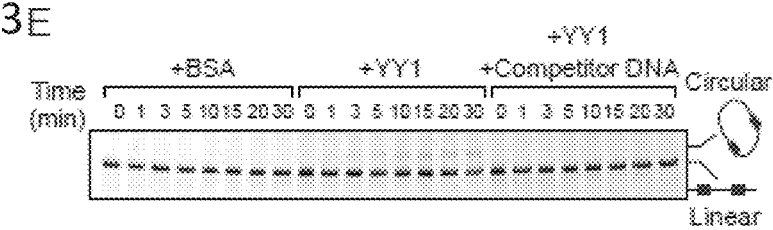
Figure 3F:
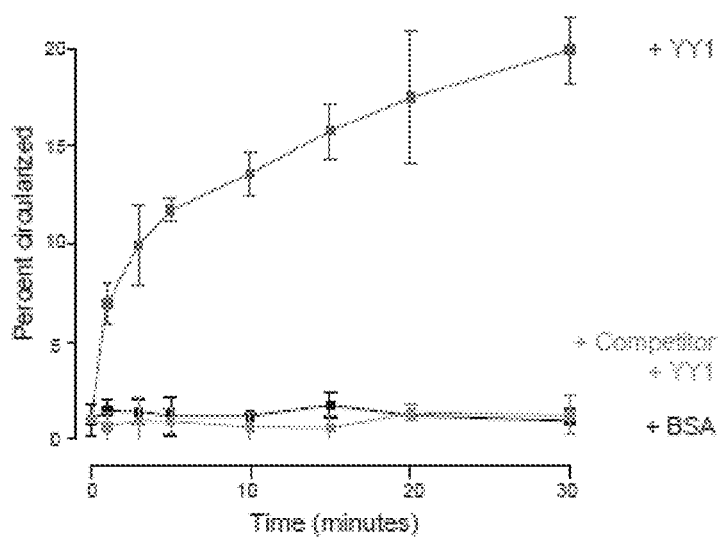
Figure 17A:
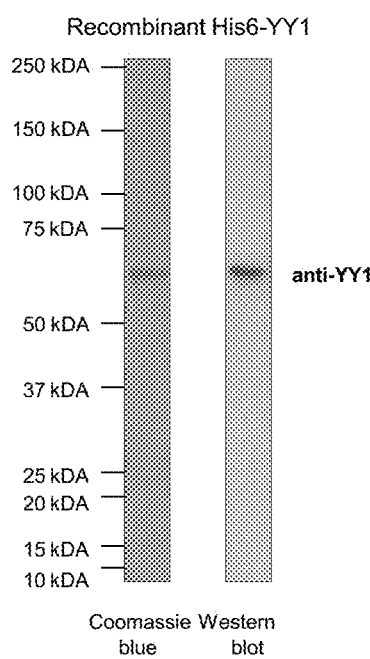
FIG. 17A-17B. YY1 can enhance DNA interactions in vitro, related to FIG. 3A-3F.

CTCF proteins can form homodimers and larger oligomers, and thus when bound to two different DNA sites can form a loop with the intervening DNA (Saldaña-Meyer et al., 2014). The observation that YY1 is bound to interacting enhancers and promoters, coupled with the evidence that YY1-YY1 interactions can occur in vitro and in cell extracts, is consistent with the idea that YY1-YY1 interactions can contribute to loop formation between enhancers and promoters. To obtain evidence that YY1 can have a direct effect on DNA interactions, we used an in vitro DNA circularization assay to determine if purified YY1 can enhance the rate of DNA interaction in vitro. The rate of DNA circularization catalyzed by T4 DNA ligase has been used previously to measure persistence length and other physical properties of DNA (Shore et al., 1981). We reasoned that if YY1 bound to DNA is capable of dimerizing and thereby forming DNA loops, then incubating a linear DNA template containing YY1 binding sites with purified YY1 protein should bring the ends into proximity and increase the rate of circularization (FIG. 3A, D). Recombinant YY1 protein was purified and shown to have DNA binding activity using a mobility shift assay (FIG. 17A, B). This recombinant YY1 was then tested in the DNA circularization assay; the results showed that YY1 increased the rate of circularization and that this depended on the presence of YY1 motifs in the DNA (FIG. 3B, 3C). The addition of an excess of a competing 200 base pair DNA fragment containing the YY1 consensus binding sequence abrogated circularization of the larger DNA molecule (FIG. 3D-F). The addition of bovine serum albumin (BSA) did not increase the rate of DNA ligation (FIG. 3C, F). These results support the idea that YY1 can directly facilitate DNA interactions. These results suggest that YY1 can multimerize, and that this multimerization is capable of looping together DNA.

Disruption of YY1 Looping Perturbs Gene Expression

Figures 4A, 4B, 4C, 4D, 4E:
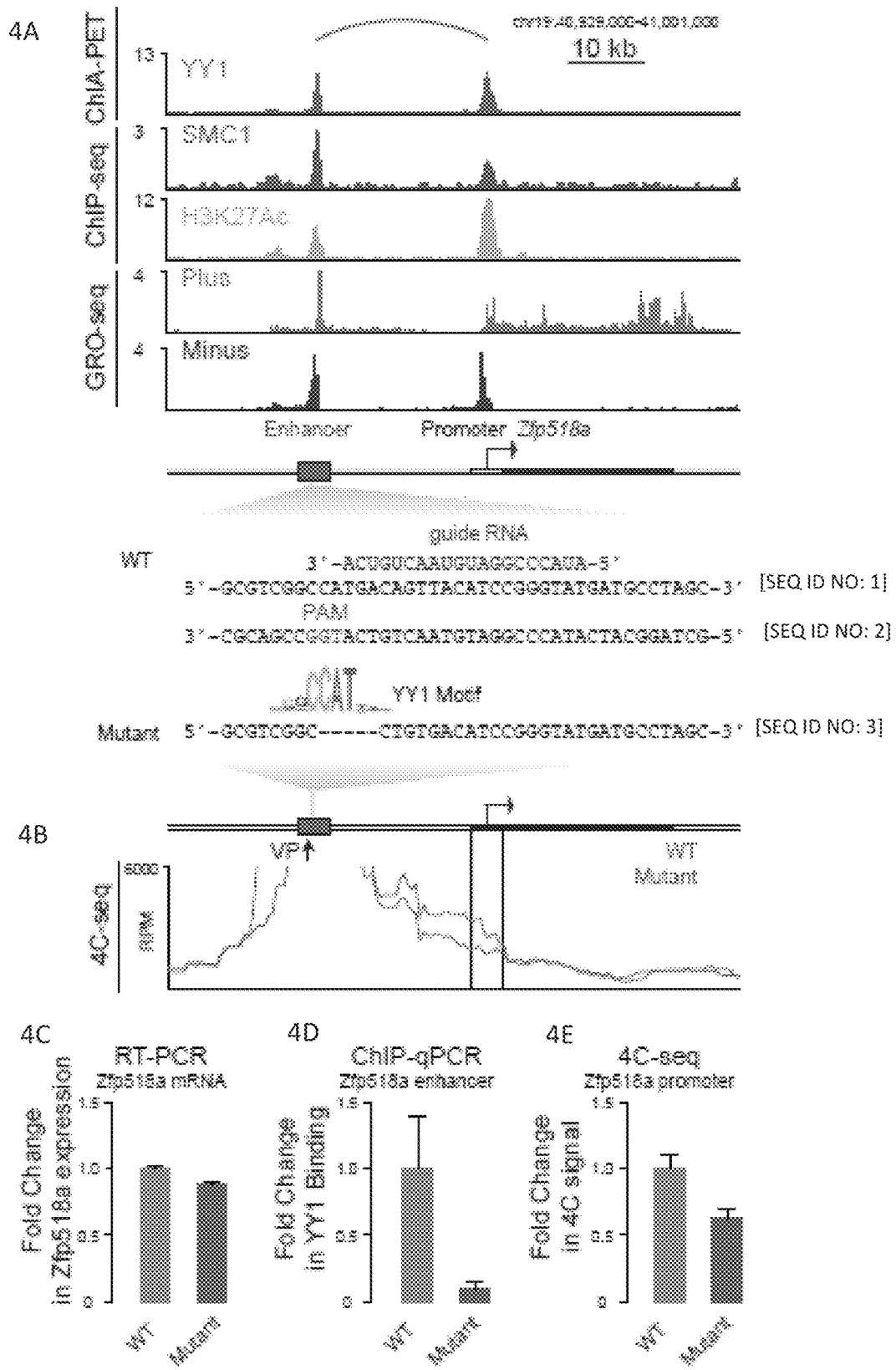
FIG. 4A-4E—Loss of YY1 causes loss of enhancer-promoter interactions.

Having shown that global depletion of YY1 perturbs gene expression and that YY1 is capable of oligomerization, we next wanted to directly test the role of YY1 binding at enhancers and promoters. We used the CRISPR/Cas9 system to generate a small deletion at the YY1 binding site in the Zfp518a enhancer and then characterized the effect on gene expression, YY1 binding, and looping (FIG. 4). We found that the mutation resulted in a decrease in the expression of Zfp518a (FIG. 4c), loss of binding of YY1 (FIG. 4d), and a decrease in looping between the enhancer and the promoter (FIG. 4b, e). These results indicate that YY1 binding at enhancers is necessary for normal looping to promoters, and that disruption of this looping perturbs gene expression suggesting that YY1 is critical for proper gene control.

Enhancer Promoter Interactions Depend on YY1 in Living Cells

Figure 6C:
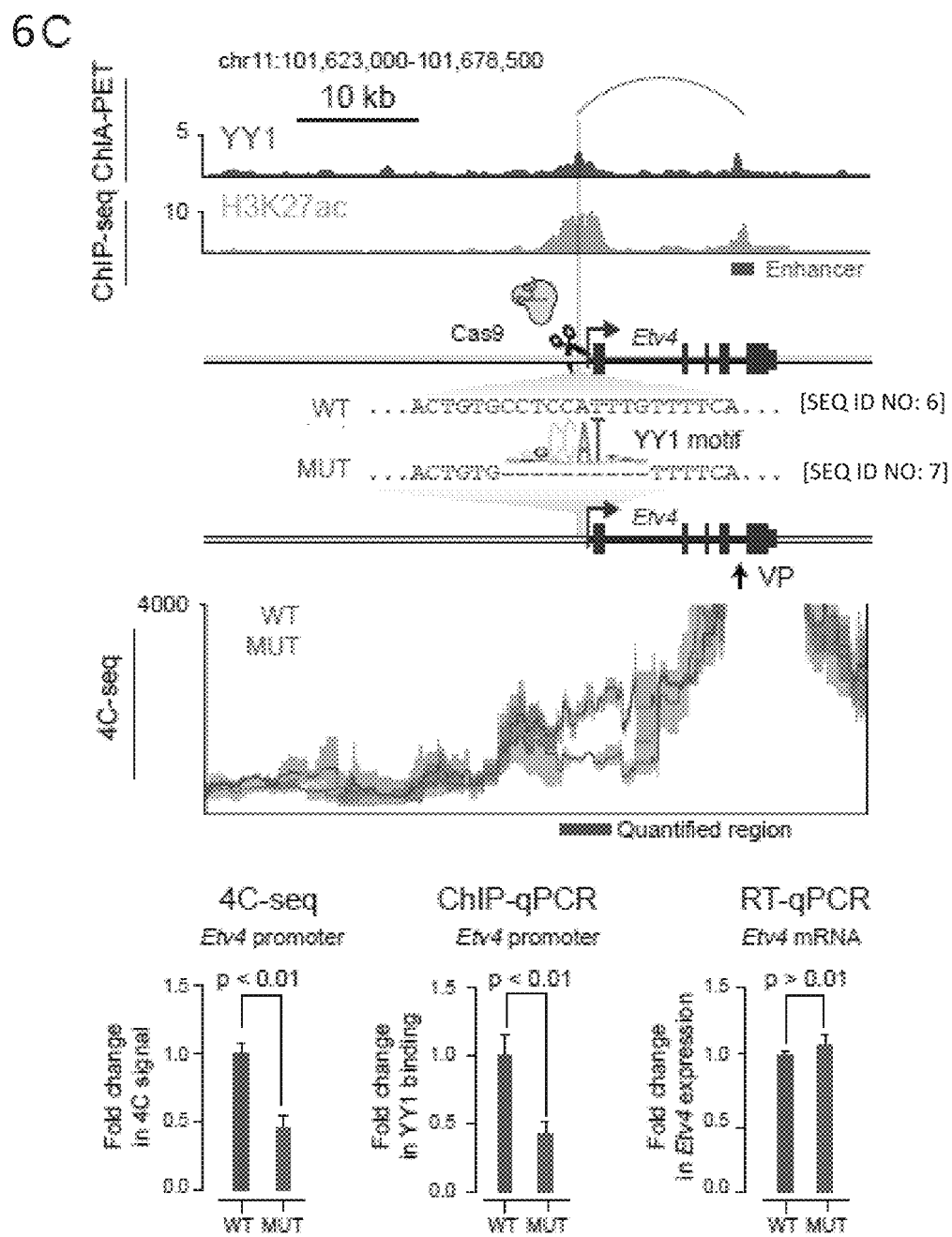
Figures 13A, 13B:
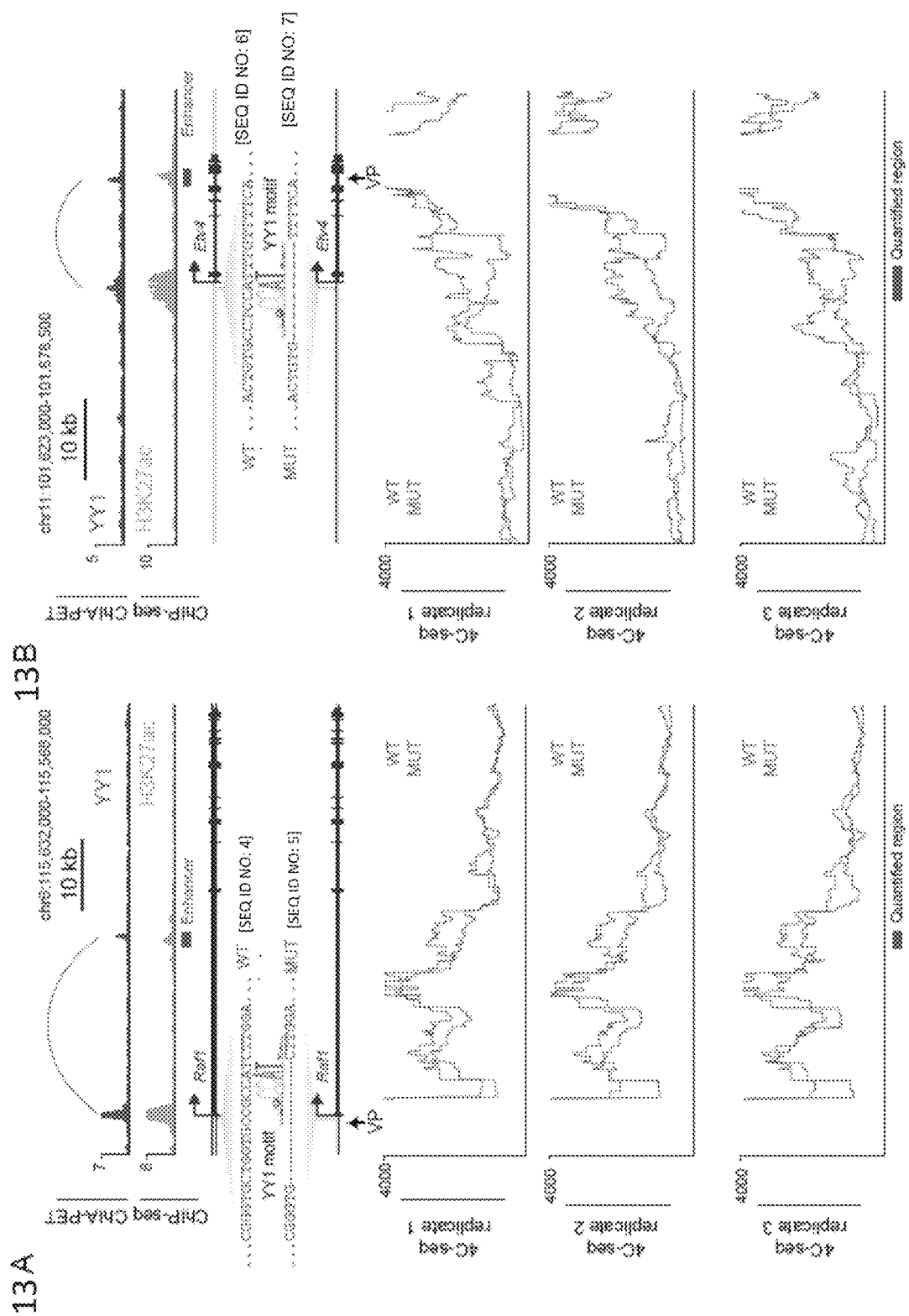
FIG. 13A-13B. Loss of YY1 binding causes loss of enhancer-promoter interactions, related to FIG. 6.
Figures 14A, 14B, 14C, 14D, 14E:
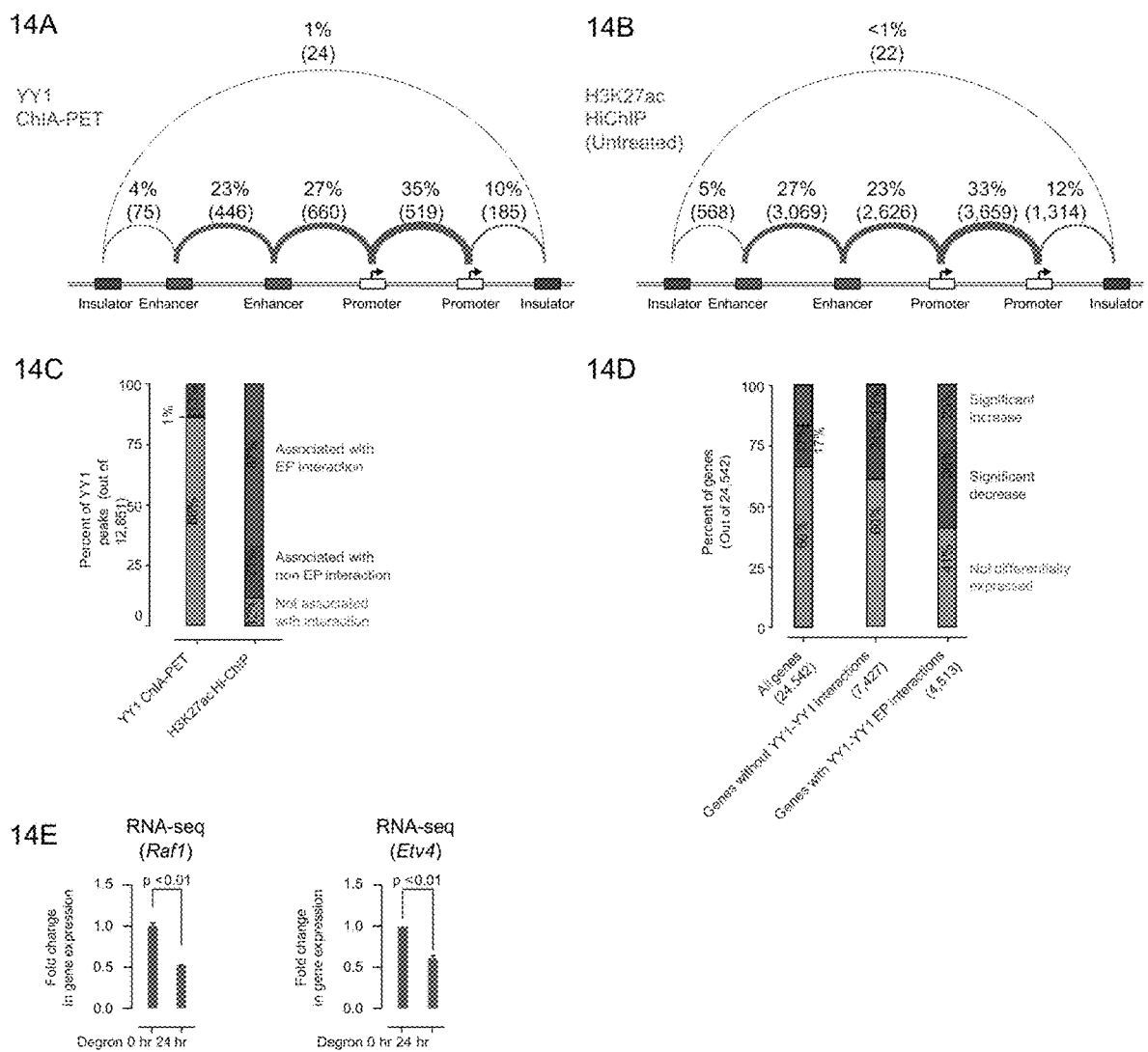
FIG. 14A-14E. Depletion of YY1 disrupts enhancer-promoter looping, related to FIG. 8.

To further test whether enhancer-promoter interactions in living cells depend on YY1 binding sites in these elements, a CRISPR/Cas9 system was used to generate a small deletion of a YY1 binding motif in the regulatory regions of two genes (FIG. 6A). Deletion of the optimal DNA-binding motif for YY1 in the promoter of the Raf1 gene resulted in decreased YY1 binding at the promoter, reduced contact frequency between the enhancer and promoter, and a decrease in Raf1 mRNA levels (FIG. 6B, FIG. 13A). Deletion of the optimal DNA-binding motif for YY1 in the promoter of the Etv4 gene also resulted in decreased YY1 binding and decreased enhancer-promoter contact frequency, although it did not significantly affect the levels of Etv4 mRNA (FIG. 6C, FIG. 13B). These results suggest that the YY1 binding sites contribute to YY1 binding and enhancer-promoter contact frequencies at both Raf1 and Etv4, although the reduction in looping frequencies at Etv4 was not sufficient to have a significant impact on Etv4 mRNA levels. The lack of an effect on Etv4 mRNA levels may be a consequence of the residual YY1 that is bound to the Etv4 promoter region, where additional CCAT motifs are observed (FIG. 6C). Indeed when YY1 protein is depleted (see below; FIG. 14E), the levels of both Raf1 and Etv4 mRNA decrease.

Figures 7A, 7B, 7C, 7D:
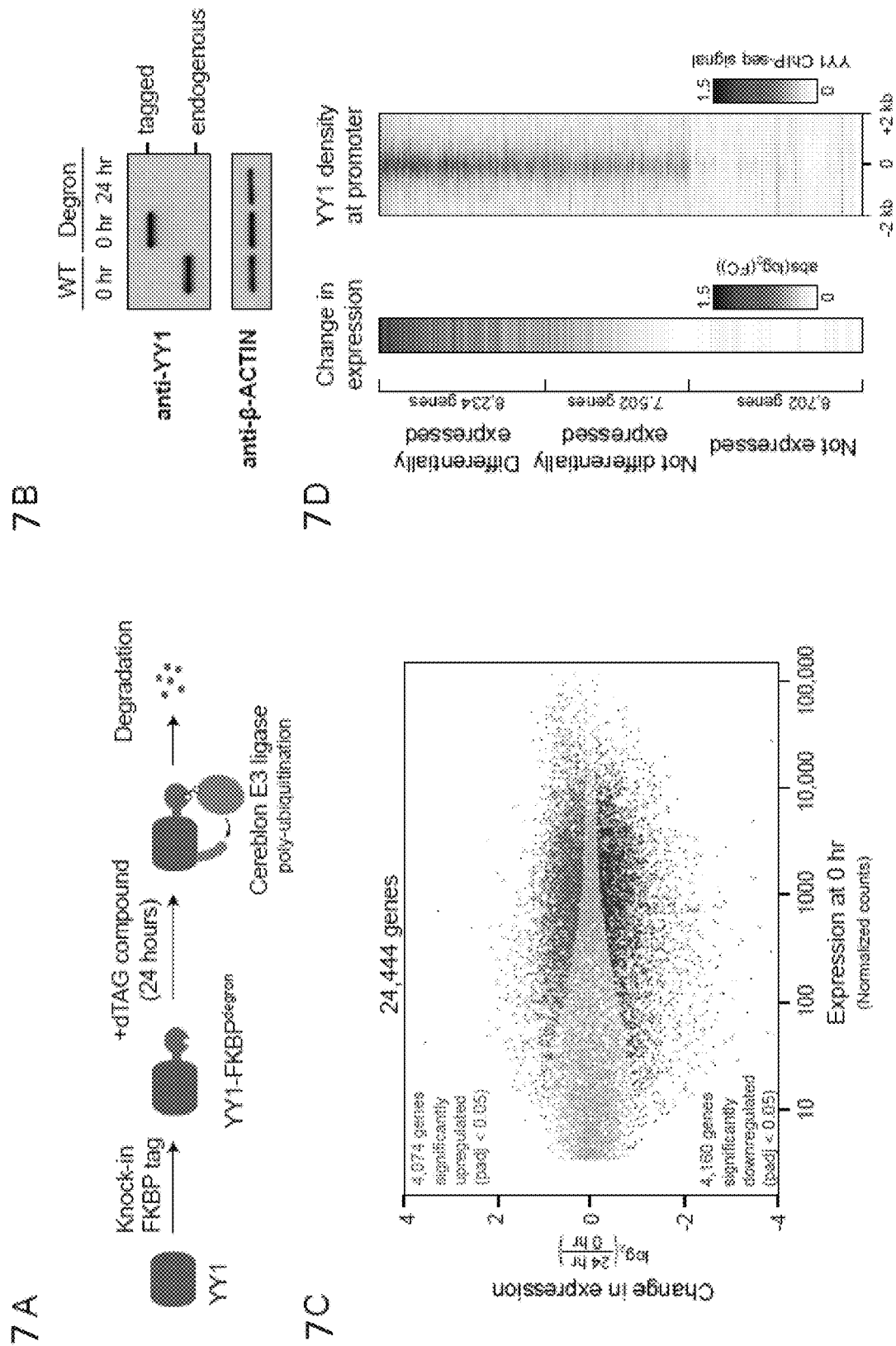
FIG. 7A-7H. Depletion of YY1 disrupts gene expression.

Previous studies have reported that YY1 is an activator of some genes and a repressor of others but a global analysis of YY1 dependencies has not been described with a complete depletion of YY1 in mES cells (Gordon et al., 2006; Shi et al., 1997; Thomas and Seto, 1999). An inducible degradation system (Erb et al., 2017; Huang et al., 2017; Winter et al., 2015) was used to fully deplete YY1 protein levels and measured the impact on gene expression in mES cells genome-wide through RNA-seq analysis (FIG. 7A, B). Depletion of YY1 led to significant (adjusted p-value<0.05) changes in expression of 8,234 genes, divided almost equally between genes with increased expression and genes with decreased expression (FIG. 7C, Table S3). The genes that experienced the greatest changes in expression with YY1 depletion were generally occupied by YY1 (FIG. 7D).

Figures 7E, 7F, 7G, 7H:
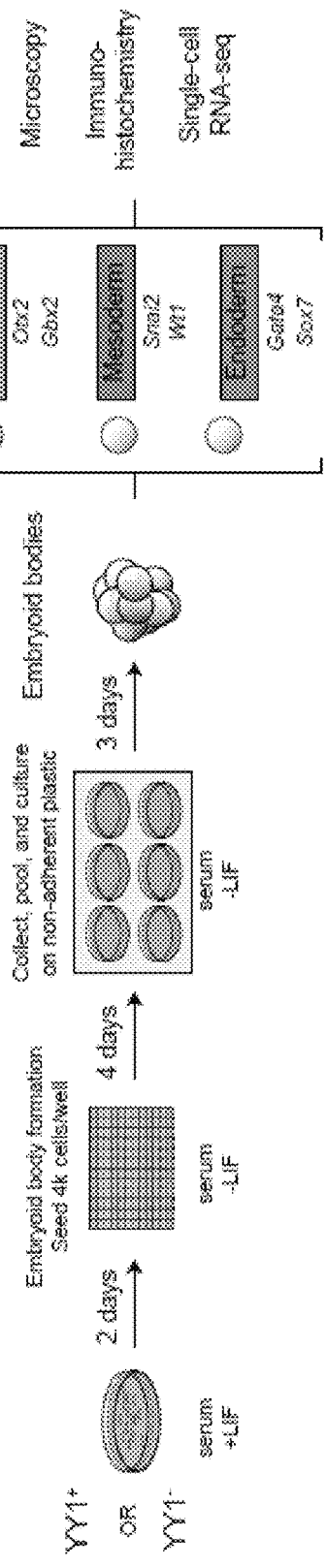
Figures 15A, 15B, 15C:
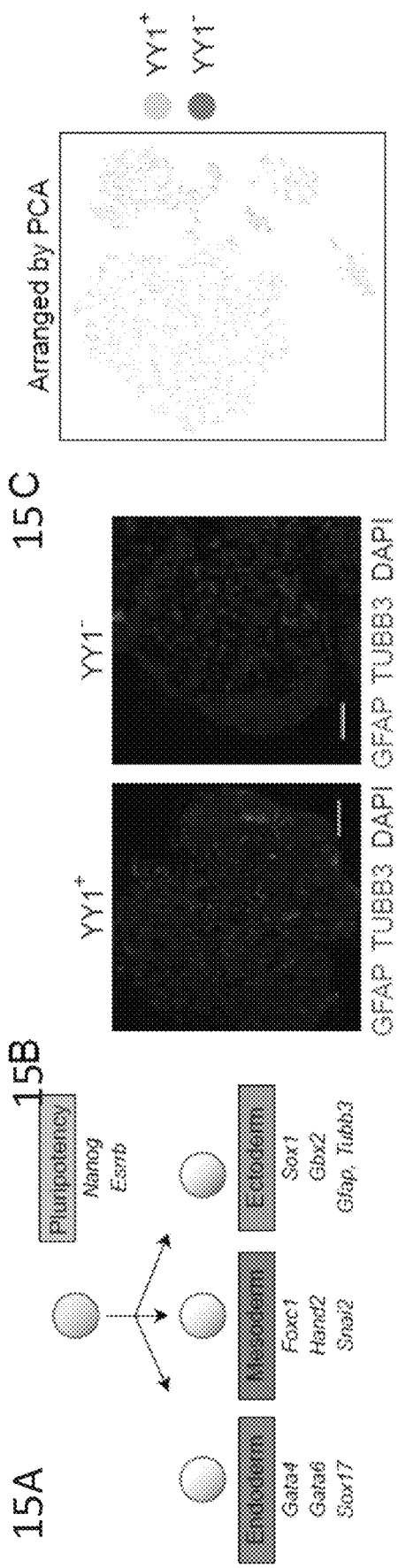
FIG. 15A-15D. Depletion of YY1 impairs ES cell differentiation, related to FIG. 7.

Previous studies have shown that YY1 is required for normal embryonic development (Donohoe et al., 1999). Whether the loss of YY1 leads to defects in embryonic stem (ES) cell differentiation into the three germ layers (FIG. 7E) was investigated. Murine ES cells, and isogenic cells that were subjected to inducible degradation of YY1, were stimulated to form embryoid bodies (FIG. 7F) and the cells in these bodies were subjected to immunohistochemistry staining and single-cell RNA-seq to monitor expression of differentiation-specific factors. The results showed that cells lacking YY1 showed pronounced defects in expression of the master transcription factors that drive normal differentiation (FIG. 7G, H; FIG. 15).

Figure 8A:
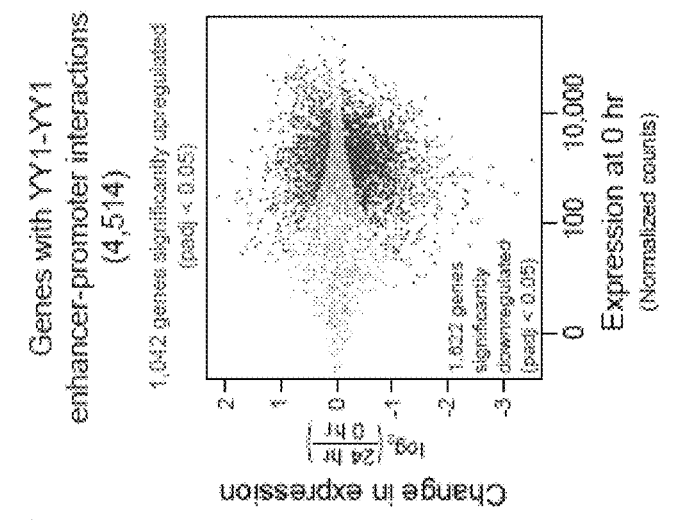
FIG. 8A-8E. Depletion of YY1 disrupts enhancer-promoter looping.

Whether changes in DNA looping occur upon global depletion of YY1 in mES cells was next investigated. HiChIP for H3K27ac, a histone modification present at both enhancers and promoters, was performed before and after YY1 depletion to detect differences in enhancer-promoter interaction frequencies. Prior to YY1 depletion, the results of the HiChIP experiment showed interactions between the various elements that were similar to the earlier YY1 ChIA-PET results (FIG. 14A, B). After YY1 depletion, the interactions between YY1-occupied enhancers and promoters decreased significantly (FIG. 8A, B). The majority (60%) of genes connected by YY1 enhancer-promoter loops showed significant changes in gene expression (FIG. 8C; FIG. 14D). Examination of the HiChIP DNA interaction profiles at specific genes confirmed these effects. For example, with YY1 depletion the Slc7a5 promoter and its enhancer showed a ~50% reduction in interaction frequency, and Slc7a5 expression levels were reduced by ~27% (FIG. 8D). Similarly, after YY1 depletion, the Klf9 promoter and its super-enhancer showed a ~40% reduction in interaction frequency and Klf9 expression levels were reduced by ~50% (FIG. 8E).

Rescue of Enhancer Promoter Interactions in Cells

Figures 9A, 9B, 9C, 9D:
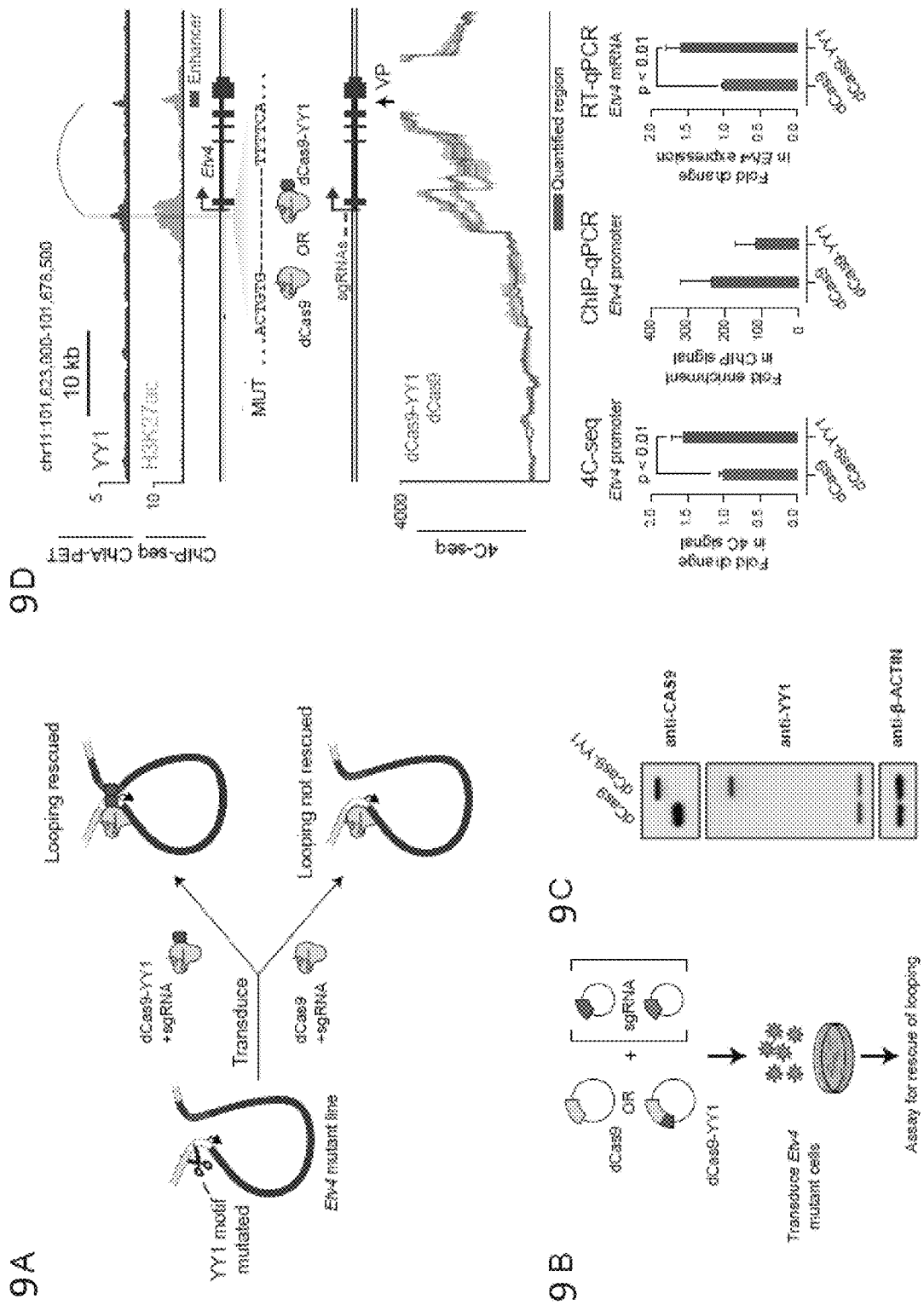
FIG. 9A-9F. Rescue of enhancer-promoter interactions in cells.

The ability of an artificially tethered YY1 protein to rescue defects associated with a YY1 binding site mutation would be a strong test of the model that YY1 mediates enhancer-promoter interactions (FIG. 9A). Such test was performed with a dCas9-YY1 fusion protein targeted to a site adjacent to a YY1 binding site mutation in the promoter-proximal region of Etv4 (FIG. 7B, C). Artificially tethering YY1 protein to the promoter was found to lead to increased contact frequency between the Etv4 promoter and its enhancer and caused increased transcription from the gene (FIG. 9D). These results support the model that YY1 is directly involved in structuring enhancer-promoter loops.

Figure 8B:
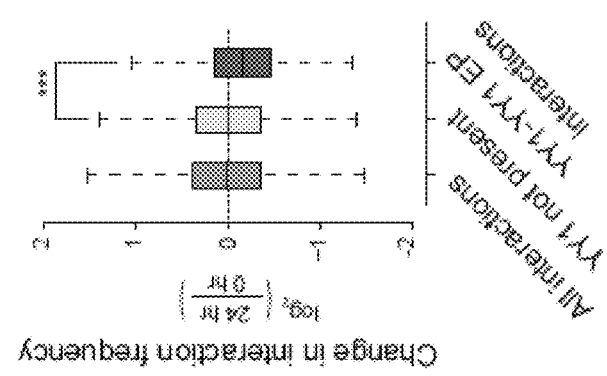
Figure 8C:
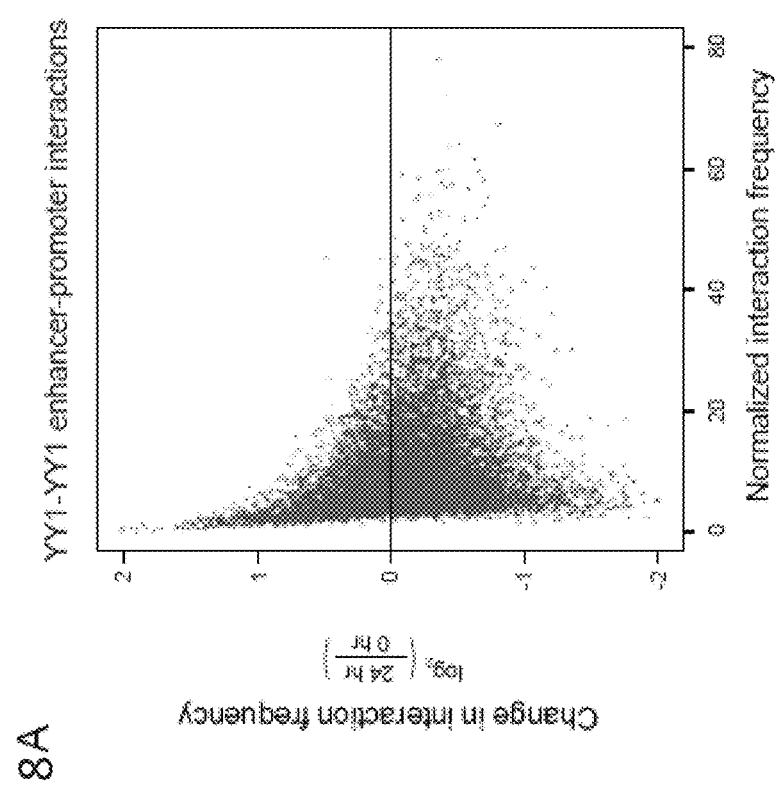
Figures 8D, 8E:
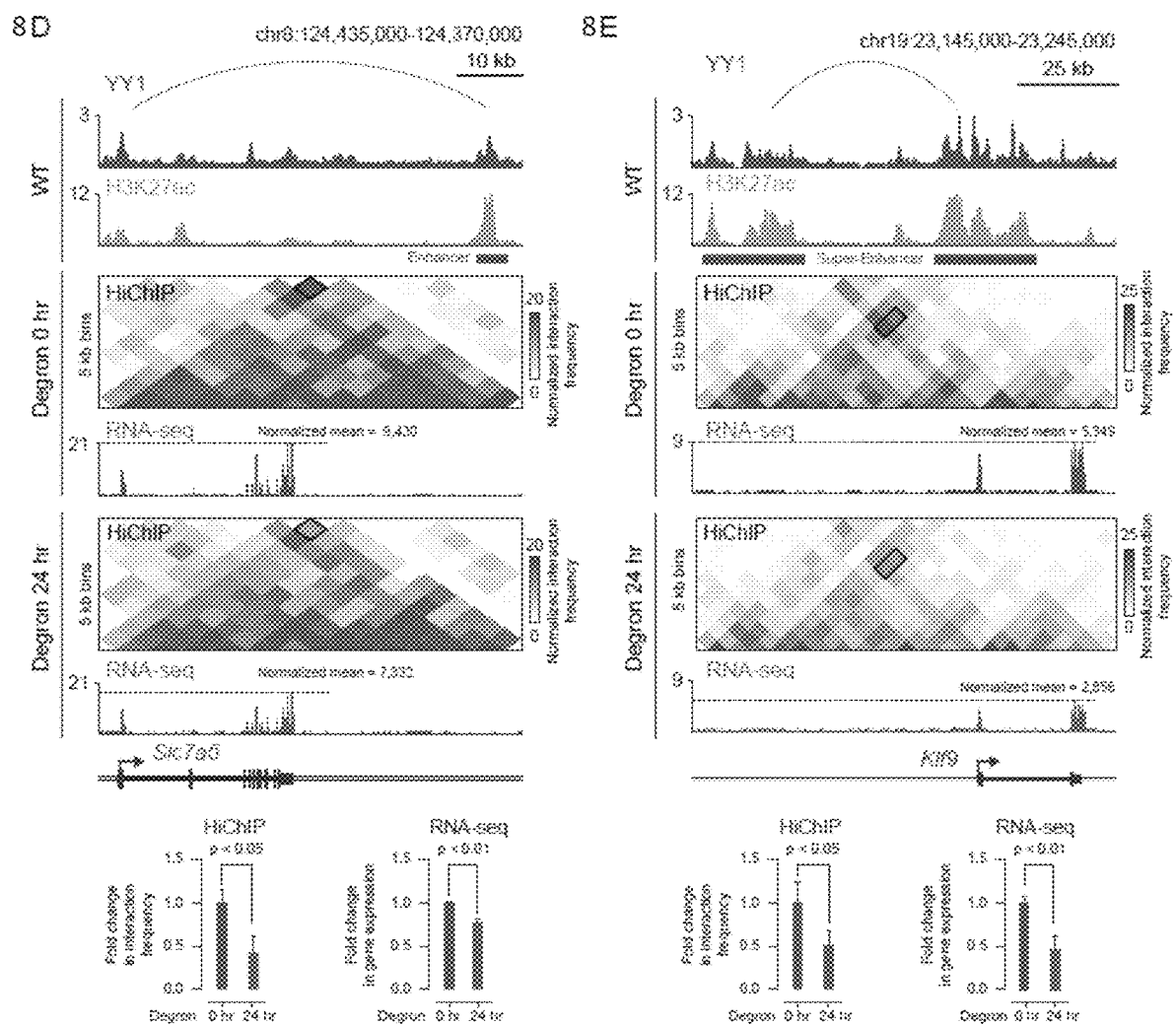
Figure 9E:
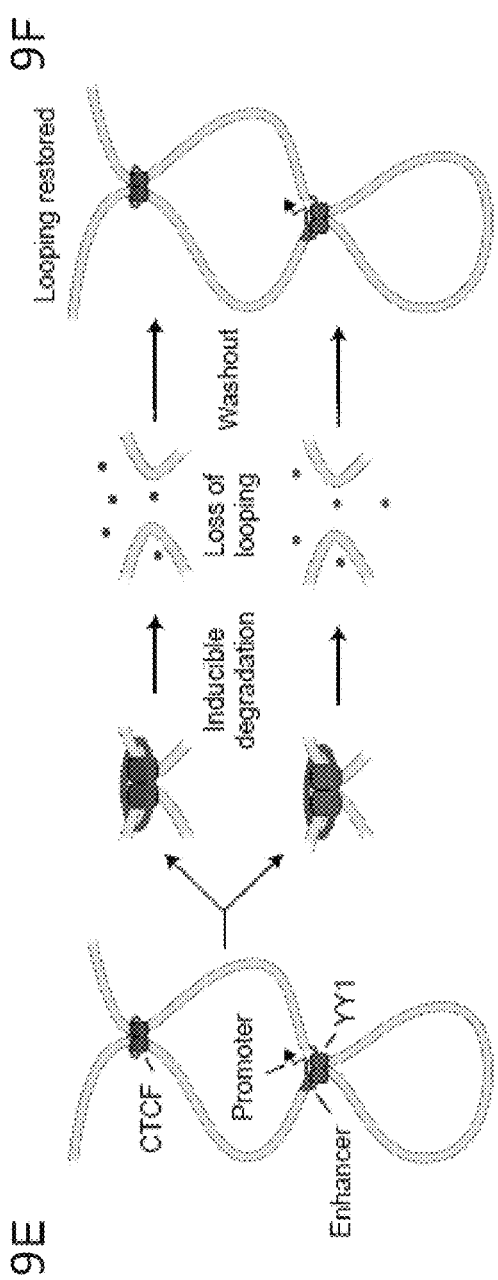
Figure 9F:
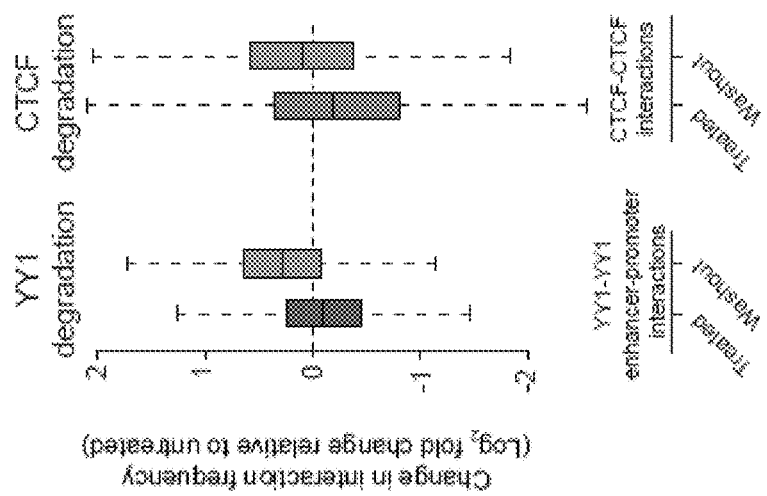
Figure 16A:
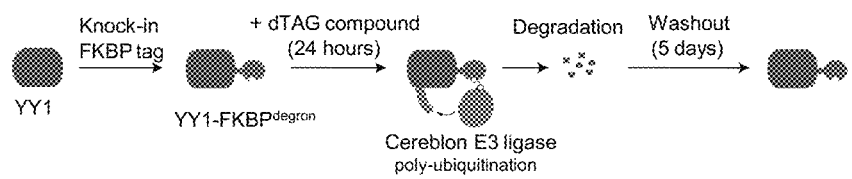
FIG. 16A-16C. Rescue of enhancer-promoter interactions in cells, related to FIG. 9.
Figure 16B:
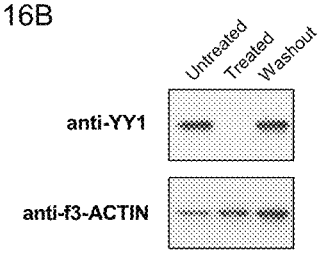
Figure 16C:
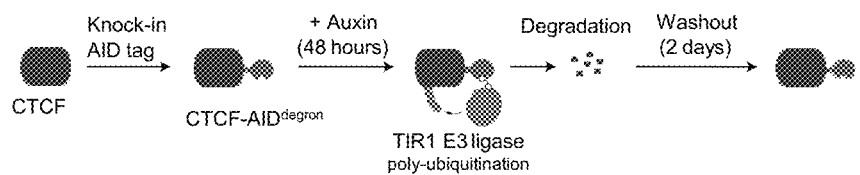

To more globally test if YY1 can rescue the loss of enhancer-promoter interactions after YY1 degradation, mES cells were subjected to YY1 degradation with the dTAG method and then washed out the dTAG compound and allowed YY1 to be restored to normal levels (FIG. 9E; FIG. 16A, B). Enhancer-promoter frequencies were monitored with H3K27ac HiChIP. Consistent with a previous experiment (FIG. 8), the loss of YY1 caused a loss in enhancer-promoter interactions, but the recovery of YY1 levels was accompanied by a substantial increase in enhancer-promoter interactions (FIG. 9F). These results were comparable to the effects observed with the rescue of CTCF-CTCF interactions in a similar experiment described recently (FIG. 9F; FIG. 16C) (Nora et al., 2017), and support the model that YY1 contributes to structuring of a large fraction of enhancer-promoter loops genome-wide.

Discussion

We describe here evidence that the transcription factor YY1 contributes to enhancer-promoter structural interactions. For a broad spectrum of genes, YY1 binds to active enhancers and promoters and is required for normal levels of enhancer-promoter interaction and gene transcription. YY1 is ubiquitously expressed, occupies enhancers and promoters in all cell types examined, is associated with sites of DNA looping in cells where such studies have been conducted, and is essential for embryonic and adult cell viability, so it is likely that YY1-mediated enhancer-promoter interactions are a general feature of mammalian gene control.

Figure 11B:
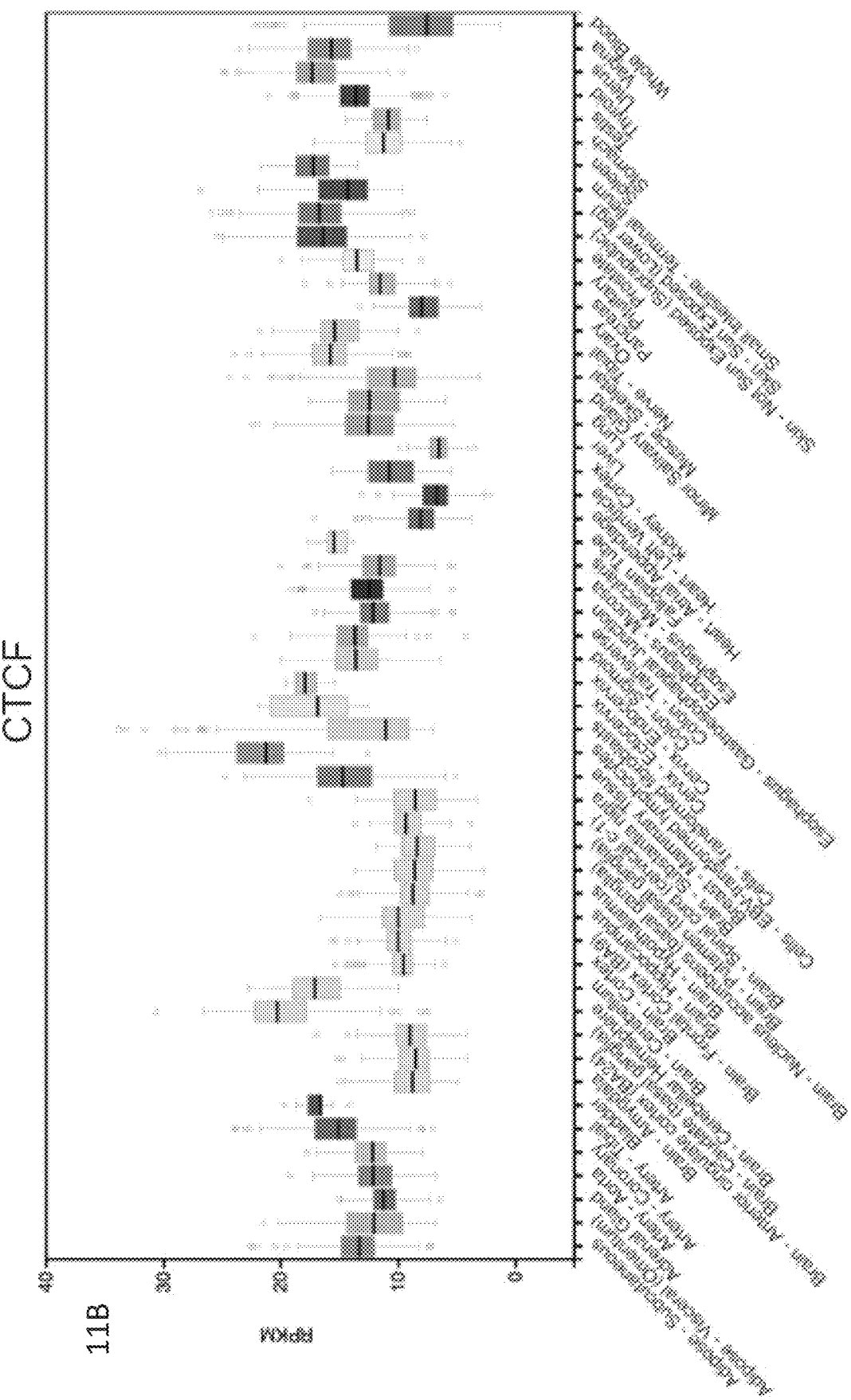
Figure 11C:
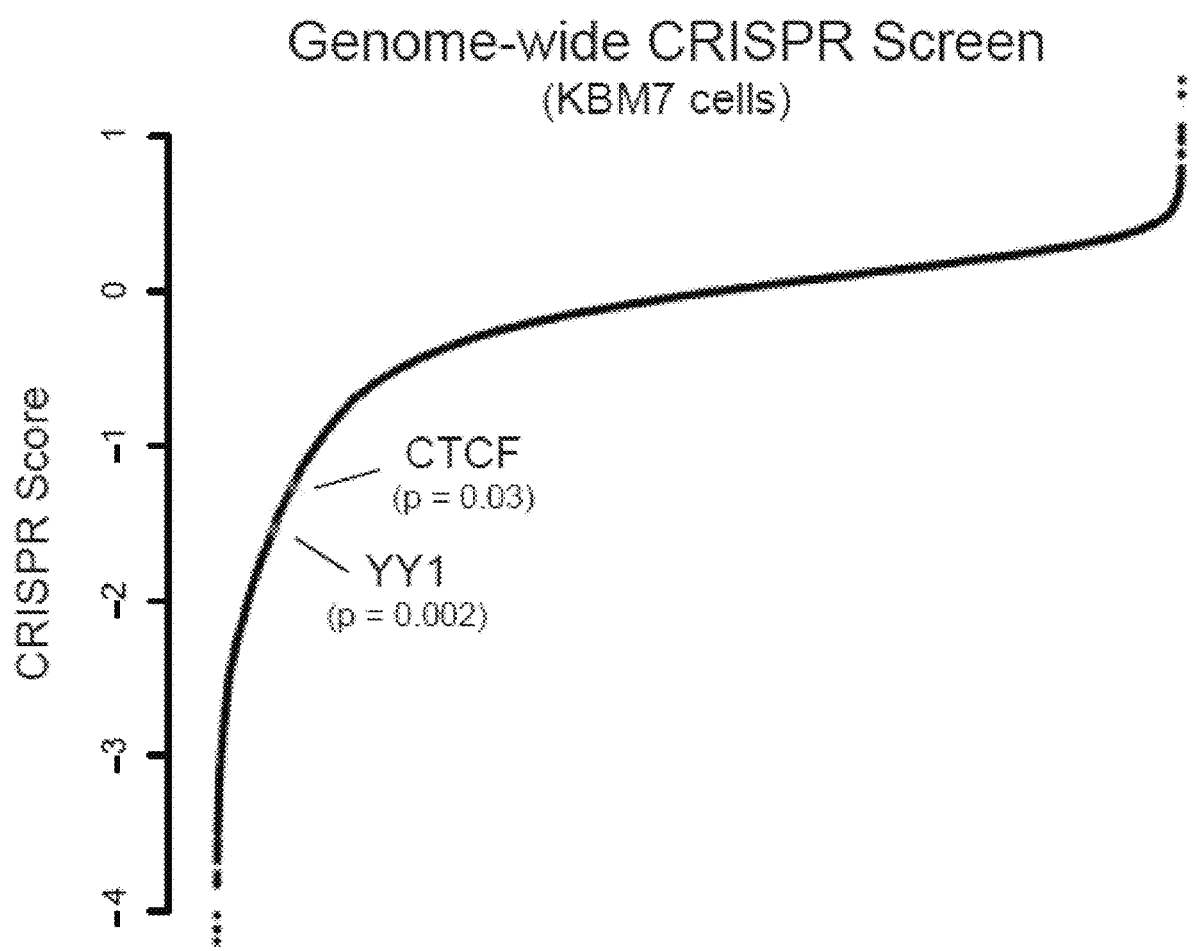
Figure 12:
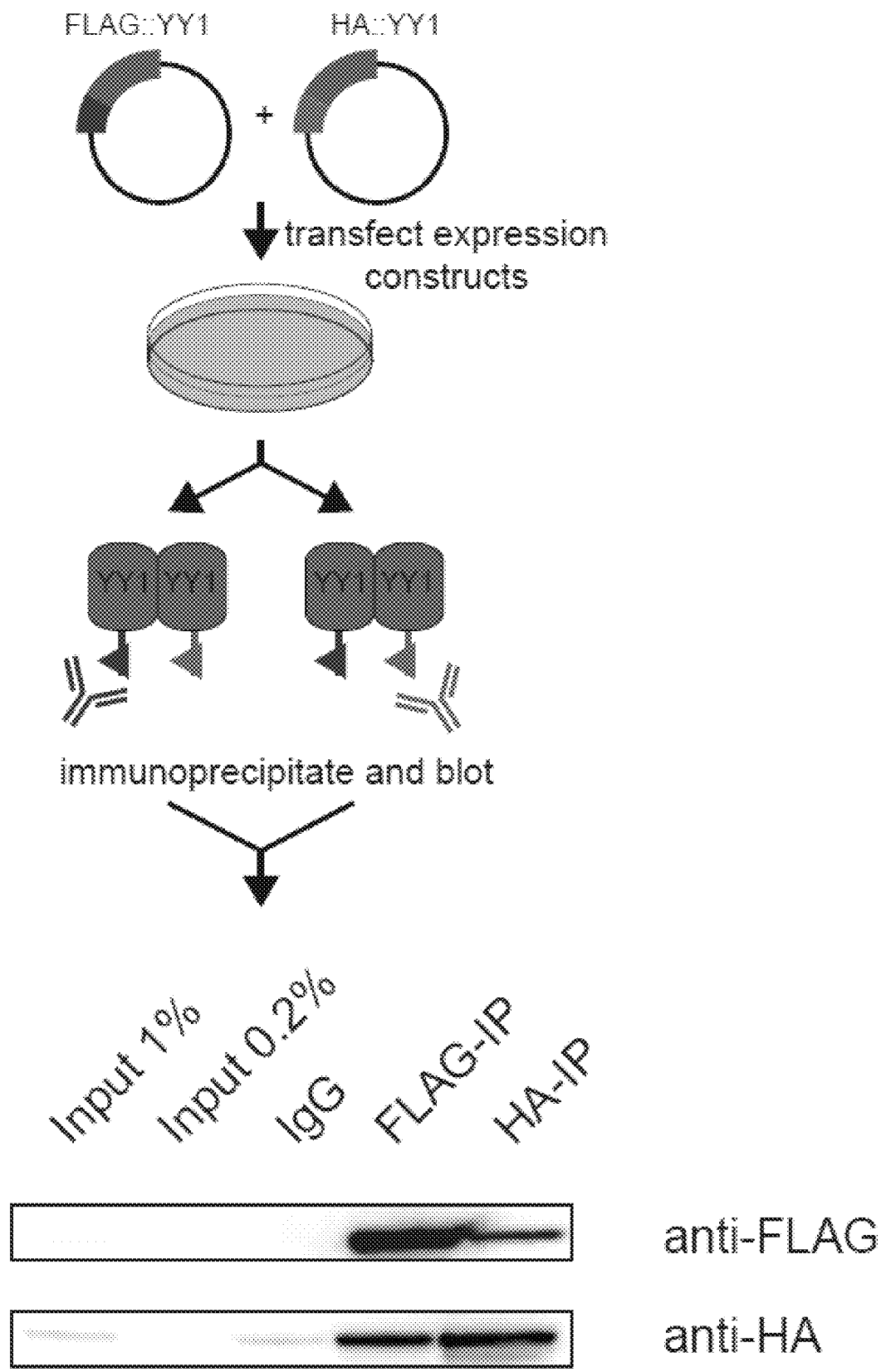

Evidence that CTCF-CTCF interactions play important roles in chromosome loop structures, but are only occasionally involved in enhancer-promoter interactions, led us to consider the possibility that a bridging protein analogous to CTCF might generally participate in enhancer-promoter interactions. CTCF and YY1 share many features: they are DNA-binding zinc-finger factors (Klenova et al., 1993; Shi et al., 1991) that selectively bind hypo-methylated DNA sequences (Bell and Felsenfeld, 2000; Yin et al., 2017), are ubiquitously expressed (FIG. 11) (Mele et al., 2015), essential for embryonic viability (Donohoe et al., 1999; Heath et al., 2008), and capable of dimerization (FIG. 12) (Lopez-Perrote et al., 2014; Saldaña-Meyer et al., 2014). The two proteins differ in several important ways. CTCF-CTCF interactions occur predominantly between sites that can act as insulators and to a lesser degree between enhancers and promoters (FIG. 1D). YY1-YY1 interactions occur predominantly between enhancers and promoters and to a lesser extent between insulators (FIG. 1D). At insulators, CTCF binds to a relatively large and conserved sequence motif (when compared to those bound by other TFs); these same sites tend to be bound in many different cell types, which may contribute to the observation that TAD boundaries tend to be preserved across cell types. At enhancers and promoters, YY1 binds to a relatively small and poorly conserved sequence motif within these regions, where RNA species are produced that can facilitate stable YY1 DNA binding (Sigova et al., 2015). The cell-type-specific activity of enhancers and promoters thus contributes to the observation that YY1-YY1 interactions tend to be cell-type-specific.

The model that YY1 contributes to structuring of enhancer-promoter loops can account for the many diverse functions previously reported for YY1, including activation and repression, differentiation, and cellular proliferation. For example, following its discovery in the early 1990's (Hariharan et al., 1991; Park and Atchison, 1991; Shi et al., 1991), YY1 was intensely studied and reported to act as a repressor for some genes and an activator for others; these context-specific effects have been attributed to many different mechanisms (reviewed in (Gordon et al., 2006; Shi et al., 1997; Thomas and Seto, 1999)). There are many similar reports of context-specific activation and repression by CTCF (reviewed in (Ohlsson et al., 2001; Phillips and Corces, 2009)). Although it is reasonable to assume that YY1 and CTCF can act directly as activators or repressors at some genes, the evidence that these proteins contribute to structuring of DNA loops makes it likely that the diverse active and repressive roles that have been attributed to them are often a consequence of their roles in DNA structuring. In this model, the loss of CTCF or YY1 could have positive or negative effects due to other regulators that were no longer properly positioned to produce their regulatory activities.

Previous studies have hinted at a role for YY1 in long distance DNA interactions. CTCF, YY1 and cohesin have been implicated in the formation of DNA loops needed for V(D)J rearrangement at the immunoglobulin locus during B cell development (Degner et al., 2011; Guo et al., 2011; Liu et al., 2007). B cell-specific deletion of YY1 causes a decrease in the contraction of the IgH locus, thought to be mediated by DNA loops, and a block in the development of B cells (Liu et al., 2007). Knockdown of YY1 has also been shown to reduce intrachromosomal interactions between the Th2 LCR and the IL4 promoter (Hwang et al., 2013). As this manuscript was completed, a paper appeared reporting that YY1 is present at the base of interactions between neuronal precursor cell specific enhancers and genes and that YY1 knockdown causes a loss of these interactions (Beagan et al., 2017). The results described here argue that YY1 is more of a general structural regulator of enhancer-promoter interactions for a large population of genes, both cell-type specific and otherwise, in all cells. Thus, the tendency of YY1 to be involved in cell-type specific loops is a reflection of the cell-type specificity of enhancers and, consequently, their interactions with genes that can be expressed in a cell-specific or a more general manner.

YY1 plays an important role in human disease; YY1 haploinsufficiency has been implicated in an intellectual disability syndrome and YY1 overexpression occurs in many cancers. A cohort of patients with various mutations in one allele and exhibiting intellectual disability have been described as having a "YY1 Syndrome", and lymphoblastoid cell lines from these patients show reduced occupancy of regulatory regions and small changes in gene expression at a subset of genes associated with YY1 binding (Gabriele et al., 2017). These results are consistent with the model we describe for YY1 in global enhancer-promoter structuring, and with the idea that higher neurological functions are especially sensitive to such gene dysregulation. YY1 is over-expressed in a broad spectrum of tumor cells, and this over-expression has been proposed to cause unchecked cellular proliferation, tumorigenesis, metastatic potential, resistance to immune-mediated apoptotic stimuli and resistance to chemotherapeutics (Gordon et al., 2006; Zhang et al., 2011). The mechanisms that have been reported to mediate these effects include YY1-mediated downregulation of p53 activity, interference with poly-ADP-ribose polymerase, alteration in c-Myc and NF-κB expression, regulation of death genes and gene products, differential YY1 binding in the presence of inflammatory mediators and YY1 binding to the oncogenic c-Myc transcription factor (Gordon et al., 2006; Zhang et al., 2011). Although it is possible that YY1 carries out all these functions, its role as a general enhancer-promoter structuring factor is a more parsimonious explanation of these pleotropic phenotypes.

Many zinc-coordinating transcription factors are capable of homo- and hetero-dimerization (Amoutzias et al., 2008; Lamb and McKnight, 1991) and because these comprise the largest class of transcription factors in mammals (Weirauch and Hughes, 2011), we suggest that a combination of cell-type-specific and cell-ubiquitous transcription factors make a substantial and underappreciated contribution to enhancer-promoter loop structures. There are compelling studies of bacterial and bacteriophage transcription factors that contribute to looping of regulatory DNA elements through oligomerization (Adhya, 1989; Schleif, 1992), and reports of several eukaryotic factors with similar capabilities (Matthews, 1992). Nonetheless, most recent study of eukaryotic enhancer-promoter interactions has focused on cofactors that lack DNA binding capabilities and bridge enhancer-bound transcription factors and promoter-bound transcription apparatus (Allen and Taatjes, 2015; Deng et al., 2012; Jeronimo et al., 2016; Kagey et al., 2010; Malik and Roeder, 2010; Petrenko et al., 2016), with the notable exception of the proposals that some enhancer-promoter interactions are determined by the nature of transcription factors bound at the two sites (Muerdter and Stark, 2016). We predict that future studies will reveal additional transcription factors that belong in the class of DNA binding proteins whose predominant role is to contribute to chromosome structure.

In conclusion, we have shown that YY1 is responsible for structuring enhancer-promoter loops in mammalian cells. YY1 occupies and connects active enhancers and promoters. YY1 dimerizes, and this dimerization is capable of looping together two pieces of DNA. The loss of YY1 causes the loss of enhancer-promoter looping. We propose that YY1 is a global enhancer-promoter structuring protein. Gene regulation depends on enhancer-promoter loops, and gene regulation is critical for proper development; thus understanding the mechanistic basis of enhancer-promoter loops is critical to understanding development. Furthermore, disease is often caused by the misregulation of gene expression and so the findings here will aid the understanding of pathogenesis.

STAR Methods:

Cell Culture Conditions:

Embryonic Stem Cells

V6.5 murine embryonic stem (mES) cells were grown on irradiated murine embryonic fibroblasts (MEFs). Cells were grown under standard mES cell conditions as described previously (1). Cells were grown on 0.2% gelatinized (Sigma, G1890) tissue culture plates in ESC media; DMEM-KO (Invitrogen, 10829-018) supplemented with 15% fetal bovine serum (Hyclone, characterized SH3007103), 1,000 U/ml LIF (ESGRO, ESG1106), 100 mM nonessential amino acids (Invitrogen, 11140-050), 2 mM L-glutamine (Invitrogen, 25030-081), 100 U/ml penicillin, 100 mg/ml streptomycin (Invitrogen, 15140-122), and 8 ul/ml of 2-mercaptoethanol (Sigma, M7522).

Protein Production and Purification:

YY1 protein was purified using methods established by the Lee Lab (Jeon and Lee, 2011) and previously described in (Sigova et al., 2015). A plasmid containing N-terminal His6-tagged human YY1 coding sequence (a gift from Dr. Yang Shi) was transformed into BL21-CodonPlus (DE3)-RIL cells (Stratagene, 230245). A fresh bacterial colony was inoculated into LB media containing ampicillin and chloramphenicol and grown overnight at 37° C. These bacteria were diluted 1:10 in 500 mL pre-warmed LB with ampicillin and chloramphenicol and grown for 1.5 hours at 37° C. After induction of YY1 expression with 1 mM IPTG, cells were grown for another 5 hours, collected, and stored frozen at −80° C. until ready to use.

Pellets from 500 mL cells were resuspended in 15 mL of Buffer A (6M GuHCl, 25 mM Tris, 100 mM NaCl, pH8.0) containing 10 mM imidazole, 5 mM 2-mercaptoethanol, cOmplete protease inhibitors (Roche, 11873580001) and sonicated (ten cycles of 15 seconds on, 60 seconds off). The lysate was cleared by centrifugation at 12,000 g for 30 minutes at 4° C. and added to 1 mL of Ni-NTA agarose (Invitrogen, R901-15) pre-equilibrated with 10× volumes of Buffer A. Tubes containing this agarose lysate slurry were rotated at room temperature for 1 hour. The slurry was poured into a column, and the packed agarose washed with 15 volumes of Buffer A containing 10 mM imidazole. Protein was eluted with 4×2 mL Buffer A containing 500 mM imidazole.

Fractions were run out by SDS-PAGE gel electrophoresis and stained with Coomassie Brilliant Blue (data not shown). Fractions containing protein of the correct size and high purity were combined and diluted 1:1 with elution buffer. DTT was added to a final concentration of 100 mM and incubated at 60° C. for 30 minutes. The protein was refolded by dialysis against 2 changes of 1 Liter of 25 mM Tris-HCl pH 8.5, 100 mM NaCl, 0.1 mM ZnCl2, and 10 mM DTT at 4° C. followed by 1 change of the same dialysis buffer with 10% glycerol. Protein was stored in aliquots at −80° C.

YY1 Characterization

Figure 17B:
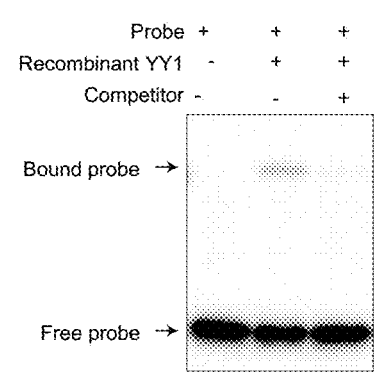

The purity of the recombinant YY1 was assessed by SDS-PAGE gel electrophoresis followed by Coomassie Brilliant Blue staining and Western blotting (FIG. 17A). The activity of the recombinant protein was assessed by EMSA (FIG. 17B).

EMSA was performed using the LightShift Chemiluminescent EMSA Kit (Thermo Scientific #20148) following the manufacturer's recommendations. Briefly, recombinant protein was incubated with a biotinylated probe in the presence or absence of a cold competitor. Reactions were separated using a native gel and transferred to a membrane. Labeled DNA was detected using chemiluminescence.

To generate the biotin labeled probe, 30-nucleotide-long 5' biotinylated single stranded oligonucleotides (IDT) were annealed in 10 mM Tris pH 7.5, 50 mM NaCl, and 1 mM EDTA at a 50 uM concentration. The same protocol was used to generate the cold competitor. The probe was serially diluted to a concentration of 10 fmol/4 and cold competitor to a concentration of 2 pmol/µL. 2 µL of diluted probe and cold competitor were used for each binding reaction for a final amount of 20 fmol labeled probe and 4 pmol cold competitor (200 fold excess) in each reaction.

Binding reactions were set-up in a 20 µL volume containing 1× Binding Buffer (10 mM Tris, 50 mM KCl, 1 mM DTT; pH 7.5), 2.5% Glycerol, 5 mM MgCl2, 50 ng/4 Poly dl dC, 0.05% Np-40, 0.1 mM ZnCl2, 10 mM Hepes, and 2 ug of recombinant YY1 protein. Binding reactions were pre-incubated for 20 mins at room temperature with or without the cold competitor. Labeled probe was then added to binding reactions and incubated for 80 minutes at room temperature. After the 80 min incubation 5× Loading Buffer (Thermo Scientific #20148) was added to the reaction and run on a 4-12% TBE gel using 0.5×TBE at 40 mA for 2.5 hrs at 4° C. The TBE gel was pre-run for 1 hr at 4° C. DNA was then electrophoretically transferred to a Biodyne B Nylon Membrane (pre-soaked in cold 0.5×TBE for 10 mins) at 380 mA for 30 mins at 4° C. The DNA was then crosslinked to the membrane by placing the membrane on a Dark Reader Transilluminator for 15 mins. The membrane was allowed to air dry at room temperature overnight and chemiluminescence detected the following day.

Detection of biotin-labeled DNA was done as follows. The membrane was blocked for 20 mins using Blocking Buffer (Thermo Scientific #20148). The membrane was then incubated in conjugate/blocking buffer (Thermo Scientific #20148) for 15 mins. The membrane was then washed four times with 1× Wash Buffer (Thermo Scientific #20148) for 5 mins. The membrane was then incubated in Substrate Equilibration Buffer (Thermo Scientific #20148) for 5 mins and then incubated in Substrate Working Solution (Thermo Scientific #20148) for 5 mins. The membrane was then imaged using a CCD camera using a 120 second exposure. All of these steps were performed at room temperature.

Genome Editing:

The CRISPR/Cas9 system was used to genetically engineer ESC lines. Target-specific oligonucleotides were cloned into a plasmid carrying a codon-optimized version of Cas9 with GFP (gift from R. Jaenisch). The oligos used for the cloning are included in Table S5.

TABLE S5

Oligos used in the study, related to STAR methods

| Name | Sequence (5'-3') | | Use |
|---|---|---|---|
| RAF1_prom_F | caccGACTCCCGCCATCCAAGATGG | SEQ ID NO: 8 | Target YY1 motif in Raf1 promoter |
| RAF1_prom_R | aaacCCATCTTGGATGGCGGGAGTC | SEQ ID NO: 9 | Target YY1 motif in Raf1 promoter |
| ETV4_prom_F | caccGAGCTACTTGAAAACAAATGG | SEQ ID NO: 10 | Target YY1 motif in Etv4 promoter |
| ETV4_prom_R | aaacCCATTTGTTTTCAAGTAGCTC | SEQ ID NO: 11 | Target YY1 motif in Etv4 promoter |
| yy1_sg1_F | CACCgtcttctctcttcttttcac | SEQ ID NO: 12 | Target YY1 for knock-in |
| yy1_sg1_R | AAACgtgaaaagaagagaagac | SEQ ID NO: 13 | Target YY1 for knock-in |
| YY1_gPCR_3F | ctgtgcagtgattgggtcct | SEQ ID NO: 14 | Genotyping knock-in |
| YY1_gPCR_3R | TTGCCGCTCTGCACTTAAGT | SEQ ID NO: 15 | Genotyping knock-in |
| Raf1_negative_F | GCTTCCTCACATTGAAACAGAA | SEQ ID NO. 16 | ChIP-qPCR |
| Raf1_negative_R | GGGAAGCTCTGAGAGTCCTTAT | SEQ ID NO: 17 | ChIP-qPCR |
| Raf1_ROI_F | CGCCACCAGGATGACAG | SEQ ID NO: 18 | ChIP-qPCR |
| Raf1_ROI_R | GAATGTGACCGCAACCAAC | SEQ ID NO: 19 | ChIP-qPCR |
| Etv4_negative_F | CATTTTACCTGCCCCCAGTA | SEQ ID NO: 20 | ChIP-qPCR |
| Etv4_negative_R | CAGCCTTAAACAGCCTGGAA | SEQ ID NO: 21 | ChIP-qPCR |
| Etv4_ROI_F | TTTCAAAGCCACCAAGGTCT | SEQ ID NO: 22 | ChIP-qPCR |
| Etv4_ROI_R | CAAGTAGCTCGGGGTCTCAG | SEQ ID NO: 23 | ChIP-qPCR |
| Bridge_linker_F | /5Phos/CGCGATATC/iBiodT/TATCTGACT | SEQ ID NO: 24 | ChIA-PET |

TABLE S5-continued

Oligos used in the study, related to STAR methods

| Name | Sequence (5'-3') | | Use |
|---|---|---|---|
| Bridge_linker_R | /5Phos/GTCAGATAAGATATCGCGT | SEQ ID NO: 25 | ChIA-PET |
| ligation_R | GTCTGGATCCTCGTCTTGAGCC | SEQ ID NO: 26 | Amplify template for ligation mediated DNA cyclization |
| ligation_F | CCAAGGATCCGTAAGCTAGGCT | SEQ ID NO: 27 | Amplify template for ligation mediated DNA cyclization |
| competitor_DNA | GAGCAACAACAACAACGAACCGGTTCGACC TCCCCGGCCATCTTTCGACCTCCCCGGCCA TCTTTCGACCTCCCCGGCCATCTTTCGACC TCCCCGGCCATCTTTCGACCTCCCCGGCCA TCTTTCGACCTCCCCGGCCATCTTTCGACC TCCCCGGCCATCTTTCGACCTCCCGTCGAC AGAGGCAGCAAAAGCCAGA | SEQ ID NO: 28 | Competitor DNA in ligation mediated DNA cyclization |
| Raf1_4C_forward | CAAGGGCAAGTAACCCGATC | SEQ ID NO: 29 | Non-tailed primer used to amplify Raf1 4C libraries |
| Raf1_4C_reverse | AATAGATACATCCCCCACCT | SEQ ID NO: 30 | Non-tailed primer used to amplify Raf1 4C libraries |
| Etv4_4C_forward | CAAGGGCAAGTAACCCGATC | SEQ ID NO: 31 | Non-tailed primer used to amplify Etv4 4C libraries |
| Etv4_4C_reverse | AATAGATACATCCCCCACCT | SEQ ID NO: 32 | Non-tailed primer used to amplify Etv4 4C libraries |
| EMSA_Forward | TCGCTCCCCGGCCATCTTGGCGGCTGGTGT | SEQ ID NO: 33 | Probe used in EMSA |
| EMSA_Reverse | ACACCAGCCGCCAAGATGGCCGGGGAGCGA | SEQ ID NO: 34 | Probe used in EMSA |
| etv4_p_sgT1_F | caccgAAGTAGCTCGGGGTCTCAGA | SEQ ID NO: 35 | Target dCas9/dCas9-YY1 to Etv4 promoter |
| etv4_p_sgT1_R | aaacTCTGAGACCCCGAGCTACTTc | SEQ ID NO: 36 | Target dCas9/dCas9-YY1 to Etv4 promoter |
| etv4_p_sgT2_F | caccGGTGCTCAGTAAATGTAAAC | SEQ ID NO: 37 | Target dCas9/dCas9-YY1 to Etv4 promoter |
| etv4_p_sgT2_R | aaacGTTTACATTTACTGAGCACC | SEQ ID NO: 38 | Target dCas9/dCas9-YY1 to Etv4 promoter |

The sequences of the DNA targeted (the protospacer adjacent motif is underlined) are listed below:

| Locus | Targeted DNA |
|---|---|
| Raf1_promoter | 5'-ACTCCCGCCATCCAAGATGGCGG-3'-SEQ ID NO: 39 |
| Etv4_promoter | 5'-GAGCTACTTGAAAACAAATGGAGG-3'-SEQ ID NO: 40 |
| YY1_stop_codon | 5'-GTCTTCTCTCTTCTTTTCACTGG-3'-SEQ ID NO: 41 |

For the motif deletions, five hundred thousand mES cells were transfected with 2.5 µg plasmid and sorted 48 hours later for the presence of GFP. Thirty thousand GFP-positive sorted cells were plated in a six-well plate in a 1:2 serial dilution (first well 15,000 cells, second well 7,500 cells, etc.). The cells were grown for approximately one week in 2i+LIF. Individual colonies were picked using a stereoscope into a 96-well plate. Cells were expanded and genotyped by PCR and Sanger sequencing. Clones with deletions spanning the motif were further expanded and used for experiments.

For the generation of the endogenously tagged lines, five hundred thousand mES cells were transfected with 2.5 ug Cas9 plasmid and 1.25 ug non-linearized repair plasmid 1 (pAW62.YY1.FKBP.knock-in.mCherry) and 1.25 ug non-linearized repair plasmid 2 (pAW63.YY1.FKBP.knock-in-.BFP). Cells were sorted after 48 hours for the presence of GFP. Cells were expanded for five days and then sorted again for double positive mCherry and BFP cells. Thirty thousand mCherry+/BFP+ sorted cells were plated in a six-well plate in a 1:2 serial dilution (first well 15,000 cells, second well 7,500 cells, etc). The cells were grown for approximately one week in 2i medium and then individual colonies were picked using a stereoscope into a 96-well plate. Cells were expanded and genotyped by PCR (YY1_gPCR_3F/3R, Table S3). Clones with a homozygous knock-in tag were further expanded and used for experiments.

TABLE S3

| GO Analysis, related to FIG. 7 | |
|---|---|
| Analysis Type: | PANTHER Overrepresentation Test (release 20170413) |
| Annotation Version and Release Date: | PANTHER version 11.1 Released 2016 Oct. 24 |
| Analyzed List: | Client Text Box Input (*Mus musculus*) |
| Reference List: | Mus musculus (all genes in database) |
| Bonferroni correction: | TRUE |
| Bonferroni count: | 241 |

| PANTHER GO Biological Process | # of mouse genes in category | # of genes diff expressed | # of expected genes | p value |
|---|---|---|---|---|
| metabolic process (GO: 0008152) | 6955 | 3136 | 2436.52 | 1.74E−60 |
| nitrogen compound metabolic process (GO: 0006807) | 2001 | 1034 | 701 | 3.96E−33 |
| biosynthetic process (GO: 0009058) | 1520 | 792 | 532.5 | 1.35E−25 |
| cellular component organization or biogenesis (GO: 0071840) | 1767 | 824 | 619.03 | 3.14E−14 |
| mRNA processing (GO: 0006397) | 247 | 171 | 86.53 | 1.16E−13 |
| transcription from RNA polymerase II promoter (GO: 0006366) | 1212 | 585 | 424.6 | 4.25E−12 |
| mRNA splicing, via spliceosome (GO: 0000398) | 185 | 127 | 64.81 | 1.07E−09 |
| cellular component organization (GO: 0016043) | 1627 | 729 | 569.98 | 3.84E−09 |
| DNA metabolic process (GO: 0006259) | 344 | 197 | 120.51 | 1.75E−08 |
| phosphate-containing compound metabolic process (GO: 0006796) | 1251 | 563 | 438.26 | 5.19E−07 |
| tRNA metabolic process (GO: 0006399) | 108 | 79 | 37.84 | 7.58E−07 |
| RNA splicing, via transesterification reactions (GO: 0000375) | 144 | 97 | 50.45 | 8.20E−07 |
| mitosis (GO: 0007067) | 355 | 194 | 124.37 | 8.23E−07 |
| DNA repair (GO: 0006281) | 162 | 104 | 56.75 | 2.55E−06 |
| protein targeting (GO: 0006605) | 151 | 95 | 52.9 | 2.59E−05 |
| protein localization (GO: 0008104) | 236 | 134 | 82.68 | 2.73E−05 |
| chromosome segregation (GO: 0007059) | 111 | 74 | 38.89 | 7.87E−05 |
| regulation of cell cycle (GO: 0051726) | 107 | 72 | 37.48 | 8.07E−05 |
| RNA catabolic process (GO: 0006401) | 58 | 46 | 20.32 | 1.60E−04 |
| rRNA metabolic process (GO: 0016072) | 118 | 76 | 41.34 | 1.95E−04 |
| regulation of transcription from RNA polymerase II promoter (GO: 0006357) | 952 | 420 | 333.51 | 4.16E−04 |
| nuclear transport (GO: 0051169) | 99 | 65 | 34.68 | 6.33E−04 |
| transcription initiation from RNA polymerase II promoter (GO: 0006367) | 50 | 37 | 17.52 | 7.84E−03 |
| localization (GO: 0051179) | 2177 | 868 | 762.66 | 1.05E−02 |
| mRNA polyadenylation (GO: 0006378) | 25 | 23 | 8.76 | 1.07E−02 |
| mRNA 3'-end processing (GO: 0031124) | 29 | 25 | 10.16 | 1.43E−02 |
| protein folding (GO: 0006457) | 119 | 69 | 41.69 | 1.53E−02 |
| cytoskeleton organization (GO: 0007010) | 154 | 83 | 53.95 | 3.31E−02 |
| cellular amino acid metabolic process (GO: 0006520) | 253 | 124 | 88.63 | 4.96E−02 |

ChIP:

ChIP was performed as described in (Lee et al., 2006) with a few adaptations. mES cells were depleted of MEFs by splitting twice onto newly gelatinized plates without MEFs. Approximately 50 million mES cells were crosslinked for 15 minutes at room temperature by the addition of one-tenth volume of fresh 11% formaldehyde solution (11% formaldehyde, 50 mM HEPES pH 7.3, 100 mM NaCl, 1 mM EDTA pH 8.0, 0.5 mM EGTA pH 8.0) to the growth media followed by 5 min quenching with 125 mM glycine. Cells were rinsed twice with 1×PBS and harvested using a silicon scraper and flash frozen in liquid nitrogen. Jurkat cells were crosslinked for 10 minutes in media at a concentration of 1 million cells/mL. Frozen crosslinked cells were stored at −80° C.

100 μl of Protein G Dynabeads (Life Technologies #10009D) were washed 3× for 5 minutes with 0.5% BSA (w/v) in PBS. Magnetic beads were bound with 10 μg of anti-YY1 antibody (Santa Cruz, sc-281X) overnight at 4° C., and then washed 3× with 0.5% BSA (w/v) in PBS.

Cells were prepared for ChIP as follows. All buffers contained freshly prepared 1× cOmplete protease inhibitors (Roche, 11873580001). Frozen crosslinked cells were thawed on ice and then resuspended in lysis buffer I (50 mM HEPES-KOH, pH 7.5, 140 mM NaCl, 1 mM EDTA, 10% glycerol, 0.5% NP-40, 0.25% Triton X-100, 1× protease inhibitors) and rotated for 10 minutes at 4° C., then spun at 1350 rcf for 5 minutes at 4° C. The pellet was resuspended in lysis buffer II (10 mM Tris-HCl, pH 8.0, 200 mM NaCl, 1 mM EDTA, 0.5 mM EGTA, 1× protease inhibitors) and rotated for 10 minutes at 4° C. and spun at 1350 rcf for 5 minutes at 4° C. The pellet was resuspended in sonication buffer (20 mM Tris-HCl pH 8.0, 150 mM NaCl, 2 mM EDTA pH 8.0, 0.1% SDS, and 1% Triton X-100, 1× protease inhibitors) and then sonicated on a Misonix 3000 sonicator for 10 cycles at 30 seconds each on ice (18-21 W) with 60 seconds on ice between cycles. Sonicated lysates were cleared once by centrifugation at 16,000 rcf for 10 minutes at 4° C. 50 μL was reserved for input, and then the remainder was incubated overnight at 4° C. with magnetic beads bound with antibody to enrich for DNA fragments bound by the indicated factor.

Beads were washed twice with each of the following buffers: wash buffer A (50 mM HEPES-KOH pH 7.5, 140 mM NaCl, 1 mM EDTA pH 8.0, 0.1% Na-Deoxycholate, 1% Triton X-100, 0.1% SDS), wash buffer B (50 mM HEPES-KOH pH 7.9, 500 mM NaCl, 1 mM EDTA pH 8.0, 0.1% Na-Deoxycholate, 1% Triton X-100, 0.1% SDS), wash buffer C (20 mM Tris-HCl pH8.0, 250 mM LiCl, 1 mM EDTA pH 8.0, 0.5% Na-Deoxycholate, 0.5% IGEPAL C-630 0.1% SDS), wash buffer D (TE with 0.2% Triton X-100), and TE buffer. DNA was eluted off the beads by incubation at 65° C. for 1 hour with intermittent vortexing in 200 μL elution buffer (50 mM Tris-HCl pH 8.0, 10 mM EDTA, 1% SDS). Cross-links were reversed overnight at 65° C. To purify eluted DNA, 200 μL TE was added and then RNA was degraded by the addition of 2.5 μL of 33 mg/mL RNase A (Sigma, R4642) and incubation at 37° C. for 2 hours. Protein was degraded by the addition of 10 μL of 20 mg/mL proteinase K (Invitrogen, 25530049) and incubation at 55° C. for 2 hours. A phenol:chloroform:isoamyl alcohol extraction was performed followed by an ethanol precipitation. The DNA was then resuspended in 50 μL TE and used for either qPCR or sequencing.

For ChIP-qPCR experiments, qPCR was performed using Power SYBR Green mix (Life Technologies #4367659) on either a QuantStudio 5 or a QuantStudio 6 System (Life Technologies). Values displayed in the figures were normalized to the input, a negative control region, and wild-type values according to the following formulas:

$$\text{Input norm} = 2^{(Ct\_input - Ct\_ChIP)}$$

$$\text{Neg norm} = \frac{Fold_{ROI}}{Fold_{neg}}$$

$$\text{WT norm} = \frac{Neg\ norm_{mut}}{Neg\ norm_{WT}}$$

qPCRs were performed in technical triplicate, and ChIPs were performed in biological triplicate. Values were comparable across replicates. The average WT norm values and standard deviation are displayed (FIG. 6A, 6B). The primers used are listed in Table S5.

For ChIP-seq experiments, purified ChIP DNA was used to prepare Illumina multiplexed sequencing libraries. Libraries for Illumina sequencing were prepared following the Illumina TruSeq DNA Sample Preparation v2 kit. Amplified libraries were size-selected using a 2% gel cassette in the Pippin Prep system from Sage Science set to capture fragments between 200 and 400 bp. Libraries were quantified by qPCR using the KAPA Biosystems Illumina Library Quantification kit according to kit protocols. Libraries were sequenced on the Illumina HiSeq 2500 for 40 bases in single read mode.

ChIA-PET

ChIA-PET was performed using a modified version (Tang et al., 2015) of a previously described protocol (Fullwood et al., 2009). mES cells (~500 million cells, grown to ~80% confluency) were crosslinked with 1% formaldehyde at room temperature for 15 min and then neutralized with 125 mM glycine. Crosslinked cells were washed three times with ice-cold PBS, snap-frozen in liquid nitrogen, and stored at ~80° C. before further processing. Nuclei were isolated as previously described above, and chromatin was fragmented using a Misonix 3000 sonicator. Either CTCF or YY1 antibodies were used to enrich protein-bound chromatin fragments exactly as described in the ChIP-seq section. A portion of ChIP DNA was eluted from antibody-coated beads for concentration quantification and for enrichment analysis using qPCR. For ChIA-PET library construction ChIP DNA fragments were end-repaired using T4 DNA polymerase (NEB #M0203) followed by A-tailing with Klenow (NEB M0212). Bridge linker oligos (Table S5) were annealed to generate a double stranded bridge linker with T-overhangs. 800 ng of bridge linker was added and the proximity ligation was performed overnight at 16° C. in 1.5 mL volume. Unligated DNA was then digested with exonuclease and lambda nuclease (NEB M0262S, M0293S). DNA was eluted off the beads by incubation at 65° C. for 1 hour with intermittent vortexing in 200 μL elution buffer (50 mM Tris-HCl pH 8.0, 10 mM EDTA, 1% SDS). Cross-links were reversed overnight at 65° C. To purify eluted DNA, 200 μL TE was added and then RNA was degraded by the addition of 2.5 μL of 33 mg/mL RNase A (Sigma, R4642) and incubation at 37° C. for 2 hours. Protein was degraded by the addition of 10 μL of 20 mg/mL proteinase K (Invitrogen, 25530049) and incubation at 55° C. for 2 hours.

A phenol:chloroform:isoamyl alcohol extraction was performed followed by an ethanol precipitation. Precipitated DNA was resuspended in Nextera DNA resuspension buffer (Illumina FC-121-1030). The DNA was then tagmented with the Nextera Tagmentation kit (Illumina FC-121-1030). 5 μL of transposon was used per 50 ng of DNA. The tagmented library was purified with a Zymo DNA Clean & Concentrator (Zymo D4003) and bound to streptavidin beads (Life Technologies #11205D) to enrich for ligation junctions (containing the biotinylated bridge linker). 12 cycles of the polymerase chain reaction were performed to amplify the library using standard Nextera primers (Illumina FC-121-1030). The amplified library was size-selected (350-500 bp) and sequenced using paired-end sequencing on an Illumina Hi-Seq 2500 platform.

HiChIP

HiChIP was performed as described in (Mumbach et al., 2016) with a few modifications. Ten million cells cross-linked for 10 min at room temperature with 1% formaldehyde in growth media and quenched in 0.125 M glycine. After washing twice with ice-cold PBS, the supernatant was aspirated and the cell pellet was flash frozen in liquid nitrogen and stored at −80° C.

Cross-linked cell pellets were thawed on ice, resuspended in 800 µL of ice-cold Hi-C lysis buffer (10 mM Tris-HCl pH 8.0, 10 mM NaCl, and 0.2% IGEPAL CA-630 with 1× cOmplete protease inhibitor (Roche, 11697498001)), and incubated at 4° C. for 30 minutes with rotation. Nuclei were pelleted by centrifugation at 2500 rcf for 5 min at 4° C. and washed once with 500 µL of ice-cold Hi-C lysis buffer. After removing supernatant, nuclei were resuspended in 100 µL of 0.5% SDS and incubated at 62° C. for 10 minutes. SDS was quenched by adding 335 µL of 1.5% Triton X-100 and incubating for 15 minutes at 37° C. After the addition of 50 µL of 10×NEB Buffer 2 (NEB, B7002) and 375 U of MboI restriction enzyme (NEB, R0147), chromatin was digested at 37° C. for 2 hours with rotation. Following digestion, MboI enzyme was heat inactivated by incubating the nuclei at 62° C. for 20 min.

To fill in the restriction fragment overhangs and mark the DNA ends with biotin, 52 µL of fill-in master mix, containing 37.5 µL of 0.4 mM biotin-dATP (Invitrogen, 19524016), 1.5 µL of 10 mM dCTP (Invitrogen, 18253013), 1.5 µL of 10 mM dGTP (Invitrogen, 18254011), 1.5 µL of 10 mM dTTP (Invitrogen, 18255018), and 10 µL of 5 U/µL DNA Polymerase I, Large (Klenow) Fragment (NEB, M0210), was added and the tubes were incubated at 37° C. for 1 hour with rotation. Proximity ligation was performed by addition of 947 µL of ligation master mix, containing 150 µL of 10×NEB T4 DNA ligase buffer (NEB, B0202), 125 µL of 10% Triton X-100, 7.5 µL of 20 mg/mL BSA (NEB, B9000), 10 µL of 400 U/pt T4 DNA ligase (NEB, M0202), and 655.5 µL of water, and incubation at room temperature for 4 hours with rotation.

After proximity ligation, nuclei were pelleted by centrifugation at 2500 rcf for 5 minutes and resuspended in 1 mL of ChIP sonication buffer (50 mM HEPES-KOH pH 7.5, 140 mM NaCl, 1 mM EDTA pH 8.0, 1 mM EGTA pH 8.0, 1% Triton X-100, 0.1% sodium deoxycholate, and 0.1% SDS with protease inhibitor). Nuclei were sonicated using a Covaris S220 for 6 minutes with the following settings: fill level 8, duty cycle 5, peak incidence power 140, cycles per burst 200. Sonicated chromatin was clarified by centrifugation at 16,100 rcf for 15 min at 4° C. and supernatant was transferred to a tube. 60 µL of protein G magnetic beads were washed three times with sonication buffer, resuspended in 50 µL of sonication buffer. Washed beads were then added to the sonicated chromatin and incubated for 1 hour at 4° C. with rotation. Beads were then separated on a magnetic stand and the supernatant was transferred to a new tube. 7.5 µg of H3K27ac antibody (Abcam, ab4729) or 7.5 ug of YY1 antibody (Abcam, ab109237) was added to the tube and the tube was incubated overnight at 4° C. with rotation. For YY1 six reactions were carried out and pooled prior to tagmentation. The next day, 60 µL, of protein G magnetic beads were washed three times in 0.5% BSA in PBS and washed once with sonication buffer before being resuspended in 100 µL of sonication buffer and added to each sample tube. Samples were incubated for 2 hours at 4° C. with rotation. Beads were then separated on a magnetic stand and washed three times with 1 mL of high salt sonication buffer (50 mM HEPES-KOH pH 7.5, 500 mM NaCl, 1 mM EDTA pH 8.0, 1 mM EGTA pH 8.0, 1% Triton X-100, 0.1% sodium deoxycholate, 0.1% SDS) followed by three times with 1 mL of LiCl wash buffer (20 mM Tris-HCl pH 8.0, 1 mM EDTA pH 8.0, 250 mM LiCl, 0.5% IGEPAL CA-630, 0.5% sodium deoxycholate, 0.1% SDS) and once with 1 mL of TE with salt (10 mM Tris-HCl pH 8.0, 1 mM EDTA pH 8.0, 50 mM NaCl). Beads were then resuspended in 200 µL of elution buffer (50 mM Tris-HCl pH 8.0, 10 mM EDTA pH 8.0, 1% SDS) and incubated at 65° C. for 15 minutes to elute. To purify eluted DNA, RNA was degraded by the addition of 2.5 µL of 33 mg/mL RNase A (Sigma, R4642) and incubation at 37° C. for 2 hours. Protein was degraded by the addition of 10 µL of 20 mg/mL proteinase K (Invitrogen, 25530049) and incubation at 55° C. for 45 minutes. Samples were then incubated at 65° C. for 5 hours to reverse cross-links. DNA was then purified using Zymo DNA Clean and Concentrate 5 columns (Zymo, D4013) according to manufacturer's protocol and eluted in 14 µL water. The amount of eluted DNA was quantified by Qubit dsDNA HS kit (Invitrogen, Q32854).

Tagmentation of ChIP DNA was performed using the Illumina Nextera DNA Library Prep Kit (Illumina, FC-121-1030). First, 5 µL of streptavidin C1 magnetic beads (Invitrogen, 65001) was washed with 1 mL of tween wash buffer (5 mM Tris-HCl pH 7.5, 0.5 mM EDTA pH 8.0, 1 M NaCl, 0.05% Tween-20) and resuspended in 10 µL of 2× biotin binding buffer (10 mM Tris-HCl pH 7.5, 1 mM EDTA pH 8.0, 2 M NaCl). 54.19 ng purified DNA was added in a total volume of 10 µL, of water to the beads and incubated at room temperature for 15 minutes with agitation every 5 minutes. After capture, beads were separated with a magnet and the supernatant was discarded. Beads were then washed twice with 500 µL of tween wash buffer, incubating at 55° C. for 2 minutes with shaking for each wash. Beads were resuspended in 25 µL of Nextera Tagment DNA buffer. To tagment the captured DNA, 3.5 µL of Nextera Tagment DNA Enzyme 1 was added with 21.5 µL of Nextera Resuspension Buffer and samples were incubated at 55° C. for 10 minutes with shaking. Beads were separated on a magnet and supernatant was discarded. Beads were washed with 500 µL of 50 mM EDTA at 50° C. for 30 minutes, then washed three times with 500 µL of tween wash buffer at 55° C. for 2 minutes each, and finally washed once with 500 µL of 10 mM Tris-HCl pH 7.5 for 1 minute at room temperature. Beads were separated on a magnet and supernatant was discarded.

To generate the sequencing library, PCR amplification of the tagmented DNA was performed while the DNA is still bound to the beads. Beads were resuspended in 15 μL of Nextera PCR Master Mix, 5 μL of Nextera PCR Primer Cocktail, 5 μL of Nextera Index Primer 1, 5 μL of Nextera Index Primer 2, and 20 μL of water. DNA was amplified with 8 cycles of PCR. After PCR, beads were separated on a magnet and the supernatant containing the PCR amplified library was transferred to a new tube, purified using the Zymo DNA Clean and Concentrate-5 (Zymo D4003T) kit according to manufacturer's protocol, and eluted in 14 μL water. Purified HiChIP libraries were size selected to 300-700 bp using a Sage Science Pippin Prep instrument according to manufacturer's protocol and subject to paired-end sequencing on an Illumina HiSeq 2500. Libraries were initially sequenced with 100×100 bp paired-end sequencing. A second round of sequencing was done on the same libraries with 50×50 bp paired-end sequencing.

4C-seq:

A modified version of 4C-seq (van de Werken et al., 2012; Van De Werken et al., 2012) was developed. The major change was the proximity ligation is performed in intact nuclei (in situ). This change was incorporated because previous work has noted that in situ ligation dramatically decreases the rate of chimeric ligations and background interactions (Nagano et al., 2015; Rao et al., 2014).

Approximately 5 million mES cells were trypsinized and then resuspended in 5 mL 10% FBS/PBS. 5 mL of 4% formaldehyde in 10% FBS/PBS was added and cells were crosslinked for 10 minutes. Glycine was added to a final concentration of 0.125 M and cells were centrifuged at 300 rcf for 5 minutes. Cells were washed twice with PBS, transferred to a 1.5 mL Eppendorf tube, snap frozen and stored at −80° C.

Pellets were gently resuspended in Hi-C lysis buffer (10 mM Tris-HCl pH 8, 10 mM NaCl, 0.2% Igepal) with 1× cOmplete protease inhibitors (Roche 11697498001). Cells were incubated on ice for 30 minutes then washed once with 500 μL of ice-cold Hi-C lysis buffer with no protease inhibitors. Pellets were resuspended in 50 μL of 0.5% SDS and incubated at 62° C. for 7 minutes. 145 μL of $H_2O$ and 25 μL of 10% Triton X-100 were added and tubes incubated at 37° C. for 15 minutes. 25 μL of the appropriate 10× New England Biolabs restriction enzyme buffer and 200 units of enzyme were added and the chromatin was incubated at 37° C. degrees in a thermomixer at 500 RPM for four hours, 200 more units of enzyme was added and the reaction was incubated overnight at 37° C. degrees in a thermomixer at 500 RPM, then 200 more units were added and the reaction was incubated another four hours at 37° C. degrees in a thermomixer at 500 RPM. DpnII (NEB) was used as the primary cutter for both Raf1 and Etv4. Restriction enzyme was inactivated by heating to 62° C. for 20 minutes while shaking at 500 rpm. Proximity ligation was performed in a total of 1200 μL with 2000 units of T4 DNA ligase (NEB M020) for six hours at room temperature. After ligation samples were spun down for 5 minutes at 2500 rcf and resuspended in 300 μL 10 mM Tris-HCl, 1% SDS and 0.5 mM NaCl with 1000 units of Proteinase K. Crosslinks were reversed by incubation overnight at 65° C.

Samples were then phenol-chloroform extracted and ethanol precipitated and the second digestion was performed overnight in 450 μL with 50 units of restriction enzyme. BfaI (NEB R0568S) was used for Etv4 and CviQI (NEB R0639S) was used for Raf1. Samples were phenol-chloroform extracted and ethanol precipitated and the second ligation was performed in 14 mL total with 6700 units of T4 DNA ligase (NEB M020) at 16° C. overnight. Samples were ethanol precipitated, resuspended in 500 μL Qiagen EB buffer, and purified with a Qiagen PCR purification kit.

PCR amplification was performed with 16 50 μL PCR reactions using Roche Expand Long Template polymerase (Roche 11759060001). Reaction conditions are as follows: 11.2 μL Roche Expand Long Template Polymerase, 80 μL of 10× Roche Buffer 1, 16 μL of 10 mM dNTPs (Promega PAU1515), 112 μL of 10 uM forward primer, 112 μL of 10 uM reverse primer (Table S5), 200 ng template, and milli-q water until 800 μL total. Reactions were mixed and then distributed into 16 50 μL reactions for amplification. Cycling conditions were a "Touchdown PCR" based on reports that this decreases non-specific amplification of 4C libraries (Ghavi-Helm et al., 2014). The conditions are: 2' 94° C., 10" 94° C., 1' 63° C., 3' 68° C., repeat steps 2-4 but decrease annealing temperature by one degree, until 53° C. is reached at which point the reaction is cycled an additional 15 times at 53° C., after 25 total cycles are performed the reaction is held for 5' at 68° C. and then 4° C. Libraries were cleaned-up using a Roche PCR purification kit (Roche 11732676001) using 4 columns per library. Reactions were then further purified with Ampure XP beads (Agencourt A63882) with a 1:1 ratio of bead solution to library following the manufactures instructions. Samples were then quantified with Qubit and the KAPA Biosystems Illumina Library Quantification kit according to kit protocols. Libraries were sequenced on the Illumina HiSeq 2500 for 40 bases in single read mode.

RNA-Isolation, qRT-PCR and Sequencing

RNA was isolated using the RNeasy Plus Mini Kit (QIAGEN, 74136) according to manufacturer's instructions.

For RT-qPCR assays, reverse transcription was performed using SuperScript III Reverse Transcriptase (Invitrogen, 18080093) with oligo-dT primers (Promega, C1101) according to manufacturers' instructions. Quantitative real-time PCR was performed on Applied Biosystems 7000, QuantStudio 5, and QuantStudio 6 instruments using TaqMan probes for Raf1 (Applied Biosystems, Mm00466513_m1) and Etv4 (Applied Biosystems, Mm00476696_m1) in conjunction with TaqMan Universal PCR Master Mix (Applied Biosystems, 4304437) according to manufacturer's instructions.

For RNA-seq experiments, stranded polyA selected libraries were prepared using the TruSeq Stranded mRNA Library Prep Kit (Illumina, RS-122-2101) according to manufacturer's standard protocol. Libraries were subject to 40 bp single end sequencing on an Illumina HiSeq 2500 instrument.

YY1 Degradation

A clonal homozygous knock-in line expressing FKBP tagged YY1 was used for the degradation experiments. Cells were grown two passages off MEFs and then treated with dTAG-47 at a concentration of 500 nM for 24 hours.

dTAG-47 Washout Experiments

The homozygous knock-in line expressing FKBP tagged YY1 was cultured on 2i+LIF media. Cells were treated with dTAG-47 at a concentration of 500 nM for 24 hours. After 24 hours of drug treatment, cells were washed three times with PBS and passaged onto a new plate. Cells were then fed daily and passaged onto a new plate every 48 hours until YY1 protein levels were restored (5 days after drug withdrawal). Cells were then harvested for protein or RNA extraction or cross-linked for ChIP or HiChIP.

dTAG-47 Synthesis

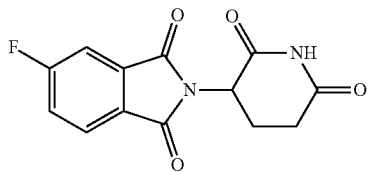 [SMILES: O=C1CCC(N2C(=O)c3ccc(F)cc3C2=O)C(=O)N1]

2-(2,6-dioxopiperidin-3-yl)-5-fluoroisoindoline-1,3-dione 4-fluorophthalic anhydride (3.32 g, 20 mmol, 1 eq) and 3-aminopiperidine-2,6-dione hydrochloride salt (3.620 g, 22 mmol, 1.1 eq) were dissolved in AcOH (50 mL) followed by potassium acetate (6.08 g, 62 mmol, 3.1 eq). The mixture was fitted with an air condenser and heated to 90° C. After 16 hours, the mixture was diluted with 200 mL water and cooled over ice. The slurry was then centrifuged (4000 rpm, 20 minutes, 4° C.) and decanted. The remaining solid was then resuspended in water, centrifuged and decanted again. The solid was then dissolved in MeOH and filtered through a silica plug (that had been pre-wetted with MeOH), washed with 50% MeOH/DCM and concentrated under reduced pressure to yield the desired product as a grey solid (2.1883 g, 7.92 mmol, 40%).

$^1$H NMR (500 MHz, DMSO-d$_6$) δ 11.13 (s, 1H), 8.01 (dd, J=8.3, 4.5 Hz, 1H), 7.85 (dd, J=7.4, 2.2 Hz, 1H), 7.72 (ddd, J=9.4, 8.4, 2.3 Hz, 1H), 5.16 (dd, J=12.9, 5.4 Hz, 1H), 2.89 (ddd, J=17.2, 13.9, 5.5 Hz, 1H), 2.65-2.51 (m, 2H), 2.07 (dtd, J=12.9, 5.3, 2.2 Hz, 1H).

LCMS 277.22 (M+H).

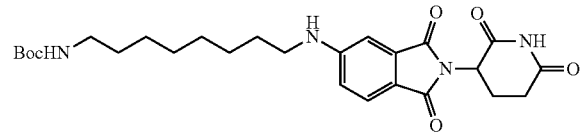 [SMILES: CC(C)(C)OC(=O)NCCCCCCCCNc1ccc2c(c1)C(=O)N(C1CCC(=O)NC1=O)C2=O]

tert-butyl (8-((2-(2,6-dioxopiperidin-3-yl)-1,3-dioxoisoindolin-5-yl)amino)octyl)carbamate 2-(2,6-dioxopiperidin-3-yl)-5-fluoroisoindoline-1,3-dione (294 mg, 1.06 mmol, 1 eq) and tert-butyl (8-aminooctyl) carbamate (286 mg, 1.17 mmol, 1.1 eq) were dissolved in NMP (5.3 mL, 0.2M). DIPEA (369 μL, 2.12 mmol, 2 eq) was added and the mixture was heated to 90° C. After 19 hours, the mixture was diluted with ethyl acetate and washed with water and three times with brine. The organic layer was dried over sodium sulfate, filtered and concentrated under reduced pressure. Purification by column chromatography (ISCO, 12 g column, 0-10% MeOH/DCM, 30 minute gradient) gave the desired product as a brown solid (0.28 g, 0.668 mmol, 63%).

$^1$H NMR (500 MHz, Chloroform-d) δ 8.12 (s, 1H), 7.62 (d, J=8.3 Hz, 1H), 7.02 (s, 1H), 6.81 (d, J=7.2 Hz, 1H), 4.93 (dd, J=12.3, 5.3 Hz, 1H), 4.51 (s, 1H), 3.21 (t, J=7.2 Hz, 2H), 3.09 (d, J=6.4 Hz, 2H), 2.90 (dd, J=18.3, 15.3 Hz, 1H), 2.82-2.68 (m, 2H), 2.16-2.08 (m, 1H), 1.66 (p, J=7.2 Hz, 2H), 1.37 (d, J=62.3 Hz, 20H).

LCMS 501.41 (M+H).

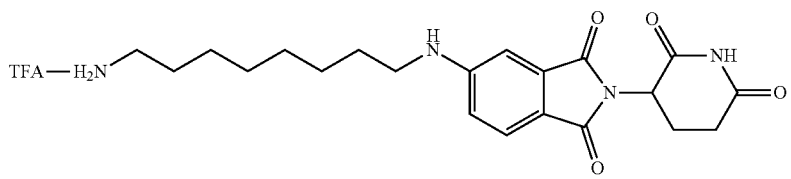

5-((8-aminooctyl)amino)-2-(2,6-dioxopiperidin-3-yl) isoindoline-1,3-dione trifluoroacetate tert-butyl (8-((2-(2,6-dioxopiperidin-3-yl)-1,3-dioxoisoindolin-5-yl)amino)octyl)carbamate (334.5 g, 0.668 mmol, 1 eq) was dissolved in TFA (6.7 mL) and heated to 50° C. After 1 hour, the mixture was cooled to room temperature, diluted with DCM and concentrated under reduced pressure. The crude material was triturated with diethyl ether and dried under vacuum to give a dark yellow foam (253.1 mg, 0.492 mmol, 74%).

$^1$H NMR (500 MHz, Methanol-d$_4$) δ 7.56 (d, J=8.4 Hz, 1H), 6.97 (d, J=2.1 Hz, 1H), 6.83 (dd, J=8.4, 2.2 Hz, 1H), 5.04 (dd, J=12.6, 5.5 Hz, 1H), 3.22 (t, J=7.1 Hz, 2H), 2.94-2.88 (m, 2H), 2.85-2.68 (m, 3H), 2.09 (ddd, J=10.4, 5.4, 3.0 Hz, 1H), 1.70-1.61 (m, 4H), 1.43 (d, J=19.0 Hz, 8H).
LCMS 401.36 (M+H).

1H), 4.11 (d, J=13.6 Hz, 1H), 3.86 (t, J=7.3 Hz, 1H), 3.80-3.76 (m, 7H), 3.71-3.65 (m, 8H), 3.14 (ddt, J=17.2, 13.3, 7.1 Hz, 4H), 2.90-2.80 (m, 1H), 2.77-2.40 (m, 6H), 2.24 (d, J=13.8 Hz, 1H), 2.12-1.97 (m, 3H), 1.92 (dq, J=14.0, 7.8 Hz, 1H), 1.67 (ddt, J=54.1, 14.7, 7.1 Hz, 5H), 1.50 (dd, J=46.1, 14.1 Hz, 3H), 1.38 (dt, J=14.5, 7.1 Hz, 4H), 1.28-1.17 (m, 6H), 0.87 (t, J=7.3 Hz, 3H).

$^{13}$C NMR (126 MHz, MeOD) δ 174.78, 174.69, 172.53, 171.71, 170.50, 169.66, 169.31, 156.22, 155.41, 154.62, 150.36, 148.83, 138.05, 136.90, 136.00, 134.93, 130.54, 128.40, 126.21, 123.14, 121.82, 117.94, 116.62, 113.58, 113.05, 112.73, 106.59, 70.69, 68.05, 61.06, 56.59, 56.51, 56.45, 53.42, 50.99, 50.31, 45.01, 44.09, 40.07, 37.44, 32.22, 32.17, 30.38, 30.32, 30.18, 29.84, 29.32, 28.05, 27.80, 27.58, 26.38, 23.87, 21.95, 12.57.
LCMS: 1077.35 (M+H)

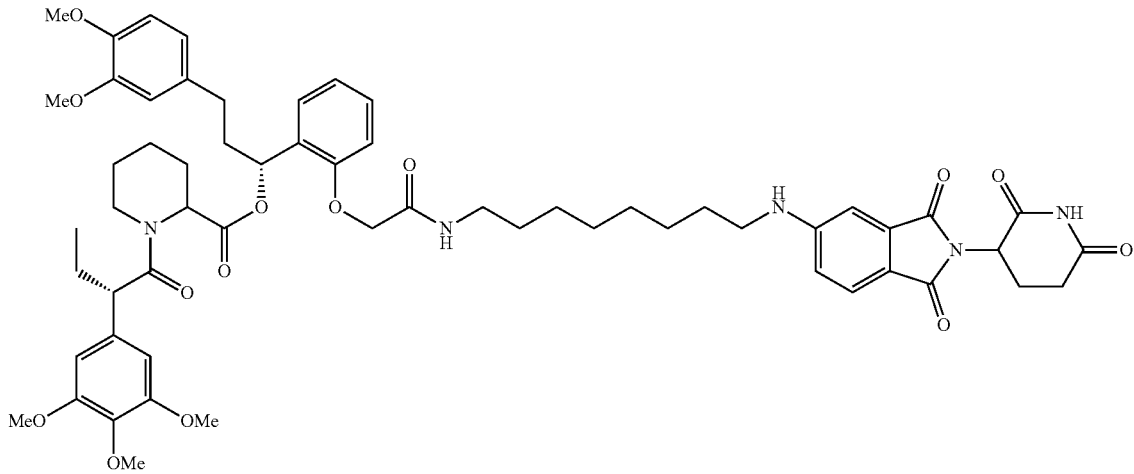 [SMILES: CC[C@H](C(=O)N1CCCCC1C(=O)O[C@H](CCc1ccc(OC)c(OC)c1)c1ccccc1OCC(=O)NCCCCCCCCNc1ccc2c(c1)C(=O)N(C1CCC(=O)NC1=O)C2=O)c1cc(OC)c(OC)c(OC)c1]

(2S)-(1R)-3-(3,4-dimethoxyphenyl)-1-(2-(2-((8-((2-(2,6-dioxopiperidin-3-yl)-1,3-dioxoisoindolin-5-yl)amino)octyl)amino)-2-oxoethoxy)phenyl)propyl 1-((S)-2-(3,4,5-trimethoxyphenyl)butanoyl)piperidine-2-carboxylate (dTAG47)

5-((8-aminooctyl)amino)-2-(2,6-dioxopiperidin-3-yl) isoindoline-1,3-dione trifluoroacetate salt (10.3 mg, 0.020 mmol, 1 eq) was added to 2-(2-((R)-3-(3,4-dimethoxyphenyl)-1-(((S)-1-((S)-2-(3,4,5-trimethoxyphenyl)butanoyl)piperidine-2-carbonyl)oxy)propyl)phenoxy)acetic acid (13.9 mg, 0.020 mmol, 1 eq) as a 0.1 M solution in DMF (200 microliters) at room temperature. DIPEA (10.5 microliters, 0.060 mmol, 3 eq) and HATU (7.6 mg, 0.020 mmol, 1 eq) were then added. After 29.5 hours, the mixture was diluted with EtOAc, and washed with 10% citric acid (aq), brine, saturated sodium bicarbonate, water and brine. The organic layer was dried over sodium sulfate, filtered and condensed. Purification by column chromatography (ISCO, 4 g silica column, 0-10% MeOH/DCM, 25 minute gradient) gave the desired product as a yellow solid (14.1 mg, 0.0131 mmol, 65%).

$^1$H NMR (500 MHz, Methanol-d$_4$) δ 7.55 (d, J=8.4 Hz, 1H), 7.26-7.20 (m, 1H), 6.99-6.93 (m, 1H), 6.89 (t, J=7.7 Hz, 2H), 6.82 (dd, J=8.4, 2.3 Hz, 2H), 6.77 (d, J=7.5 Hz, 1H), 6.74 (d, J=1.9 Hz, 1H), 6.63 (d, J=9.6 Hz, 2H), 6.12 (dd, J=8.1, 6.0 Hz, 1H), 5.40 (d, J=4.3 Hz, 1H), 5.03 (dd, J=13.1, 5.5 Hz, 1H), 4.57 (d, J=14.9 Hz, 1H), 4.46-4.39 (m, In Vitro DNA Circularization Assay First, two plasmids (pAW49, pAW79) were generated. pAW49 contains YY1 binding sites separated by ~3.5 kb of intervening DNA. pAW79 is identical except it contains filler DNA instead of the YY1 motifs. The intervening DNA was chosen based on looking at YY1 ChIP-seq and motif distribution in mES cells to identify regions that lacked YY1 occupancy and YY1 binding motifs. The YY1 binding motifs were chosen based on successful EMSAs (Sigova et al., 2015). Approximately 200 bp of sequence was added between the binding motifs and the termini in order to provide flexibility for the termini to ligate. The plasmid was built using Gibson assembly.

Next, a PCR was run using plasmid as a template to generate a linear piece of DNA (Table S5). This PCR product was PCR purified (Qiagen 28104) and then digested with BamHI (NEB R3136) and PCR purified. The BamHI digested template was used in the ligation assay.

The ligation assay was carried out as follows. Reactions were prepared on ice in 66 μL with the following components:

BSA control: 0.25 nM DNA, 1× T4 DNA ligase buffer (NEB B0202S), H2O, 0.12 μg/μL of BSA
YY1: 0.25 nM DNA, 1× T4 DNA ligase buffer (NEB B0202S), H2O, 0.12 μg/μL of YY1
YY1+competitor: 0.25 nM DNA, 1× T4 DNA ligase buffer (NEB B0202S), H2O, 0.12 μg/μL of YY1, 100 nM competitor DNA (Table S5)

Assuming an extinction coefficient for YY1 of 19940 M$^{-1}$ cm$^{-1}$ and 75% purity, that gives an approximate YY1 molar concentration of ~3 uM.

Reactions were incubated at 20° C. for 20 minutes to allow binding of YY1 to the DNA. For each timepoint 6 µL of the reaction was withdrawn and quenched in a total volume of 9 µL with a final concentration of 30 mM EDTA, 1×NEB loading dye (NEB, B7024S), 1 ug/µL of proteinase K, and heated at 65° C. for 5 minutes. Timepoint 0 was taken and then 600 units of T4 DNA ligase (NEB M0202) was added and the reaction was carried out at 20° C. Indicated timepoints were taken and then samples were run on a 4-20% TBE gradient gel for three hours at 120 V. The gel was stained with SYBR Gold (Life Technologies S11494) and imaged with a CCD camera.

Quantification was done using Image Lab version 5.2.1 (Bio-Rad Laboratories). First, band density of the starting product and ligation product were measured. Then the percent circularized was calculated: (ligation product)/(ligation product+starting band)*100. In FIG. 3 to facilitate visualization overexposed gels are shown. For the quantification exposures were used that did not have any overexposed pixels.

Co-Immunoprecipitation

V6.5 mESCs were transfected with pcDNA3 FLAG YY1 and pcDNA3 FLAG HA using Lipofectamine 3000 (Life Technologies #L3000001) according to the manufacturer's instructions. Briefly, cells were split and 8 million cells were plated onto a gelatinized 15 cm plate. 7.5 µg of each plasmid was mixed with 30 µL P3000 reagent and 75 µL Lipofectamine 3000 reagent (Life Technologies #L3000001) in 1250 µL of DMEM (Life technologies #11995-073). After ~12-16 hours media was changed.

Cells were harvested 48 hours after transfection by washing twice with ice-cold PBS and collected by scraping in ice-cold PBS. Harvested cells were centrifuged at 1,000 rcf for 3 minutes to pellet cells. Supernatant was discarded and cell pellets were flash frozen and stored at −80° C. until ready to prepare nuclear extract. For each 15 cm plate of cells, frozen cell pellets were resuspended in 5 mL of ice-cold hypotonic lysis buffer (20 mM HEPES-KOH pH 7.5, 20% glycerol, 10 mM NaCl, 0.1% Triton X-100, 1.5 mM MgCl$_2$, 0.5 mM DTT and protease inhibitor (Roche, 11697498001)) and incubated on ice for 10 minutes to extract nuclei. Nuclei were pelleted by centrifugation at 14,000 rcf for 10 minutes at 4° C. Supernatant was discarded and nuclei were resuspended in 0.5 mL of ice-cold nuclear extraction buffer (20 mM HEPES-KOH pH 7.5, 20% glycerol, 250 mM NaCl, 0.1% Triton X-100, 1.5 mM MgCl$_2$ and protease inhibitor) and incubated for 1 hour at 4° C. with rotation. Lysates were clarified by centrifugation at 14,000 rcf for 10 minutes at 4° C. Nuclear extract, supernatant, was transferred to a new tube and diluted with 1 mL of ice-cold dilution buffer (20 mM HEPES-KOH pH 7.5, 10% glycerol, 100 mM NaCl, 0.1% Triton X-100, 1.5 mM MgCl$_2$, 0.2 mM EDTA, 0.5 mM DTT and protease inhibitor). Protein concentration of extracts was quantified by BCA assay (Thermo Scientific, 23225) and protein concentration was adjusted to 400 µg/mL by addition of appropriate volume of 1:2 nuclear extraction buffer:dilution buffer. For RNase A-treated nuclear extract experiments, 250 µL of nuclear extract (100 µg) was treated by addition of 7.5 µL of 33 mg/mL RNase A (Sigma, R4642) or 18.75 µL of 20 U/µL SUPERase In RNase Inhibitor (Invitrogen, AM2696) followed by incubation at 37° C. for 10 minutes. For all experiments, an aliquot of extract was saved and stored at −80° C. for use as an input sample after immunoprecipitation.

To prepare beads for immunoprecipitation of FLAG-tagged and HA-tagged YY1 from nuclear extract, 50 µL of protein G magnetic beads per immunoprecipitation was washed three times with 1 mL of blocking buffer (0.5% BSA in PBS), rotating for 5 minutes at 4° C. for each wash. After separation on a magnet, beads were resuspended in 250 µL of blocking buffer. After addition of 5 µg of anti-FLAG (Sigma, F7425)), anti-HA (Abcam, ab9110), or normal IgG (Millipore, 12-370) antibody, beads were allowed to incubate for at least 1 hour at 4° C. with rotation to bind antibody. After incubation, beads were washed three times with 1 mL of blocking buffer, rotating for 5 minutes at 4° C. for each wash.

Washed beads were separated on a magnet and the supernatant was discarded before resuspending in 250 µL of nuclear extract (100 µg). Beads were allowed to incubate with extract overnight at 4° C. with rotation. The following morning, beads were washed five times with 1 mL of ice-cold wash buffer, rotating for 5 minutes at 4° C. for each wash. Washed beads were resuspended in 100 µL of 1× XT sample buffer (Biorad, 1610791) with 100 mM DTT and incubated at 95° C. for 10 min. Beads were separated on a magnet and supernatant containing immunoprecipitated material was transferred to a new tube.

To assay immunoprecipitation results by western blot, 10 µL of each samples was run on a 4-20% Bis-Tris gel (Bio-rad, 3450124) using XT MOPS running buffer (Bio-rad, 1610788) at 80 V for 20 minutes, followed by 150 V until dye front reached the end of the gel. Protein was then wet transferred to a 0.45 µm PVDF membrane (Millipore, IPVH00010) in ice-cold transfer buffer (25 mM Tris, 192 mM glycine, 20% methanol) at 250 mA for 2 hours at 4° C. After transfer the membrane was blocked with 5% non-fat milk in TBS for 1 hour at room temperature, shaking. Membrane was then incubated with 1:50,000 anti-FLAG-HRP (Sigma, A8592), 1:25:000 anti-HA-HRP (Cell Signaling, 2999), or anti-OCT3/4 (C-10, Santa Cruz sc-5279) 1:2000 antibody diluted in 5% non-fat milk in TBST and incubated overnight at 4° C., with shaking. In the morning, the membrane was washed three times with TBST for 5 min at room temperature shaking for each wash. Membranes were developed with ECL substrate (Thermo Scientific, 34080) and imaged using a CCD camera or exposed using film.

Embryoid Body Formation

Prior to differentiation, YY1-FKBP tagged knock-in mESCs were cultured in serum+LIF on irradiated MEFs. Starting 48 hours prior to the differentiation and continuing throughout the entire experiment the YY1$^-$ condition were exposed to 500 nM dTAG-47. 4,000 cells (either YY1$^-$ or YY1$^+$) were then plated into each well of a 96-well plate (Nunclon Sphera, ThermoFisher) in Embryoid Body formation media (serum-LIF). Three plates were generated for each condition. The EBs were cultured in 96-well plates for 4 days and then pooled and cultured in ultra-low attachment culture plates (Costar, Corning). After three days, cells were harvested for single-cell RNA-seq (day 7 of differentiation). Cells were harvested for single-cell RNA-seq by dissociation with Accutase for 30 minutes at 37° C. The cells were then resuspended in PBS with 0.04% BSA and then prepared for sequencing (see section on single-cell RNA-seq). Immunohistochemistry was performed after four days (day 8 of differentiation).

Immunohistochemistry

Cells were fixed in 4% paraformaldehyde in PBS and embedded in paraffin. Cells were sectioned and stained according to standard protocols using TUJI (Biolegend 801201, 1:1000), GFAP (Dako Z0344, 1:200), and Gata-4 (Abcam ab84593 1:100) primary antibodies and appropriate Alexa Fluor dye conjugated secondary antibodies (1:1000, ThermoFisher) and DAPI. Slides were mounted with Fluoro-mount G (Electron Microscopy Science) and imaged using a Zeiss LSM 710 laser scanning confocal microscope. In all images scale bars are 50 µm.

Single-Cell RNA-Seq Library Preparation

Single-cell RNA-seq libraries were prepared using the Chromium Controller (10× Genomics). Briefly, single cells in 0.04% BSA in PBS were separated into droplets and then reverse transcription and library construction was performed according to the 10× Chromium Single Cell 3' Reagent Kit User Guide and sequenced on an Illumina Hi-seq 2500.

dCas9-YY1 Tethering

First two lentiviral constructs were generated by modifying *lenti* dCAS-VP64_Blast (*lenti* dCAS-VP64 Blast was a gift from Feng Zhang (Addgene plasmid #61425), (Konermann et al., 2014)). The VP64 was removed to generate dCas9 alone (pAW91) or the human YY1 cDNA was inserted to the C-terminus to generate dCas9-YY1 (pAW90).

For virus production, HEK293T cells grown to 50-75% confluency on a 15 cm dish and then transfected with 15 ug of pAW90 or pAW91, 11.25 µg psPAX (Addgene 12260), and 3.75 µg pMD2.G (Addgene 12259). psPAX and pMD2.G were kind gifts of Didier Trono. After 12 hours, media was replaced. Viral supernatant was collected 24 hours after media replacement (36 hrs post transfection) and fresh media was added. Viral supernatant was collected again 48 hours after the media replacement (60 hours post transfection). Viral supernatant was cleared of cells by either centrifugation at 500×g for 10 minutes. The virus was concentrated with Lenti-X concentrator (Clontech 631231) per manufacturers' instructions. Concentrated virus was resuspended in mES media (serum+LIF) and added to 5 million cells in the presence of polybrene (Millipore TR-1003) at 8 ug/mL. After 24 hours, viral media was removed and fresh media containing Blasticidin (Invitrogen ant-bl-1) at 10 ug/mL. Cells were selected until all cells on non-transduced plates died.

Two additional lentiviral constructs were generated (pAW12.lentiguide-GFP, pAW13.1entiguide-mCherry) by modifying lentiGuide-puro (lentiGuide-Puro was a gift from Feng Zhang (Addgene plasmid #52963) (Sanjana et al., 2014)) to remove the puromycin and replace it either GFP or mCherry. The tethering guide RNAs (Table S5, etv4_p_sgT1_F&R, etv4p_sgT2_F&R) were then cloned into pAW12 and pAW13. Virus was generated as described above and mES cells were transduced. Double positive cells were identified and collected by flow cytometry and expanded. These expanded cell lines were analyzed by 4C-seq, ChIP-qPCR (anti-Cas9, CST 14697), and RT-qPCR exactly as described elsewhere in the methods.

Bioinformatic Analysis

ChIP-MS Data Analysis

Previously published ChIP-ms data was downloaded (Ji et al., 2015). For each mark the log 2 ratio of the immunoprecipitation over the input and over IgG was calculated. Then a high confidence set of proteins was identified by filtering out all proteins that had a log 2 fold change less than or equal to one in either the input or IgG control. Then we filtered for transcription factors using the annotation provided in the original table to end up with the 26 candidates.

Tissue Specific Expression Analysis

In order to identify candidate structuring factors that are broadly expressed across many tissues, tissue specific expression data from RNA-seq was downloaded from the Genotype-Tissue Expression (GTEx) Project (release V6p). Genes were considered to be expressed in a particular tissues if the median reads per million per kilobase for that tissue was greater than 5 (RPKM>5). Broadly expressed genes were identified as genes that were expressed in greater than 90% of the 53 tissues surveyed by GTEx.

Definition of Regulatory Regions

Throughout the disclosure, multiple analyses rely on overlaps with different regulatory regions, namely enhancers, promoters, and insulators. Here we explain how these regulatory regions were defined.

Promoters

Promoters were defined as +/−2 kilobases from the transcription start site.

Active Promoters

Active promoters were defined as +/−2 kilobases from the transcription start site that overlapped with a H3K27ac peak.

Enhancers

Enhancers were defined as H3K27ac peaks that did not overlap with a promoter.

Insulators

Insulators were defined by downloading the called insulated neighborhoods from (Hnisz et al., 2016a) (available at: http://younglab.wi.mit.edu/insulatedneighborhoods.htm). Each row represents an insulated neighborhood (defined as a SMC1 cohesin ChIA-PET interaction with both anchors overlapping a CTCF peak). The file contains six columns, columns 1-3 contain the coordinates for the left interaction anchors of the insulated neighborhoods, and columns 4-6 contain the coordinates for the right interaction anchors of the insulated neighborhoods. Columns 1-3 and 4-6 were concatenated and then filtered to identify the unique anchors. The unique loop anchors regions correspond to SMC1 ChIA-PET peaks. Insulators elements were identified as the subset of CTCF ChIP-seq peaks that overlapped the unique anchors.

Super-Enhancers

Oct4/Sox2/Nanog/Med1 super-enhancers and constituents were downloaded from (Whyte et al., 2013)

Typical-Enhancer Constituents

Oct4/Sox2/Nanog/Med1 typical-enhancer constituents were downloaded from (Whyte et al., 2013)

ChIP-Seq Data Analysis

Alignment

Reads from ChIP-seq experiments were aligned to the mm9 revision of the mouse reference genome using only annotated chromosomes 1-19, chrX, chrY, and chrM or to the hg19 revision of the human genome using only annotated chromosomes 1-22, chrX, chrY, and chrM. Alignment was performed using bowtie (Langmead et al., 2009) with parameters -best -k 1 -m 1 -sam and −1 set to read length.

Read Pileup for Display

Wiggle files representing counts of ChIP-Seq reads across the reference genome were created using MACS (Zhang et al., 2008) with parameters -w -S -space=50 -nomodel -shiftsize=200. Resulting wiggle files were normalized for sequencing depth by dividing the read counts in each bin by the millions of mapped reads in each sample and were visualized in the UCSC genome browser (Kent et al., 2002).

Gene List and Promoter List

For mouse data analysis 36,796 RefSeq transcripts were downloaded in the GTF format from the UCSC genome browser on Feb. 1, 2017. For human data analysis, 39,967 RefSeq transcripts were downloaded on Dec. 7, 2016 in the GTF format from the UCSC genome browser on Feb. 1, 2017. For each transcript, a promoter was created that is a 4,000 bp window centered on the transcription start site.

Peak Calling

Regions with an exceptionally high coverage of ChIP-Seq reads (i.e. peaks) were identified using MACS with parameters -keep-dup=auto -p1e-9 and with corresponding input control.

Heatmaps and Metagenes

Profiles of ChIP-seq and GRO-seq signal at individual regions of interest were created by quantifying the signal in reads per million per base pair (rpm/bp) in bins that equally divide each region of interest using bamToGFF (https://github.com/BradnerLab/pipeline) with parameters -m 200 -r -d. Reads used for quantification were removed of presumed PCR duplicate reads using samtools v0.1.19-44428cd rmdup (Li et al., 2009). Promoters with the same gene id, chromosome, start, and end coordinates were collapsed into one instance.

Figures 10A, 10B:
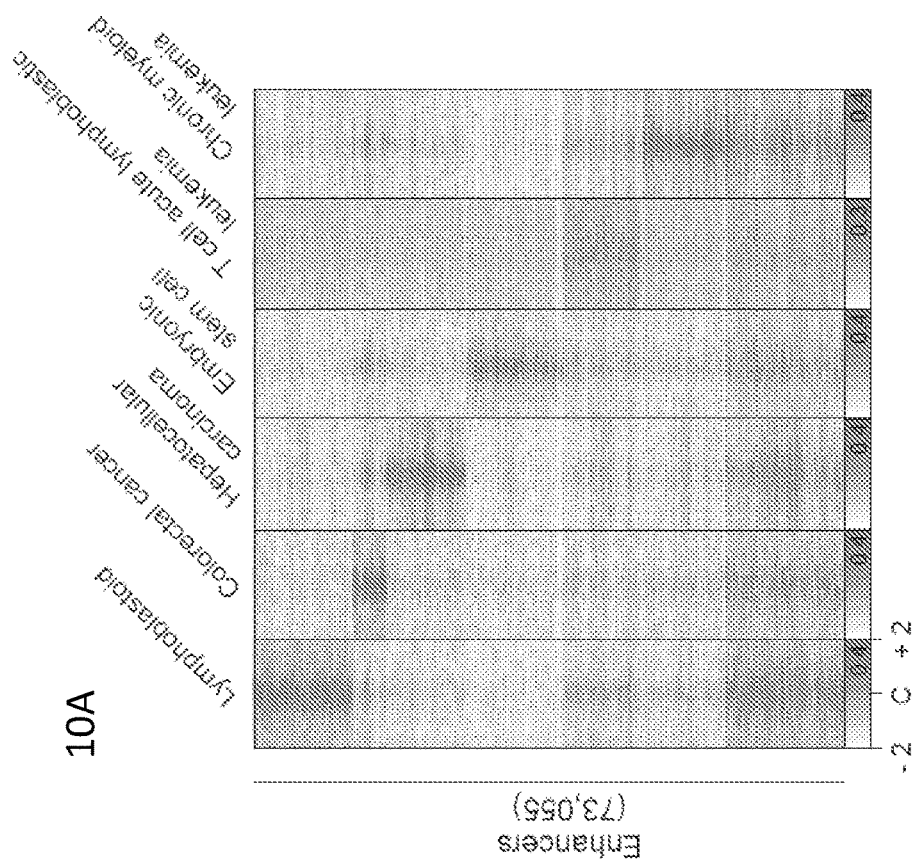
FIG. 10A-10K. YY1 generally occupies enhancers and promoters in mammalian cells.

Heatmaps of ChIP-seq profiles were used to display ChIP-seq signal at enhancer and active promoters. Each row of a heatmap represents an individual region of interest with the ChIP-seq signal profile at that region displayed in rpm/bp in a ±2 kb region centered on the region of interest. For each heatmap, the number of regions of interest are displayed in parentheses in the figure panel. See FIG. 10A-B. For murine ES cell heatmaps, ChIP-seq signal was quantified in 200 bins per region of interest. For human tissues and non-ES cell murine tissues, heatmaps were generated by quantifying ChIP-seq signal in 50 bins per region of interest.

Metagene plots were used to display the average ChIP-seq signal across related regions of interest. Metagene plots were generated for enhancer, promoter, and insulator elements, separately. The average profile (metagene) was calculated by calculating the mean ChIP-seq or GRO-seq signal profiles across the related regions of interest. For each metagene plot, the average profile is displayed in rpm/bp in a ±2 kb region centered on the regions of interest. The number of enhancers, promoters, and insulators surveyed are noted in parentheses. To facilitate comparisons of the ChIP-seq signal from a single factor between different sets of regions, the total ChIP-seq signal for each metagene analysis was quantified and is displayed in the top right corner of each metagene plot. We note that different antibodies have different immunoprecipitation efficiencies resulting in different signal intensities. Therefore, we believe that quantitative comparisons should be made across different sites in the same ChIP rather than across different ChIPs at the same site.

RNA-Seq Data Analysis

RNA-Seq Analysis

RNA-seq data was aligned and quantified using kallisto (version 0.43.0) (Bray et al., 2016) with the following parameters: -b 100 --single -l 180 -s 20 using the mm9 RefSeq transcriptome (downloaded on Feb. 1, 2017). The output files represent the estimated transcript counts.

Figure 5:
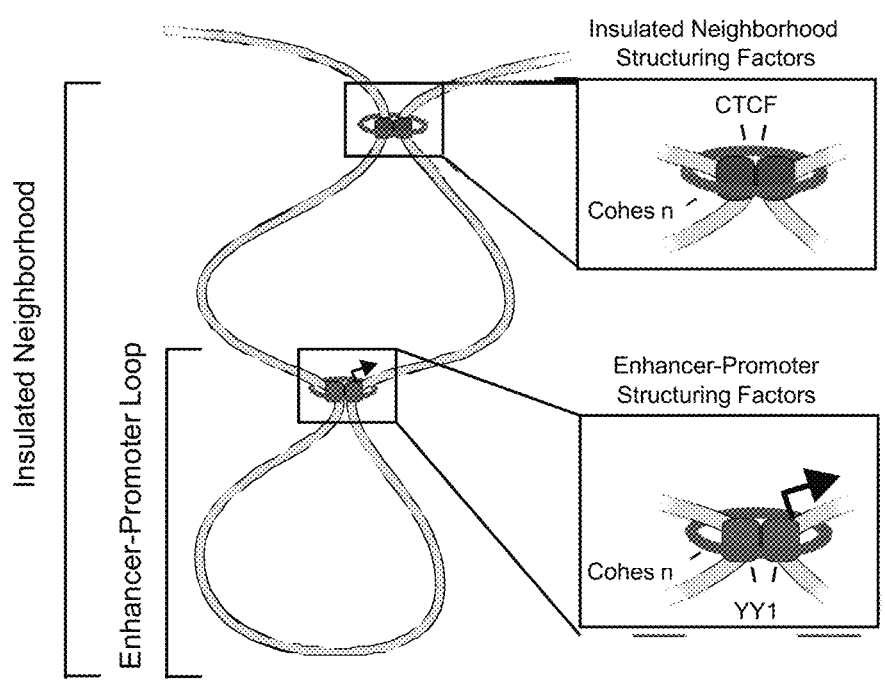
FIG. 5—Model of YY1 as an enhancer-promoter structuring factor. Model depicting YY1 (red globules) structuring an enhancer-promoter loop. The enhancer-promoter loop is contained within an insulated neighborhood that is structured by CTCF (purple globules). Both YY1 and CTCF structure DNA loops through homodimerization.

Differential gene expression analysis was performed using deseq2 (version 1.14.1) (Love et al., 2014). Analysis was performed on the gene level. To calculate the gene-level read counts, the estimated transcript counts were summed across all the isoforms of the gene. This was then input into deseq2 and adjusted p values were calculated using the default settings. Log 2 fold changes and adjusted p values are included in Table S2. An FDR value of 0.05 was used as a cut off for significant differential expression. For FIG. 5C, the values on the y axis are the deseq2-calculated log 2 fold change values. The values on the x axis are the deseq2 calculated baseMean values.

For FIG. 7D, the absolute value of the deseq2 calculated log 2 fold change is plotted on the left side. On the right side the YY1 density at the promoter is plotted. Because the analysis is done on the gene level, the YY1 promoter signal for genes with multiple isoforms was averaged.

For the GO analysis the list of differentially expressed genes (Table S3) was input into the PANTHER GO analysis web tool (http://pantherdb.org/, Version 11.1) (Mi et al., 2013, 2017) and a statistical overrepresentation test was performed using the default settings.

RNA-Seq Display

For displaying RNA-seq tracks, the RNA-seq data was mapped with Tophat to the mm9 RefSeq transcriptome (downloaded on Feb. 1, 2017) using the following parameters: -n 10 tophat -p 10 --no-novel-juncs -o. Wiggle files representing counts of RNA-Seq reads across the reference genome were created using MACS (Zhang et al., 2008) with parameters -w -S -space=50 -nomodel -shiftsize=200. Resulting wiggle files were normalized for sequencing depth by dividing the read counts in each bin by the millions of mapped reads in each sample and were visualized in the UCSC genome browser (Kent et al., 2002).

Single-Cell RNA-Seq Analysis

Figure 15D:
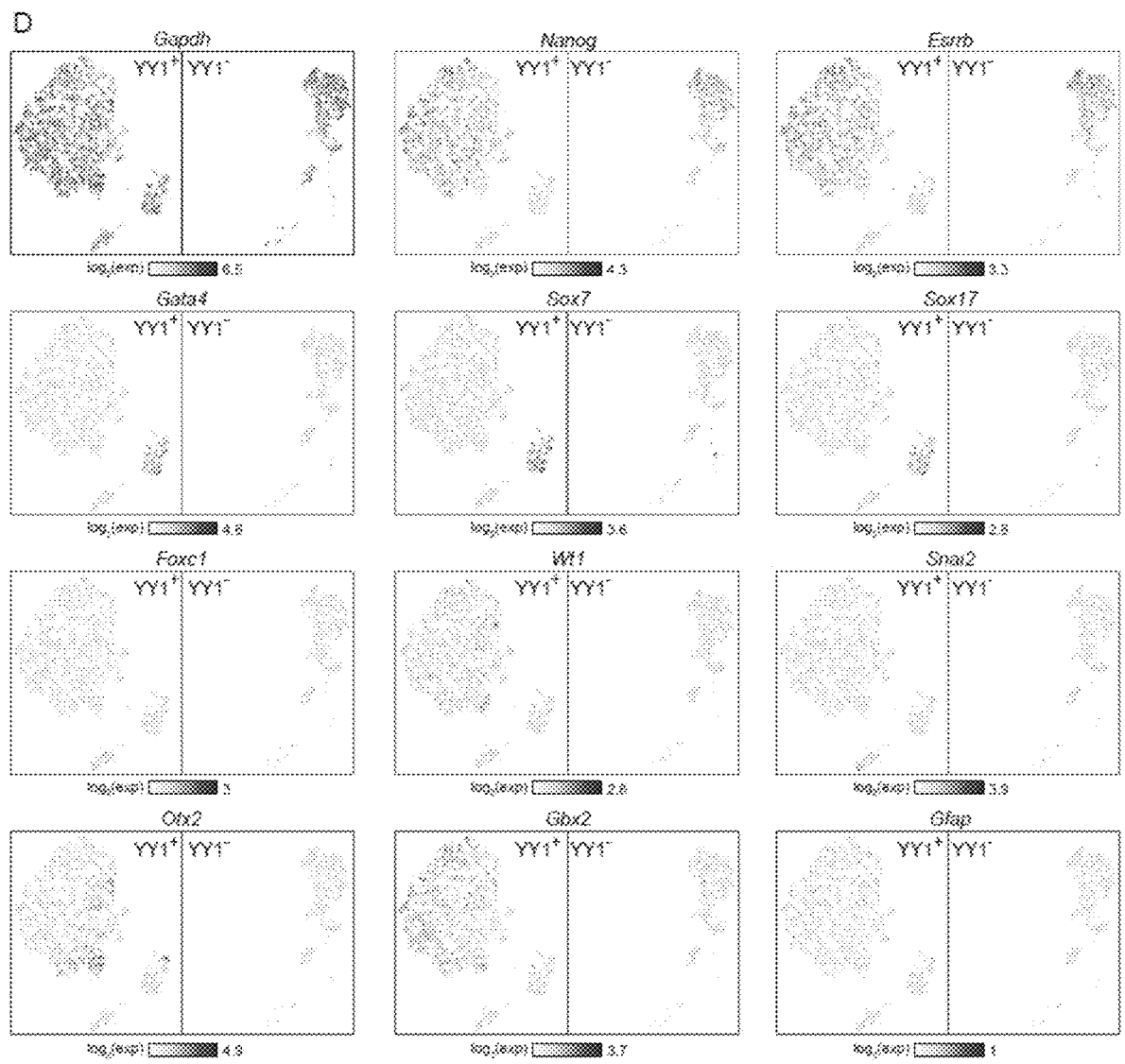

Sequencing data was demultiplexed using the 10× Genomics Cell Ranger software (version 2.0.0) and aligned to the mm10 transcriptome. Unique molecular identifiers were collapsed into a gene-barcode matrix representing the counts of molecules per cell as determined and filtered by Cell Ranger using default parameters. Normalized expression values were generated using Cell Ranger using the default parameters. For FIG. 7H the number of cells with a >1 normalized expression value for the specified transcript were counted. For FIG. 15C the cells were arranged by principal component analysis using the default Cell Ranger parameters. In FIG. 15D cells were split into the two panels based on what condition they came from. The arrangement is the same as in FIG. 15C. Individual cells are then colored by normalized expression level.

4C-Seq Data Analysis

4C-Seq Analysis

The 4C-seq samples were first processed by removing their associated read primer sequences (Table S5) from the 5' end of each FASTQ read. To improve mapping efficiency of the trimmed reads by making the read longer, the restriction enzyme digest site was kept on the trimmed read. After trimming the reads, the reads were mapped using bowtie with options -k 1 -m 1 against the mm9 genome assembly. All unmapped or repetitively mapping reads were discarded from further analysis. The mm9 genome was then "digested" in silico according to the restriction enzyme pair used for that sample to identify all the fragments that could be generated by a 4C experiment given a restriction enzyme pair. All mapped reads were assigned to their corresponding fragment based on where they mapped to the genome. The digestion of a sample in a 4C experiment creates a series of "blind" and "non-blind" fragments as described by the Tanay and De Laat labs (van de Werken et al., 2012). In brief, "blind" fragments lack a secondary restriction enzyme site whereas "non-blind" fragments contain a secondary restriction enzyme site. Because of this we expect to only observe reads derived from non-blind fragments. We therefore only used reads derived from non-blind fragments.

Experiments were conducted in biological triplicate and the mutant and WT samples were quantile normalized with each other.

If no reads were detected at a non-blind fragment for a given sample when reads were detected in at least one other sample, we assigned a "0" to that non-blind fragment for the sample(s) missing reads.

4C-Seq Display

To display 4C-seq genomic coverage tracks, we first smoothed the normalized 4C-seq signal using a 5 kb running mean at 50 bp steps across the genome for each sample. Individual replicates are displayed in FIG. 13. Next, biological replicates of the same condition were combined and the mean and 95% confidence interval of the 4C-seq signal for each bin across the genome was calculated. In FIG. 6 and FIG. 9, the 4C-seq signal tracks display the mean 4C-seq signal along the genome as a line and the 95% confidence interval as the shaded area around the line. For each 4C-seq signal track, the viewpoint used in the 4C-seq experiment is indicated as an arrow labeled VP.

To quantify the change in 4C-seq signal in a specific region of interest, the normalized 4C-seq signal (non-smoothed) was counted for each sample and the mean and standard deviation of the quantified signal was calculated for biological replicates of the same condition. The mean and standard deviation of the quantified signal was normalized to the appropriate control condition (either WT or dCas9) before plotting. Below each 4C-seq signal track, the quantified region is indicated as a red bar labeled "Quantified region". The coordinates of the quantified region for Raf1 are chr6:115598005-115604631, and for Etv4 are chr11:101644625-101648624.

ChIA-PET Data Analysis

ChIA-PET Read Processing

For each ChIA-PET dataset, raw reads were processed in order to identify a set of putative interactions that connect interaction anchors for further statistical modeling and analysis. First, paired-end tags (PETs), each containing two paired reads, were analyzed for the presence of the bridge-linker sequence and trimmed to facilitate read mapping. PETs containing at least one instance of the bridge-linker sequence in either of the two reads were kept for further processing and reads containing the bridge-linker sequence were trimmed immediately before the linker sequence using cutadapt with options "-n 3 -O 3 -m 15 -a forward=ACGCGATATCTTATCTGACT (SEQ ID NO: 42)-a reverse=AGTCAGATAAGATATCGCGT" (SEQ ID NO: 43) (http://cutadapt.readthedocs.io/en/stable/). PETs that did not contain an instance of the bridge-linker sequence were not processed further. Trimmed read were mapped individually to the mm9 mouse reference genome using Bowtie with options "-n 1 -m 1 -p 6" (Langmead et al., Genome Biology, 2009). After alignment, paired reads were re-linked with an in-house script using read identifiers. To avoid potential artifacts arising from PCR bias, redundant PETs with identical genomic mapping coordinates and strand information were collapsed into a single PET. Potential interaction anchors were determined by identifying regions of local enrichment in the individually mapped reads using MACS with options "-g mm -p 1e-9 --nolambda --nomodel --shiftsize=100" (Zhang et al., Genome Biology, 2008). PETs with two mapped reads that each overlapped a different potential interaction anchor by at least 1 bp were used to identify putative interactions between the overlapped interaction anchors. Each putative interaction represents a connection between two interaction anchors and is supported by the number of PETs (PET count) that connect the two interaction anchors.

ChIA-PET Statistical Analysis Overview

In processing our chromatin interaction data, we sought to identify the putative interactions that represent structured chromatin contacts, defined as chromatin contacts that are structured by forces other than the fiber dynamics resulting from the linear genomic distance between the two contacting regions. In contrast, we sought to filter out putative interactions that likely result from PETs arising from non-structured chromatin contacts, defined as contacts resulting from the close linear genomic proximity of the two contacting regions, or from technical artifacts of the ChIA-PET protocol. We expect that putative interactions that represent structured chromatin contacts should be detected with greater frequency, or PET count, than expected given the linear genomic distance between the two contacting regions, allowing us to distinguish between these two classes of interactions.

To this end, we developed Origami, a statistical method to identify high confidence interactions that are likely to represent structured chromatin contacts. Conceptually, Origami uses a semi-Bayesian two-component mixture model to estimate the probability that a putative interaction corresponds to one of two groups: structured chromatin contacts, or non-structured chromatin contacts and technical artifacts. Origami estimates this as a probability score for each putative interaction by modeling the relationship between PET count, linear genomic distance between interaction anchors, and read depth at the interaction anchors. High confidence interactions are then identified as the subset of putative interactions that are likely to represent structured chromatin contacts, by requiring high confidence interactions to have a probability score >0.9.

All the methods below were developed within the origami software that is available at https://github.com/younglab/origami. The version used was version 1.1 (tagged on GitHub repository as v1.1). The software below was run with the following parameters: --iterations=10000 --burn-in=100 --prune=0 --min-dist=4000 --peak-count-filter=5.

Origami Statistical Model

We developed Origami, a method to analyze ChIA-PET data, in order to identify putative interactions that likely represent structured chromatin contacts, and to filter out putative interactions that likely represent non-structured chromatin contacts that occur as a result of the close linear genomic proximity of contacting regions and interactions that represent technical artifacts of the ChIA-PET protocol. This includes modeling of the relationship between the number of PETs observed to support each interaction ($I_i$), linear genomic distance between interaction anchors ($d_i$), and the sequencing depth at the interaction anchors, to estimate the probability that each putative interaction (i) represents a structured chromatin contact given the observed PET count ($I_i$).

We initially assume that putative interactions classify into one of two groups, $j \in \{0,1\}$, such that each putative interaction, $i \in 1 \ldots N$), has a latent group identity $Z_i$ that corresponds to a value of j. Group 1 is designated as the set of putative interactions resulting from structured chromatin contacts that we expect to detect with greater frequencies than expected given the linear genomic distance between the contacting regions. Group 0 is designated as the set of putative interactions resulting from non-structured chromatin contacts due to close linear genomic proximity of the contacting regions, or from technical artifacts of the ChIA-PET protocol.

We developed a semi-Bayesian two-component mixture model to estimate the probability that each putative interaction represents a structured chromatin contact. For each group, we modeled the likelihood to observe the PET count ($I_i$) under that group as a Poisson process with two underlying factors. These factors are the number of PETs observed as a result of being part of the group ($G_{ij}$), and the number of PETs observed as a result of the linear genomic distance between the anchors given the group ($D_{ij}$). We modeled the number of PETs observed as a result of being part of the group ($G_{ij}$) as a Poisson process with mean, $\lambda_j$. We modeled the number of PETs observed as a result of the linear genomic distance between the anchors given the group ($D_{ij}$) as a Poisson process with mean, $\mu_{ij}$. Since these two factors are thought to be independent (Phanstiel et al., Bioinformatics, 2015), the total Poisson process is the summation of these two underlying factors.

We modeled the data variables under the following distributions:

$$I_i \sim \Sigma_{j \in \{0,1\}} w_{ij} * (G_{ij} + D_{ij})$$

$$G_{ij} \sim \text{Poisson}(\lambda_j)$$

$$D_{ij} \sim \text{Poisson}[\mu_{ij}(d_i)]$$

$$I_i \sim \text{Poisson}[+_{ij}(d_i)]$$

We modeled our parameters with the following prior distributions:

$$\lambda_j \sim \text{Gamma}(1,1)$$

$$w_{i1} \sim \text{Beta}(1+a_i, 1+b_i)$$

Since $w_{i1}$ is a binomial probability, $w_{i0} = 1 - w_{i1}$.

From these priors and likelihood distributions, the posterior distributions of these parameters are as follows:

$$\lambda_j \sim \text{Gamma}[1 + \Sigma_{Z_i = j} G_{ij}, 1 + \#(Z_i = j)]$$

$$w_{i1} \sim \text{Beta}[1 + \alpha_i + Zi, 1 + \beta_i + (1 - Zi)]$$

Aside from $D_{ij}$ and $\mu_{ij}$, we estimated the parameters using the iterative process Markov Chain Monte Carlo (MCMC) with Gibbs Sampling with the appropriate posterior to sample from (Gelman et al., 2004).

To estimate $\mu_{ij}$, we modeled the function between $D_{ij}$ and the linear genomic distance ($d_i$) on the log 10 scale using a smoothed cubic spline (via smooth.spline in R), taking $\mu_{ij}$ to be the expected number of PETs to be observed due to distance ($D_{ij}$) given the linear genomic distance ($d_i$), for each putative interaction (i).

The constants $\alpha_i$ and $\beta_i$ were set to be as minimally informative as possible. The constant $\alpha_i$ was set equal to the number of putative interactions sharing one anchor with i that have PET counts less than $I_i$. The constant $\beta_i$ was set equal to the number of putative interactions sharing one anchor with i that have PET counts greater than $I_i$ plus the ratio of the depth score ($s_i$) to the median depth score with all values<1 floored to 0. The depth score ($s_i$) for each putative interaction is defined as the product of the number of reads that map to its interaction anchors.

Origami Implementation

We implemented the model described above by Markov Chain Monte Carlo simulation. By iteratively estimating the group identity ($Z_i$) of each putative interaction, we sought to explore the probability space for $Z_i$ and determined a probability score ($p_i$) for each putative interaction that reflects the probability that the interaction results from a structured chromatin contact (belongs to group 1). The steps in our implementation are as follows.

For each putative interaction, we recorded the number of PETs observed that support the interaction ($I_i$), the linear genomic distance of the interaction between the outermost basepairs of the putative interaction's two anchors ($d_i$), and a depth score ($s_i$), which is defined as the product of the number of the reads in the dataset that map to each anchor of the putative interaction.

To seed the parameters of the model for the first iteration, the following was performed. The mixing weights ($w_{ij}$) were set to be equal at 0.5 for each interaction. The group process means ($\lambda_j$) were assigned values of 5 and 1 for group 1 and 0, respectively. The distance process mean ($\mu_{ij}$) was initially set to 0 for all interactions.

Additionally values of $\alpha_i$ and $\beta_i$ were computed for each interaction, but not used in the first iteration. In all subsequent iterations, $\alpha_i$ and $\beta_i$, are used in updating the values of the mixing weights ($w_{ij}$). The parameter $\alpha_i$ was set equal to the number of putative interactions sharing one anchor with i that have PET counts less than $I_i$. The parameter $\beta_i$ was set equal to the number of putative interactions sharing one anchor with i that have PET counts greater than $I_i$ plus the ratio of the depth score ($s_i$) over the median depth score for all putative interactions, where when this ratio is less than 1 it is floored to 0.

For each putative interaction, we estimated the likelihood (i) that the putative interaction is observed with PET count ($I_i$), given that the putative interaction belongs to group 1 and group 0, as follows.

$$l_{ij} = \text{dPoisson}(I_i; \lambda_j + \mu_{ij})$$

Where dPoisson is the density function of the Poisson distribution for the mean $\mu_j + \mu_{ij}$ and evaluated on $I_i$.

We calculated the relative weighted likelihood ($r_i$) of each putative interaction belonging to group 1. To do this we multiplied each of the two likelihoods calculated for each putative interaction by their respective mixing weights ($w_{ij}$) and evaluated as follows.

$$r_i = \frac{w_{i1} * L_{i1}}{(w_{i1} * L_{i1}) + (w_{i0} * L_{i0})}$$

We update the group identity ($Z_i$) of each interaction by drawing from the binomial distribution with a probability of $r_i$ as follows.

$$Z_i = \text{rBinomial}(1, r_i)$$

Where rBinomial means we randomly draw 1 or 0 with the probability of $r_i$ for drawing 1.

We update the mixing weights ($w_{ij}$) using our newly updated group identies ($Z_i$), by drawing from the Beta distribution in the following way.

$$w_{i1} = \text{rBeta}[1 + \alpha_i + Zi, 1 + \beta + (1 - Zi)]$$

Where rBeta means we randomly draw from the beta distribution with the above parameters. Since $w_{i1}$ is a binomial probability, $w_{i0} = 1 - w_{i1}$.

In order to estimate the PET counts for $G_{ij}$ and $D_{ij}$, we randomly sampled the number of PETs for $G_{ij}$ and $D_{ij}$ by taking advantage of the fact that when two Poisson variables are known to sum to a given count, then the distribution of either variable follows a binomial distribution with probability $\lambda_j/(\lambda_j+\mu_{ij})$. Accordingly, we estimated the PET counts for $G_{ij}$ and $D_{ij}$ in the following way:

$$G_{ij} = rBinomial\left(I_i, \frac{\lambda_j}{\lambda_j + \mu_{ij}}\right)$$

$$D_{ij} = I_i - G_{ij}$$

Where rBinomial means we randomly draw up to $I_i$ PETs with the probability $\lambda_j/(\lambda_j+\mu_{ij})$ of drawing each PET.

We update the group process mean $(\lambda_j)$ using the following identity, requiring that $\lambda_1 > \lambda_0$ in order to maintain identifiability of the two groups (although during our runs this constraint was not necessary).

$$\lambda_j = rGamma(1+\Sigma_{Z_i=j}G_{ij},1+\#(Z_i=j))$$

Where rGamma means we randomly draw from the Gamma distribution with the above parameters.

To update the distance process means $(\mu_{ij})$, we calculated the function between $D_{ij}$ and the $\log_{10}(d_i+1)$, using a smoothed cubic spline (via smooth. spline in R). To simplify estimation of $\mu_{ij}$, we chose to take the maximum likelihood estimate of this process.

We iterated steps 4-10 in the following way. We performed an initial 1,000 iterations as a burn-in, which were discarded. Then we performed 10,000 iterations.

We estimated the probability that each putative interaction belongs to group 1 by calculating a probability score $(p_i)$ for each putative interaction that equals the mean value of $Z_i$ across the 10,000 iterations. High confidence interactions were identified as putative interactions with $p_i > 0.9$.

$$p_i = \frac{1}{\#\text{(iterations)}}\sum Z_i \approx P(Z_i = 1)$$

HiChIP Data Analysis
HiChIP Processing

The HiChIP samples were processed by first identifying reads with a restriction fragment junction (i.e. a site where ligation occurred). Reads containing the restriction fragment junction were trimmed such that the information 5' to the junction was kept. Reads without restriction fragment junctions were left untrimmed. Reads were then mapped using bowtie with options -k 1 -m 1 against the mm9 genome assembly. All unmapped or repetitively mapping reads were discarded from further analysis. Reads were joined back together in pairs by their read identifier. The genome was binned and for every pair of bins the number of PETs joining them was calculated. These data were then used as input into the Origami pipeline described above to identify significant bin to bin interaction pairs.

HiChIP Analysis

Quantitative analysis of HiChIP and Hi-C data (FIGS. 8, 9) was done as follows. High confidence interactions were identified by Origami. A union of high confidence interactions was then created for each experiment.

| Experiment | FIG. | Condition | Replicate |
|---|---|---|---|
| Degron | 8, 14 | noDrug | 1 |
| Degron | 8, 14 | noDrug | 2 |
| Degron | 8, 14 | noDrug | 3 |
| Degron | 8, 14 | yesDrug | 1 |
| Degron | 8, 14 | yesDrug | 2 |
| Degron | 8, 14 | yesDrug | 3 |
| Washout | 9 | Untreated (UT) | 1 |
| Washout | 9 | Untreated (UT) | 2 |
| Washout | 9 | Untreated (UT) | 3 |
| Washout | 9 | Treated (TR) | 1 |
| Washout | 9 | Treated (TR) | 2 |
| Washout | 9 | Washout (WO) | 1 |
| Washout | 9 | Washout (WO) | 2 |
| Washout | 9 | Washout (WO) | 3 |
| CTCF Washout | 9 | Untreated (UT) | 1 |
| CTCF Washout | 9 | Untreated (UT) | 2 |
| CTCF Washout | 9 | Treated (TR) | 1 |
| CTCF Washout | 9 | Treated (TR) | 2 |
| CTCF Washout | 9 | Washout (WO) | 1 |
| CTCF Washout | 9 | Washout (WO) | 2 |

For example, the degron high confidence set would consist of the union of the 6 degron samples listed above. The PET counts were then normalized to each other using deseq2 (Love et al., 2014). The mean of each group was then calculated and then the fold change was then calculated by taking the ratio of the perturbed condition to the non-perturbed condition (i.e. yesDrug to noDrug or TR/UT;WO/UT) with a pseudocount of 0.5 added to both. This complete set of significant interactions is what is displayed in FIG. 8B as "All Interactions."

For subset analysis the anchor of each interaction was classified by overlapping with known genomic features as defined earlier. This resulted in a binary score for whether an anchor overlapped with an enhancer, promoter, insulator, YY1, or CTCF. The interactions were then subset to identify the following groups:

YY1 not present (FIG. 8): no YY1 at either end of the interaction.

YY1 enhancer-promoter interactions (FIG. 8, FIG. 9): YY1 at both ends AND an enhancer or promoter at both ends.

CTCF-CTCF interaction: CTCF at both ends.

The log 2 fold change for these groups is plotted in FIG. 8B, 9F.

The analysis in FIG. 6C was done by identifying the gene at the end of YY1 enhancer-promoter loops. This was done by intersecting promoters (as defined above) with the significant loop anchors. Genes with multiple promoters were collapsed after the intersection to generate a list of genes at the end of YY1 enhancer-promoter loops. The deseq2 calculated log 2 fold change for these genes is then plotted in FIG. 8C. Genes are colored based on the deseq2 calculated adjusted p value (as in FIG. 7).

HiChIP Display

HiChIP interaction matrices displayed in FIGS. 8D and 8E. For these interaction matrices, all putative interactions are displayed and the intensity of each pixel represents the mean of the deseq2 normalized interaction frequency of all biological replicates of that condition. In FIGS. 8D & 8E the outlined pixel, which reflects the frequency of interaction between sites at the base of the diagonals, was used to quantify the change in normalized interaction frequency upon YY1 degradation.

Figures 10C, 10D, 10E, 10F, 10G, 10H, 10I, 10J, 10K:
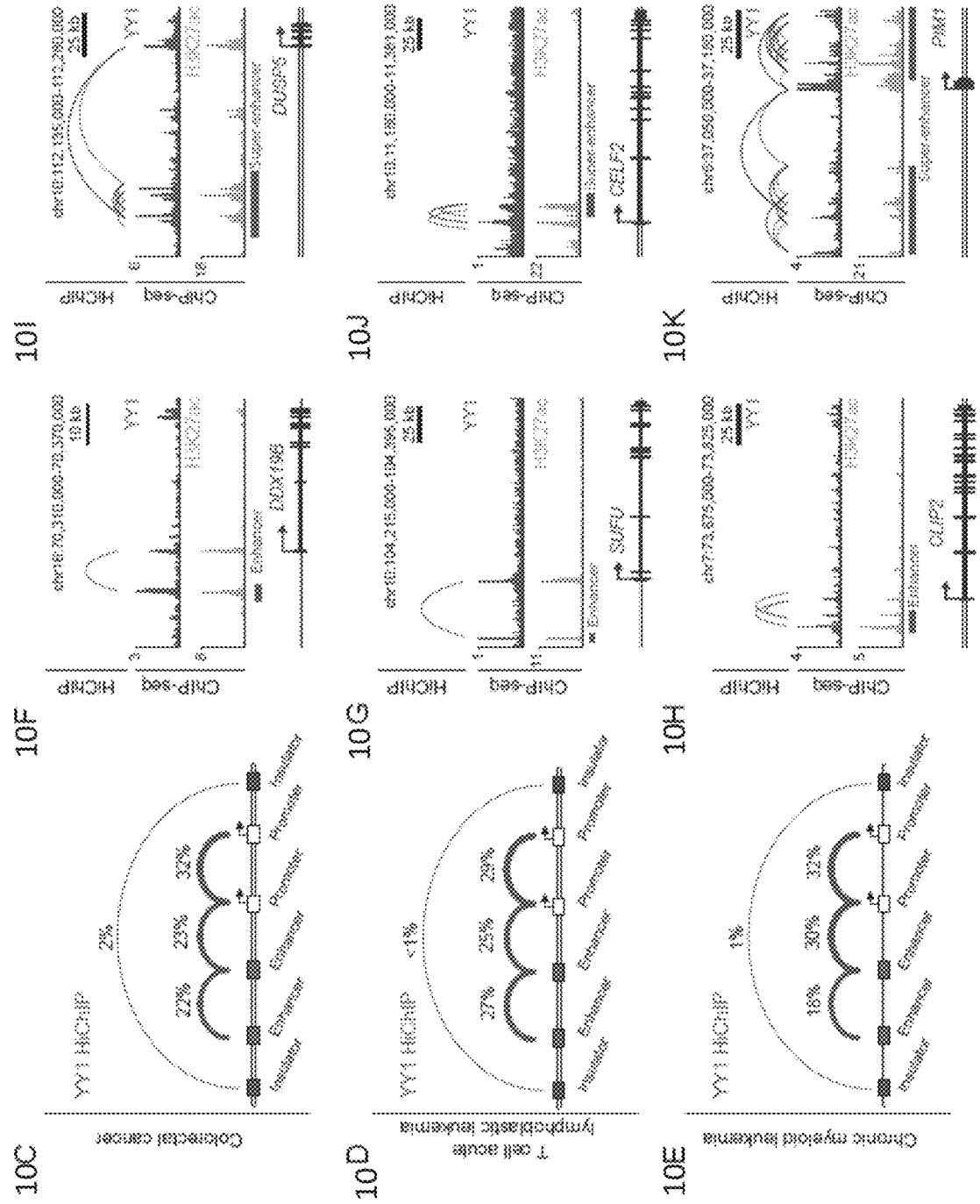

In FIG. 10, high-confidence HiChIP interactions are displayed as arcs. For display, the interactions displayed were filtered to remove bin to adjacent bin contacts and non-enhancer-promoter interactions. Arcs were centered on the relevant genomic feature within the bin (for example a ChIP-seq peak summit or transcription start site).

Interaction Classification

High-confidence ChIA-PET and HiChIP interactions were classified based on the presence of enhancer, promoter, and insulator elements at the anchors of each interaction as defined above. In the case where an interaction anchor overlapped both an enhancer and an insulator or a promoter and an insulator a hierarchy where anchors were considered first as promoters, then enhancers, then insulators. For example, if there is an interaction where the left anchor is insulator/promoter and the right anchor is enhancer/insulator it would be counted as an enhancer-promoter interaction and not an insulator-insulator interaction.

To display summaries of the classes of high-confidence interactions, each class of interactions is displayed as an arc between the relevant enhancer, promoter, and insulator elements. The thickness of the arcs approximately reflects the percentage of interactions of that class relative to the total number of interactions that were classified. In the main figures, enhancer-enhancer, enhancer-promoter, promoter-promoter, and insulator-insulator interaction classes are displayed. Extended summaries that additionally include enhancer-insulator and promoter-insulator interactions are displayed in the supplemental figures.

Figure Display

In certain figure panels displaying genome tracks, enhancer elements are indicated as red boxes labelled "Enhancer". These regions represent our interpretation of the ChIP-seq data and are distinct from the algorithmically defined enhancers used in the quantitative genome-wide analysis.

Statistical Analysis

In order to use the unpaired t-test we made two assumptions.

1) Populations are distributed according to a Gaussian distribution. For most experiments three replicates were used, and so sample sizes were too small to reliably calculate departure from normality (i.e. with a D'Agostino test).

2) The two populations have the same variance. A test for variance was not carried out.

Full p values are listed here*:

| FIG. | Sub panel | Test | Biological Replicates | P value |
|---|---|---|---|---|
| 6B | 4C-seq | Student's T-Test | 3 | 0.011 |
| 6B | ChIP-qPCR | Student's T-Test | 3 | 0.0066 |
| 6B | RT-qPCR | Student's T-Test | 6 | <0.0001 |
| 6C | 4C-seq | Student's T-Test | 3 | 0.0013 |
| 6C | ChIP-qPCR | Student's T-Test | 3 | 0.0048 |
| 6C | RT-qPCR | Student's T-Test | 6 | 0.0394 |
| 8B | | Welch Two Sample T-Test | 3 | <2.2e−16 |
| 8D | HiChIP | Student's T-Test | 3 | 0.0162 |
| 8D | RNA-seq | Wald | 2 | 7.22E−13 |
| 8E | HiChIP | Student's T-Test | 3 | 0.0446 |
| 8E | RNA-seq | Wald | 2 | 1.25E−58 |
| 9D | 4c-seq | Student's T-Test | 3 | 0.004717003 |
| 9D | RT-qPCR | Student's T-Test | 6 | <0.0001 |
| 14D | Raf1 | Wald | 2 | 1.63E−53 |
| 14D | Etv4 | Wald | 2 | 2.88E−34 |

*note that the Student's T-test was conducted using GraphPad Prism which sets a lower limit at 0.0001, the Welch Two Sample T-test was conducted using R which sets a lower limit at 2.2e-16, Wald test was conducted using deseq2 in R which does not have a lower limit on the p value.

Data and Software Availability

All datasets used are summarized in Table S4 below.

| Species | Cell | Type | Name | GEO | This study or previous publication |
|---|---|---|---|---|---|
| Human | KBM7 | CRISPR Screen | Wang et al 2015 | N/A | Previous publication |
| Human | 54 types | RNA-seq | GTEX | N/A | Previous publication |
| Mouse | V6.5 | ChIP-seq | CTCF_merged | GSM747534, GSM747535, GSM747536 | Previous publication |
| Mouse | V6.5 | ChIP-seq | CTCF_rep1 | GSM747534 | Previous publication |
| Mouse | V6.5 | ChIP-seq | CTCF_rep2 | GSM747535 | Previous publication |
| Mouse | V6.5 | ChIP-seq | CTCF_rep3 | GSM747536 | Previous publication |
| Mouse | V6.5 | ChIP-seq | CTCF_input_merged | GSM747545, GSM747546 | Previous publication |
| Mouse | V6.5 | ChIP-seq | CTCF_input_rep1 | GSM747545 | Previous publication |
| Mouse | V6.5 | ChIP-seq | CTCF_input_rep2 | GSM747546 | Previous publication |
| Mouse | V6.5 | ChIP-seq | YY1 | GSM2645432 | This paper |
| Mouse | V6.5 | ChIP-seq | YY1_input | GSM2645433 | This paper |
| Mouse | V6.5 | ChIP-seq | H3K27Ac | GSM1526287 | This paper |
| Mouse | V6.5 | ChIP-seq | H3K27AC_input | GSM1526285 | This paper |
| Mouse | V6.5 | ChIA-PET | YY1 | GSM2645440 | This paper |

-continued

| Species | Cell | Type | Name | GEO | This study or previous publication |
|---|---|---|---|---|---|
| Mouse | V6.5 | ChIA-PET | CTCF | GSM2645441 | This paper |
| Mouse | V6.5 | RNA-seq | 0 hr_rep1 | GSM2645362 | This paper |
| Mouse | V6.5 | RNA-seq | 0 hr_rep2 | GSM2645363 | This paper |
| Mouse | V6.5 | Hi-ChIP | H3K27Ac_0 hr_rep1 | GSM2645434 | This paper |
| Mouse | V6.6 | Hi-ChIP | H3K27Ac_0 hr_rep2 | GSM2645435 | This paper |
| Mouse | V6.5 | Hi-ChIP | H3K27Ac_0 hr_rep3 | GSM2645436 | This paper |
| Mouse | V6.5 | RNA-seq | mES_24 hr_rep1 | GSM2645364 | This paper |
| Mouse | V6.5 | RNA-seq | mES_24 hr_rep2 | GSM2645365 | This paper |
| Mouse | V6.5 | Hi-ChIP | H3K27Ac_24 hr_rep1 | GSM2645435 | This paper |
| Mouse | V6.5 | Hi-ChIP | H3K27Ac_24 hr_rep2 | GSM2645436 | This paper |
| Mouse | V6.5 | Hi-ChIP | H3K27Ac_24 hr_rep3 | GSM2645437 | This paper |
| Human | GM12878 | ChIP-seq | H3K27AC_input | GSM733742 | Previous publication |
| Human | GM12878 | ChIP-seq | H3K27Ac | GSM733771 | Previous publication |
| Human | GM12878 | ChIP-seq | CTCF_input | GSM749669 | Previous publication |
| Human | GM12878 | ChIP-seq | CTCF | GSM749704 | Previous publication |
| Human | GM12878 | ChIP-seq | YY1 | GSM803406 | Previous publication |
| Human | K562 | ChIP-seq | CTCF_input | GSM749719 | Previous publication |
| Human | K562 | ChIP-Seq | CTCF_1 | GSM749690 | Previous publication |
| Human | K562 | ChIP-Seq | H3k27Ac_input | GSM733780 | Previous publication |
| Human | K562 | ChIP-Seq | H3K27Ac | GSM733656 | Previous publication |
| Human | K562 | ChIP-Seq | YY1 | GSM803470 | Previous publication |
| Human | K562 | Hi-ChIP | YY1 | GSM2774002 | This paper |
| Human | ESC | ChIP-Seq | CTCF | GSM1705263 | Previous publication |
| Human | ESC | ChIP-Seq | H3K27Ac | GSM1705260 | Previous publication |
| Human | ESC | ChIP-Seq | CTCF_H3K27Ac_input | GSM1705264 | Previous publication |
| Human | ESC | ChIP-Seq | YY1 | GSM803513 | Previous publication |
| Human | HEPG2 | ChIP-Seq | CTCF | GSM803486 | Previous publication |
| Human | HEPG2 | ChIP-Seq | YY1 | GSM803381 | Previous publication |
| Human | HEPG2 | ChIP-Seq | CTCF_YY1_input | GSM803463 | Previous publication |
| Human | HEPG2 | ChIP-Seq | H3K27Ac | GSM733743 | Previous publication |
| Human | HEPG2 | ChIP-Seq | H3K27Ac_input | GSM733732 | Previous publication |
| Human | HCT-116 | ChIP-Seq | YY1 | GSM803354 | Previous publication |
| Human | HCT-116 | ChIP-Seq | CTCF | GSM1022652 | Previous publication |
| Human | HCT-116 | ChIP-Seq | CTCF_input | GSM749774 | Previous publication |
| Human | HCT-116 | ChIP-Seq | H3K27Ac | GSM945853 | Previous publication |
| Human | HCT-116 | ChIP-Seq | H3K27Ac_input | GSM817344 | Previous publication |
| Human | HCT-116 | Hi-ChIP | YY1 | GSM2774000 | This paper |
| Human | Jurkat | ChIP-seq | YY1 | GSM2773998 | This paper |
| Human | Jurkat | ChIP-seq | YY1_input | GSM2773999 | This paper |
| Human | Jurkat | ChIP-seq | H3K27ac | GSM1697882 | Previous publication |
| Human | Jurkat | ChIP-seq | H3K27ac_input | GSM1697880 | Previous publication |
| Human | Jurkat | ChIP-seq | CTCF | GSM1689152 | Previous publication |
| Human | Jurkat | ChIP-seq | CTCF_input | GSM1689151 | Previous publication |

| Species | Cell | Type | Name | GEO | This study or previous publication |
|---|---|---|---|---|---|
| Human | Jurkat | Hi-ChIP | YY1 | GSM2774001 | This paper |
| Mouse | NPC | ChIP-Seq | YY1 | GSM628032 | Previous publication |
| Mouse | NPC | ChIP-Seq | CTCF | GSM2259909 | Previous publication |
| Mouse | NPC | ChIP-Seq | CTCF_input | GSM2259910 | Previous publication |
| Mouse | NPC | ChIP-Seq | H3K27Ac | GSM594585 | Previous publication |
| Mouse | NPC | ChIP-Seq | H3K27AC_input* | GSM2259910 | Previous publication |
| Mouse | B cell | ChIP-Seq | YY1 | GSM1897387 | Previous publication |
| Mouse | B cell | ChIP-Seq | CTCF | GSM546526 | Previous publication |
| Mouse | B cell | ChIP-Seq | CTCF_input | GSM546540 | Previous publication |
| Mouse | B cell | ChIP-Seq | H3K27Ac | GSM594592 | Previous publication |
| Mouse | B cell | ChIP-Seq | H3K27Ac_input* | GSM546540 | Previous publication |
| Mouse | V6.5 | GRO-seq | mES_GRO-seq | GSM1665566 | Previous publication |
| Mouse | V6.5 | single cell RNA-seq | noDrug | GSM2774584 | This paper |
| Mouse | V6.5 | single cell RNA-seq | yesDrug | GSM2774585 | This paper |
| Mouse | V6.5 | Hi-ChIP | H3K27Ac_UT_rep1 | GSM2774003 | This paper |
| Mouse | V6.6 | Hi-ChIP | H3K27Ac_UT_rep2 | GSM2774004 | This paper |
| Mouse | V6.5 | Hi-ChIP | H3K27Ac_UT_rep3 | GSM2774005 | This paper |
| Mouse | V6.5 | Hi-ChIP | H3K27Ac_TR_rep1 | GSM2774006 | This paper |
| Mouse | V6.6 | Hi-ChIP | H3K27Ac_TR_rep2 | GSM2774007 | This paper |
| Mouse | V6.5 | Hi-ChIP | H3K27Ac_WO_rep1 | GSM2774008 | This paper |
| Mouse | V6.6 | Hi-ChIP | H3K27Ac_WO_rep2 | GSM2774009 | This paper |
| Mouse | V6.5 | Hi-ChIP | H3K27Ac_WO_rep3 | GSM2774010 | This paper |
| Mouse | 129/Ola, XY | Hi-C | CTCF_UT_rep1 | GSM2644945 | Previous publication |
| Mouse | 129/Ola, XY | Hi-C | CTCF_UT_rep2 | GSM2644946 | Previous publication |
| Mouse | 129/Ola, XY | Hi-C | CTCF_TR_rep1 | GSM2644947 | Previous publication |
| Mouse | 129/Ola, XY | Hi-C | CTCF_TR_rep2 | GSM2644948 | Previous publication |
| Mouse | 129/Ola, XY | Hi-C | CTCF_WO_rep1 | GSM2644949 | Previous publication |
| Mouse | 129/Ola, XY | Hi-C | CTCF_WO_rep2 | GSM2644950 | Previous publication |
| Mouse | V6.5 | 4C | DB7938357_Etv4_Prom_B3_mES_situ_rep1 | GSM2645350 | This paper |
| Mouse | V6.6 | 4C | DB7938357_Etv4_Prom_B3_mES_situ_rep2 | GSM2645351 | This paper |
| Mouse | V6.5 | 4C | DB7938357_Etv4_Prom_B3_mES_situ_rep3 | GSM2645352 | This paper |
| Mouse | V6.5 | 4C | DB7938357_WT_mES_situ_rep1 | GSM2645353 | This paper |
| Mouse | V6.6 | 4C | DB7938357_WT_mES_situ_rep2 | GSM2645354 | This paper |
| Mouse | V6.5 | 4C | DB7938357_WT_mES_situ_rep3 | GSM2645355 | This paper |
| Mouse | V6.6 | 4C | DC4688024_Raf1_Prom_G2_mES_situ.rep1 | GSM2645356 | This paper |
| Mouse | V6.5 | 4C | DC4688024_Raf1_Prom_G2_mES_situ.rep2 | GSM2645357 | This paper |
| Mouse | V6.5 | 4C | DC4688024_Raf1_Prom_G2_mES_situ.rep3 | GSM2645358 | This paper |
| Mouse | V6.6 | 4C | DC4688024_WT_mES_situ_rep1 | GSM2645359 | This paper |
| Mouse | V6.5 | 4C | DC4688024_WT_mES_situ_rep2 | GSM2645360 | This paper |
| Mouse | V6.5 | 4C | DC4688024_WT_mES_situ_rep3 | GSM2645361 | This paper |
| Mouse | V6.6 | 4C | 8357_Etv4_Prom_B3_dCas9_mES_sit | GSM2773992 | This paper |
| Mouse | V6.5 | 4C | 8357_Etv4_Prom_B3_dCas9_mES_sit | GSM2773993 | This paper |
| Mouse | V6.6 | 4C | 8357_Etv4_Prom_B3_dCas9_mES_sit | GSM2773994 | This paper |
| Mouse | V6.5 | 4C | 57_Etv4_Prom_B3_dCas9-YY1_mES_ | GSM2773995 | This paper |
| Mouse | V6.5 | 4C | 57_Etv4_Prom_B3_dCas9-YY1_mES_ | GSM2773996 | This paper |
| Mouse | V6.6 | 4C | 57_Etv4_Prom_B3_dCas9-YY1_mES_ | GSM2773997 | This paper |

Origami: https://github.com/younglab/origami using version v1.1-alpha-2.

The data associated with this study have been deposited in the Gene Expression Omnibus (GEO) under ID code GSE99521.

REFERENCES

Adhya, S. (1989). Multipartite genetic control elements: communication by DNA loop. Annu. Rev. Genet. 23, 227-250.

Allen, B. L., and Taatjes, D. J. (2015). The Mediator complex: a central integrator of transcription. Nat. Rev. Mol. Cell Biol. 16, 155-166.

Amoutzias, G. D., Robertson, D. L., Van de Peer, Y., and Oliver, S. G. (2008). Choose your partners: dimerization in eukaryotic transcription factors. Trends Biochem. Sci. 33, 220-229.

Beagan, J. A., Duong, M. T., Titus, K. R., Zhou, L., Cao, Z., Ma, J., Lachanski, C. V, Gillis, D. R., and Phillips-cremins, J. E. (2017). YY1 and CTCF orchestrate a 3-D chromatin looping switch during early neural lineage commitment. Genome Res.

Bell, A. C., and Felsenfeld, G. (2000). Methylation of a CTCF-dependent boundary controls imprinted expression of the Igf2 gene. Nature 405, 2-5.

Bonev, B., and Cavalli, G. (2016). Organization and function of the 3D genome. Nat. Rev. Genet. 17, 772-772.

Buecker, C., and Wysocka, J. (2012). Enhancers as information integration hubs in development: Lessons from genomics. Trends Genet. 28, 276-284.

Bulger, M., and Groudine, M. (2011). Functional and mechanistic diversity of distal transcription enhancers. Cell.

Creyghton, M. P., Cheng, A. W., Welstead, G. G., Kooistra, T., Carey, B. W., Steine, E. J., Hanna, J., Lodato, M. A., Frampton, G. M., Sharp, P. A., et al. (2010). Histone H3K27ac separates active from poised enhancers and predicts developmental state. Proc. Natl. Acad. Sci. U.S.A. 107, 21931-21936.

Cuddapah, S., Jothi, R., Schones, D. E., Roh, T. Y., Cui, K., and Zhao, K. (2009). Global analysis of the insulator binding protein CTCF in chromatin barrier regions reveals demarcation of active and repressive domains. Genome Res. 19, 24-32.

Degner, S. C., Verma-Gaur, J., Wong, T. P., Bossen, C., Iverson, G. M., Torkamani, A., Vettermann, C., Lin, Y. C., Ju, Z., Schulz, D., et al. (2011). CCCTC-binding factor (CTCF) and cohesin influence the genomic architecture of the Igh locus and antisense transcription in pro-B cells. Proc. Natl. Acad. Sci. 108, 9566-9571.

Deng, W., Lee, J., Wang, H., Miller, J., Reik, A., Gregory, P. D., Dean, A., and Blobel, G. A. (2012). Controlling long-range genomic interactions at a native locus by targeted tethering of a looping factor. Cell 149, 1233-1244.

Dixon, J. R., Selvaraj, S., Yue, F., Kim, A., Li, Y., Shen, Y., Hu, M., Liu, J. S., and Ren, B. (2012). Topological domains in mammalian genomes identified by analysis of chromatin interactions. Nature 485, 376-380.

Donohoe, M. E., Zhang, X., McGinnis, L., Biggers, J., Li, E., and Shi, Y. (1999). Targeted disruption of mouse Yin Yang 1 transcription factor results in peri-implantation lethality. Mol. Cell. Biol. 19, 7237-7244.

Dowen, J. M., Fan, Z. P., Hnisz, D., Ren, G., Abraham, B. J., Zhang, L. N., Weintraub, A. S., Schuijers, J., Lee, T. I., Zhao, K., et al. (2014). Control of Cell Identity Genes Occurs in Insulated Neighborhoods in Mammalian Chromosomes. Cell 159, 374-387.

Erb, M. A., Scott, T. G., Li, B. E., Xie, H., Paulk, J., Seo, H.-S., Souza, A., Roberts, J. M., Dastjerdi, S., Buckley, D. L., et al. (2017). Transcription control by the ENL YEATS domain in acute leukaemia. Nature 543, 270-274.

Fraser, J., Williamson, I., Bickmore, W. a, and Dostie, J. (2015). An Overview of Genome Organization and How We Got There: from FISH to Hi-C. Microbiol. Mol. Biol. Rev. 79, 347-372.

Fullwood, M. J., Liu, M. H., Pan, Y. F., Liu, J., Xu, H., Mohamed, Y. Bin, Orlov, Y. L., Velkov, S., Ho, A., Mei, P. H., et al. (2009). An oestrogen-receptor-alpha-bound human chromatin interactome. Nature 462, 58-64.

Gabriele, M., Vulto-van Silfhout, A. T., Germain, P.-L., Vitriolo, A., Kumar, R., Douglas, E., Haan, E., Kosaki, K., Takenouchi, T., Rauch, A., et al. (2017). YY1 Haploinsufficiency Causes an Intellectual Disability Syndrome Featuring Transcriptional and Chromatin Dysfunction. Am. J. Hum. Genet. 100, 907-925.

Gibcus, J. H., and Dekker, J. (2013). The hierarchy of the 3D genome. Mol. Cell 49, 773-782. Gordon, S., Akopyan, G., Garban, H., and Bonavida, B. (2006). Transcription factor YY1: structure, function, and therapeutic implications in cancer biology. Oncogene 25, 1125-1142.

Gorkin, D. U., Leung, D., and Ren, B. (2014). The 3D Genome in Transcriptional Regulation and Pluripotency. Cell Stem Cell 14, 762-775.

Guo, C., Yoon, H. S., Franklin, A., Jain, S., Ebert, A., Cheng, H.-L., Hansen, E., Despo, O., Bossen, C., Vettermann, C., et al. (2011). CTCF-binding elements mediate control of V(D)J recombination. Nature 477, 424-430.

Guo, Y., Xu, Q., Canzio, D., Shou, J., Li, J., Gorkin, D. U., Jung, I., Wu, H., Zhai, Y., Tang, Y., et al. (2015). CRISPR Inversion of CTCF Sites Alters Genome Topology and Enhancer/Promoter Function. Cell 162, 900-910.

Hariharan, N., Kelley, D. E., and Perry, R. P. (1991). Delta, a transcription factor that binds to downstream elements in several polymerase II promoters, is a functionally versatile zinc finger protein. Proc. Natl. Acad. Sci. U.S.A. 88, 9799-9803.

Heard, E., and Bickmore, W. (2007). The ins and outs of gene regulation and chromosome territory organisation. Curr. Opin. Cell Biol. 19, 311-316.

Heath, H., Ribeiro de Almeida, C., Sleutels, F., Dingjan, G., van de Nobelen, S., Jonkers, I., Ling, K.-W., Gribnau, J., Renkawitz, R., Grosveld, F., et al. (2008). CTCF regulates cell cycle progression of alphabeta T cells in the thymus. EMBO J. 27, 2839-2850.

Hnisz, D., Day, D. S., and Young, R. A. (2016a). Insulated Neighborhoods: Structural and Functional Units of Mammalian Gene Control. Cell 167, 1188-1200.

Hnisz, D., Weintraub, A. S., Day, D. S., Valton, A.-L., Bak, R. O., Li, C. H., Goldmann, J., Lajoie, B. R., Fan, Z. P., Sigova, A. A., et al. (2016b). Activation of proto-oncogenes by disruption of chromosome neighborhoods. Science (80-.). 351, 1454-1458.

Huang, H., Seo, H., Zhang, T., Wang, Y., Jiang, B., Li, Q., Buckley, D. L., Nabet, B., Roberts, J. M., Paulk, J., et al. (2017). MELK is not necessary for the proliferation of basal-like breast cancer cells. 1-29.

Hwang, S. S., Kim, Y. U., Lee, S., Jang, S. W., Kim, M. K., Koh, B. H., Lee, W., Kim, J., Souabni, A., Busslinger, M., et al. (2013). Transcription factor YY1 is essential for regulation of the Th2 cytokine locus and for Th2 cell differentiation. Proc. Natl. Acad. Sci. 110, 276-281.

Jeronimo, C., Langelier, M. F., Bataille, A. R., Pascal, J. M., Pugh, B. F., and Robert, F. (2016). Tail and Kinase Modules Differently Regulate Core Mediator Recruitment and Function In Vivo. Mol. Cell 64, 455-466.

Ji, X., Dadon, D. B., Abraham, B. J., Ihn, T., Jaenisch, R., Bradner, J. E., and Young, R. A. (2015). Chromatin proteomic profiling reveals novel proteins associated with histone-marked genomic regions. Proc. Natl. Acad. Sci. 112, 3841-3846.

Ji, X., Dadon, D., Powell, B., Fan, Z. P., Borges-Rivera, D., Shachar, S., Weintraub, A. S., Hnisz, D., Pegoraro, G., Lee, T. I., et al. (2016). 3D Chromosome Regulatory Landscape of Human Pluripotent Cells. Cell Stem Cell 18, 1-14.

Kagey, M. H., Newman, J. J., Bilodeau, S., Zhan, Y., Orlando, D. a, van Berkum, N. L., Ebmeier, C. C., Goossens, J., Rahl, P. B., Levine, S. S., et al. (2010). Mediator and cohesin connect gene expression and chromatin architecture. Nature 467, 430-435.

Kim, T. H., Abdullaev, Z. K., Smith, A. D., Ching, K. A., Loukinov, D. I., Green, R. D. D., Zhang, M. Q., Lobanenkov, V. V., and Ren, B. (2007). Analysis of the Vertebrate Insulator Protein CTCF-Binding Sites in the Human Genome. Cell 128, 1231-1245.

Klenova, E. M., Nicolas, R. H., Paterson, H. F., Came, A. F., Heath, C. M., Goodwin, G. H., Neiman, P. E., and Lobanenkov, V. V (1993). CTCF, a conserved nuclear factor required for optimal transcriptional activity of the chicken c-myc gene, is an 11-Zn-finger protein differentially expressed in multiple forms. Mol. Cell. Biol. 13, 7612-7624.

de Laat, W., and Duboule, D. (2013). Topology of mammalian developmental enhancers and their regulatory landscapes. Nature 502, 499-506.

Lamb, P., and McKnight, S. L. (1991). Diversity and specificity in transcriptional regulation: the benefits of heterotypic dimerization. Trends Biochem. Sci. 16, 417-422.

Levine, M., Cattoglio, C., and Tjian, R. (2014). Looping back to leap forward: Transcription enters a new era. Cell 157, 13-25.

Liu, H., Schmidt-supprian, M., Shi, Y., Hobeika, E., Barteneva, N., Jumaa, H., Pelanda, R., Reth, M., Skok, J., Rajewsky, K., et al. (2007). Yin Yang 1 is a critical regulator of B-cell development. 1179-1189.

Lopez-Perrote, A., Alatwi, H. E., Torreira, E., Ismail, A., Ayora, S., Downs, J. A., and Llorca, O. (2014). Structure of Yin Yang 1 oligomers that cooperate with RuvBL1-RuvBL2 ATPases. J. Biol. Chem. 289, 22614-22629.

Lupiáñez, D. G., Kraft, K., Heinrich, V., Krawitz, P., Brancati, F., Klopocki, E., Horn, D., Kayserili, H., Opitz, J. M., Laxova, R., et al. (2015). Disruptions of Topological Chromatin Domains Cause Pathogenic Rewiring of Gene-Enhancer Interactions. Cell 1-14.

Malik, S., and Roeder, R. G. (2010). The metazoan Mediator co-activator complex as an integrative hub for transcriptional regulation. Nat. Rev. Genet. 11, 761-772.

Matthews, K. S. (1992). DNA looping. Microbiol. Rev. 56, 123-136.

Mele, M., Ferreira, P. G., Reverter, F., DeLuca, D. S., Monlong, J., Sammeth, M., Young, T. R., Goldmann, J. M., Pervouchine, D. D., Sullivan, T. J., et al. (2015). The human transcriptome across tissues and individuals. Science (80-.). 348, 660-665.

Merkenschlager, M., and Nora, E. P. (2016). CTCF and Cohesin in Genome Folding and Transcriptional Gene Regulation. Annu. Rev. Genomics Hum. Genet. 17, 1-27.

Muerdter, F., and Stark, A. (2016). Gene Regulation: Activation through Space. Curr. Biol. 26, R895-R898.

Mumbach, M. R., Rubin, A. J., Flynn, R. A., Dai, C., Khavari, P. A., Greenleaf, W. J., and Chang, H. Y. (2016). HiChIP: efficient and sensitive analysis of protein-directed genome architecture. Nat. Methods 13, 919-922.

Narendra, V., Rocha, P. P., An, D., Raviram, R., Skok, J. A., Mazzoni, E. O., and Reinberg, D. (2015). CTCF establishes discrete functional chromatin domains at the Hox clusters during differentiation. 347, 1017-1022.

Nora, E. P., Lajoie, B. R., Schulz, E. G., Giorgetti, L., Okamoto, I., Servant, N., Piolot, T., van Berkum, N. L., Meisig, J., Sedat, J., et al. (2012). Spatial partitioning of the regulatory landscape of the X-inactivation centre. Nature 485, 381-385.

Nora, E. P., Goloborodko, A., Valton, A.-L., Gibcus, J. H., Uebersohn, A., Abdennur, N., Dekker, J., Mirny, L. A., and Bruneau, B. G. (2017). Targeted Degradation of CTCF Decouples Local Insulation of Chromosome Domains from Genomic Compartmentalization. Cell 169, 930-944.e22.

Ohlsson, R., Renkawitz, R., and Lobanenkov, V. (2001). CTCF is a uniquely versatile transcription regulator linked to epigenetics and disease. Trends Genet. 17, 520-527.

Ong, C., and Corces, V. (2011). Enhancer function: new insights into the regulation of tissue-specific gene expression. Nat. Rev. Genet. 12, 283-293.

Park, K., and Atchison, M. L. (1991). Isolation of a candidate repressor/activator, NF-E1 (YY1, d), that binds to the immunoglobulin k 3' enhancer and the immunoglobulin heavy-chain mE1 site. Proc. Natl. Acad. Sci. 88, 9804-9808.

Petrenko, N., Jin, Y., Wong, K. H., and Struhl, K. (2016). Mediator Undergoes a Compositional Change during Transcriptional Activation. Mol. Cell 64, 443-454.

Phillips, J. E., and Corces, V. G. (2009). CTCF: master weaver of the genome. Cell 137, 1194-1211.

Phillips-Cremins, J. E., Sauria, M. E. G., Sanyal, A., Gerasimova, T. I., Lajoie, B. R., Bell, J. S. K., Ong, C.-T., Hookway, T. a, Guo, C., Sun, Y., et al. (2013). Architectural protein subclasses shape 3D organization of genomes during lineage commitment. Cell 153, 1281-1295.

Pombo, A., and Dillon, N. (2015). Three-dimensional genome architecture: players and mechanisms. Nat. Rev. Mol. Cell Biol. 12.

Rao, S. S. P., Huntley, M. H., Durand, N. C., Stamenova, E. K., Bochkov, I. D., Robinson, J. T., Sanborn, A. L., Machol, I., Omer, A. D., Lander, E. S., et al. (2014). A 3D Map of the Human Genome at Kilobase Resolution Reveals Principles of Chromatin Looping. Cell 1-16.

Ren, B., and Yue, F. (2016). Transcriptional enhancers: Bridging the genome and phenome. In Cold Spring Harbor Symposia on Quantitative Biology, pp. 17-26.

Saldaña-Meyer, R., Gonzalez-Buendia, E., Guerrero, G., Narendra, V., Bonasio, R., Recillas-Targa, F., and Reinberg, D. (2014). CTCF regulates the human p53 gene through direct interaction with its natural antisense transcript, Wrap53. Genes Dev. 28, 723-734.

Schleif, R. (1992). DNA looping. Annu. Rev. Biochem. 61, 199-223.

Schmidt, D., Schwalie, P. C., Ross-Innes, C. S., Hurtado, A., Brown, G. D., Carroll, J. S., Flicek, P., and Odom, D. T. (2010). A CTCF-independent role for cohesin in tissue-specific transcription. Genome Res. 20, 578-588.

Shi, Y., Seto, E., Chang, L. S., and Shenk, T. (1991). Transcriptional repression by YY1, a human GLI-Krüppel-related protein, and relief of repression by adenovirus E1A protein. Cell 67, 377-388.

Shi, Y., Lee, J. S., and Galvin, K. M. (1997). Everything you have ever wanted to know about Yin Yang 1 . . . Biochim. Biophys. Acta-Rev. Cancer 1332.

Shore, D., Langowski, J., and Baldwin, R. L. (1981). DNA flexibility studied by covalent closure of short fragments into circles. Proc. Natl. Acad. Sci. U.S.A. 78, 4833-4837.

Sigova, A. A., Abraham, B. J., Ji, X., Molinie, B., Hannett, N. M., Guo, Y. E., Jangi, M., Giallourakis, C. C., Sharp, P. a., and Young, R. A. (2015). Transcription factor trapping by RNA in gene regulatory elements. Science (80-.). 350, 978-981.

Spitz, F. (2016). Gene regulation at a distance: From remote enhancers to 3D regulatory ensembles. Semin. Cell Dev. Biol. 57, 57-67.

Splinter, E., Heath, H., Kooren, J., Palstra, R.-J., Klous, P., Grosveld, F., Galjart, N., and de Laat, W. (2006). CTCF mediates long-range chromatin looping and local histone modification in the beta-globin locus. Genes Dev. 2349-2354.

Tang, Z., Luo, O. J., Li, X., Zheng, M., Zhu, J. J., Szalaj, P., Trzaskoma, P., Magalska, A., Wlodarczyk, J., Ruszczycki, B., et al. (2015). CTCF-Mediated Human 3D Genome Architecture Reveals Chromatin Topology for Transcription. Cell 163, 1611-1627.

Thomas, M. J., and Seto, E. (1999). Unlocking the mechanisms of transcription factor YY1: Are chromatin modifying enzymes the key? Gene 236, 197-208.

Wang, T., Birsoy, K., Hughes, N. W., Krupczak, K. M., Post, Y., Wei, J. J., Lander, E. S., and Sabatini, D. M. (2015). Identification and characterization of essential genes in the human genome. Science (80-.). 350, 1096-1101.

Weirauch, M. T., and Hughes, T. R. (2011). A catalogue of eukaryotic transcription factor types, their evolutionary origin, and species distribution. In A Handbook of Transcription Factors, Subcellular Biochemistry, pp. 25-73.

Wendt, K. S., Yoshida, K., Itoh, T., Bando, M., Koch, B., Schirghuber, E., Tsutsumi, S., Nagae, G., Ishihara, K., Mishiro, T., et al. (2008). Cohesin mediates transcriptional insulation by CCCTC-binding factor. Nature 451, 796-801.

Winter, G. E., Buckley, D. L., Paulk, J., Roberts, J. M., Souza, A., Dhe-Paganon, S., and Bradner, J. E. (2015). Phthalimide conjugation as a strategy for in vivo target protein degradation. Science 348, 1376-1381.

Yin, Y., Morgunova, E., Jolma, A., Kaasinen, E., Sahu, B., Khund-Sayeed, S., Das, P. K., Kivioja, T., Dave, K., Zhong, F., et al. (2017). Impact of cytosine methylation on DNA binding specificities of human transcription factors. Science (80-.). 356, eaaj2239.

Zhang, Q., Stovall, D. B., Inoue, K., and Sui, G. (2011). The Oncogenic Role of Yin Yang 1.

The invention claimed is:

1. A method of decreasing expression of one or more genes in a cell, comprising contacting the cell with a composition for decreasing binding of Yin Yang 1 (YY1) to a YY1 binding site, wherein the composition comprises a site-specific DNA binding domain (DBD) that binds a promoter or an enhancer of the one or more genes and an effector domain having DNA methylation activity, or one or more nucleic acids encoding the site-specific DBD and/or effector domain, and wherein the YY1 binding site is in the promoter or the enhancer of the one or more genes, thereby decreasing expression of the one or more genes.

2. The method of claim 1, wherein the site-specific DBD comprises a zinc finger (ZF).

3. The method of claim 1, wherein the site-specific DBD comprises a transcription activator-like effector (TALE).

4. The method of claim 1, wherein the site-specific DBD comprises a catalytically inactive nuclease and a guide sequence that binds the target sequence.

5. The method of claim 4, wherein the catalytically inactive nuclease is a catalytically inactive Cas protein.

6. The method of claim 1, wherein the site-specific DBD is operably linked to the effector domain.

7. The method of claim 1, wherein the composition comprises a nucleic acid comprising a nucleotide sequence encoding the site-specific DBD operably linked to the effector domain.

8. The method of claim 7, wherein the composition comprises the nucleic acid formulated in a lipid nanoparticle.

9. The method of claim 1, wherein the YY1 binding site is in the enhancer of the one or more genes.

10. The method of claim 1, wherein the YY1 binding site is in the promoter of the one or more genes.

11. The method of claim 1, wherein the effector domain having DNA methylation activity increases DNA methylation of the one or more genes in a region of about 25 bases about 50 bases, about 100 bases, about 200 bases, about 300 bases, about 400 bases, about 500 bases, about 600 bases, about 700 bases, about 800 bases, about 900 bases, or about 1000 bases spanning the YY1 binding site.

12. The method of claim 1, wherein the one or more genes comprises an oncogene.

13. The method of claim 1, wherein binding of YY1 to the YY1 binding site is decreased compared to a control cell not contacted with the composition.

14. A method of decreasing expression of one or more genes in a cell, comprising contacting the cell with a composition for inhibiting formation of an enhancer-promoter DNA loop comprising the one or more genes, wherein the formation of the enhancer-promoter DNA loop is YY1 dependent, wherein the composition comprises a polypeptide for decreasing YY1 multimerization, or one or more nucleic acids encoding the polypeptide.

15. The method of claim 14, wherein the one or more genes comprises an oncogene.

16. The method of claim 14, wherein the composition comprises the polypeptide.

17. The method of claim 14, wherein the composition comprises one or more nucleic acids encoding the polypeptide.

18. The method of claim 17, wherein the composition comprises the one or more nucleic acids formulated in a lipid nanoparticle.

* * * * *